US012612469B2

(12) United States Patent
Kim et al.

(10) Patent No.: US 12,612,469 B2
(45) Date of Patent: Apr. 28, 2026

(54) FUSION POLYPEPTIDE COMPRISING POLYPEPTIDE REGION THAT CAN BE O-GLYCOSYLATED

(71) Applicant: LG CHEM, LTD., Seoul (KR)

(72) Inventors: Yeonchul Kim, Daejeon (KR); Seung Joo Lee, Daejeon (KR); Jong Uk Koh, Daejeon (KR); Kyuyong Kim, Daejeon (KR); Saem Jung, Daejeon (KR); Young Dok Son, Daejeon (KR)

(73) Assignee: LG CHEM, LTD., Seoul (KR)

( * ) Notice: Subject to any disclaimer, the term of this patent is extended or adjusted under 35 U.S.C. 154(b) by 799 days.

(21) Appl. No.: 17/273,591

(22) PCT Filed: Sep. 4, 2019

(86) PCT No.: PCT/KR2019/011409

§ 371 (c)(1),
(2) Date: Mar. 4, 2021

(87) PCT Pub. No.: WO2020/050626

PCT Pub. Date: Mar. 12, 2020

(65) Prior Publication Data

US 2021/0340281 A1     Nov. 4, 2021

(30) Foreign Application Priority Data

Sep. 5, 2018     (KR) ........................ 10-2018-0105741

(51) Int. Cl.
| | |
|---|---|
| *C07K 19/00* | (2006.01) |
| *C07K 14/605* | (2006.01) |
| *C07K 14/61* | (2006.01) |
| *C12N 5/10* | (2006.01) |
| *C12N 15/62* | (2006.01) |
| *C12N 15/63* | (2006.01) |
| *A61K 38/00* | (2006.01) |
| *A61K 39/00* | (2006.01) |
| *C12N 15/00* | (2006.01) |

(52) U.S. Cl.
CPC ............ *C07K 19/00* (2013.01); *C07K 14/605* (2013.01); *C07K 14/61* (2013.01); *A61K 38/00* (2013.01); *A61K 2039/505* (2013.01); *C07K 2317/41* (2013.01); *C07K 2317/53* (2013.01); *C07K 2317/94* (2013.01); *C07K 2319/30* (2013.01); *C07K 2319/31* (2013.01); *C12N 5/10* (2013.01); *C12N 15/00* (2013.01); *C12N 15/62* (2013.01); *C12N 15/63* (2013.01)

(58) Field of Classification Search
CPC ................ C07K 2317/53; C07K 19/00; C07K 2319/31; C07K 2317/41; C07K 2317/94
See application file for complete search history.

(56) References Cited

U.S. PATENT DOCUMENTS

| | | | |
|---|---|---|---|
| 5,416,017 A | | 5/1995 | Burton et al. |
| 6,165,476 A | * | 12/2000 | Strom .................... C07K 14/55 |
| | | | 435/325 |
| 8,304,386 B2 | | 11/2012 | Fares et al. |
| 2003/0044423 A1 | * | 3/2003 | Gillies ................... C07K 16/30 |
| | | | 424/192.1 |
| 2005/0069521 A1 | | 3/2005 | Gillies et al. |
| 2006/0051844 A1 | * | 3/2006 | Heavner ................. A61P 25/00 |
| | | | 435/325 |
| 2008/0300188 A1 | | 12/2008 | Yang et al. |
| 2012/0094356 A1 | | 4/2012 | Chung et al. |

FOREIGN PATENT DOCUMENTS

| | | |
|---|---|---|
| CN | 102439044 A | 5/2012 |
| CN | 105198998 A | 12/2015 |
| CN | 106256835 A | 12/2016 |
| CN | 107286248 A | 10/2017 |
| JP | H01-287041 A | 11/1989 |
| JP | H02-213 A | 1/1990 |
| JP | 2010-531134 A | 9/2010 |
| KR | 10-0545720 B1 | 1/2006 |
| KR | 10-1038126 B1 | 5/2011 |
| KR | 10-1183262 B1 | 9/2012 |
| KR | 10-2014-0015152 A | 2/2014 |
| KR | 10-1380729 B1 | 4/2014 |
| KR | 10-1380732 B1 | 4/2014 |
| KR | 10-2014-0083973 A | 7/2014 |
| KR | 10-2015-0125402 A | 11/2015 |
| WO | 2017-198435 A1 | 11/2017 |

OTHER PUBLICATIONS

Novak et al., Mol Immunol, 2000, 37: 1047-1056.*
Schmidt, "Controlling Glycosylation in Fusion Protein Manufacturing to Generate Potent Biobetters", BioProcess International, 2017, 15(8), p. 12-21.
Plomp et al., "Hinge-Region O-Glycosylation of Human Immunoglobulin G3 (IgG3)", Molecular Cell Proteomics, 2015, 14(5), p. 1373-1384.
Extended European Search Report dated Oct. 18, 2021, of the corresponding European Patent Application No. 19857094.7, 6 pages.
Fares, et al., Design of a long-acting follitropin agonist by fusing the C-terminal sequence of the chorionic gonadotropin beta subunit to the follitropin beta subunit, Proc Natl Acad Sci U S A. May 15, 1992; 89(10): 4304-4308.

(Continued)

*Primary Examiner* — Hong Sang
(74) *Attorney, Agent, or Firm* — ROTHWELL, FIGG, ERNST & MANBECK, P.C.

(57)     ABSTRACT

Disclosed are a fusion polypeptide comprising a target polypeptide and a hinge region of an immunoglobulin; a pharmaceutical composition containing the fusion polypeptide; and a method for increasing the in vivo period of a target polypeptide, comprising a step of fusing a hinge region of an immunoglobulin with the target polypeptide.

10 Claims, 8 Drawing Sheets

Specification includes a Sequence Listing.

(56)            References Cited

OTHER PUBLICATIONS

Fuad Fares, Half-Life Extension Through O-Glycosylation, Therapeutic Proteins, Feb. 6, 2012, Wiley-Blackwell, Weinheim, Germany, pp. 81-94.

International Search Report and Written Opinion issued for International Application No. PCT/KR2019/011409 on Nov. 29, 2019, 20 pages.

Ilum, et al., "Hyaluronic acid ester microspheres as a nasal delivery system for insulin", J. Controlled Rel., 1994, 29, 133-141.

* cited by examiner

【FIG. 1】
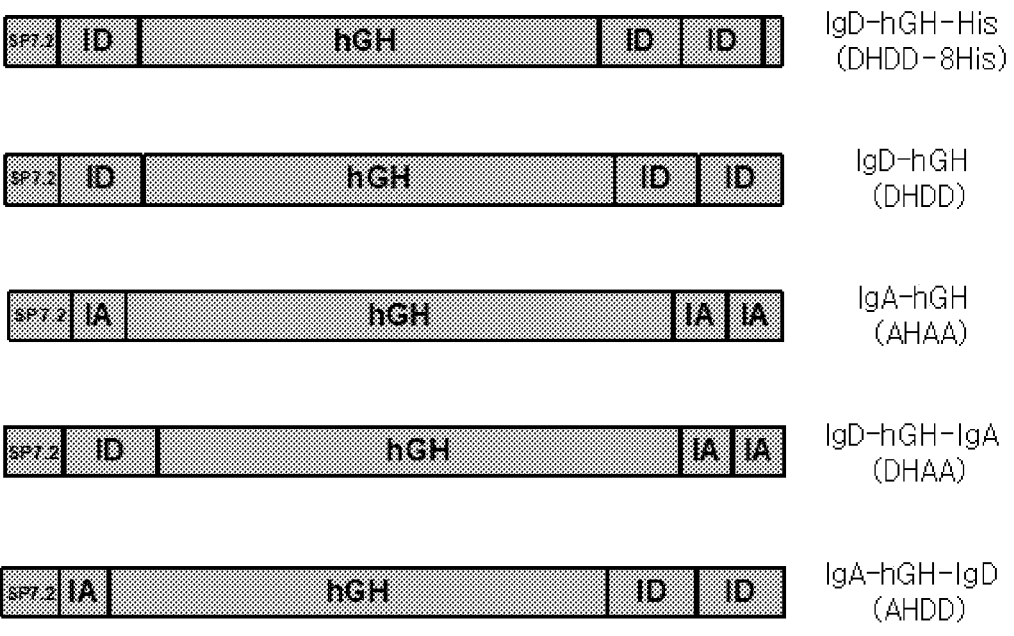
ID: ESPKAQASSVPTAQPQAEGSLAKATTAPATT RNT
(SEQ ID NO: 1)
IA: VPSTPPTPSPSTPPTPSPS (SEQ ID NO: 2)

[FIG. 2]
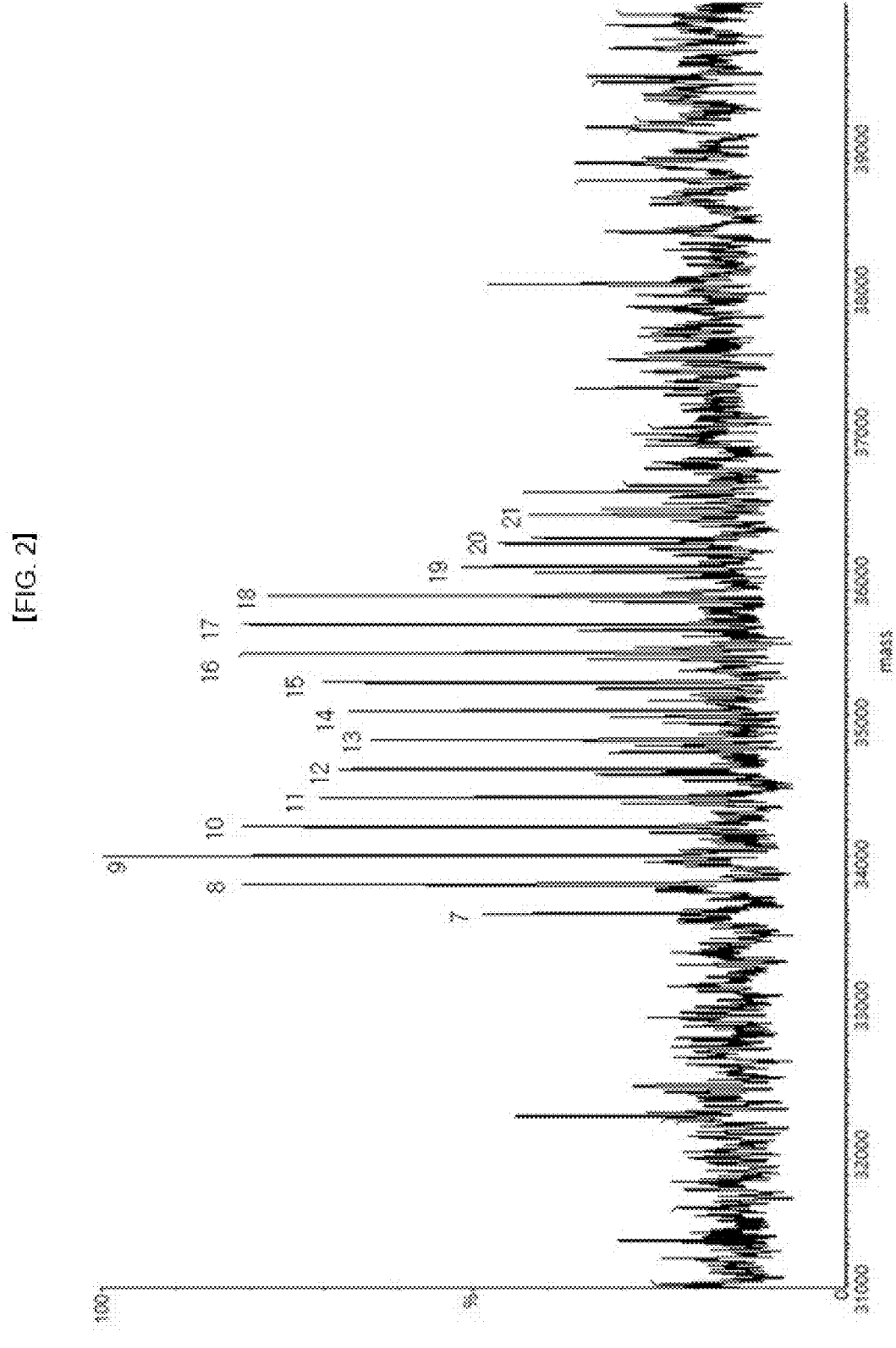

【FIG. 3】
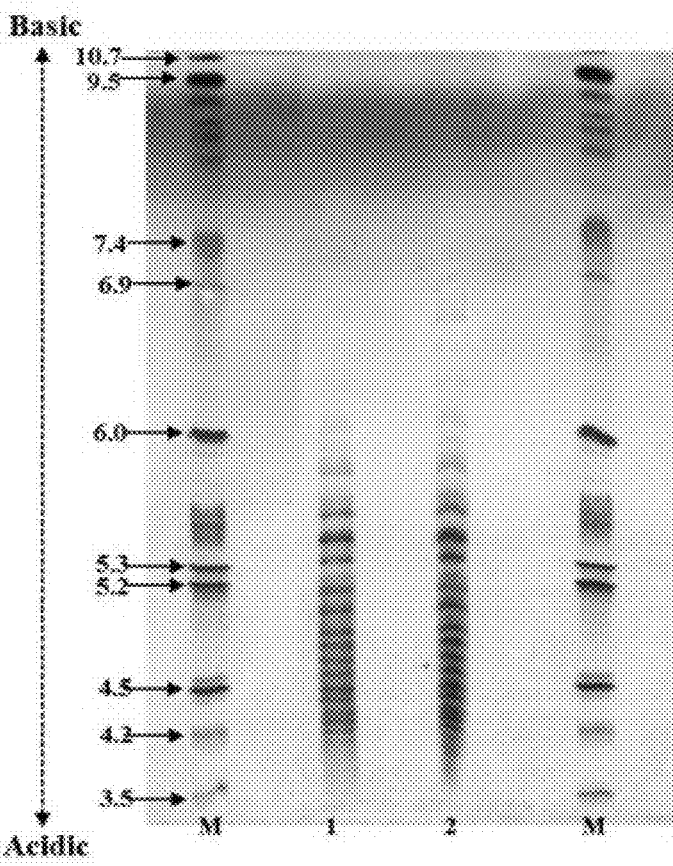
M: PI Marker
1: Isomer distribution of IgD-hGH-His (40μg)
2: Isomer distribution of IgD-hGH-His (60μg)

[FIG. 4]
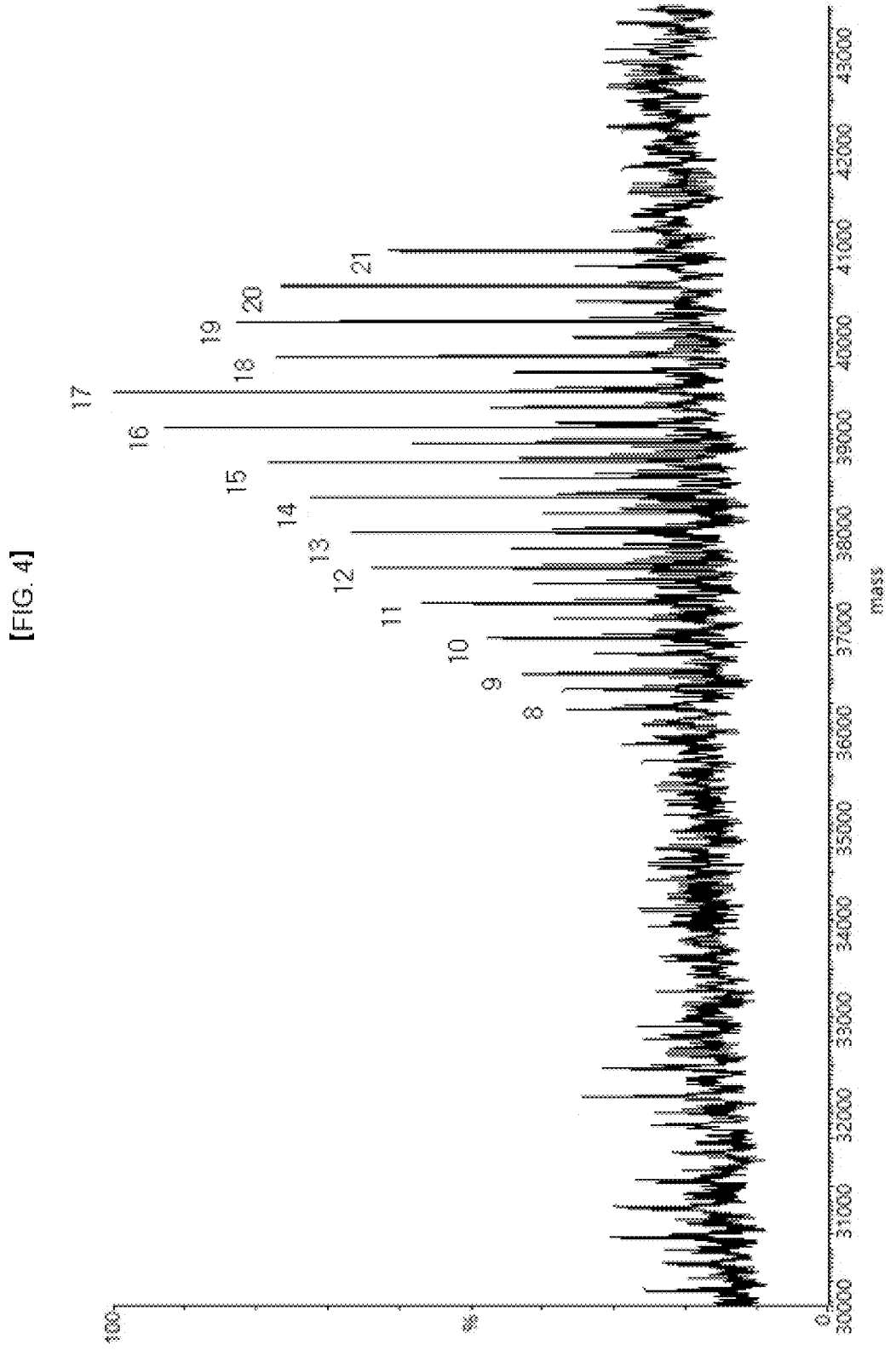

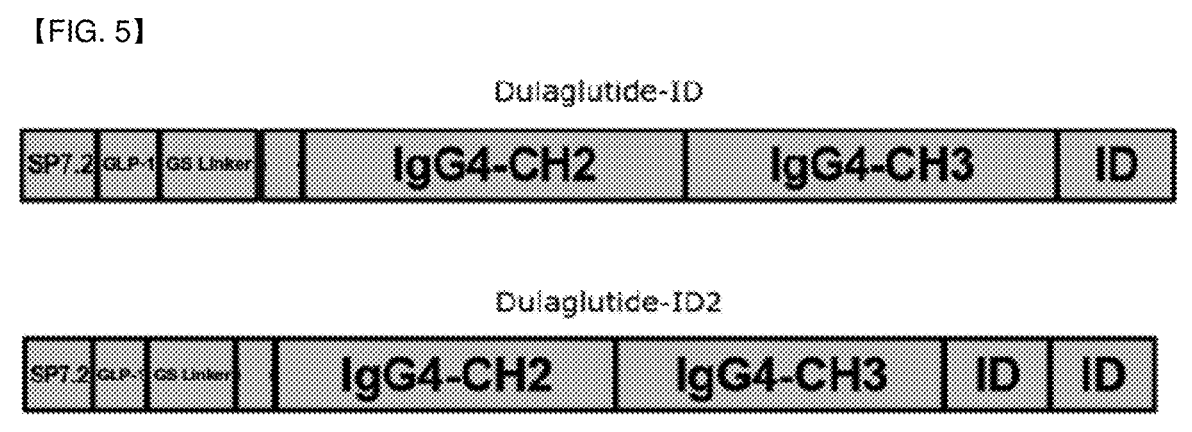

【FIG. 5】

Dulaglutide-ID

| SP7.2 | GLP-1 | GS Linker | | | IgG4-CH2 | IgG4-CH3 | ID |

Dulaglutide-ID2

| SP7.2 | GLP | GS Linker | | | IgG4-CH2 | IgG4-CH3 | ID | ID |

【FIG. 6】
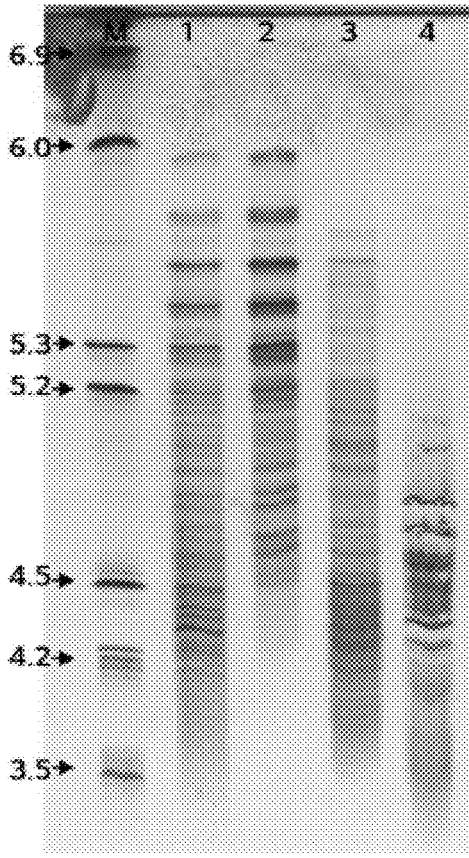
M: pI Marker
1: Dulaglutide-ID2 Pool
2: Dulaglutide-ID2 Fr#1
3: Dulaglutide-ID2 Fr#2
4: Dulaglutide-ID2 Fr#3

【FIG. 7】
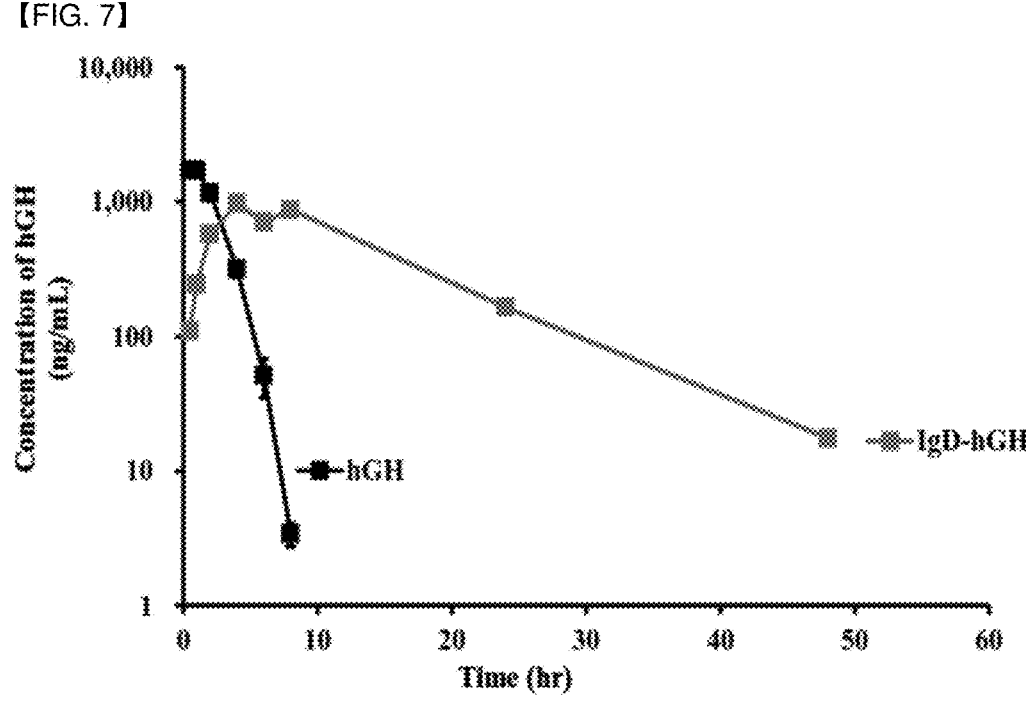
【FIG. 8】
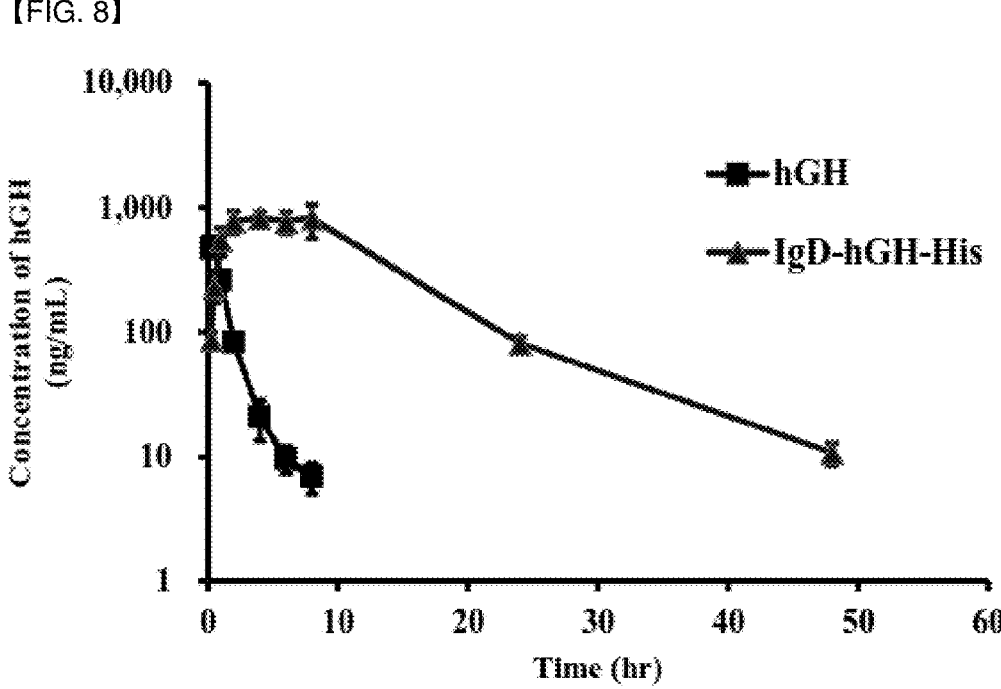

【FIG. 9】
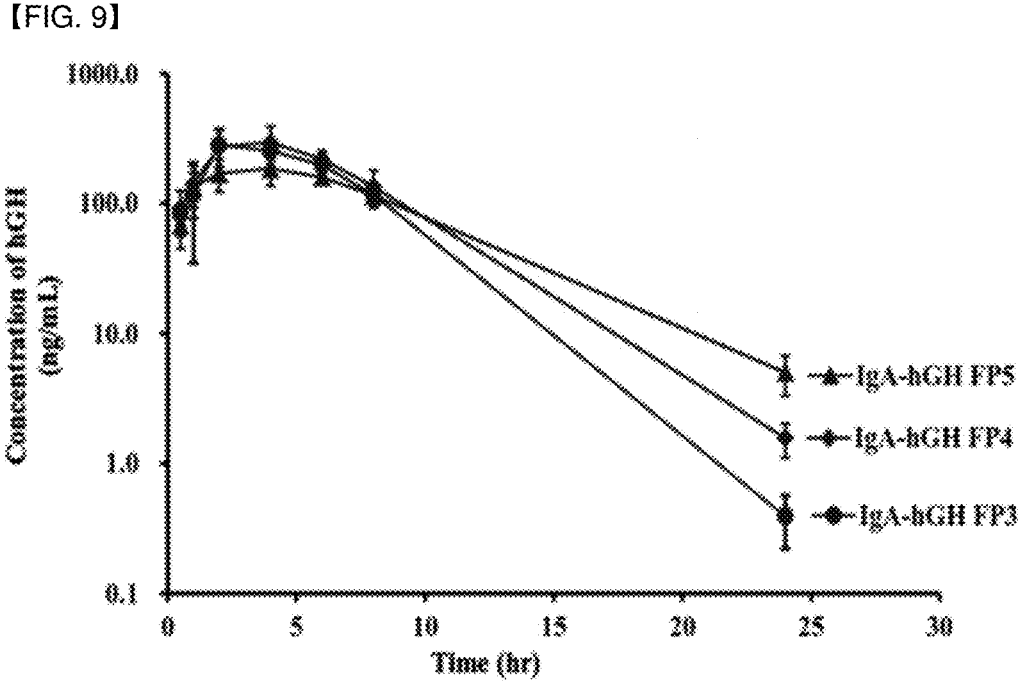
【FIG. 10】
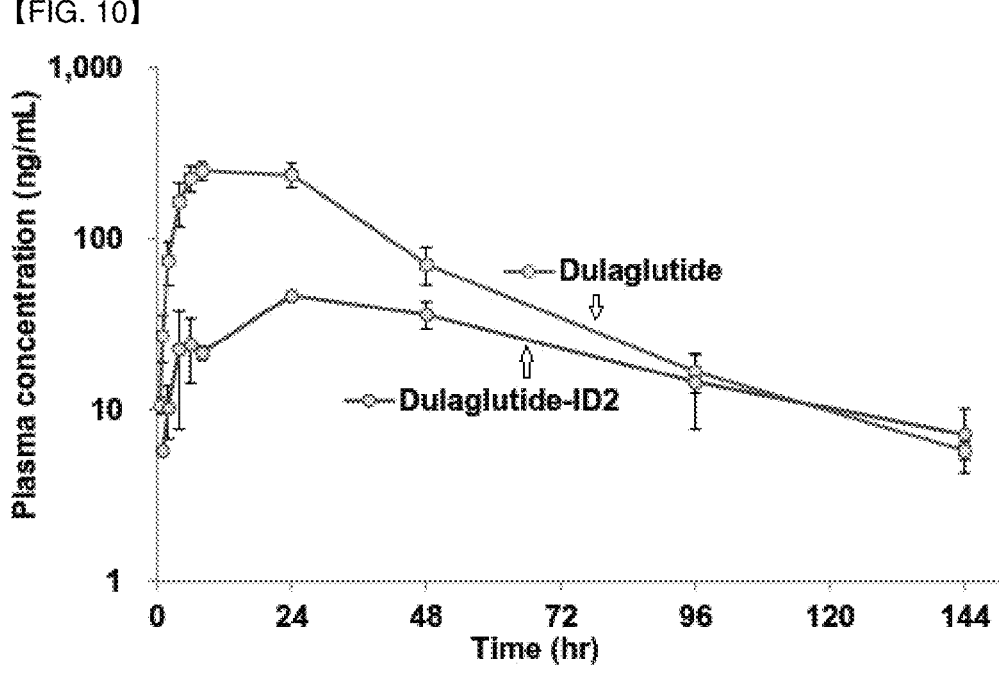

SEQUENCE LISTING

```
<160> NUMBER OF SEQ ID NOS: 114

<210> SEQ ID NO 1
<211> LENGTH: 34
<212> TYPE: PRT
<213> ORGANISM: Artificial Sequence
<220> FEATURE:
<223> OTHER INFORMATION: Synthetic_Human IgD hinge region

<400> SEQUENCE: 1

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
            20                  25                  30

Asn Thr

<210> SEQ ID NO 2
<211> LENGTH: 19
<212> TYPE: PRT
<213> ORGANISM: Artificial Sequence
<220> FEATURE:
<223> OTHER INFORMATION: Synthetic_Human IgA1 hinge region

<400> SEQUENCE: 2

Val Pro Ser Thr Pro Pro Thr Pro Ser Pro Ser Thr Pro Pro Thr Pro
1               5                   10                  15

Ser Pro Ser

<210> SEQ ID NO 3
<211> LENGTH: 191
<212> TYPE: PRT
<213> ORGANISM: Artificial Sequence
<220> FEATURE:
<223> OTHER INFORMATION: Synthetic_Human growth hormone

<400> SEQUENCE: 3

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60
```

-continued

```
Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
        130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
                180                 185                 190

<210> SEQ ID NO 4
<211> LENGTH: 22
<212> TYPE: PRT
<213> ORGANISM: Artificial Sequence
<220> FEATURE:
<223> OTHER INFORMATION: Synthetic_signal peptide

<400> SEQUENCE: 4

Met His Arg Pro Glu Ala Met Leu Leu Leu Leu Thr Leu Ala Leu Leu
1               5                   10                  15

Gly Gly Pro Thr Trp Ala
            20

<210> SEQ ID NO 5
<211> LENGTH: 8
<212> TYPE: PRT
<213> ORGANISM: Artificial Sequence
<220> FEATURE:
<223> OTHER INFORMATION: Synthetic_His-Tag

<400> SEQUENCE: 5

His His His His His His His His
1               5

<210> SEQ ID NO 6
<211> LENGTH: 275
<212> TYPE: PRT
<213> ORGANISM: Artificial Sequence
<220> FEATURE:
<223> OTHER INFORMATION: Synthetic_GLP-1-Fc

<400> SEQUENCE: 6

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Gly Ser Gly Gly Gly Gly Ser Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80
```

-continued

```
Met Ile Ser Arg Thr Pro Glu Val Thr Cys Val Val Val Asp Val Ser
                85              90              95

Gln Glu Asp Pro Glu Val Gln Phe Asn Trp Tyr Val Asp Gly Val Glu
            100             105             110

Val His Asn Ala Lys Thr Lys Pro Arg Glu Glu Gln Phe Asn Ser Thr
            115             120             125

Tyr Arg Val Val Ser Val Leu Thr Val Leu His Gln Asp Trp Leu Asn
    130             135             140

Gly Lys Glu Tyr Lys Cys Lys Val Ser Asn Lys Gly Leu Pro Ser Ser
145             150             155             160

Ile Glu Lys Thr Ile Ser Lys Ala Lys Gly Gln Pro Arg Glu Pro Gln
                165             170             175

Val Tyr Thr Leu Pro Pro Ser Gln Glu Glu Met Thr Lys Asn Gln Val
            180             185             190

Ser Leu Thr Cys Leu Val Lys Gly Phe Tyr Pro Ser Asp Ile Ala Val
            195             200             205

Glu Trp Glu Ser Asn Gly Gln Pro Glu Asn Asn Tyr Lys Thr Thr Pro
    210             215             220

Pro Val Leu Asp Ser Asp Gly Ser Phe Phe Leu Tyr Ser Arg Leu Thr
225             230             235             240

Val Asp Lys Ser Arg Trp Gln Glu Gly Asn Val Phe Ser Cys Ser Val
            245             250             255

Met His Glu Ala Leu His Asn His Tyr Thr Gln Lys Ser Leu Ser Leu
            260             265             270

Ser Leu Gly
        275

<210> SEQ ID NO 7
<211> LENGTH: 384
<212> TYPE: PRT
<213> ORGANISM: Artificial Sequence
<220> FEATURE:
<223> OTHER INFORMATION: Synthetic_Human IgD heavy chain constant region
      (UniProtKB P01880)

<400> SEQUENCE: 7

Ala Pro Thr Lys Ala Pro Asp Val Phe Pro Ile Ile Ser Gly Cys Arg
1               5               10              15

His Pro Lys Asp Asn Ser Pro Val Val Leu Ala Cys Leu Ile Thr Gly
            20              25              30

Tyr His Pro Thr Ser Val Thr Val Thr Trp Tyr Met Gly Thr Gln Ser
        35              40              45

Gln Pro Gln Arg Thr Phe Pro Glu Ile Gln Arg Arg Asp Ser Tyr Tyr
    50              55              60

Met Thr Ser Ser Gln Leu Ser Thr Pro Leu Gln Gln Trp Arg Gln Gly
65              70              75              80

Glu Tyr Lys Cys Val Val Gln His Thr Ala Ser Lys Ser Lys Lys Glu
                85              90              95

Ile Phe Arg Trp Pro Glu Ser Pro Lys Ala Gln Ala Ser Ser Val Pro
            100             105             110

Thr Ala Gln Pro Gln Ala Glu Gly Ser Leu Ala Lys Ala Thr Thr Ala
            115             120             125

Pro Ala Thr Thr Arg Asn Thr Gly Arg Gly Gly Glu Glu Lys Lys Lys
    130             135             140

Glu Lys Glu Lys Glu Glu Gln Glu Glu Arg Glu Thr Lys Thr Pro Glu
145             150             155             160
```

Cys Pro Ser His Thr Gln Pro Leu Gly Val Tyr Leu Leu Thr Pro Ala
              165             170             175

Val Gln Asp Leu Trp Leu Arg Asp Lys Ala Thr Phe Thr Cys Phe Val
              180             185             190

Val Gly Ser Asp Leu Lys Asp Ala His Leu Thr Trp Glu Val Ala Gly
              195             200             205

Lys Val Pro Thr Gly Gly Val Glu Glu Gly Leu Leu Glu Arg His Ser
      210             215             220

Asn Gly Ser Gln Ser Gln His Ser Arg Leu Thr Leu Pro Arg Ser Leu
225             230             235             240

Trp Asn Ala Gly Thr Ser Val Thr Cys Thr Leu Asn His Pro Ser Leu
              245             250             255

Pro Pro Gln Arg Leu Met Ala Leu Arg Glu Pro Ala Ala Gln Ala Pro
              260             265             270

Val Lys Leu Ser Leu Asn Leu Leu Ala Ser Ser Asp Pro Pro Glu Ala
              275             280             285

Ala Ser Trp Leu Leu Cys Glu Val Ser Gly Phe Ser Pro Pro Asn Ile
      290             295             300

Leu Leu Met Trp Leu Glu Asp Gln Arg Glu Val Asn Thr Ser Gly Phe
305             310             315             320

Ala Pro Ala Arg Pro Pro Pro Gln Pro Arg Ser Thr Thr Phe Trp Ala
              325             330             335

Trp Ser Val Leu Arg Val Pro Ala Pro Pro Ser Pro Gln Pro Ala Thr
              340             345             350

Tyr Thr Cys Val Val Ser His Glu Asp Ser Arg Thr Leu Leu Asn Ala
              355             360             365

Ser Arg Ser Leu Glu Val Ser Tyr Val Thr Asp His Gly Pro Met Lys
      370             375             380

<210> SEQ ID NO 8
<211> LENGTH: 353
<212> TYPE: PRT
<213> ORGANISM: Artificial Sequence
<220> FEATURE:
<223> OTHER INFORMATION: Synthetic_Human IgA heavy chain constant region
      (UniProtKB P01876)

<400> SEQUENCE: 8

Ala Ser Pro Thr Ser Pro Lys Val Phe Pro Leu Ser Leu Cys Ser Thr
1               5               10              15

Gln Pro Asp Gly Asn Val Val Ile Ala Cys Leu Val Gln Gly Phe Phe
              20              25              30

Pro Gln Glu Pro Leu Ser Val Thr Trp Ser Glu Ser Gly Gln Gly Val
              35              40              45

Thr Ala Arg Asn Phe Pro Pro Ser Gln Asp Ala Ser Gly Asp Leu Tyr
      50              55              60

Thr Thr Ser Ser Gln Leu Thr Leu Pro Ala Thr Gln Cys Leu Ala Gly
65              70              75              80

Lys Ser Val Thr Cys His Val Lys His Tyr Thr Asn Pro Ser Gln Asp
              85              90              95

Val Thr Val Pro Cys Pro Val Pro Ser Thr Pro Pro Thr Pro Ser Pro
              100             105             110

Ser Thr Pro Pro Thr Pro Ser Pro Ser Cys Cys His Pro Arg Leu Ser
      115             120             125

Leu His Arg Pro Ala Leu Glu Asp Leu Leu Leu Gly Ser Glu Ala Asn

-continued

```
       130               135                140

Leu Thr Cys Thr Leu Thr Gly Leu Arg Asp Ala Ser Gly Val Thr Phe
145              150                155                160

Thr Trp Thr Pro Ser Ser Gly Lys Ser Ala Val Gln Gly Pro Pro Glu
                 165                170                175

Arg Asp Leu Cys Gly Cys Tyr Ser Val Ser Ser Val Leu Pro Gly Cys
              180                185                190

Ala Glu Pro Trp Asn His Gly Lys Thr Phe Thr Cys Thr Ala Ala Tyr
           195                200                205

Pro Glu Ser Lys Thr Pro Leu Thr Ala Thr Leu Ser Lys Ser Gly Asn
           210                215                220

Thr Phe Arg Pro Glu Val His Leu Leu Pro Pro Pro Ser Glu Glu Leu
225                230                235                240

Ala Leu Asn Glu Leu Val Thr Leu Thr Cys Leu Ala Arg Gly Phe Ser
                 245                250                255

Pro Lys Asp Val Leu Val Arg Trp Leu Gln Gly Ser Gln Glu Leu Pro
              260                265                270

Arg Glu Lys Tyr Leu Thr Trp Ala Ser Arg Gln Glu Pro Ser Gln Gly
           275                280                285

Thr Thr Thr Phe Ala Val Thr Ser Ile Leu Arg Val Ala Ala Glu Asp
        290                295                300

Trp Lys Lys Gly Asp Thr Phe Ser Cys Met Val Gly His Glu Ala Leu
305                310                315                320

Pro Leu Ala Phe Thr Gln Lys Thr Ile Asp Arg Leu Ala Gly Lys Pro
                 325                330                335

Thr His Val Asn Val Ser Val Val Met Ala Glu Val Asp Gly Thr Cys
                 340                345                350

Tyr
```

```
<210> SEQ ID NO 9
<211> LENGTH: 5
<212> TYPE: PRT
<213> ORGANISM: Artificial Sequence
<220> FEATURE:
<223> OTHER INFORMATION: Synthetic_a part of human IgD hinge region

<400> SEQUENCE: 9

Ser Ser Val Pro Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic_a part of human IgD hinge region

<400> SEQUENCE: 10

Thr Thr Ala Pro Ala Thr Thr
1               5

<210> SEQ ID NO 11
<211> LENGTH: 58
<212> TYPE: PRT
<213> ORGANISM: Artificial Sequence
<220> FEATURE:
<223> OTHER INFORMATION: Synthetic_a extended part of human IgD hinge
      region

<400> SEQUENCE: 11
```

```
Glu Ser Pro Lys Ala Gln Ala Ser Ser Val Pro Thr Ala Gln Pro Gln
1               5               10              15

Ala Glu Gly Ser Leu Ala Lys Ala Thr Thr Ala Pro Ala Thr Thr Arg
            20              25              30

Asn Thr Gly Arg Gly Gly Glu Glu Lys Lys Lys Glu Lys Glu Lys Glu
        35              40              45

Glu Gln Glu Glu Arg Glu Thr Lys Thr Pro
    50              55
```

```
<210> SEQ ID NO 12
<211> LENGTH: 8
<212> TYPE: PRT
<213> ORGANISM: Artificial Sequence
<220> FEATURE:
<223> OTHER INFORMATION: Synthetic_a part of human IgA1 hinge region

<400> SEQUENCE: 12

Ser Thr Pro Pro Thr Pro Ser Pro
1               5
```

```
<210> SEQ ID NO 13
<211> LENGTH: 5
<212> TYPE: PRT
<213> ORGANISM: Artificial Sequence
<220> FEATURE:
<223> OTHER INFORMATION: Synthetic_peptide linker

<400> SEQUENCE: 13

Gly Gly Gly Gly Ser
1               5
```

```
<210> SEQ ID NO 14
<211> LENGTH: 27
<212> TYPE: DNA
<213> ORGANISM: Artificial Sequence
<220> FEATURE:
<223> OTHER INFORMATION: Synthetic_hGH-Pst_F primer

<400> SEQUENCE: 14
aagtattcct tcctgcagaa cccccag                                        27
```

```
<210> SEQ ID NO 15
<211> LENGTH: 30
<212> TYPE: DNA
<213> ORGANISM: Artificial Sequence
<220> FEATURE:
<223> OTHER INFORMATION: Synthetic_DD_R primer

<400> SEQUENCE: 15
cctgtgcctt tggagactct gtgttacggg                                     30
```

```
<210> SEQ ID NO 16
<211> LENGTH: 30
<212> TYPE: DNA
<213> ORGANISM: Artificial Sequence
<220> FEATURE:
<223> OTHER INFORMATION: Synthetic_DD_F primer

<400> SEQUENCE: 16
gagtctccaa aggcacaggc ctcctccgtg                                     30
```

```
<210> SEQ ID NO 17
<211> LENGTH: 33
<212> TYPE: DNA
```

-continued

```
<213> ORGANISM: Artificial Sequence
<220> FEATURE:
<223> OTHER INFORMATION: Synthetic_DHis_R primer

<400> SEQUENCE: 17
gtggtgatga tggtgtgtgt tacgggtggt ggc                                    33

<210> SEQ ID NO 18
<211> LENGTH: 36
<212> TYPE: DNA
<213> ORGANISM: Artificial Sequence
<220> FEATURE:
<223> OTHER INFORMATION: Synthetic_His-Not_R primer

<400> SEQUENCE: 18
gcggccgctt tagtgatggt ggtggtgatg atggtg                                 36

<210> SEQ ID NO 19
<211> LENGTH: 30
<212> TYPE: DNA
<213> ORGANISM: Artificial Sequence
<220> FEATURE:
<223> OTHER INFORMATION: Synthetic_IgG4mCH2_F primer

<400> SEQUENCE: 19
cacctgaggc cgccggggga ccgtcagtct                                        30

<210> SEQ ID NO 20
<211> LENGTH: 30
<212> TYPE: DNA
<213> ORGANISM: Artificial Sequence
<220> FEATURE:
<223> OTHER INFORMATION: Synthetic_IgG4ID_R primer

<400> SEQUENCE: 20
ctttggagac tcgcccaggg acagggacag                                        30

<210> SEQ ID NO 21
<211> LENGTH: 30
<212> TYPE: DNA
<213> ORGANISM: Artificial Sequence
<220> FEATURE:
<223> OTHER INFORMATION: Synthetic_IgG4ID_F primer

<400> SEQUENCE: 21
ctgggcgagt ctccaaaggc acaggcctcc                                        30

<210> SEQ ID NO 22
<211> LENGTH: 30
<212> TYPE: DNA
<213> ORGANISM: Artificial Sequence
<220> FEATURE:
<223> OTHER INFORMATION: Synthetic_ID_NotR primer

<400> SEQUENCE: 22
ttcttcttcg cggccgcttt atgtgttacg                                        30

<210> SEQ ID NO 23
<211> LENGTH: 90
<212> TYPE: PRT
<213> ORGANISM: Artificial Sequence
<220> FEATURE:
<223> OTHER INFORMATION: Synthetic_MUCL1_HUMAN

<400> SEQUENCE: 23

Met Lys Phe Leu Ala Val Leu Val Leu Leu Gly Val Ser Ile Phe Leu
```

-continued

```
1               5                   10                  15

Val Ser Ala Gln Asn Pro Thr Thr Ala Ala Pro Ala Asp Thr Tyr Pro
              20                  25                  30

Ala Thr Gly Pro Ala Asp Asp Glu Ala Pro Asp Ala Glu Thr Thr Ala
          35                  40                  45

Ala Ala Thr Thr Ala Thr Thr Ala Ala Pro Thr Thr Ala Thr Thr Ala
      50                  55                  60

Ala Ser Thr Thr Ala Arg Lys Asp Ile Pro Val Leu Pro Lys Trp Val
65                  70                  75                  80

Gly Asp Leu Pro Asn Gly Arg Val Cys Pro
              85                  90
```

<210> SEQ ID NO 24
<211> LENGTH: 97
<212> TYPE: PRT
<213> ORGANISM: Artificial Sequence
<220> FEATURE:
<223> OTHER INFORMATION: Synthetic_SMAGP_HUMAN

<400> SEQUENCE: 24

```
Met Thr Ser Leu Leu Thr Thr Pro Ser Pro Arg Glu Glu Leu Met Thr
1               5                   10                  15

Thr Pro Ile Leu Gln Pro Thr Glu Ala Leu Ser Pro Glu Asp Gly Ala
              20                  25                  30

Ser Thr Ala Leu Ile Ala Val Val Ile Thr Val Val Phe Leu Thr Leu
          35                  40                  45

Leu Ser Val Val Ile Leu Ile Phe Phe Tyr Leu Tyr Lys Asn Lys Gly
      50                  55                  60

Ser Tyr Val Thr Tyr Glu Pro Thr Glu Gly Glu Pro Ser Ala Ile Val
65                  70                  75                  80

Gln Met Glu Ser Asp Leu Ala Lys Gly Ser Glu Lys Glu Glu Tyr Phe
              85                  90                  95

Ile
```

<210> SEQ ID NO 25
<211> LENGTH: 128
<212> TYPE: PRT
<213> ORGANISM: Artificial Sequence
<220> FEATURE:
<223> OTHER INFORMATION: Synthetic_GLPC_HUMAN

<400> SEQUENCE: 25

```
Met Trp Ser Thr Arg Ser Pro Asn Ser Thr Ala Trp Pro Leu Ser Leu
1               5                   10                  15

Glu Pro Asp Pro Gly Met Ala Ser Ala Ser Thr Thr Met His Thr Thr
              20                  25                  30

Thr Ile Ala Glu Pro Asp Pro Gly Met Ser Gly Trp Pro Asp Gly Arg
          35                  40                  45

Met Glu Thr Ser Thr Pro Thr Ile Met Asp Ile Val Val Ile Ala Gly
      50                  55                  60

Val Ile Ala Ala Val Ala Ile Val Leu Val Ser Leu Leu Phe Val Met
65                  70                  75                  80

Leu Arg Tyr Met Tyr Arg His Lys Gly Thr Tyr His Thr Asn Glu Ala
              85                  90                  95

Lys Gly Thr Glu Phe Ala Glu Ser Ala Asp Ala Ala Leu Gln Gly Asp
              100                 105                 110

Pro Ala Leu Gln Asp Ala Gly Asp Ser Ser Arg Lys Glu Tyr Phe Ile
```

-continued

```
        115             120             125

<210> SEQ ID NO 26
<211> LENGTH: 134
<212> TYPE: PRT
<213> ORGANISM: Artificial Sequence
<220> FEATURE:
<223> OTHER INFORMATION: Synthetic_ANFB_HUMAN

<400> SEQUENCE: 26

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
            115                 120                 125

Lys Val Leu Arg Arg His
    130

<210> SEQ ID NO 27
<211> LENGTH: 144
<212> TYPE: PRT
<213> ORGANISM: Artificial Sequence
<220> FEATURE:
<223> OTHER INFORMATION: Synthetic_CSF2_HUMAN

<400> SEQUENCE: 27

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
    130                 135                 140

<210> SEQ ID NO 28
<211> LENGTH: 150
```

```
<212> TYPE: PRT
<213> ORGANISM: Artificial Sequence
<220> FEATURE:
<223> OTHER INFORMATION: Synthetic_GLPA_HUMAN

<400> SEQUENCE: 28

Met Tyr Gly Lys Ile Ile Phe Val Leu Leu Leu Ser Glu Ile Val Ser
1               5                   10                  15

Ile Ser Ala Ser Ser Thr Thr Gly Val Ala Met His Thr Ser Thr Ser
            20                  25                  30

Ser Ser Val Thr Lys Ser Tyr Ile Ser Ser Gln Thr Asn Asp Thr His
        35                  40                  45

Lys Arg Asp Thr Tyr Ala Ala Thr Pro Arg Ala His Glu Val Ser Glu
    50                  55                  60

Ile Ser Val Arg Thr Val Tyr Pro Pro Glu Glu Glu Thr Gly Glu Arg
65                  70                  75                  80

Val Gln Leu Ala His His Phe Ser Glu Pro Glu Ile Thr Leu Ile Ile
                85                  90                  95

Phe Gly Val Met Ala Gly Val Ile Gly Thr Ile Leu Leu Ile Ser Tyr
            100                 105                 110

Gly Ile Arg Arg Leu Ile Lys Lys Ser Pro Ser Asp Val Lys Pro Leu
        115                 120                 125

Pro Ser Pro Asp Thr Asp Val Pro Leu Ser Ser Val Glu Ile Glu Asn
    130                 135                 140

Pro Glu Thr Ser Asp Gln
145                 150

<210> SEQ ID NO 29
<211> LENGTH: 158
<212> TYPE: PRT
<213> ORGANISM: Artificial Sequence
<220> FEATURE:
<223> OTHER INFORMATION: Synthetic_SRGN_HUMAN

<400> SEQUENCE: 29

Met Met Gln Lys Leu Leu Lys Cys Ser Arg Leu Val Leu Ala Leu Ala
1               5                   10                  15

Leu Ile Leu Val Leu Glu Ser Ser Val Gln Gly Tyr Pro Thr Arg Arg
            20                  25                  30

Ala Arg Tyr Gln Trp Val Arg Cys Asn Pro Asp Ser Asn Ser Ala Asn
        35                  40                  45

Cys Leu Glu Glu Lys Gly Pro Met Phe Glu Leu Leu Pro Gly Glu Ser
    50                  55                  60

Asn Lys Ile Pro Arg Leu Arg Thr Asp Leu Phe Pro Lys Thr Arg Ile
65                  70                  75                  80

Gln Asp Leu Asn Arg Ile Phe Pro Leu Ser Glu Asp Tyr Ser Gly Ser
                85                  90                  95

Gly Phe Gly Ser Gly Ser Gly Ser Gly Ser Gly Ser Gly Ser Gly Phe
            100                 105                 110

Leu Thr Glu Met Glu Gln Asp Tyr Gln Leu Val Asp Glu Ser Asp Ala
        115                 120                 125

Phe His Asp Asn Leu Arg Ser Leu Asp Arg Asn Leu Pro Ser Asp Ser
    130                 135                 140

Gln Asp Leu Gly Gln His Gly Leu Glu Glu Asp Phe Met Leu
145                 150                 155

<210> SEQ ID NO 30
```

```
<211> LENGTH: 162
<212> TYPE: PRT
<213> ORGANISM: Artificial Sequence
<220> FEATURE:
<223> OTHER INFORMATION: Synthetic_PDPN_HUMAN

<400> SEQUENCE: 30

Met Trp Lys Val Ser Ala Leu Leu Phe Val Leu Gly Ser Ala Ser Leu
1               5                   10                  15

Trp Val Leu Ala Glu Gly Ala Ser Thr Gly Gln Pro Glu Asp Asp Thr
            20                  25                  30

Glu Thr Thr Gly Leu Glu Gly Gly Val Ala Met Pro Gly Ala Glu Asp
        35                  40                  45

Asp Val Val Thr Pro Gly Thr Ser Glu Asp Arg Tyr Lys Ser Gly Leu
    50                  55                  60

Thr Thr Leu Val Ala Thr Ser Val Asn Ser Val Thr Gly Ile Arg Ile
65                  70                  75                  80

Glu Asp Leu Pro Thr Ser Glu Ser Thr Val His Ala Gln Glu Gln Ser
                85                  90                  95

Pro Ser Ala Thr Ala Ser Asn Val Ala Thr Ser His Ser Thr Glu Lys
            100                 105                 110

Val Asp Gly Asp Thr Gln Thr Thr Val Glu Lys Asp Gly Leu Ser Thr
        115                 120                 125

Val Thr Leu Val Gly Ile Ile Val Gly Val Leu Leu Ala Ile Gly Phe
    130                 135                 140

Ile Gly Ala Ile Ile Val Val Val Met Arg Lys Met Ser Gly Arg Tyr
145                 150                 155                 160

Ser Pro

<210> SEQ ID NO 31
<211> LENGTH: 165
<212> TYPE: PRT
<213> ORGANISM: Artificial Sequence
<220> FEATURE:
<223> OTHER INFORMATION: Synthetic_CGB7_HUMAN

<400> SEQUENCE: 31

Met Glu Met Phe Gln Gly Leu Leu Leu Leu Leu Leu Leu Ser Met Gly
1               5                   10                  15

Gly Thr Trp Ala Ser Arg Glu Met Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Ala Ser Ser Ser Ser Lys Ala Pro
    130                 135                 140

Pro Pro Ser Leu Pro Ser Pro Ser Arg Leu Pro Gly Pro Ser Asp Thr
145                 150                 155                 160
```

```
Pro Ile Leu Pro Gln
                165

<210> SEQ ID NO 32
<211> LENGTH: 165
<212> TYPE: PRT
<213> ORGANISM: Artificial Sequence
<220> FEATURE:
<223> OTHER INFORMATION: Synthetic_CGB3_HUMAN

<400> SEQUENCE: 32

Met Glu Met Phe Gln Gly Leu Leu Leu Leu Leu Leu Ser Met Gly
1               5                  10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
        50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
            115                 120                 125

Thr Cys Asp Asp Pro Arg Phe Gln Asp Ser Ser Ser Ser Lys Ala Pro
        130                 135                 140

Pro Pro Ser Leu Pro Ser Pro Ser Arg Leu Pro Gly Pro Ser Asp Thr
145                 150                 155                 160

Pro Ile Leu Pro Gln
                165

<210> SEQ ID NO 33
<211> LENGTH: 180
<212> TYPE: PRT
<213> ORGANISM: Artificial Sequence
<220> FEATURE:
<223> OTHER INFORMATION: Synthetic_IGF2_HUMAN

<400> SEQUENCE: 33

Met Gly Ile Pro Met Gly Lys Ser Met Leu Val Leu Leu Thr Phe Leu
1               5                  10                  15

Ala Phe Ala Ser Cys Cys Ile Ala Ala Tyr Arg Pro Ser Glu Thr Leu
                20                  25                  30

Cys Gly Gly Glu Leu Val Asp Thr Leu Gln Phe Val Cys Gly Asp Arg
            35                  40                  45

Gly Phe Tyr Phe Ser Arg Pro Ala Ser Arg Val Ser Arg Arg Ser Arg
        50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
                100                 105                 110

Phe Phe Gln Tyr Asp Thr Trp Lys Gln Ser Thr Gln Arg Leu Arg Arg
```

```
                115                 120                 125

Gly Leu Pro Ala Leu Leu Arg Ala Arg Arg Gly His Val Leu Ala Lys
    130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                165                 170                 175

Ser Asn Arg Lys
            180

<210> SEQ ID NO 34
<211> LENGTH: 182
<212> TYPE: PRT
<213> ORGANISM: Artificial Sequence
<220> FEATURE:
<223> OTHER INFORMATION: Synthetic_CASK_HUMAN

<400> SEQUENCE: 34

Met Lys Ser Phe Leu Leu Val Val Asn Ala Leu Ala Leu Thr Leu Pro
1               5                   10                  15

Phe Leu Ala Val Glu Val Gln Asn Gln Lys Gln Pro Ala Cys His Glu
                20                  25                  30

Asn Asp Glu Arg Pro Phe Tyr Gln Lys Thr Ala Pro Tyr Val Pro Met
            35                  40                  45

Tyr Tyr Val Pro Asn Ser Tyr Pro Tyr Tyr Gly Thr Asn Leu Tyr Gln
    50                  55                  60

Arg Arg Pro Ala Ile Ala Ile Asn Asn Pro Tyr Val Pro Arg Thr Tyr
65                  70                  75                  80

Tyr Ala Asn Pro Ala Val Val Arg Pro His Ala Gln Ile Pro Gln Arg
                85                  90                  95

Gln Tyr Leu Pro Asn Ser His Pro Pro Thr Val Val Arg Arg Pro Asn
            100                 105                 110

Leu His Pro Ser Phe Ile Ala Ile Pro Pro Lys Lys Ile Gln Asp Lys
            115                 120                 125

Ile Ile Ile Pro Thr Ile Asn Thr Ile Ala Thr Val Glu Pro Thr Pro
    130                 135                 140

Ala Pro Ala Thr Glu Pro Thr Val Asp Ser Val Val Thr Pro Glu Ala
145                 150                 155                 160

Phe Ser Glu Ser Ile Ile Thr Ser Thr Pro Glu Thr Thr Thr Val Ala
                165                 170                 175

Val Thr Pro Pro Thr Ala
            180

<210> SEQ ID NO 35
<211> LENGTH: 198
<212> TYPE: PRT
<213> ORGANISM: Artificial Sequence
<220> FEATURE:
<223> OTHER INFORMATION: Synthetic_SDC4_HUMAN

<400> SEQUENCE: 35

Met Ala Pro Ala Arg Leu Phe Ala Leu Leu Leu Phe Phe Val Gly Gly
1               5                   10                  15

Val Ala Glu Ser Ile Arg Glu Thr Glu Val Ile Asp Pro Gln Asp Leu
                20                  25                  30

Leu Glu Gly Arg Tyr Phe Ser Gly Ala Leu Pro Asp Asp Glu Asp Val
            35                  40                  45
```

-continued

```
Val Gly Pro Gly Gln Glu Ser Asp Asp Phe Glu Leu Ser Gly Ser Gly
    50                  55                  60

Asp Leu Asp Asp Leu Glu Asp Ser Met Ile Gly Pro Glu Val Val His
65                  70                  75                  80

Pro Leu Val Pro Leu Asp Asn His Ile Pro Glu Arg Ala Gly Ser Gly
                85                  90                  95

Ser Gln Val Pro Thr Glu Pro Lys Lys Leu Glu Glu Asn Glu Val Ile
            100                 105                 110

Pro Lys Arg Ile Ser Pro Val Glu Glu Ser Glu Asp Val Ser Asn Lys
            115                 120                 125

Val Ser Met Ser Ser Thr Val Gln Gly Ser Asn Ile Phe Glu Arg Thr
    130                 135                 140

Glu Val Leu Ala Ala Leu Ile Val Gly Gly Ile Val Gly Ile Leu Phe
145                 150                 155                 160

Ala Val Phe Leu Ile Leu Leu Leu Met Tyr Arg Met Lys Lys Lys Asp
                165                 170                 175

Glu Gly Ser Tyr Asp Leu Gly Lys Lys Pro Ile Tyr Lys Lys Ala Pro
            180                 185                 190

Thr Asn Glu Phe Tyr Ala
        195
```

```
<210> SEQ ID NO 36
<211> LENGTH: 201
<212> TYPE: PRT
<213> ORGANISM: Artificial Sequence
<220> FEATURE:
<223> OTHER INFORMATION: Synthetic_SDC2_HUMAN

<400> SEQUENCE: 36
```

```
Met Arg Arg Ala Trp Ile Leu Leu Thr Leu Gly Leu Val Ala Cys Val
1               5                   10                  15

Ser Ala Glu Ser Arg Ala Glu Leu Thr Ser Asp Lys Asp Met Tyr Leu
            20                  25                  30

Asp Asn Ser Ser Ile Glu Glu Ala Ser Gly Val Tyr Pro Ile Asp Asp
        35                  40                  45

Asp Asp Tyr Ala Ser Ala Ser Gly Ser Gly Ala Asp Glu Asp Val Glu
    50                  55                  60

Ser Pro Glu Leu Thr Thr Ser Arg Pro Leu Pro Lys Ile Leu Leu Thr
65                  70                  75                  80

Ser Ala Ala Pro Lys Val Glu Thr Thr Thr Leu Asn Ile Gln Asn Lys
                85                  90                  95

Ile Pro Ala Gln Thr Lys Ser Pro Glu Glu Thr Asp Lys Glu Lys Val
            100                 105                 110

His Leu Ser Asp Ser Glu Arg Lys Met Asp Pro Ala Glu Glu Asp Thr
            115                 120                 125

Asn Val Tyr Thr Glu Lys His Ser Asp Ser Leu Phe Lys Arg Thr Glu
    130                 135                 140

Val Leu Ala Ala Val Ile Ala Gly Gly Val Ile Gly Phe Leu Phe Ala
145                 150                 155                 160

Ile Phe Leu Ile Leu Leu Leu Val Tyr Arg Met Arg Lys Lys Asp Glu
                165                 170                 175

Gly Ser Tyr Asp Leu Gly Glu Arg Lys Pro Ser Ser Ala Ala Tyr Gln
            180                 185                 190

Lys Ala Pro Thr Lys Glu Phe Tyr Ala
            195                 200
```

-continued

<210> SEQ ID NO 37
<211> LENGTH: 208
<212> TYPE: PRT
<213> ORGANISM: Artificial Sequence
<220> FEATURE:
<223> OTHER INFORMATION: Synthetic_HBEGF_HUMAN

<400> SEQUENCE: 37

```
Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Thr Val Ser Thr Asp
            35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
            115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
        195                 200                 205
```

<210> SEQ ID NO 38
<211> LENGTH: 222
<212> TYPE: PRT
<213> ORGANISM: Artificial Sequence
<220> FEATURE:
<223> OTHER INFORMATION: Synthetic_PRG2_HUMAN

<400> SEQUENCE: 38

```
Met Lys Leu Pro Leu Leu Leu Ala Leu Leu Phe Gly Ala Val Ser Ala
1               5                   10                  15

Leu His Leu Arg Ser Glu Thr Ser Thr Phe Glu Thr Pro Leu Gly Ala
            20                  25                  30

Lys Thr Leu Pro Glu Asp Glu Glu Thr Pro Glu Gln Glu Met Glu Glu
            35                  40                  45

Thr Pro Cys Arg Glu Leu Glu Glu Glu Glu Trp Gly Ser Gly Ser
    50                  55                  60

Glu Asp Ala Ser Lys Lys Asp Gly Ala Val Glu Ser Ile Ser Val Pro
65                  70                  75                  80

Asp Met Val Asp Lys Asn Leu Thr Cys Pro Glu Glu Glu Asp Thr Val
                85                  90                  95

Lys Val Val Gly Ile Pro Gly Cys Gln Thr Cys Arg Tyr Leu Leu Val
            100                 105                 110
```

```
Arg Ser Leu Gln Thr Phe Ser Gln Ala Trp Phe Thr Cys Arg Arg Cys
        115             120             125

Tyr Arg Gly Asn Leu Val Ser Ile His Asn Phe Asn Ile Asn Tyr Arg
    130             135             140

Ile Gln Cys Ser Val Ser Ala Leu Asn Gln Gly Gln Val Trp Ile Gly
145             150             155             160

Gly Arg Ile Thr Gly Ser Gly Arg Cys Arg Arg Phe Gln Trp Val Asp
            165             170             175

Gly Ser Arg Trp Asn Phe Ala Tyr Trp Ala Ala His Gln Pro Trp Ser
            180             185             190

Arg Gly Gly His Cys Val Ala Leu Cys Thr Arg Gly Gly His Trp Arg
        195             200             205

Arg Ala His Cys Leu Arg Arg Leu Pro Phe Ile Cys Ser Tyr
    210             215             220

<210> SEQ ID NO 39
<211> LENGTH: 240
<212> TYPE: PRT
<213> ORGANISM: Artificial Sequence
<220> FEATURE:
<223> OTHER INFORMATION: Synthetic_IBP6_HUMAN

<400> SEQUENCE: 39

Met Thr Pro His Arg Leu Leu Pro Pro Leu Leu Leu Leu Leu Ala Leu
1               5               10              15

Leu Leu Ala Ala Ser Pro Gly Gly Ala Leu Ala Arg Cys Pro Gly Cys
            20              25              30

Gly Gln Gly Val Gln Ala Gly Cys Pro Gly Gly Cys Val Glu Glu Glu
        35              40              45

Asp Gly Gly Ser Pro Ala Glu Gly Cys Ala Glu Ala Glu Gly Cys Leu
    50              55              60

Arg Arg Glu Gly Gln Glu Cys Gly Val Tyr Thr Pro Asn Cys Ala Pro
65              70              75              80

Gly Leu Gln Cys His Pro Pro Lys Asp Asp Glu Ala Pro Leu Arg Ala
            85              90              95

Leu Leu Leu Gly Arg Gly Arg Cys Leu Pro Ala Arg Ala Pro Ala Val
            100             105             110

Ala Glu Glu Asn Pro Lys Glu Ser Lys Pro Gln Ala Gly Thr Ala Arg
        115             120             125

Pro Gln Asp Val Asn Arg Arg Asp Gln Gln Arg Asn Pro Gly Thr Ser
    130             135             140

Thr Thr Pro Ser Gln Pro Asn Ser Ala Gly Val Gln Asp Thr Glu Met
145             150             155             160

Gly Pro Cys Arg Arg His Leu Asp Ser Val Leu Gln Gln Leu Gln Thr
            165             170             175

Glu Val Tyr Arg Gly Ala Gln Thr Leu Tyr Val Pro Asn Cys Asp His
            180             185             190

Arg Gly Phe Tyr Arg Lys Arg Gln Cys Arg Ser Ser Gln Gly Gln Arg
        195             200             205

Arg Gly Pro Cys Trp Cys Val Asp Arg Met Gly Lys Ser Leu Pro Gly
    210             215             220

Ser Pro Asp Gly Asn Gly Ser Ser Ser Cys Pro Thr Gly Ser Ser Gly
225             230             235             240

<210> SEQ ID NO 40
```

```
<211> LENGTH: 260
<212> TYPE: PRT
<213> ORGANISM: Artificial Sequence
<220> FEATURE:
<223> OTHER INFORMATION: Synthetic_PCSK1_HUMAN

<400> SEQUENCE: 40

Met Ala Gly Ser Pro Leu Leu Trp Gly Pro Arg Ala Gly Gly Val Gly
1               5                   10                  15

Leu Leu Val Leu Leu Leu Leu Gly Leu Phe Arg Pro Pro Pro Ala Leu
                20                  25                  30

Cys Ala Arg Pro Val Lys Glu Pro Arg Gly Leu Ser Ala Ala Ser Pro
            35                  40                  45

Pro Leu Ala Glu Thr Gly Ala Pro Arg Arg Phe Arg Arg Ser Val Pro
        50                  55                  60

Arg Gly Glu Ala Ala Gly Ala Val Gln Glu Leu Ala Arg Ala Leu Ala
65                  70                  75                  80

His Leu Leu Glu Ala Glu Arg Gln Glu Arg Ala Arg Ala Glu Ala Gln
                85                  90                  95

Glu Ala Glu Asp Gln Gln Ala Arg Val Leu Ala Gln Leu Leu Arg Val
                100                 105                 110

Trp Gly Ala Pro Arg Asn Ser Asp Pro Ala Leu Gly Leu Asp Asp Asp
            115                 120                 125

Pro Asp Ala Pro Ala Ala Gln Leu Ala Arg Ala Leu Leu Arg Ala Arg
        130                 135                 140

Leu Asp Pro Ala Ala Leu Ala Ala Gln Leu Val Pro Ala Pro Val Pro
145                 150                 155                 160

Ala Ala Ala Leu Arg Pro Arg Pro Val Tyr Asp Asp Gly Pro Ala
                165                 170                 175

Gly Pro Asp Ala Glu Glu Ala Gly Asp Glu Thr Pro Asp Val Asp Pro
                180                 185                 190

Glu Leu Leu Arg Tyr Leu Leu Gly Arg Ile Leu Ala Gly Ser Ala Asp
            195                 200                 205

Ser Glu Gly Val Ala Ala Pro Arg Arg Leu Arg Arg Ala Ala Asp His
        210                 215                 220

Asp Val Gly Ser Glu Leu Pro Pro Glu Gly Val Leu Gly Ala Leu Leu
225                 230                 235                 240

Arg Val Lys Arg Leu Glu Thr Pro Ala Pro Gln Val Pro Ala Arg Arg
                245                 250                 255

Leu Leu Pro Pro
            260

<210> SEQ ID NO 41
<211> LENGTH: 272
<212> TYPE: PRT
<213> ORGANISM: Artificial Sequence
<220> FEATURE:
<223> OTHER INFORMATION: Synthetic_IL2RA_HUMAN

<400> SEQUENCE: 41

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
                20                  25                  30

His Ala Thr Phe Lys Ala Met Ala Tyr Lys Glu Gly Thr Met Leu Asn
            35                  40                  45

Cys Glu Cys Lys Arg Gly Phe Arg Arg Ile Lys Ser Gly Ser Leu Tyr
```

-continued

```
        50              55              60

Met Leu Cys Thr Gly Asn Ser Ser His Ser Ser Trp Asp Asn Gln Cys
65              70              75              80

Gln Cys Thr Ser Ser Ala Thr Arg Asn Thr Thr Lys Gln Val Thr Pro
                85              90              95

Gln Pro Glu Glu Gln Lys Glu Arg Lys Thr Thr Glu Met Gln Ser Pro
            100             105             110

Met Gln Pro Val Asp Gln Ala Ser Leu Pro Gly His Cys Arg Glu Pro
        115             120             125

Pro Pro Trp Glu Asn Glu Ala Thr Glu Arg Ile Tyr His Phe Val Val
        130             135             140

Gly Gln Met Val Tyr Tyr Gln Cys Val Gln Gly Tyr Arg Ala Leu His
145             150             155             160

Arg Gly Pro Ala Glu Ser Val Cys Lys Met Thr His Gly Lys Thr Arg
                165             170             175

Trp Thr Gln Pro Gln Leu Ile Cys Thr Gly Glu Met Glu Thr Ser Gln
            180             185             190

Phe Pro Gly Glu Glu Lys Pro Gln Ala Ser Pro Glu Gly Arg Pro Glu
            195             200             205

Ser Glu Thr Ser Cys Leu Val Thr Thr Thr Asp Phe Gln Ile Gln Thr
        210             215             220

Glu Met Ala Ala Thr Met Glu Thr Ser Ile Phe Thr Thr Glu Tyr Gln
225             230             235             240

Val Ala Val Ala Gly Cys Val Phe Leu Leu Ile Ser Val Leu Leu Leu
                245             250             255

Ser Gly Leu Thr Trp Gln Arg Arg Gln Arg Lys Ser Arg Arg Thr Ile
            260             265             270
```

<210> SEQ ID NO 42
<211> LENGTH: 273
<212> TYPE: PRT
<213> ORGANISM: Artificial Sequence
<220> FEATURE:
<223> OTHER INFORMATION: Synthetic_SCF_HUMAN

<400> SEQUENCE: 42

```
Met Lys Lys Thr Gln Thr Trp Ile Leu Thr Cys Ile Tyr Leu Gln Leu
1               5               10              15

Leu Leu Phe Asn Pro Leu Val Lys Thr Glu Gly Ile Cys Arg Asn Arg
                20              25              30

Val Thr Asn Asn Val Lys Asp Val Thr Lys Leu Val Ala Asn Leu Pro
            35              40              45

Lys Asp Tyr Met Ile Thr Leu Lys Tyr Val Pro Gly Met Asp Val Leu
        50              55              60

Pro Ser His Cys Trp Ile Ser Glu Met Val Val Gln Leu Ser Asp Ser
65              70              75              80

Leu Thr Asp Leu Leu Asp Lys Phe Ser Asn Ile Ser Glu Gly Leu Ser
                85              90              95

Asn Tyr Ser Ile Ile Asp Lys Leu Val Asn Ile Val Asp Asp Leu Val
            100             105             110

Glu Cys Val Lys Glu Asn Ser Ser Lys Asp Leu Lys Lys Ser Phe Lys
            115             120             125

Ser Pro Glu Pro Arg Leu Phe Thr Pro Glu Glu Phe Phe Arg Ile Phe
        130             135             140

Asn Arg Ser Ile Asp Ala Phe Lys Asp Phe Val Val Ala Ser Glu Thr
```

-continued

```
145                 150                 155                 160

Ser Asp Cys Val Val Ser Ser Thr Leu Ser Pro Glu Lys Asp Ser Arg
                165                 170                 175

Val Ser Val Thr Lys Pro Phe Met Leu Pro Pro Val Ala Ala Ser Ser
                180                 185                 190

Leu Arg Asn Asp Ser Ser Ser Ser Asn Arg Lys Ala Lys Asn Pro Pro
                195                 200                 205

Gly Asp Ser Ser Leu His Trp Ala Ala Met Ala Leu Pro Ala Leu Phe
        210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
                245                 250                 255

Asp Asn Glu Ile Ser Met Leu Gln Glu Lys Glu Arg Glu Phe Gln Glu
                260                 265                 270

Val
```

```
<210> SEQ ID NO 43
<211> LENGTH: 279
<212> TYPE: PRT
<213> ORGANISM: Artificial Sequence
<220> FEATURE:
<223> OTHER INFORMATION: Synthetic_ODAM_HUMAN

<400> SEQUENCE: 43

Met Lys Ile Ile Ile Leu Leu Gly Phe Leu Gly Ala Thr Leu Ser Ala
1               5                   10                  15

Pro Leu Ile Pro Gln Arg Leu Met Ser Ala Ser Asn Ser Asn Glu Leu
                20                  25                  30

Leu Leu Asn Leu Asn Asn Gly Gln Leu Leu Pro Leu Gln Leu Gln Gly
            35                  40                  45

Pro Leu Asn Ser Trp Ile Pro Pro Phe Ser Gly Ile Leu Gln Gln Gln
        50                  55                  60

Gln Gln Ala Gln Ile Pro Gly Leu Ser Gln Phe Ser Leu Ser Ala Leu
65                  70                  75                  80

Asp Gln Phe Ala Gly Leu Leu Pro Asn Gln Ile Pro Leu Thr Gly Glu
                85                  90                  95

Ala Ser Phe Ala Gln Gly Ala Gln Ala Gly Gln Val Asp Pro Leu Gln
                100                 105                 110

Leu Gln Thr Pro Pro Gln Thr Gln Pro Gly Pro Ser His Val Met Pro
            115                 120                 125

Tyr Val Phe Ser Phe Lys Met Pro Gln Glu Gln Gly Gln Met Phe Gln
        130                 135                 140

Tyr Tyr Pro Val Tyr Met Val Leu Pro Trp Glu Gln Pro Gln Gln Thr
145                 150                 155                 160

Val Pro Arg Ser Pro Gln Gln Thr Arg Gln Gln Gln Tyr Glu Glu Gln
                165                 170                 175

Ile Pro Phe Tyr Ala Gln Phe Gly Tyr Ile Pro Gln Leu Ala Glu Pro
                180                 185                 190

Ala Ile Ser Gly Gly Gln Gln Gln Leu Ala Phe Asp Pro Gln Leu Gly
            195                 200                 205

Thr Ala Pro Glu Ile Ala Val Met Ser Thr Gly Glu Glu Ile Pro Tyr
        210                 215                 220

Leu Gln Lys Glu Ala Ile Asn Phe Arg His Asp Ser Ala Gly Val Phe
225                 230                 235                 240
```

```
Met Pro Ser Thr Ser Pro Lys Pro Ser Thr Thr Asn Val Phe Thr Ser
            245                 250                 255

Ala Val Asp Gln Thr Ile Thr Pro Glu Leu Pro Glu Glu Lys Asp Lys
            260                 265                 270

Thr Asp Ser Leu Arg Glu Pro
        275

<210> SEQ ID NO 44
<211> LENGTH: 314
<212> TYPE: PRT
<213> ORGANISM: Artificial Sequence
<220> FEATURE:
<223> OTHER INFORMATION: Synthetic_OSTP_HUMAN

<400> SEQUENCE: 44

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
            115                 120                 125

Ser Asp Glu Leu Val Thr Asp Phe Pro Thr Asp Leu Pro Ala Thr Glu
            130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
            195                 200                 205

Gln Asp Leu Asn Ala Pro Ser Asp Trp Asp Ser Arg Gly Lys Asp Ser
        210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
            275                 280                 285

Pro Lys Ser Lys Glu Glu Asp Lys His Leu Lys Phe Arg Ile Ser His
        290                 295                 300

Glu Leu Asp Ser Ala Ser Ser Glu Val Asn
305                 310
```

<210> SEQ ID NO 45
<211> LENGTH: 317
<212> TYPE: PRT
<213> ORGANISM: Artificial Sequence
<220> FEATURE:
<223> OTHER INFORMATION: Synthetic_SIAL_HUMAN

<400> SEQUENCE: 45

Met Lys Thr Ala Leu Ile Leu Leu Ser Ile Leu Gly Met Ala Cys Ala
1               5                   10                  15

Phe Ser Met Lys Asn Leu His Arg Arg Val Lys Ile Glu Asp Ser Glu
                20                  25                  30

Glu Asn Gly Val Phe Lys Tyr Arg Pro Arg Tyr Tyr Leu Tyr Lys His
            35                  40                  45

Ala Tyr Phe Tyr Pro His Leu Lys Arg Phe Pro Val Gln Gly Ser Ser
        50                  55                  60

Asp Ser Ser Glu Glu Asn Gly Asp Asp Ser Ser Glu Glu Glu Glu
65                  70                  75                  80

Glu Glu Glu Thr Ser Asn Glu Gly Glu Asn Asn Glu Glu Ser Asn Glu
                85                  90                  95

Asp Glu Asp Ser Glu Ala Glu Asn Thr Thr Leu Ser Ala Thr Thr Leu
            100                 105                 110

Gly Tyr Gly Glu Asp Ala Thr Pro Gly Thr Gly Tyr Thr Gly Leu Ala
        115                 120                 125

Ala Ile Gln Leu Pro Lys Lys Ala Gly Asp Ile Thr Asn Lys Ala Thr
    130                 135                 140

Lys Glu Lys Glu Ser Asp Glu Glu Glu Glu Glu Glu Glu Gly Asn
145                 150                 155                 160

Glu Asn Glu Glu Ser Glu Ala Glu Val Asp Glu Asn Glu Gln Gly Ile
                165                 170                 175

Asn Gly Thr Ser Thr Asn Ser Thr Glu Ala Glu Asn Gly Asn Gly Ser
            180                 185                 190

Ser Gly Gly Asp Asn Gly Glu Glu Gly Glu Glu Glu Ser Val Thr Gly
        195                 200                 205

Ala Asn Ala Glu Asp Thr Thr Glu Thr Gly Arg Gln Gly Lys Gly Thr
    210                 215                 220

Ser Lys Thr Thr Thr Ser Pro Asn Gly Gly Phe Glu Pro Thr Thr Pro
225                 230                 235                 240

Pro Gln Val Tyr Arg Thr Thr Ser Pro Pro Phe Gly Lys Thr Thr Thr
            245                 250                 255

Val Glu Tyr Glu Gly Glu Tyr Glu Tyr Thr Gly Ala Asn Glu Tyr Asp
            260                 265                 270

Asn Gly Tyr Glu Ile Tyr Glu Ser Glu Asn Gly Glu Pro Arg Gly Asp
        275                 280                 285

Asn Tyr Arg Ala Tyr Glu Asp Glu Tyr Ser Tyr Phe Lys Gly Gln Gly
    290                 295                 300

Tyr Asp Gly Tyr Asp Gly Gln Asn Tyr Tyr His His Gln
305                 310                 315

<210> SEQ ID NO 46
<211> LENGTH: 317
<212> TYPE: PRT
<213> ORGANISM: Artificial Sequence
<220> FEATURE:
<223> OTHER INFORMATION: Synthetic_APOE_HUMAN -continued

```
<400> SEQUENCE: 46

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
                20                  25                  30

Arg Gln Gln Thr Glu Trp Gln Ser Gly Gln Arg Trp Glu Leu Ala Leu
            35                  40                  45

Gly Arg Phe Trp Asp Tyr Leu Arg Trp Val Gln Thr Leu Ser Glu Gln
        50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
                100                 105                 110

Lys Glu Leu Gln Ala Ala Gln Ala Arg Leu Gly Ala Asp Met Glu Asp
            115                 120                 125

Val Cys Gly Arg Leu Val Gln Tyr Arg Gly Glu Val Gln Ala Met Leu
        130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
                180                 185                 190

Ser Ala Ile Arg Glu Arg Leu Gly Pro Leu Val Glu Gln Gly Arg Val
            195                 200                 205

Arg Ala Ala Thr Val Gly Ser Leu Ala Gly Gln Pro Leu Gln Glu Arg
        210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
                260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
        290                 295                 300

Val Gly Thr Ser Ala Ala Pro Val Pro Ser Asp Asn His
305                 310                 315

<210> SEQ ID NO 47
<211> LENGTH: 322
<212> TYPE: PRT
<213> ORGANISM: Artificial Sequence
<220> FEATURE:
<223> OTHER INFORMATION: Synthetic_EPYC_HUMAN

<400> SEQUENCE: 47

Met Lys Thr Leu Ala Gly Leu Val Leu Gly Leu Val Ile Phe Asp Ala
1               5                   10                  15

Ala Val Thr Ala Pro Thr Leu Glu Ser Ile Asn Tyr Asp Ser Glu Thr
                20                  25                  30

Tyr Asp Ala Thr Leu Glu Asp Leu Asp Asn Leu Tyr Asn Tyr Glu Asn
```

```
              35                    40                    45
Ile Pro Val Asp Lys Val Glu Ile Glu Ile Ala Thr Val Met Pro Ser
    50                    55                    60
Gly Asn Arg Glu Leu Leu Thr Pro Pro Gln Pro Glu Lys Ala Gln
65                    70                    75                    80
Glu Glu Glu Glu Glu Glu Ser Thr Pro Arg Leu Ile Asp Gly Ser
                          85                    90                    95
Ser Pro Gln Glu Pro Glu Phe Thr Gly Val Leu Gly Pro His Thr Asn
                  100                   105                   110
Glu Asp Phe Pro Thr Cys Leu Leu Cys Thr Cys Ile Ser Thr Thr Val
                  115                   120                   125
Tyr Cys Asp Asp His Glu Leu Asp Ala Ile Pro Pro Leu Pro Lys Asn
    130                   135                   140
Thr Ala Tyr Phe Tyr Ser Arg Phe Asn Arg Ile Lys Lys Ile Asn Lys
145                   150                   155                   160
Asn Asp Phe Ala Ser Leu Ser Asp Leu Lys Arg Ile Asp Leu Thr Ser
                  165                   170                   175
Asn Leu Ile Ser Glu Ile Asp Glu Asp Ala Phe Arg Lys Leu Pro Gln
                  180                   185                   190
Leu Arg Glu Leu Val Leu Arg Asp Asn Lys Ile Arg Gln Leu Pro Glu
                  195                   200                   205
Leu Pro Thr Thr Leu Thr Phe Ile Asp Ile Ser Asn Asn Arg Leu Gly
    210                   215                   220
Arg Lys Gly Ile Lys Gln Glu Ala Phe Lys Asp Met Tyr Asp Leu His
225                   230                   235                   240
His Leu Tyr Leu Thr Asp Asn Asn Leu Asp His Ile Pro Leu Pro Leu
                  245                   250                   255
Pro Glu Asn Leu Arg Ala Leu His Leu Gln Asn Asn Asn Ile Leu Glu
                  260                   265                   270
Met His Glu Asp Thr Phe Cys Asn Val Lys Asn Leu Thr Tyr Ile Arg
                  275                   280                   285
Lys Ala Leu Glu Asp Ile Arg Leu Asp Gly Asn Pro Ile Asn Leu Ser
    290                   295                   300
Lys Thr Pro Gln Ala Tyr Met Cys Leu Pro Arg Leu Pro Val Gly Ser
305                   310                   315                   320
Leu Val
```

```
<210> SEQ ID NO 48
<211> LENGTH: 332
<212> TYPE: PRT
<213> ORGANISM: Artificial Sequence
<220> FEATURE:
<223> OTHER INFORMATION: Synthetic_CLM9_HUMAN

<400> SEQUENCE: 48

Met Arg Leu Leu Val Leu Leu Trp Gly Cys Leu Leu Leu Pro Gly Tyr
1                 5                     10                    15
Glu Ala Leu Glu Gly Pro Glu Glu Ile Ser Gly Phe Glu Gly Asp Thr
                  20                    25                    30
Val Ser Leu Gln Cys Thr Tyr Arg Glu Glu Leu Arg Asp His Arg Lys
          35                    40                    45
Tyr Trp Cys Arg Lys Gly Gly Ile Leu Phe Ser Arg Cys Ser Gly Thr
    50                    55                    60
Ile Tyr Ala Glu Glu Glu Gly Gln Glu Thr Met Lys Gly Arg Val Ser
65                    70                    75                    80
```

```
Ile Arg Asp Ser Arg Gln Glu Leu Ser Leu Ile Val Thr Leu Trp Asn
                85                  90                  95

Leu Thr Leu Gln Asp Ala Gly Glu Tyr Trp Cys Gly Val Glu Lys Arg
            100                 105                 110

Gly Pro Asp Glu Ser Leu Leu Ile Ser Leu Phe Val Phe Pro Gly Pro
        115                 120                 125

Cys Cys Pro Pro Ser Pro Ser Pro Thr Phe Gln Pro Leu Ala Thr Thr
    130                 135                 140

Arg Leu Gln Pro Lys Ala Lys Ala Gln Gln Thr Gln Pro Pro Gly Leu
145                 150                 155                 160

Thr Ser Pro Gly Leu Tyr Pro Ala Ala Thr Thr Ala Lys Gln Gly Lys
                165                 170                 175

Thr Gly Ala Glu Ala Pro Pro Leu Pro Gly Thr Ser Gln Tyr Gly His
            180                 185                 190

Glu Arg Thr Ser Gln Tyr Thr Gly Thr Ser Pro His Pro Ala Thr Ser
        195                 200                 205

Pro Pro Ala Gly Ser Ser Arg Pro Pro Met Gln Leu Asp Ser Thr Ser
    210                 215                 220

Ala Glu Asp Thr Ser Pro Ala Leu Ser Ser Gly Ser Ser Lys Pro Arg
225                 230                 235                 240

Val Ser Ile Pro Met Val Arg Ile Leu Ala Pro Val Leu Val Leu Leu
                245                 250                 255

Ser Leu Leu Ser Ala Ala Gly Leu Ile Ala Phe Cys Ser His Leu Leu
            260                 265                 270

Leu Trp Arg Lys Glu Ala Gln Gln Ala Thr Glu Thr Gln Arg Asn Glu
        275                 280                 285

Lys Phe Cys Leu Ser Arg Leu Thr Ala Glu Glu Lys Glu Ala Pro Ser
    290                 295                 300

Gln Ala Pro Glu Gly Asp Val Ile Ser Met Pro Pro Leu His Thr Ser
305                 310                 315                 320

Glu Glu Glu Leu Gly Phe Ser Lys Phe Val Ser Ala
                325                 330
```

```
<210> SEQ ID NO 49
<211> LENGTH: 350
<212> TYPE: PRT
<213> ORGANISM: Artificial Sequence
<220> FEATURE:
<223> OTHER INFORMATION: Synthetic_YIPF3_HUMAN

<400> SEQUENCE: 49
```

```
Met Ala Thr Thr Ala Ala Pro Ala Gly Gly Ala Arg Asn Gly Ala Gly
1               5                   10                  15

Pro Glu Trp Gly Gly Phe Glu Glu Asn Ile Gln Gly Gly Gly Ser Ala
                20                  25                  30

Val Ile Asp Met Glu Asn Met Asp Asp Thr Ser Gly Ser Ser Phe Glu
            35                  40                  45

Asp Met Gly Glu Leu His Gln Arg Leu Arg Glu Glu Glu Val Asp Ala
        50                  55                  60

Asp Ala Ala Asp Ala Ala Ala Ala Glu Glu Glu Asp Gly Glu Phe Leu
65                  70                  75                  80

Gly Met Lys Gly Phe Lys Gly Gln Leu Ser Arg Gln Val Ala Asp Gln
                85                  90                  95

Met Trp Gln Ala Gly Lys Arg Gln Ala Ser Arg Ala Phe Ser Leu Tyr
            100                 105                 110
```

Ala Asn Ile Asp Ile Leu Arg Pro Tyr Phe Asp Val Glu Pro Ala Gln
        115                 120                 125

Val Arg Ser Arg Leu Leu Glu Ser Met Ile Pro Ile Lys Met Val Asn
        130                 135                 140

Phe Pro Gln Lys Ile Ala Gly Glu Leu Tyr Gly Pro Leu Met Leu Val
145                 150                 155                 160

Phe Thr Leu Val Ala Ile Leu Leu His Gly Met Lys Thr Ser Asp Thr
                165                 170                 175

Ile Ile Arg Glu Gly Thr Leu Met Gly Thr Ala Ile Gly Thr Cys Phe
                180                 185                 190

Gly Tyr Trp Leu Gly Val Ser Ser Phe Ile Tyr Phe Leu Ala Tyr Leu
        195                 200                 205

Cys Asn Ala Gln Ile Thr Met Leu Gln Met Leu Ala Leu Leu Gly Tyr
        210                 215                 220

Gly Leu Phe Gly His Cys Ile Val Leu Phe Ile Thr Tyr Asn Ile His
225                 230                 235                 240

Leu His Ala Leu Phe Tyr Leu Phe Trp Leu Leu Val Gly Gly Leu Ser
                245                 250                 255

Thr Leu Arg Met Val Ala Val Leu Val Ser Arg Thr Val Gly Pro Thr
                260                 265                 270

Gln Arg Leu Leu Leu Cys Gly Thr Leu Ala Ala Leu His Met Leu Phe
        275                 280                 285

Leu Leu Tyr Leu His Phe Ala Tyr His Lys Val Val Glu Gly Ile Leu
        290                 295                 300

Asp Thr Leu Glu Gly Pro Asn Ile Pro Pro Ile Gln Arg Val Pro Arg
305                 310                 315                 320

Asp Ile Pro Ala Met Leu Pro Ala Ala Arg Leu Pro Thr Thr Val Leu
                325                 330                 335

Asn Ala Thr Ala Lys Ala Val Ala Val Thr Leu Gln Ser His
                340                 345                 350

<210> SEQ ID NO 50
<211> LENGTH: 352
<212> TYPE: PRT
<213> ORGANISM: Artificial Sequence
<220> FEATURE:
<223> OTHER INFORMATION: Synthetic_CCR5_HUMAN

<400> SEQUENCE: 50

Met Asp Tyr Gln Val Ser Ser Pro Ile Tyr Asp Ile Asn Tyr Tyr Thr
1                   5                   10                  15

Ser Glu Pro Cys Gln Lys Ile Asn Val Lys Gln Ile Ala Ala Arg Leu
                20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
        50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
                100                 105                 110

Phe Ser Gly Ile Phe Phe Ile Ile Leu Leu Thr Ile Asp Arg Tyr Leu
        115                 120                 125

-continued

```
Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
                180                 185                 190

Phe Gln Thr Leu Lys Ile Val Ile Leu Gly Leu Val Leu Pro Leu Leu
                195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
                260                 265                 270

Asn Arg Leu Asp Gln Ala Met Gln Val Thr Glu Thr Leu Gly Met Thr
                275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
                340                 345                 350
```

```
<210> SEQ ID NO 51
<211> LENGTH: 353
<212> TYPE: PRT
<213> ORGANISM: Artificial Sequence
<220> FEATURE:
<223> OTHER INFORMATION: Synthetic_TPO_HUMAN

<400> SEQUENCE: 51
```

```
Met Glu Leu Thr Glu Leu Leu Leu Val Val Met Leu Leu Leu Thr Ala
1                   5                   10                  15

Arg Leu Thr Leu Ser Ser Pro Ala Pro Pro Ala Cys Asp Leu Arg Val
                20                  25                  30

Leu Ser Lys Leu Leu Arg Asp Ser His Val Leu His Ser Arg Leu Ser
                35                  40                  45

Gln Cys Pro Glu Val His Pro Leu Pro Thr Pro Val Leu Leu Pro Ala
    50                  55                  60

Val Asp Phe Ser Leu Gly Glu Trp Lys Thr Gln Met Glu Glu Thr Lys
65                  70                  75                  80

Ala Gln Asp Ile Leu Gly Ala Val Thr Leu Leu Leu Glu Gly Val Met
                85                  90                  95

Ala Ala Arg Gly Gln Leu Gly Pro Thr Cys Leu Ser Ser Leu Leu Gly
                100                 105                 110

Gln Leu Ser Gly Gln Val Arg Leu Leu Leu Gly Ala Leu Gln Ser Leu
                115                 120                 125

Leu Gly Thr Gln Leu Pro Pro Gln Gly Arg Thr Thr Ala His Lys Asp
    130                 135                 140
```

-continued

```
Pro Asn Ala Ile Phe Leu Ser Phe Gln His Leu Leu Arg Gly Lys Val
145             150             155             160

Arg Phe Leu Met Leu Val Gly Gly Ser Thr Leu Cys Val Arg Arg Ala
            165             170             175

Pro Pro Thr Thr Ala Val Pro Ser Arg Thr Ser Leu Val Leu Thr Leu
            180             185             190

Asn Glu Leu Pro Asn Arg Thr Ser Gly Leu Leu Glu Thr Asn Phe Thr
            195             200             205

Ala Ser Ala Arg Thr Thr Gly Ser Gly Leu Leu Lys Trp Gln Gln Gly
            210             215             220

Phe Arg Ala Lys Ile Pro Gly Leu Leu Asn Gln Thr Ser Arg Ser Leu
225             230             235             240

Asp Gln Ile Pro Gly Tyr Leu Asn Arg Ile His Glu Leu Leu Asn Gly
            245             250             255

Thr Arg Gly Leu Phe Pro Gly Pro Ser Arg Arg Thr Leu Gly Ala Pro
            260             265             270

Asp Ile Ser Ser Gly Thr Ser Asp Thr Gly Ser Leu Pro Pro Asn Leu
            275             280             285

Gln Pro Gly Tyr Ser Pro Ser Pro Thr His Pro Pro Thr Gly Gln Tyr
            290             295             300

Thr Leu Phe Pro Leu Pro Pro Thr Leu Pro Thr Pro Val Val Gln Leu
305             310             315             320

His Pro Leu Leu Pro Asp Pro Ser Ala Pro Thr Pro Thr Pro Thr Ser
            325             330             335

Pro Leu Leu Asn Thr Ser Tyr Thr His Ser Gln Asn Leu Ser Gln Glu
            340             345             350

Gly
```

```
<210> SEQ ID NO 52
<211> LENGTH: 367
<212> TYPE: PRT
<213> ORGANISM: Artificial Sequence
<220> FEATURE:
<223> OTHER INFORMATION: Synthetic_FETUA_HUMAN

<400> SEQUENCE: 52
```

```
Met Lys Ser Leu Val Leu Leu Leu Cys Leu Ala Gln Leu Trp Gly Cys
1               5               10              15

His Ser Ala Pro His Gly Pro Gly Leu Ile Tyr Arg Gln Pro Asn Cys
            20              25              30

Asp Asp Pro Glu Thr Glu Glu Ala Ala Leu Val Ala Ile Asp Tyr Ile
            35              40              45

Asn Gln Asn Leu Pro Trp Gly Tyr Lys His Thr Leu Asn Gln Ile Asp
            50              55              60

Glu Val Lys Val Trp Pro Gln Gln Pro Ser Gly Glu Leu Phe Glu Ile
65              70              75              80

Glu Ile Asp Thr Leu Glu Thr Thr Cys His Val Leu Asp Pro Thr Pro
            85              90              95

Val Ala Arg Cys Ser Val Arg Gln Leu Lys Glu His Ala Val Glu Gly
            100             105             110

Asp Cys Asp Phe Gln Leu Leu Lys Leu Asp Gly Lys Phe Ser Val Val
            115             120             125

Tyr Ala Lys Cys Asp Ser Ser Pro Asp Ser Ala Glu Asp Val Arg Lys
            130             135             140
```

-continued

```
Val Cys Gln Asp Cys Pro Leu Leu Ala Pro Leu Asn Asp Thr Arg Val
145                 150                 155                 160

Val His Ala Ala Lys Ala Ala Leu Ala Ala Phe Asn Ala Gln Asn Asn
                165                 170                 175

Gly Ser Asn Phe Gln Leu Glu Glu Ile Ser Arg Ala Gln Leu Val Pro
                180                 185                 190

Leu Pro Pro Ser Thr Tyr Val Glu Phe Thr Val Ser Gly Thr Asp Cys
                195                 200                 205

Val Ala Lys Glu Ala Thr Glu Ala Ala Lys Cys Asn Leu Leu Ala Glu
        210                 215                 220

Lys Gln Tyr Gly Phe Cys Lys Ala Thr Leu Ser Glu Lys Leu Gly Gly
225                 230                 235                 240

Ala Glu Val Ala Val Thr Cys Met Val Phe Gln Thr Gln Pro Val Ser
                245                 250                 255

Ser Gln Pro Gln Pro Glu Gly Ala Asn Glu Ala Val Pro Thr Pro Val
                260                 265                 270

Val Asp Pro Asp Ala Pro Pro Ser Pro Pro Leu Gly Ala Pro Gly Leu
        275                 280                 285

Pro Pro Ala Gly Ser Pro Pro Asp Ser His Val Leu Leu Ala Ala Pro
    290                 295                 300

Pro Gly His Gln Leu His Arg Ala His Tyr Asp Leu Arg His Thr Phe
305                 310                 315                 320

Met Gly Val Val Ser Leu Gly Ser Pro Ser Gly Glu Val Ser His Pro
                325                 330                 335

Arg Lys Thr Arg Thr Val Val Gln Pro Ser Val Gly Ala Ala Ala Gly
                340                 345                 350

Pro Val Val Pro Pro Cys Pro Gly Arg Ile Arg His Phe Lys Val
                355                 360                 365
```

```
<210> SEQ ID NO 53
<211> LENGTH: 368
<212> TYPE: PRT
<213> ORGANISM: Artificial Sequence
<220> FEATURE:
<223> OTHER INFORMATION: Synthetic_PGS1_HUMAN

<400> SEQUENCE: 53
```

```
Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
                20                  25                  30

Pro Phe Met Met Asn Asp Glu Glu Ala Ser Gly Ala Asp Thr Ser Gly
                35                  40                  45

Val Leu Asp Pro Asp Ser Val Thr Pro Thr Tyr Ser Ala Met Cys Pro
        50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
                100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
        130                 135                 140
```

-continued

```
Ile Ser Lys Asn His Leu Val Glu Ile Pro Pro Asn Leu Pro Ser Ser
145             150             155             160

Leu Val Glu Leu Arg Ile His Asp Asn Arg Ile Arg Lys Val Pro Lys
            165             170             175

Gly Val Phe Ser Gly Leu Arg Asn Met Asn Cys Ile Glu Met Gly Gly
            180             185             190

Asn Pro Leu Glu Asn Ser Gly Phe Glu Pro Gly Ala Phe Asp Gly Leu
            195             200             205

Lys Leu Asn Tyr Leu Arg Ile Ser Glu Ala Lys Leu Thr Gly Ile Pro
            210             215             220

Lys Asp Leu Pro Glu Thr Leu Asn Glu Leu His Leu Asp His Asn Lys
225             230             235             240

Ile Gln Ala Ile Glu Leu Glu Asp Leu Leu Arg Tyr Ser Lys Leu Tyr
            245             250             255

Arg Leu Gly Leu Gly His Asn Gln Ile Arg Met Ile Glu Asn Gly Ser
            260             265             270

Leu Ser Phe Leu Pro Thr Leu Arg Glu Leu His Leu Asp Asn Asn Lys
            275             280             285

Leu Ala Arg Val Pro Ser Gly Leu Pro Asp Leu Lys Leu Leu Gln Val
            290             295             300

Val Tyr Leu His Ser Asn Asn Ile Thr Lys Val Gly Val Asn Asp Phe
305             310             315             320

Cys Pro Met Gly Phe Gly Val Lys Arg Ala Tyr Tyr Asn Gly Ile Ser
            325             330             335

Leu Phe Asn Asn Pro Val Pro Tyr Trp Glu Val Gln Pro Ala Thr Phe
            340             345             350

Arg Cys Val Thr Asp Arg Leu Ala Ile Gln Phe Gly Asn Tyr Lys Lys
            355             360             365

<210> SEQ ID NO 54
<211> LENGTH: 377
<212> TYPE: PRT
<213> ORGANISM: Artificial Sequence
<220> FEATURE:
<223> OTHER INFORMATION: Synthetic_IGHG3_HUMAN

<400> SEQUENCE: 54

Ala Ser Thr Lys Gly Pro Ser Val Phe Pro Leu Ala Pro Cys Ser Arg
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
            50              55              60

Leu Ser Ser Val Val Thr Val Pro Ser Ser Ser Leu Gly Thr Gln Thr
65              70              75              80

Tyr Thr Cys Asn Val Asn His Lys Pro Ser Asn Thr Lys Val Asp Lys
            85              90              95

Arg Val Glu Leu Lys Thr Pro Leu Gly Asp Thr Thr His Thr Cys Pro
            100             105             110

Arg Cys Pro Glu Pro Lys Ser Cys Asp Thr Pro Pro Pro Cys Pro Arg
            115             120             125

Cys Pro Glu Pro Lys Ser Cys Asp Thr Pro Pro Pro Cys Pro Arg Cys
            130             135             140
```

```
Pro Glu Pro Lys Ser Cys Asp Thr Pro Pro Pro Cys Pro Arg Cys Pro
145             150             155             160

Ala Pro Glu Leu Leu Gly Gly Pro Ser Val Phe Leu Phe Pro Pro Lys
                165             170             175

Pro Lys Asp Thr Leu Met Ile Ser Arg Thr Pro Glu Val Thr Cys Val
            180             185             190

Val Val Asp Val Ser His Glu Asp Pro Glu Val Gln Phe Lys Trp Tyr
        195             200             205

Val Asp Gly Val Glu Val His Asn Ala Lys Thr Lys Pro Arg Glu Glu
    210             215             220

Gln Tyr Asn Ser Thr Phe Arg Val Val Ser Val Leu Thr Val Leu His
225             230             235             240

Gln Asp Trp Leu Asn Gly Lys Glu Tyr Lys Cys Lys Val Ser Asn Lys
            245             250             255

Ala Leu Pro Ala Pro Ile Glu Lys Thr Ile Ser Lys Thr Lys Gly Gln
            260             265             270

Pro Arg Glu Pro Gln Val Tyr Thr Leu Pro Pro Ser Arg Glu Glu Met
            275             280             285

Thr Lys Asn Gln Val Ser Leu Thr Cys Leu Val Lys Gly Phe Tyr Pro
    290             295             300

Ser Asp Ile Ala Val Glu Trp Glu Ser Ser Gly Gln Pro Glu Asn Asn
305             310             315             320

Tyr Asn Thr Thr Pro Pro Met Leu Asp Ser Asp Gly Ser Phe Phe Leu
            325             330             335

Tyr Ser Lys Leu Thr Val Asp Lys Ser Arg Trp Gln Gln Gly Asn Ile
            340             345             350

Phe Ser Cys Ser Val Met His Glu Ala Leu His Asn Arg Phe Thr Gln
            355             360             365

Lys Ser Leu Ser Leu Ser Pro Gly Lys
            370             375
```

```
<210> SEQ ID NO 55
<211> LENGTH: 383
<212> TYPE: PRT
<213> ORGANISM: Artificial Sequence
<220> FEATURE:
<223> OTHER INFORMATION: Synthetic_DLK1_HUMAN

<400> SEQUENCE: 55

Met Thr Ala Thr Glu Ala Leu Leu Arg Val Leu Leu Leu Leu Leu Ala
1               5               10              15

Phe Gly His Ser Thr Tyr Gly Ala Glu Cys Phe Pro Ala Cys Asn Pro
                20              25              30

Gln Asn Gly Phe Cys Glu Asp Asp Asn Val Cys Arg Cys Gln Pro Gly
            35              40              45

Trp Gln Gly Pro Leu Cys Asp Gln Cys Val Thr Ser Pro Gly Cys Leu
    50              55              60

His Gly Leu Cys Gly Glu Pro Gly Gln Cys Ile Cys Thr Asp Gly Trp
65              70              75              80

Asp Gly Glu Leu Cys Asp Arg Asp Val Arg Ala Cys Ser Ser Ala Pro
                85              90              95

Cys Ala Asn Asn Arg Thr Cys Val Ser Leu Asp Asp Gly Leu Tyr Glu
            100             105             110

Cys Ser Cys Ala Pro Gly Tyr Ser Gly Lys Asp Cys Gln Lys Lys Asp
            115             120             125
```

-continued

```
Gly Pro Cys Val Ile Asn Gly Ser Pro Cys Gln His Gly Gly Thr Cys
    130                 135                 140

Val Asp Asp Glu Gly Arg Ala Ser His Ala Ser Cys Leu Cys Pro Pro
145                 150                 155                 160

Gly Phe Ser Gly Asn Phe Cys Glu Ile Val Ala Asn Ser Cys Thr Pro
                165                 170                 175

Asn Pro Cys Glu Asn Asp Gly Val Cys Thr Asp Ile Gly Gly Asp Phe
                180                 185                 190

Arg Cys Arg Cys Pro Ala Gly Phe Ile Asp Lys Thr Cys Ser Arg Pro
                195                 200                 205

Val Thr Asn Cys Ala Ser Ser Pro Cys Gln Asn Gly Gly Thr Cys Leu
    210                 215                 220

Gln His Thr Gln Val Ser Tyr Glu Cys Leu Cys Lys Pro Glu Phe Thr
225                 230                 235                 240

Gly Leu Thr Cys Val Lys Lys Arg Ala Leu Ser Pro Gln Gln Val Thr
                245                 250                 255

Arg Leu Pro Ser Gly Tyr Gly Leu Ala Tyr Arg Leu Thr Pro Gly Val
                260                 265                 270

His Glu Leu Pro Val Gln Gln Pro Glu His Arg Ile Leu Lys Val Ser
                275                 280                 285

Met Lys Glu Leu Asn Lys Lys Thr Pro Leu Leu Thr Glu Gly Gln Ala
    290                 295                 300

Ile Cys Phe Thr Ile Leu Gly Val Leu Thr Ser Leu Val Val Leu Gly
305                 310                 315                 320

Thr Val Gly Ile Val Phe Leu Asn Lys Cys Glu Thr Trp Val Ser Asn
                325                 330                 335

Leu Arg Tyr Asn His Met Leu Arg Lys Lys Lys Asn Leu Leu Leu Gln
                340                 345                 350

Tyr Asn Ser Gly Glu Asp Leu Ala Val Asn Ile Ile Phe Pro Glu Lys
                355                 360                 365

Ile Asp Met Thr Thr Phe Ser Lys Glu Ala Gly Asp Glu Glu Ile
    370                 375                 380
```

<210> SEQ ID NO 56
<211> LENGTH: 392
<212> TYPE: PRT
<213> ORGANISM: Artificial Sequence
<220> FEATURE:
<223> OTHER INFORMATION: Synthetic_MCP_HUMAN

<400> SEQUENCE: 56

```
Met Glu Pro Pro Gly Arg Arg Glu Cys Pro Phe Pro Ser Trp Arg Phe
1               5                   10                  15

Pro Gly Leu Leu Leu Ala Ala Met Val Leu Leu Leu Tyr Ser Phe Ser
            20                  25                  30

Asp Ala Cys Glu Glu Pro Pro Thr Phe Glu Ala Met Glu Leu Ile Gly
        35                  40                  45

Lys Pro Lys Pro Tyr Tyr Glu Ile Gly Glu Arg Val Asp Tyr Lys Cys
    50                  55                  60

Lys Lys Gly Tyr Phe Tyr Ile Pro Pro Leu Ala Thr His Thr Ile Cys
65                  70                  75                  80

Asp Arg Asn His Thr Trp Leu Pro Val Ser Asp Asp Ala Cys Tyr Arg
                85                  90                  95

Glu Thr Cys Pro Tyr Ile Arg Asp Pro Leu Asn Gly Gln Ala Val Pro
                100                 105                 110
```

```
Ala Asn Gly Thr Tyr Glu Phe Gly Tyr Gln Met His Phe Ile Cys Asn
        115                 120                 125

Glu Gly Tyr Tyr Leu Ile Gly Glu Glu Ile Leu Tyr Cys Glu Leu Lys
        130                 135                 140

Gly Ser Val Ala Ile Trp Ser Gly Lys Pro Pro Ile Cys Glu Lys Val
145                 150                 155                 160

Leu Cys Thr Pro Pro Pro Lys Ile Lys Asn Gly Lys His Thr Phe Ser
                165                 170                 175

Glu Val Glu Val Phe Glu Tyr Leu Asp Ala Val Thr Tyr Ser Cys Asp
        180                 185                 190

Pro Ala Pro Gly Pro Asp Pro Phe Ser Leu Ile Gly Glu Ser Thr Ile
        195                 200                 205

Tyr Cys Gly Asp Asn Ser Val Trp Ser Arg Ala Ala Pro Glu Cys Lys
        210                 215                 220

Val Val Lys Cys Arg Phe Pro Val Val Glu Asn Gly Lys Gln Ile Ser
225                 230                 235                 240

Gly Phe Gly Lys Lys Phe Tyr Tyr Lys Ala Thr Val Met Phe Glu Cys
                245                 250                 255

Asp Lys Gly Phe Tyr Leu Asp Gly Ser Asp Thr Ile Val Cys Asp Ser
        260                 265                 270

Asn Ser Thr Trp Asp Pro Pro Val Pro Lys Cys Leu Lys Val Leu Pro
        275                 280                 285

Pro Ser Ser Thr Lys Pro Pro Ala Leu Ser His Ser Val Ser Thr Ser
        290                 295                 300

Ser Thr Thr Lys Ser Pro Ala Ser Ser Ala Ser Gly Pro Arg Pro Thr
305                 310                 315                 320

Tyr Lys Pro Pro Val Ser Asn Tyr Pro Gly Tyr Pro Lys Pro Glu Glu
                325                 330                 335

Gly Ile Leu Asp Ser Leu Asp Val Trp Val Ile Ala Val Ile Val Ile
                340                 345                 350

Ala Ile Val Val Gly Val Ala Val Ile Cys Val Val Pro Tyr Arg Tyr
                355                 360                 365

Leu Gln Arg Arg Lys Lys Lys Gly Thr Tyr Leu Thr Asp Glu Thr His
        370                 375                 380

Arg Glu Val Lys Phe Thr Ser Leu
385                 390
```

<210> SEQ ID NO 57
<211> LENGTH: 392
<212> TYPE: PRT
<213> ORGANISM: Artificial Sequence
<220> FEATURE:
<223> OTHER INFORMATION: Synthetic_PRP1_HUMAN

<400> SEQUENCE: 57

```
Met Leu Leu Ile Leu Leu Ser Val Ala Leu Leu Ala Leu Ser Ser Ala
1               5                   10                  15

Gln Asn Leu Asn Glu Asp Val Ser Gln Glu Glu Ser Pro Ser Leu Ile
        20                  25                  30

Ala Gly Asn Pro Gln Gly Pro Ser Pro Gln Gly Gly Asn Lys Pro Gln
        35                  40                  45

Gly Pro Pro Pro Pro Gly Lys Pro Gln Gly Pro Pro Pro Gln Gly
        50                  55                  60

Gly Asn Lys Pro Gln Gly Pro Pro Pro Gly Lys Pro Gln Gly Pro
65                  70                  75                  80
```

```
Pro Pro Gln Gly Asp Lys Ser Arg Ser Pro Arg Ser Pro Pro Gly Lys
                85              90              95

Pro Gln Gly Pro Pro Pro Gln Gly Gly Asn Gln Pro Gln Gly Pro Pro
            100             105             110

Pro Pro Pro Gly Lys Pro Gln Gly Pro Pro Pro Gln Gly Gly Asn Lys
            115             120             125

Pro Gln Gly Pro Pro Pro Gly Lys Pro Gln Gly Pro Pro Pro Gln
        130             135             140

Gly Asp Lys Ser Gln Ser Pro Arg Ser Pro Pro Gly Lys Pro Gln Gly
145             150             155             160

Pro Pro Pro Gln Gly Gly Asn Gln Pro Gln Gly Pro Pro Pro Pro
                165             170             175

Gly Lys Pro Gln Gly Pro Pro Pro Gln Gly Gly Asn Lys Pro Gln Gly
            180             185             190

Pro Pro Pro Pro Gly Lys Pro Gln Gly Pro Pro Pro Gln Gly Asp Lys
            195             200             205

Ser Gln Ser Pro Arg Ser Pro Pro Gly Lys Pro Gln Gly Pro Pro Pro
    210             215             220

Gln Gly Gly Asn Gln Pro Gln Gly Pro Pro Pro Pro Gly Lys Pro
225             230             235             240

Gln Gly Pro Pro Gln Gln Gly Gly Asn Arg Pro Gln Gly Pro Pro Pro
            245             250             255

Pro Gly Lys Pro Gln Gly Pro Pro Pro Gln Gly Asp Lys Ser Arg Ser
            260             265             270

Pro Gln Ser Pro Pro Gly Lys Pro Gln Gly Pro Pro Pro Gln Gly Gly
            275             280             285

Asn Gln Pro Gln Gly Pro Pro Pro Pro Pro Gly Lys Pro Gln Gly Pro
    290             295             300

Pro Pro Gln Gly Gly Asn Lys Pro Gln Gly Pro Pro Pro Pro Gly Lys
305             310             315             320

Pro Gln Gly Pro Pro Ala Gln Gly Gly Ser Lys Ser Gln Ser Ala Arg
            325             330             335

Ser Pro Pro Gly Lys Pro Gln Gly Pro Pro Gln Gln Glu Gly Asn Asn
            340             345             350

Pro Gln Gly Pro Pro Pro Ala Gly Gly Asn Pro Gln Gln Pro Gln
            355             360             365

Ala Pro Pro Ala Gly Gln Pro Gln Gly Pro Pro Arg Pro Pro Gln Gly
    370             375             380

Gly Arg Pro Ser Arg Pro Pro Gln
385             390
```

<210> SEQ ID NO 58
<211> LENGTH: 397
<212> TYPE: PRT
<213> ORGANISM: Artificial Sequence
<220> FEATURE:
<223> OTHER INFORMATION: Synthetic_X3CL1_HUMAN

<400> SEQUENCE: 58

```
Met Ala Pro Ile Ser Leu Ser Trp Leu Leu Arg Leu Ala Thr Phe Cys
1               5               10              15

His Leu Thr Val Leu Leu Ala Gly Gln His His Gly Val Thr Lys Cys
                20              25              30

Asn Ile Thr Cys Ser Lys Met Thr Ser Lys Ile Pro Val Ala Leu Leu
            35              40              45
```

-continued

```
Ile His Tyr Gln Gln Asn Gln Ala Ser Cys Gly Lys Arg Ala Ile Ile
    50              55                  60

Leu Glu Thr Arg Gln His Arg Leu Phe Cys Ala Asp Pro Lys Glu Gln
65              70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
            115                 120                 125

Pro Glu Ala Thr Gly Glu Ser Ser Ser Leu Glu Pro Thr Pro Ser Ser
    130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
            180                 185                 190

Thr Ala Ala Thr Trp Gln Ser Ser Ala Pro His Gln Pro Gly Pro Ser
            195                 200                 205

Leu Trp Ala Glu Ala Lys Thr Ser Glu Ala Pro Ser Thr Gln Asp Pro
    210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                245                 250                 255

Glu Asn Ser Leu Glu Arg Glu Glu Met Gly Pro Val Pro Ala His Thr
            260                 265                 270

Asp Ala Phe Gln Asp Trp Gly Pro Gly Ser Met Ala His Val Ser Val
            275                 280                 285

Val Pro Val Ser Ser Glu Gly Thr Pro Ser Arg Glu Pro Val Ala Ser
    290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                325                 330                 335

Ala Thr Arg Arg Gln Ala Val Gly Leu Leu Ala Phe Leu Gly Leu Leu
            340                 345                 350

Phe Cys Leu Gly Val Ala Met Phe Thr Tyr Gln Ser Leu Gln Gly Cys
            355                 360                 365

Pro Arg Lys Met Ala Gly Glu Met Ala Glu Gly Leu Arg Tyr Ile Pro
    370                 375                 380

Arg Ser Cys Gly Ser Asn Ser Tyr Val Leu Val Pro Val
385                 390                 395
```

<210> SEQ ID NO 59
<211> LENGTH: 400
<212> TYPE: PRT
<213> ORGANISM: Artificial Sequence
<220> FEATURE:
<223> OTHER INFORMATION: Synthetic_LEUK_HUMAN

<400> SEQUENCE: 59

```
Met Ala Thr Leu Leu Leu Leu Leu Gly Val Leu Val Val Ser Pro Asp
1               5                   10                  15
```

```
Ala Leu Gly Ser Thr Thr Ala Val Gln Thr Pro Thr Ser Gly Glu Pro
        20              25              30

Leu Val Ser Thr Ser Glu Pro Leu Ser Ser Lys Met Tyr Thr Thr Ser
        35              40              45

Ile Thr Ser Asp Pro Lys Ala Asp Ser Thr Gly Asp Gln Thr Ser Ala
    50              55              60

Leu Pro Pro Ser Thr Ser Ile Asn Glu Gly Ser Pro Leu Trp Thr Ser
65              70              75              80

Ile Gly Ala Ser Thr Gly Ser Pro Leu Pro Glu Pro Thr Thr Tyr Gln
                85              90              95

Glu Val Ser Ile Lys Met Ser Ser Val Pro Gln Glu Thr Pro His Ala
            100             105             110

Thr Ser His Pro Ala Val Pro Ile Thr Ala Asn Ser Leu Gly Ser His
            115             120             125

Thr Val Thr Gly Gly Thr Ile Thr Thr Asn Ser Pro Glu Thr Ser Ser
    130             135             140

Arg Thr Ser Gly Ala Pro Val Thr Thr Ala Ala Ser Ser Leu Glu Thr
145             150             155             160

Ser Arg Gly Thr Ser Gly Pro Pro Leu Thr Met Ala Thr Val Ser Leu
                165             170             175

Glu Thr Ser Lys Gly Thr Ser Gly Pro Pro Val Thr Met Ala Thr Asp
            180             185             190

Ser Leu Glu Thr Ser Thr Gly Thr Thr Gly Pro Pro Val Thr Met Thr
            195             200             205

Thr Gly Ser Leu Glu Pro Ser Ser Gly Ala Ser Gly Pro Gln Val Ser
    210             215             220

Ser Val Lys Leu Ser Thr Met Met Ser Pro Thr Thr Ser Thr Asn Ala
225             230             235             240

Ser Thr Val Pro Phe Arg Asn Pro Asp Glu Asn Ser Arg Gly Met Leu
                245             250             255

Pro Val Ala Val Leu Val Ala Leu Leu Ala Val Ile Val Leu Val Ala
            260             265             270

Leu Leu Leu Leu Trp Arg Arg Arg Gln Lys Arg Arg Thr Gly Ala Leu
            275             280             285

Val Leu Ser Arg Gly Gly Lys Arg Asn Gly Val Val Asp Ala Trp Ala
    290             295             300

Gly Pro Ala Gln Val Pro Glu Glu Gly Ala Val Thr Val Thr Val Gly
305             310             315             320

Gly Ser Gly Gly Asp Lys Gly Ser Gly Phe Pro Asp Gly Glu Gly Ser
                325             330             335

Ser Arg Arg Pro Thr Leu Thr Thr Phe Phe Gly Arg Arg Lys Ser Arg
                340             345             350

Gln Gly Ser Leu Ala Met Glu Glu Leu Lys Ser Gly Ser Gly Pro Ser
            355             360             365

Leu Lys Gly Glu Glu Glu Pro Leu Val Ala Ser Glu Asp Gly Ala Val
            370             375             380

Asp Ala Pro Ala Pro Asp Glu Pro Glu Gly Gly Asp Gly Ala Ala Pro
385             390             395             400
```

<210> SEQ ID NO 60
<211> LENGTH: 410
<212> TYPE: PRT
<213> ORGANISM: Artificial Sequence
<220> FEATURE:
<223> OTHER INFORMATION: Synthetic_LAMP2_HUMAN -continued

<400> SEQUENCE: 60

Met Val Cys Phe Arg Leu Phe Pro Val Pro Gly Ser Gly Leu Val Leu
1                   5                   10                  15

Val Cys Leu Val Leu Gly Ala Val Arg Ser Tyr Ala Leu Glu Leu Asn
                20                  25                  30

Leu Thr Asp Ser Glu Asn Ala Thr Cys Leu Tyr Ala Lys Trp Gln Met
            35                  40                  45

Asn Phe Thr Val Arg Tyr Glu Thr Thr Asn Lys Thr Tyr Lys Thr Val
        50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Asp Cys
        355                 360                 365

Ser Ala Asp Asp Asp Asn Phe Leu Val Pro Ile Ala Val Gly Ala Ala
    370                 375                 380

Leu Ala Gly Val Leu Ile Leu Val Leu Leu Ala Tyr Phe Ile Gly Leu
385                 390                 395                 400

Lys His His His Ala Gly Tyr Glu Gln Phe

-continued

```
            405                 410
```

<210> SEQ ID NO 61
<211> LENGTH: 417
<212> TYPE: PRT
<213> ORGANISM: Artificial Sequence
<220> FEATURE:
<223> OTHER INFORMATION: Synthetic_LAMP1_HUMAN

<400> SEQUENCE: 61

```
Met Ala Ala Pro Gly Ser Ala Arg Arg Pro Leu Leu Leu Leu Leu Leu
1               5                   10                  15

Leu Leu Leu Leu Gly Leu Met His Cys Ala Ser Ala Ala Met Phe Met
            20                  25                  30

Val Lys Asn Gly Asn Gly Thr Ala Cys Ile Met Ala Asn Phe Ser Ala
        35                  40                  45

Ala Phe Ser Val Asn Tyr Asp Thr Lys Ser Gly Pro Lys Asn Met Thr
    50                  55                  60

Phe Asp Leu Pro Ser Asp Ala Thr Val Val Leu Asn Arg Ser Ser Cys
65                  70                  75                  80

Gly Lys Glu Asn Thr Ser Asp Pro Ser Leu Val Ile Ala Phe Gly Arg
                85                  90                  95

Gly His Thr Leu Thr Leu Asn Phe Thr Arg Asn Ala Thr Arg Tyr Ser
            100                 105                 110

Val Gln Leu Met Ser Phe Val Tyr Asn Leu Ser Asp Thr His Leu Phe
            115                 120                 125

Pro Asn Ala Ser Ser Lys Glu Ile Lys Thr Val Glu Ser Ile Thr Asp
    130                 135                 140

Ile Arg Ala Asp Ile Asp Lys Lys Tyr Arg Cys Val Ser Gly Thr Gln
145                 150                 155                 160

Val His Met Asn Asn Val Thr Val Thr Leu His Asp Ala Thr Ile Gln
                165                 170                 175

Ala Tyr Leu Ser Asn Ser Ser Phe Ser Arg Gly Glu Thr Arg Cys Glu
            180                 185                 190

Gln Asp Arg Pro Ser Pro Thr Thr Ala Pro Pro Ala Pro Pro Ser Pro
            195                 200                 205

Ser Pro Ser Pro Val Pro Lys Ser Pro Ser Val Asp Lys Tyr Asn Val
    210                 215                 220

Ser Gly Thr Asn Gly Thr Cys Leu Leu Ala Ser Met Gly Leu Gln Leu
225                 230                 235                 240

Asn Leu Thr Tyr Glu Arg Lys Asp Asn Thr Thr Val Thr Arg Leu Leu
                245                 250                 255

Asn Ile Asn Pro Asn Lys Thr Ser Ala Ser Gly Ser Cys Gly Ala His
            260                 265                 270

Leu Val Thr Leu Glu Leu His Ser Glu Gly Thr Thr Val Leu Leu Phe
            275                 280                 285

Gln Phe Gly Met Asn Ala Ser Ser Ser Arg Phe Phe Leu Gln Gly Ile
    290                 295                 300

Gln Leu Asn Thr Ile Leu Pro Asp Ala Arg Asp Pro Ala Phe Lys Ala
305                 310                 315                 320

Ala Asn Gly Ser Leu Arg Ala Leu Gln Ala Thr Val Gly Asn Ser Tyr
                325                 330                 335

Lys Cys Asn Ala Glu Glu His Val Arg Val Thr Lys Ala Phe Ser Val
            340                 345                 350

Asn Ile Phe Lys Val Trp Val Gln Ala Phe Lys Val Glu Gly Gly Gln
```

```
          355                 360                 365
Phe Gly Ser Val Glu Glu Cys Leu Leu Asp Glu Asn Ser Met Leu Ile
    370                 375                 380

Pro Ile Ala Val Gly Gly Ala Leu Ala Gly Leu Val Leu Ile Val Leu
385                 390                 395                 400

Ile Ala Tyr Leu Val Gly Arg Lys Arg Ser His Ala Gly Tyr Gln Thr
                405                 410                 415

Ile

<210> SEQ ID NO 62
<211> LENGTH: 424
<212> TYPE: PRT
<213> ORGANISM: Artificial Sequence
<220> FEATURE:
<223> OTHER INFORMATION: Synthetic_ZP3_HUMAN

<400> SEQUENCE: 62

Met Glu Leu Ser Tyr Arg Leu Phe Ile Cys Leu Leu Leu Trp Gly Ser
1                   5                   10                  15

Thr Glu Leu Cys Tyr Pro Gln Pro Leu Trp Leu Leu Gln Gly Gly Ala
                20                  25                  30

Ser His Pro Glu Thr Ser Val Gln Pro Val Leu Val Glu Cys Gln Glu
            35                  40                  45

Ala Thr Leu Met Val Met Val Ser Lys Asp Leu Phe Gly Thr Gly Lys
        50                  55                  60

Leu Ile Arg Ala Ala Asp Leu Thr Leu Gly Pro Glu Ala Cys Glu Pro
65                  70                  75                  80

Leu Val Ser Met Asp Thr Glu Asp Val Val Arg Phe Glu Val Gly Leu
                85                  90                  95

His Glu Cys Gly Asn Ser Met Gln Val Thr Asp Asp Ala Leu Val Tyr
            100                 105                 110

Ser Thr Phe Leu Leu His Asp Pro Arg Pro Val Gly Asn Leu Ser Ile
        115                 120                 125

Val Arg Thr Asn Arg Ala Glu Ile Pro Ile Glu Cys Arg Tyr Pro Arg
    130                 135                 140

Gln Gly Asn Val Ser Ser Gln Ala Ile Leu Pro Thr Trp Leu Pro Phe
145                 150                 155                 160

Arg Thr Thr Val Phe Ser Glu Glu Lys Leu Thr Phe Ser Leu Arg Leu
                165                 170                 175

Met Glu Glu Asn Trp Asn Ala Glu Lys Arg Ser Pro Thr Phe His Leu
            180                 185                 190

Gly Asp Ala Ala His Leu Gln Ala Glu Ile His Thr Gly Ser His Val
        195                 200                 205

Pro Leu Arg Leu Phe Val Asp His Cys Val Ala Thr Pro Thr Pro Asp
    210                 215                 220

Gln Asn Ala Ser Pro Tyr His Thr Ile Val Asp Phe His Gly Cys Leu
225                 230                 235                 240

Val Asp Gly Leu Thr Asp Ala Ser Ser Ala Phe Lys Val Pro Arg Pro
                245                 250                 255

Gly Pro Asp Thr Leu Gln Phe Thr Val Asp Val Phe His Phe Ala Asn
                260                 265                 270

Asp Ser Arg Asn Met Ile Tyr Ile Thr Cys His Leu Lys Val Thr Leu
            275                 280                 285

Ala Glu Gln Asp Pro Asp Glu Leu Asn Lys Ala Cys Ser Phe Ser Lys
        290                 295                 300
```

-continued

```
Pro Ser Asn Ser Trp Phe Pro Val Glu Gly Ser Ala Asp Ile Cys Gln
305                 310                 315                 320

Cys Cys Asn Lys Gly Asp Cys Gly Thr Pro Ser His Ser Arg Arg Gln
                325                 330                 335

Pro His Val Met Ser Gln Trp Ser Arg Ser Ala Ser Arg Asn Arg Arg
            340                 345                 350

His Val Thr Glu Glu Ala Asp Val Thr Val Gly Pro Leu Ile Phe Leu
            355                 360                 365

Asp Arg Arg Gly Asp His Glu Val Glu Gln Trp Ala Leu Pro Ser Asp
        370                 375                 380

Thr Ser Val Val Leu Leu Gly Val Gly Leu Ala Val Val Val Ser Leu
385                 390                 395                 400

Thr Leu Thr Ala Val Ile Leu Val Leu Thr Arg Arg Cys Arg Thr Ala
                405                 410                 415

Ser His Pro Val Ser Ala Ser Glu
                420

<210> SEQ ID NO 63
<211> LENGTH: 430
<212> TYPE: PRT
<213> ORGANISM: Artificial Sequence
<220> FEATURE:
<223> OTHER INFORMATION: Synthetic_K1C18_HUMAN

<400> SEQUENCE: 63

Met Ser Phe Thr Thr Arg Ser Thr Phe Ser Thr Asn Tyr Arg Ser Leu
1               5                   10                  15

Gly Ser Val Gln Ala Pro Ser Tyr Gly Ala Arg Pro Val Ser Ser Ala
                20                  25                  30

Ala Ser Val Tyr Ala Gly Ala Gly Gly Ser Gly Ser Arg Ile Ser Val
            35                  40                  45

Ser Arg Ser Thr Ser Phe Arg Gly Gly Met Gly Ser Gly Gly Leu Ala
        50                  55                  60

Thr Gly Ile Ala Gly Gly Leu Ala Gly Met Gly Gly Ile Gln Asn Glu
65                  70                  75                  80

Lys Glu Thr Met Gln Ser Leu Asn Asp Arg Leu Ala Ser Tyr Leu Asp
                85                  90                  95

Arg Val Arg Ser Leu Glu Thr Glu Asn Arg Arg Leu Glu Ser Lys Ile
                100                 105                 110

Arg Glu His Leu Glu Lys Lys Gly Pro Gln Val Arg Asp Trp Ser His
            115                 120                 125

Tyr Phe Lys Ile Ile Glu Asp Leu Arg Ala Gln Ile Phe Ala Asn Thr
        130                 135                 140

Val Asp Asn Ala Arg Ile Val Leu Gln Ile Asp Asn Ala Arg Leu Ala
145                 150                 155                 160

Ala Asp Asp Phe Arg Val Lys Tyr Glu Thr Glu Leu Ala Met Arg Gln
                165                 170                 175

Ser Val Glu Asn Asp Ile His Gly Leu Arg Lys Val Ile Asp Asp Thr
                180                 185                 190

Asn Ile Thr Arg Leu Gln Leu Glu Thr Glu Ile Glu Ala Leu Lys Glu
            195                 200                 205

Glu Leu Leu Phe Met Lys Lys Asn His Glu Glu Glu Val Lys Gly Leu
        210                 215                 220

Gln Ala Gln Ile Ala Ser Ser Gly Leu Thr Val Glu Val Asp Ala Pro
225                 230                 235                 240
```

```
Lys Ser Gln Asp Leu Ala Lys Ile Met Ala Asp Ile Arg Ala Gln Tyr
            245                 250                 255

Asp Glu Leu Ala Arg Lys Asn Arg Glu Glu Leu Asp Lys Tyr Trp Ser
            260                 265                 270

Gln Gln Ile Glu Glu Ser Thr Thr Val Val Thr Thr Gln Ser Ala Glu
        275                 280                 285

Val Gly Ala Ala Glu Thr Thr Leu Thr Glu Leu Arg Arg Thr Val Gln
        290                 295                 300

Ser Leu Glu Ile Asp Leu Asp Ser Met Arg Asn Leu Lys Ala Ser Leu
305                 310                 315                 320

Glu Asn Ser Leu Arg Glu Val Glu Ala Arg Tyr Ala Leu Gln Met Glu
            325                 330                 335

Gln Leu Asn Gly Ile Leu Leu His Leu Glu Ser Glu Leu Ala Gln Thr
            340                 345                 350

Arg Ala Glu Gly Gln Arg Gln Ala Gln Glu Tyr Glu Ala Leu Leu Asn
            355                 360                 365

Ile Lys Val Lys Leu Glu Ala Glu Ile Ala Thr Tyr Arg Arg Leu Leu
        370                 375                 380

Glu Asp Gly Glu Asp Phe Asn Leu Gly Asp Ala Leu Asp Ser Ser Asn
385                 390                 395                 400

Ser Met Gln Thr Ile Gln Lys Thr Thr Thr Arg Arg Ile Val Asp Gly
            405                 410                 415

Lys Val Val Ser Glu Thr Asn Asp Thr Lys Val Leu Arg His
            420                 425                 430
```

<210> SEQ ID NO 64
<211> LENGTH: 439
<212> TYPE: PRT
<213> ORGANISM: Artificial Sequence
<220> FEATURE:
<223> OTHER INFORMATION: Synthetic_TICN1_HUMAN

<400> SEQUENCE: 64

```
Met Pro Ala Ile Ala Val Leu Ala Ala Ala Ala Ala Ala Trp Cys Phe
1               5                   10                  15

Leu Gln Val Glu Ser Arg His Leu Asp Ala Leu Ala Gly Gly Ala Gly
            20                  25                  30

Pro Asn His Gly Asn Phe Leu Asp Asn Asp Gln Trp Leu Ser Thr Val
            35                  40                  45

Ser Gln Tyr Asp Arg Asp Lys Tyr Trp Asn Arg Phe Arg Asp Asp Asp
        50                  55                  60

Tyr Phe Arg Asn Trp Asn Pro Asn Lys Pro Phe Asp Gln Ala Leu Asp
65                  70                  75                  80

Pro Ser Lys Asp Pro Cys Leu Lys Val Lys Cys Ser Pro His Lys Val
            85                  90                  95

Cys Val Thr Gln Asp Tyr Gln Thr Ala Leu Cys Val Ser Arg Lys His
            100                 105                 110

Leu Leu Pro Arg Gln Lys Lys Gly Asn Val Ala Gln Lys His Trp Val
            115                 120                 125

Gly Pro Ser Asn Leu Val Lys Cys Lys Pro Cys Pro Val Ala Gln Ser
        130                 135                 140

Ala Met Val Cys Gly Ser Asp Gly His Ser Tyr Thr Ser Lys Cys Lys
145                 150                 155                 160

Leu Glu Phe His Ala Cys Ser Thr Gly Lys Ser Leu Ala Thr Leu Cys
            165                 170                 175
```

-continued

```
Asp Gly Pro Cys Pro Cys Leu Pro Glu Pro Glu Pro Lys His Lys
        180             185             190

Ala Glu Arg Ser Ala Cys Thr Asp Lys Glu Leu Arg Asn Leu Ala Ser
        195             200             205

Arg Leu Lys Asp Trp Phe Gly Ala Leu His Glu Asp Ala Asn Arg Val
        210             215             220

Ile Lys Pro Thr Ser Ser Asn Thr Ala Gln Gly Arg Phe Asp Thr Ser
225             230             235             240

Ile Leu Pro Ile Cys Lys Asp Ser Leu Gly Trp Met Phe Asn Lys Leu
            245             250             255

Asp Met Asn Tyr Asp Leu Leu Leu Asp Pro Ser Glu Ile Asn Ala Ile
            260             265             270

Tyr Leu Asp Lys Tyr Glu Pro Cys Ile Lys Pro Leu Phe Asn Ser Cys
        275             280             285

Asp Ser Phe Lys Asp Gly Lys Leu Ser Asn Asn Glu Trp Cys Tyr Cys
        290             295             300

Phe Gln Lys Pro Gly Gly Leu Pro Cys Gln Asn Glu Met Asn Arg Ile
305             310             315             320

Gln Lys Leu Ser Lys Gly Lys Ser Leu Leu Gly Ala Phe Ile Pro Arg
            325             330             335

Cys Asn Glu Glu Gly Tyr Tyr Lys Ala Thr Gln Cys His Gly Ser Thr
            340             345             350

Gly Gln Cys Trp Cys Val Asp Lys Tyr Gly Asn Glu Leu Ala Gly Ser
            355             360             365

Arg Lys Gln Gly Ala Val Ser Cys Glu Glu Glu Gln Glu Thr Ser Gly
        370             375             380

Asp Phe Gly Ser Gly Gly Ser Val Val Leu Leu Asp Asp Leu Glu Tyr
385             390             395             400

Glu Arg Glu Leu Gly Pro Lys Asp Lys Glu Gly Lys Leu Arg Val His
            405             410             415

Thr Arg Ala Val Thr Glu Asp Asp Glu Asp Glu Asp Asp Lys Glu
            420             425             430

Asp Glu Val Gly Tyr Ile Trp
        435
```

```
<210> SEQ ID NO 65
<211> LENGTH: 442
<212> TYPE: PRT
<213> ORGANISM: Artificial Sequence
<220> FEATURE:
<223> OTHER INFORMATION: Synthetic_SDC3_HUMAN

<400> SEQUENCE: 65

Met Lys Pro Gly Pro Pro His Arg Ala Gly Ala Ala His Gly Ala Gly
1               5               10              15

Ala Gly Ala Gly Ala Ala Ala Gly Pro Gly Ala Arg Gly Leu Leu Leu
            20              25              30

Pro Pro Leu Leu Leu Leu Leu Leu Ala Gly Arg Ala Ala Gly Ala Gln
        35              40              45

Arg Trp Arg Ser Glu Asn Phe Glu Arg Pro Val Asp Leu Glu Gly Ser
        50              55              60

Gly Asp Asp Asp Ser Phe Pro Asp Asp Glu Leu Asp Asp Leu Tyr Ser
65              70              75              80

Gly Ser Gly Ser Gly Tyr Phe Glu Gln Glu Ser Gly Ile Glu Thr Ala
            85              90              95
```

```
Met Arg Phe Ser Pro Asp Val Ala Leu Ala Val Ser Thr Thr Pro Ala
            100                 105                 110

Val Leu Pro Thr Thr Asn Ile Gln Pro Val Gly Thr Pro Phe Glu Glu
            115                 120                 125

Leu Pro Ser Glu Arg Pro Thr Leu Glu Pro Ala Thr Ser Pro Leu Val
            130                 135                 140

Val Thr Glu Val Pro Glu Glu Pro Ser Gln Arg Ala Thr Thr Val Ser
145                 150                 155                 160

Thr Thr Met Ala Thr Thr Ala Ala Thr Ser Thr Gly Asp Pro Thr Val
                165                 170                 175

Ala Thr Val Pro Ala Thr Val Ala Thr Ala Thr Pro Ser Thr Pro Ala
                180                 185                 190

Ala Pro Pro Phe Thr Ala Thr Thr Ala Val Ile Arg Thr Thr Gly Val
                195                 200                 205

Arg Arg Leu Leu Pro Leu Pro Leu Thr Thr Val Ala Thr Ala Arg Ala
            210                 215                 220

Thr Thr Pro Glu Ala Pro Ser Pro Pro Thr Thr Ala Ala Val Leu Asp
225                 230                 235                 240

Thr Glu Ala Pro Thr Pro Arg Leu Val Ser Thr Ala Thr Ser Arg Pro
                245                 250                 255

Arg Ala Leu Pro Arg Pro Ala Thr Thr Gln Glu Pro Asp Ile Pro Glu
            260                 265                 270

Arg Ser Thr Leu Pro Leu Gly Thr Thr Ala Pro Gly Pro Thr Glu Val
            275                 280                 285

Ala Gln Thr Pro Thr Pro Glu Thr Phe Leu Thr Thr Ile Arg Asp Glu
            290                 295                 300

Pro Glu Val Pro Val Ser Gly Gly Pro Ser Gly Asp Phe Glu Leu Pro
305                 310                 315                 320

Glu Glu Glu Thr Thr Gln Pro Asp Thr Ala Asn Glu Val Val Ala Val
                325                 330                 335

Gly Gly Ala Ala Ala Lys Ala Ser Ser Pro Pro Gly Thr Leu Pro Lys
                340                 345                 350

Gly Ala Arg Pro Gly Pro Gly Leu Leu Asp Asn Ala Ile Asp Ser Gly
                355                 360                 365

Ser Ser Ala Ala Gln Leu Pro Gln Lys Ser Ile Leu Glu Arg Lys Glu
            370                 375                 380

Val Leu Val Ala Val Ile Val Gly Gly Val Val Gly Ala Leu Phe Ala
385                 390                 395                 400

Ala Phe Leu Val Thr Leu Leu Ile Tyr Arg Met Lys Lys Lys Asp Glu
                405                 410                 415

Gly Ser Tyr Thr Leu Glu Glu Pro Lys Gln Ala Ser Val Thr Tyr Gln
                420                 425                 430

Lys Pro Asp Lys Gln Glu Glu Phe Tyr Ala
            435                 440
```

```
<210> SEQ ID NO 66
<211> LENGTH: 457
<212> TYPE: PRT
<213> ORGANISM: Artificial Sequence
<220> FEATURE:
<223> OTHER INFORMATION: Synthetic_CMGA_HUMAN

<400> SEQUENCE: 66
```

```
Met Arg Ser Ala Ala Val Leu Ala Leu Leu Leu Cys Ala Gly Gln Val
1               5                   10                  15
```

```
Thr Ala Leu Pro Val Asn Ser Pro Met Asn Lys Gly Asp Thr Glu Val
            20              25              30

Met Lys Cys Ile Val Glu Val Ile Ser Asp Thr Leu Ser Lys Pro Ser
            35              40              45

Pro Met Pro Val Ser Gln Glu Cys Phe Glu Thr Leu Arg Gly Asp Glu
        50              55              60

Arg Ile Leu Ser Ile Leu Arg His Gln Asn Leu Leu Lys Glu Leu Gln
65              70              75              80

Asp Leu Ala Leu Gln Gly Ala Lys Glu Arg Ala His Gln Gln Lys Lys
                85              90              95

His Ser Gly Phe Glu Asp Glu Leu Ser Glu Val Leu Glu Asn Gln Ser
            100             105             110

Ser Gln Ala Glu Leu Lys Glu Ala Val Glu Glu Pro Ser Ser Lys Asp
            115             120             125

Val Met Glu Lys Arg Glu Asp Ser Lys Glu Ala Glu Lys Ser Gly Glu
        130             135             140

Ala Thr Asp Gly Ala Arg Pro Gln Ala Leu Pro Glu Pro Met Gln Glu
145             150             155             160

Ser Lys Ala Glu Gly Asn Asn Gln Ala Pro Gly Glu Glu Glu Glu Glu
                165             170             175

Glu Glu Glu Ala Thr Asn Thr His Pro Pro Ala Ser Leu Pro Ser Gln
            180             185             190

Lys Tyr Pro Gly Pro Gln Ala Glu Gly Asp Ser Glu Gly Leu Ser Gln
            195             200             205

Gly Leu Val Asp Arg Glu Lys Gly Leu Ser Ala Glu Pro Gly Trp Gln
        210             215             220

Ala Lys Arg Glu Glu Glu Glu Glu Glu Glu Glu Ala Glu Ala Gly
225             230             235             240

Glu Glu Ala Val Pro Glu Glu Glu Gly Pro Thr Val Val Leu Asn Pro
                245             250             255

His Pro Ser Leu Gly Tyr Lys Glu Ile Arg Lys Gly Glu Ser Arg Ser
            260             265             270

Glu Ala Leu Ala Val Asp Gly Ala Gly Lys Pro Gly Ala Glu Glu Ala
            275             280             285

Gln Asp Pro Glu Gly Lys Gly Glu Gln Glu His Ser Gln Gln Lys Glu
        290             295             300

Glu Glu Glu Glu Met Ala Val Val Pro Gln Gly Leu Phe Arg Gly Gly
305             310             315             320

Lys Ser Gly Glu Leu Glu Gln Glu Glu Glu Arg Leu Ser Lys Glu Trp
            325             330             335

Glu Asp Ser Lys Arg Trp Ser Lys Met Asp Gln Leu Ala Lys Glu Leu
            340             345             350

Thr Ala Glu Lys Arg Leu Glu Gly Gln Glu Glu Glu Asp Asn Arg
            355             360             365

Asp Ser Ser Met Lys Leu Ser Phe Arg Ala Arg Ala Tyr Gly Phe Arg
        370             375             380

Gly Pro Gly Pro Gln Leu Arg Arg Gly Trp Arg Pro Ser Ser Arg Glu
385             390             395             400

Asp Ser Leu Glu Ala Gly Leu Pro Leu Gln Val Arg Gly Tyr Pro Glu
                405             410             415

Glu Lys Lys Glu Glu Glu Gly Ser Ala Asn Arg Arg Pro Glu Asp Gln
            420             425             430
```

-continued

```
Glu Leu Glu Ser Leu Ser Ala Ile Glu Ala Glu Leu Glu Lys Val Ala
        435                 440                 445

His Gln Leu Gln Ala Leu Arg Arg Gly
    450                 455

<210> SEQ ID NO 67
<211> LENGTH: 458
<212> TYPE: PRT
<213> ORGANISM: Artificial Sequence
<220> FEATURE:
<223> OTHER INFORMATION: Synthetic_CBPN_HUMAN

<400> SEQUENCE: 67

Met Ser Asp Leu Leu Ser Val Phe Leu His Leu Leu Leu Leu Phe Lys
1               5                   10                  15

Leu Val Ala Pro Val Thr Phe Arg His His Arg Tyr Asp Asp Leu Val
            20                  25                  30

Arg Thr Leu Tyr Lys Val Gln Asn Glu Cys Pro Gly Ile Thr Arg Val
        35                  40                  45

Tyr Ser Ile Gly Arg Ser Val Glu Gly Arg His Leu Tyr Val Leu Glu
    50                  55                  60

Phe Ser Asp His Pro Gly Ile His Glu Pro Leu Glu Pro Glu Val Lys
65                  70                  75                  80

Tyr Val Gly Asn Met His Gly Asn Glu Ala Leu Gly Arg Glu Leu Met
                85                  90                  95

Leu Gln Leu Ser Glu Phe Leu Cys Glu Glu Phe Arg Asn Arg Asn Gln
            100                 105                 110

Arg Ile Val Gln Leu Ile Gln Asp Thr Arg Ile His Ile Leu Pro Ser
        115                 120                 125

Met Asn Pro Asp Gly Tyr Glu Val Ala Ala Ala Gln Gly Pro Asn Lys
    130                 135                 140

Pro Gly Tyr Leu Val Gly Arg Asn Asn Ala Asn Gly Val Asp Leu Asn
145                 150                 155                 160

Arg Asn Phe Pro Asp Leu Asn Thr Tyr Ile Tyr Tyr Asn Glu Lys Tyr
                165                 170                 175

Gly Gly Pro Asn His His Leu Pro Leu Pro Asp Asn Trp Lys Ser Gln
            180                 185                 190

Val Glu Pro Glu Thr Arg Ala Val Ile Arg Trp Met His Ser Phe Asn
        195                 200                 205

Phe Val Leu Ser Ala Asn Leu His Gly Gly Ala Val Val Ala Asn Tyr
    210                 215                 220

Pro Tyr Asp Lys Ser Phe Glu His Arg Val Arg Gly Val Arg Arg Thr
225                 230                 235                 240

Ala Ser Thr Pro Thr Pro Asp Asp Lys Leu Phe Gln Lys Leu Ala Lys
                245                 250                 255

Val Tyr Ser Tyr Ala His Gly Trp Met Phe Gln Gly Trp Asn Cys Gly
            260                 265                 270

Asp Tyr Phe Pro Asp Gly Ile Thr Asn Gly Ala Ser Trp Tyr Ser Leu
        275                 280                 285

Ser Lys Gly Met Gln Asp Phe Asn Tyr Leu His Thr Asn Cys Phe Glu
    290                 295                 300

Ile Thr Leu Glu Leu Ser Cys Asp Lys Phe Pro Pro Glu Glu Glu Leu
305                 310                 315                 320

Gln Arg Glu Trp Leu Gly Asn Arg Glu Ala Leu Ile Gln Phe Leu Glu
                325                 330                 335
```

```
Gln Val His Gln Gly Ile Lys Gly Met Val Leu Asp Glu Asn Tyr Asn
            340                 345                 350

Asn Leu Ala Asn Ala Val Ile Ser Val Ser Gly Ile Asn His Asp Val
            355                 360                 365

Thr Ser Gly Asp His Gly Asp Tyr Phe Arg Leu Leu Leu Pro Gly Ile
    370                 375                 380

Tyr Thr Val Ser Ala Thr Ala Pro Gly Tyr Asp Pro Glu Thr Val Thr
385                 390                 395                 400

Val Thr Val Gly Pro Ala Glu Pro Thr Leu Val Asn Phe His Leu Lys
                405                 410                 415

Arg Ser Ile Pro Gln Val Ser Pro Val Arg Arg Ala Pro Ser Arg Arg
            420                 425                 430

His Gly Val Arg Ala Lys Val Gln Pro Gln Ala Arg Lys Lys Glu Met
            435                 440                 445

Glu Met Arg Gln Leu Gln Arg Gly Pro Ala
    450                 455
```

```
<210> SEQ ID NO 68
<211> LENGTH: 461
<212> TYPE: PRT
<213> ORGANISM: Artificial Sequence
<220> FEATURE:
<223> OTHER INFORMATION: Synthetic_FA9_HUMAN

<400> SEQUENCE: 68

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240
```

-continued

```
Gln Val Val Leu Asn Gly Lys Val Asp Ala Phe Cys Gly Gly Ser Ile
            245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
            275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
            325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
            405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr
    450                 455                 460
```

```
<210> SEQ ID NO 69
<211> LENGTH: 461
<212> TYPE: PRT
<213> ORGANISM: Artificial Sequence
<220> FEATURE:
<223> OTHER INFORMATION: Synthetic_TNR1B_HUMAN

<400> SEQUENCE: 69
```

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
            85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
            115                 120                 125

Ser Lys Gln Glu Gly Cys Arg Leu Cys Ala Pro Leu Arg Lys Cys Arg
    130                 135                 140
```

```
Pro Gly Phe Gly Val Ala Arg Pro Gly Thr Glu Thr Ser Asp Val Val
145             150             155             160

Cys Lys Pro Cys Ala Pro Gly Thr Phe Ser Asn Thr Thr Ser Ser Thr
                165             170             175

Asp Ile Cys Arg Pro His Gln Ile Cys Asn Val Val Ala Ile Pro Gly
            180             185             190

Asn Ala Ser Met Asp Ala Val Cys Thr Ser Thr Ser Pro Thr Arg Ser
            195             200             205

Met Ala Pro Gly Ala Val His Leu Pro Gln Pro Val Ser Thr Arg Ser
    210             215             220

Gln His Thr Gln Pro Thr Pro Glu Pro Ser Thr Ala Pro Ser Thr Ser
225             230             235             240

Phe Leu Leu Pro Met Gly Pro Ser Pro Ala Glu Gly Ser Thr Gly
            245             250             255

Asp Phe Ala Leu Pro Val Gly Leu Ile Val Gly Val Thr Ala Leu Gly
            260             265             270

Leu Leu Ile Ile Gly Val Val Asn Cys Val Ile Met Thr Gln Val Lys
            275             280             285

Lys Lys Pro Leu Cys Leu Gln Arg Glu Ala Lys Val Pro His Leu Pro
    290             295             300

Ala Asp Lys Ala Arg Gly Thr Gln Gly Pro Glu Gln Gln His Leu Leu
305             310             315             320

Ile Thr Ala Pro Ser Ser Ser Ser Ser Ser Leu Glu Ser Ser Ala Ser
            325             330             335

Ala Leu Asp Arg Arg Ala Pro Thr Arg Asn Gln Pro Gln Ala Pro Gly
            340             345             350

Val Glu Ala Ser Gly Ala Gly Glu Ala Arg Ala Ser Thr Gly Ser Ser
            355             360             365

Asp Ser Ser Pro Gly Gly His Gly Thr Gln Val Asn Val Thr Cys Ile
    370             375             380

Val Asn Val Cys Ser Ser Ser Asp His Ser Ser Gln Cys Ser Ser Gln
385             390             395             400

Ala Ser Ser Thr Met Gly Asp Thr Asp Ser Ser Pro Ser Glu Ser Pro
            405             410             415

Lys Asp Glu Gln Val Pro Phe Ser Lys Glu Glu Cys Ala Phe Arg Ser
            420             425             430

Gln Leu Glu Thr Pro Glu Thr Leu Leu Gly Ser Thr Glu Glu Lys Pro
            435             440             445

Leu Pro Leu Gly Val Pro Asp Ala Gly Met Lys Pro Ser
    450             455             460
```

<210> SEQ ID NO 70
<211> LENGTH: 466
<212> TYPE: PRT
<213> ORGANISM: Artificial Sequence
<220> FEATURE:
<223> OTHER INFORMATION: Synthetic_VIME_HUMAN

<400> SEQUENCE: 70

```
Met Ser Thr Arg Ser Val Ser Ser Ser Tyr Arg Arg Met Phe Gly
1               5               10              15

Gly Pro Gly Thr Ala Ser Arg Pro Ser Ser Ser Arg Ser Tyr Val Thr
                20              25              30

Thr Ser Thr Arg Thr Tyr Ser Leu Gly Ser Ala Leu Arg Pro Ser Thr
            35              40              45
```

-continued

```
Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
            115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
            195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
            245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
    275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
            325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
            355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
            405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
    450                 455                 460

Leu Glu
```

465

<210> SEQ ID NO 71
<211> LENGTH: 468
<212> TYPE: PRT
<213> ORGANISM: Artificial Sequence
<220> FEATURE:
<223> OTHER INFORMATION: Synthetic_SCG3_HUMAN

<400> SEQUENCE: 71

Met Gly Phe Leu Gly Thr Gly Thr Trp Ile Leu Val Leu Val Leu Pro
1               5                   10                  15

Ile Gln Ala Phe Pro Lys Pro Gly Gly Ser Gln Asp Lys Ser Leu His
            20                  25                  30

Asn Arg Glu Leu Ser Ala Glu Arg Pro Leu Asn Glu Gln Ile Ala Glu
        35                  40                  45

Ala Glu Glu Asp Lys Ile Lys Lys Thr Tyr Pro Pro Glu Asn Lys Pro
    50                  55                  60

Gly Gln Ser Asn Tyr Ser Phe Val Asp Asn Leu Asn Leu Leu Lys Ala
65                  70                  75                  80

Ile Thr Glu Lys Glu Lys Ile Glu Lys Glu Arg Gln Ser Ile Arg Ser
                85                  90                  95

Ser Pro Leu Asp Asn Lys Leu Asn Val Glu Asp Val Asp Ser Thr Lys
            100                 105                 110

Asn Arg Lys Leu Ile Asp Asp Tyr Asp Ser Thr Lys Ser Gly Leu Asp
            115                 120                 125

His Lys Phe Gln Asp Asp Pro Asp Gly Leu His Gln Leu Asp Gly Thr
    130                 135                 140

Pro Leu Thr Ala Glu Asp Ile Val His Lys Ile Ala Ala Arg Ile Tyr
145                 150                 155                 160

Glu Glu Asn Asp Arg Ala Val Phe Asp Lys Ile Val Ser Lys Leu Leu
                165                 170                 175

Asn Leu Gly Leu Ile Thr Glu Ser Gln Ala His Thr Leu Glu Asp Glu
            180                 185                 190

Val Ala Glu Val Leu Gln Lys Leu Ile Ser Lys Glu Ala Asn Asn Tyr
            195                 200                 205

Glu Glu Asp Pro Asn Lys Pro Thr Ser Trp Thr Glu Asn Gln Ala Gly
    210                 215                 220

Lys Ile Pro Glu Lys Val Thr Pro Met Ala Ala Ile Gln Asp Gly Leu
225                 230                 235                 240

Ala Lys Gly Glu Asn Asp Glu Thr Val Ser Asn Thr Leu Thr Leu Thr
                245                 250                 255

Asn Gly Leu Glu Arg Arg Thr Lys Thr Tyr Ser Glu Asp Asn Phe Glu
            260                 265                 270

Glu Leu Gln Tyr Phe Pro Asn Phe Tyr Ala Leu Leu Lys Ser Ile Asp
            275                 280                 285

Ser Glu Lys Glu Ala Lys Glu Lys Glu Thr Leu Ile Thr Ile Met Lys
    290                 295                 300

Thr Leu Ile Asp Phe Val Lys Met Met Val Lys Tyr Gly Thr Ile Ser
305                 310                 315                 320

Pro Glu Glu Gly Val Ser Tyr Leu Glu Asn Leu Asp Glu Met Ile Ala
                325                 330                 335

Leu Gln Thr Lys Asn Lys Leu Glu Lys Asn Ala Thr Asp Asn Ile Ser
            340                 345                 350

Lys Leu Phe Pro Ala Pro Ser Glu Lys Ser His Glu Glu Thr Asp Ser

-continued

```
              355                    360                    365

Thr Lys Glu Glu Ala Ala Lys Met Glu Lys Glu Tyr Gly Ser Leu Lys
    370                    375                    380

Asp Ser Thr Lys Asp Asp Asn Ser Asn Pro Gly Gly Lys Thr Asp Glu
385                    390                    395                    400

Pro Lys Gly Lys Thr Glu Ala Tyr Leu Glu Ala Ile Arg Lys Asn Ile
                   405                    410                    415

Glu Trp Leu Lys Lys His Asp Lys Lys Gly Asn Lys Glu Asp Tyr Asp
                   420                    425                    430

Leu Ser Lys Met Arg Asp Phe Ile Asn Lys Gln Ala Asp Ala Tyr Val
                   435                    440                    445

Glu Lys Gly Ile Leu Asp Lys Glu Glu Ala Glu Ala Ile Lys Arg Ile
        450                    455                    460

Tyr Ser Ser Leu
465

<210> SEQ ID NO 72
<211> LENGTH: 473
<212> TYPE: PRT
<213> ORGANISM: Artificial Sequence
<220> FEATURE:
<223> OTHER INFORMATION: Synthetic_KCC4_HUMAN

<400> SEQUENCE: 72

Met Leu Lys Val Thr Val Pro Ser Cys Ser Ala Ser Ser Cys Ser Ser
1                   5                    10                    15

Val Thr Ala Ser Ala Ala Pro Gly Thr Ala Ser Leu Val Pro Asp Tyr
                   20                    25                    30

Trp Ile Asp Gly Ser Asn Arg Asp Ala Leu Ser Asp Phe Phe Glu Val
                   35                    40                    45

Glu Ser Glu Leu Gly Arg Gly Ala Thr Ser Ile Val Tyr Arg Cys Lys
        50                    55                    60

Gln Lys Gly Thr Gln Lys Pro Tyr Ala Leu Lys Val Leu Lys Lys Thr
65                    70                    75                    80

Val Asp Lys Lys Ile Val Arg Thr Glu Ile Gly Val Leu Leu Arg Leu
                   85                    90                    95

Ser His Pro Asn Ile Ile Lys Leu Lys Glu Ile Phe Glu Thr Pro Thr
                   100                   105                   110

Glu Ile Ser Leu Val Leu Glu Leu Val Thr Gly Gly Glu Leu Phe Asp
                   115                   120                   125

Arg Ile Val Glu Lys Gly Tyr Tyr Ser Glu Arg Asp Ala Ala Asp Ala
        130                   135                   140

Val Lys Gln Ile Leu Glu Ala Val Ala Tyr Leu His Glu Asn Gly Ile
145                   150                   155                   160

Val His Arg Asp Leu Lys Pro Glu Asn Leu Leu Tyr Ala Thr Pro Ala
                   165                   170                   175

Pro Asp Ala Pro Leu Lys Ile Ala Asp Phe Gly Leu Ser Lys Ile Val
                   180                   185                   190

Glu His Gln Val Leu Met Lys Thr Val Cys Gly Thr Pro Gly Tyr Cys
                   195                   200                   205

Ala Pro Glu Ile Leu Arg Gly Cys Ala Tyr Gly Pro Glu Val Asp Met
        210                   215                   220

Trp Ser Val Gly Ile Ile Thr Tyr Ile Leu Leu Cys Gly Phe Glu Pro
225                   230                   235                   240

Phe Tyr Asp Glu Arg Gly Asp Gln Phe Met Phe Arg Arg Ile Leu Asn
```

-continued

```
                    245                 250                 255

Cys Glu Tyr Tyr Phe Ile Ser Pro Trp Trp Asp Glu Val Ser Leu Asn
            260                 265                 270

Ala Lys Asp Leu Val Arg Lys Leu Ile Val Leu Asp Pro Lys Lys Arg
            275                 280                 285

Leu Thr Thr Phe Gln Ala Leu Gln His Pro Trp Val Thr Gly Lys Ala
    290                 295                 300

Ala Asn Phe Val His Met Asp Thr Ala Gln Lys Lys Leu Gln Glu Phe
305                 310                 315                 320

Asn Ala Arg Arg Lys Leu Lys Ala Ala Val Lys Ala Val Val Ala Ser
                325                 330                 335

Ser Arg Leu Gly Ser Ala Ser Ser Ser His Gly Ser Ile Gln Glu Ser
            340                 345                 350

His Lys Ala Ser Arg Asp Pro Ser Pro Ile Gln Asp Gly Asn Glu Asp
            355                 360                 365

Met Lys Ala Ile Pro Glu Gly Glu Lys Ile Gln Gly Asp Gly Ala Gln
    370                 375                 380

Ala Ala Val Lys Gly Ala Gln Ala Glu Leu Met Lys Val Gln Ala Leu
385                 390                 395                 400

Glu Lys Val Lys Gly Ala Asp Ile Asn Ala Glu Glu Ala Pro Lys Met
                405                 410                 415

Val Pro Lys Ala Val Glu Asp Gly Ile Lys Val Ala Asp Leu Glu Leu
                420                 425                 430

Glu Glu Gly Leu Ala Glu Glu Lys Leu Lys Thr Val Glu Glu Ala Ala
            435                 440                 445

Ala Pro Arg Glu Gly Gln Gly Ser Ser Ala Val Gly Phe Glu Val Pro
    450                 455                 460

Gln Gln Asp Val Ile Leu Pro Glu Tyr
465                 470

<210> SEQ ID NO 73
<211> LENGTH: 480
<212> TYPE: PRT
<213> ORGANISM: Artificial Sequence
<220> FEATURE:
<223> OTHER INFORMATION: Synthetic_AKT1_HUMAN

<400> SEQUENCE: 73

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
```

-continued

```
        130                135                140

Val Thr Met Asn Glu Phe Glu Tyr Leu Lys Leu Leu Gly Lys Gly Thr
145                150                155                160

Phe Gly Lys Val Ile Leu Val Lys Glu Lys Ala Thr Gly Arg Tyr Tyr
                165                170                175

Ala Met Lys Ile Leu Lys Lys Glu Val Ile Val Ala Lys Asp Glu Val
                180                185                190

Ala His Thr Leu Thr Glu Asn Arg Val Leu Gln Asn Ser Arg His Pro
        195                200                205

Phe Leu Thr Ala Leu Lys Tyr Ser Phe Gln Thr His Asp Arg Leu Cys
        210                215                220

Phe Val Met Glu Tyr Ala Asn Gly Gly Glu Leu Phe Phe His Leu Ser
225                230                235                240

Arg Glu Arg Val Phe Ser Glu Asp Arg Ala Arg Phe Tyr Gly Ala Glu
                245                250                255

Ile Val Ser Ala Leu Asp Tyr Leu His Ser Glu Lys Asn Val Val Tyr
                260                265                270

Arg Asp Leu Lys Leu Glu Asn Leu Met Leu Asp Lys Asp Gly His Ile
        275                280                285

Lys Ile Thr Asp Phe Gly Leu Cys Lys Glu Gly Ile Lys Asp Gly Ala
        290                295                300

Thr Met Lys Thr Phe Cys Gly Thr Pro Glu Tyr Leu Ala Pro Glu Val
305                310                315                320

Leu Glu Asp Asn Asp Tyr Gly Arg Ala Val Asp Trp Trp Gly Leu Gly
                325                330                335

Val Val Met Tyr Glu Met Met Cys Gly Arg Leu Pro Phe Tyr Asn Gln
                340                345                350

Asp His Glu Lys Leu Phe Glu Leu Ile Leu Met Glu Glu Ile Arg Phe
        355                360                365

Pro Arg Thr Leu Gly Pro Glu Ala Lys Ser Leu Leu Ser Gly Leu Leu
        370                375                380

Lys Lys Asp Pro Lys Gln Arg Leu Gly Gly Gly Ser Glu Asp Ala Lys
385                390                395                400

Glu Ile Met Gln His Arg Phe Phe Ala Gly Ile Val Trp Gln His Val
                405                410                415

Tyr Glu Lys Lys Leu Ser Pro Pro Phe Lys Pro Gln Val Thr Ser Glu
                420                425                430

Thr Asp Thr Arg Tyr Phe Asp Glu Glu Phe Thr Ala Gln Met Ile Thr
                435                440                445

Ile Thr Pro Pro Asp Gln Asp Asp Ser Met Glu Cys Val Asp Ser Glu
        450                455                460

Arg Arg Pro His Phe Pro Gln Phe Ser Tyr Ser Ala Ser Gly Thr Ala
465                470                475                480

<210> SEQ ID NO 74
<211> LENGTH: 481
<212> TYPE: PRT
<213> ORGANISM: Artificial Sequence
<220> FEATURE:
<223> OTHER INFORMATION: Synthetic_AKT2_HUMAN

<400> SEQUENCE: 74

Met Asn Glu Val Ser Val Ile Lys Glu Gly Trp Leu His Lys Arg Gly
1                5                10                15

Glu Tyr Ile Lys Thr Trp Arg Pro Arg Tyr Phe Leu Leu Lys Ser Asp
```

-continued

```
                20                  25                  30

Gly Ser Phe Ile Gly Tyr Lys Glu Arg Pro Glu Ala Pro Asp Gln Thr
        35                  40                  45

Leu Pro Pro Leu Asn Asn Phe Ser Val Ala Glu Cys Gln Leu Met Lys
    50                  55                  60

Thr Glu Arg Pro Arg Pro Asn Thr Phe Val Ile Arg Cys Leu Gln Trp
65                  70                  75                  80

Thr Thr Val Ile Glu Arg Thr Phe His Val Asp Ser Pro Asp Glu Arg
                85                  90                  95

Glu Glu Trp Met Arg Ala Ile Gln Met Val Ala Asn Ser Leu Lys Gln
            100                 105                 110

Arg Ala Pro Gly Glu Asp Pro Met Asp Tyr Lys Cys Gly Ser Pro Ser
        115                 120                 125

Asp Ser Ser Thr Thr Glu Glu Met Glu Val Ala Val Ser Lys Ala Arg
        130                 135                 140

Ala Lys Val Thr Met Asn Asp Phe Asp Tyr Leu Lys Leu Leu Gly Lys
145                 150                 155                 160

Gly Thr Phe Gly Lys Val Ile Leu Val Arg Glu Lys Ala Thr Gly Arg
                165                 170                 175

Tyr Tyr Ala Met Lys Ile Leu Arg Lys Glu Val Ile Ile Ala Lys Asp
            180                 185                 190

Glu Val Ala His Thr Val Thr Glu Ser Arg Val Leu Gln Asn Thr Arg
        195                 200                 205

His Pro Phe Leu Thr Ala Leu Lys Tyr Ala Phe Gln Thr His Asp Arg
    210                 215                 220

Leu Cys Phe Val Met Glu Tyr Ala Asn Gly Gly Glu Leu Phe Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
            260                 265                 270

Tyr Arg Asp Ile Lys Leu Glu Asn Leu Met Leu Asp Lys Asp Gly His
        275                 280                 285

Ile Lys Ile Thr Asp Phe Gly Leu Cys Lys Glu Gly Ile Ser Asp Gly
    290                 295                 300

Ala Thr Met Lys Thr Phe Cys Gly Thr Pro Glu Tyr Leu Ala Pro Glu
305                 310                 315                 320

Val Leu Glu Asp Asn Asp Tyr Gly Arg Ala Val Asp Trp Trp Gly Leu
                325                 330                 335

Gly Val Val Met Tyr Glu Met Met Cys Gly Arg Leu Pro Phe Tyr Asn
            340                 345                 350

Gln Asp His Glu Arg Leu Phe Glu Leu Ile Leu Met Glu Glu Ile Arg
        355                 360                 365

Phe Pro Arg Thr Leu Ser Pro Glu Ala Lys Ser Leu Leu Ala Gly Leu
    370                 375                 380

Leu Lys Lys Asp Pro Lys Gln Arg Leu Gly Gly Gly Pro Ser Asp Ala
385                 390                 395                 400

Lys Glu Val Met Glu His Arg Phe Phe Leu Ser Ile Asn Trp Gln Asp
                405                 410                 415

Val Val Gln Lys Lys Leu Leu Pro Pro Phe Lys Pro Gln Val Thr Ser
            420                 425                 430

Glu Val Asp Thr Arg Tyr Phe Asp Asp Glu Phe Thr Ala Gln Ser Ile
        435                 440                 445
```

-continued

```
Thr Ile Thr Pro Pro Asp Arg Tyr Asp Ser Leu Gly Leu Leu Glu Leu
    450                 455                 460

Asp Gln Arg Thr His Phe Pro Gln Phe Ser Tyr Ser Ala Ser Ile Arg
465                 470                 475                 480

Glu

<210> SEQ ID NO 75
<211> LENGTH: 481
<212> TYPE: PRT
<213> ORGANISM: Artificial Sequence
<220> FEATURE:
<223> OTHER INFORMATION: Synthetic_G37L1_HUMAN

<400> SEQUENCE: 75

Met Arg Trp Leu Trp Pro Leu Ala Val Ser Leu Ala Val Ile Leu Ala
1               5                   10                  15

Val Gly Leu Ser Arg Val Ser Gly Gly Ala Pro Leu His Leu Gly Arg
            20                  25                  30

His Arg Ala Glu Thr Gln Glu Gln Gln Ser Arg Ser Lys Arg Gly Thr
        35                  40                  45

Glu Asp Glu Glu Ala Lys Gly Val Gln Gln Tyr Val Pro Glu Glu Trp
    50                  55                  60

Ala Glu Tyr Pro Arg Pro Ile His Pro Ala Gly Leu Gln Pro Thr Lys
65                  70                  75                  80

Pro Leu Val Ala Thr Ser Pro Asn Pro Gly Lys Asp Gly Gly Thr Pro
            85                  90                  95

Asp Ser Gly Gln Glu Leu Arg Gly Asn Leu Thr Gly Ala Pro Gly Gln
            100                 105                 110

Arg Leu Gln Ile Gln Asn Pro Leu Tyr Pro Val Thr Glu Ser Ser Tyr
        115                 120                 125

Ser Ala Tyr Ala Ile Met Leu Leu Ala Leu Val Val Phe Ala Val Gly
    130                 135                 140

Ile Val Gly Asn Leu Ser Val Met Cys Ile Val Trp His Ser Tyr Tyr
145                 150                 155                 160

Leu Lys Ser Ala Trp Asn Ser Ile Leu Ala Ser Leu Ala Leu Trp Asp
            165                 170                 175

Phe Leu Val Leu Phe Phe Cys Leu Pro Ile Val Ile Phe Asn Glu Ile
            180                 185                 190

Thr Lys Gln Arg Leu Leu Gly Asp Val Ser Cys Arg Ala Val Pro Phe
        195                 200                 205

Met Glu Val Ser Ser Leu Gly Val Thr Thr Phe Ser Leu Cys Ala Leu
    210                 215                 220

Gly Ile Asp Arg Phe His Val Ala Thr Ser Thr Leu Pro Lys Val Arg
225                 230                 235                 240

Pro Ile Glu Arg Cys Gln Ser Ile Leu Ala Lys Leu Ala Val Ile Trp
            245                 250                 255

Val Gly Ser Met Thr Leu Ala Val Pro Glu Leu Leu Leu Trp Gln Leu
            260                 265                 270

Ala Gln Glu Pro Ala Pro Thr Met Gly Thr Leu Asp Ser Cys Ile Met
        275                 280                 285

Lys Pro Ser Ala Ser Leu Pro Glu Ser Leu Tyr Ser Leu Val Met Thr
    290                 295                 300

Tyr Gln Asn Ala Arg Met Trp Trp Tyr Phe Gly Cys Tyr Phe Cys Leu
305                 310                 315                 320
```

-continued

```
Pro Ile Leu Phe Thr Val Thr Cys Gln Leu Val Thr Trp Arg Val Arg
            325             330             335

Gly Pro Pro Gly Arg Lys Ser Glu Cys Arg Ala Ser Lys His Glu Gln
            340             345             350

Cys Glu Ser Gln Leu Asn Ser Thr Val Val Gly Leu Thr Val Val Tyr
            355             360             365

Ala Phe Cys Thr Leu Pro Glu Asn Val Cys Asn Ile Val Val Ala Tyr
    370             375             380

Leu Ser Thr Glu Leu Thr Arg Gln Thr Leu Asp Leu Leu Gly Leu Ile
385             390             395             400

Asn Gln Phe Ser Thr Phe Phe Lys Gly Ala Ile Thr Pro Val Leu Leu
            405             410             415

Leu Cys Ile Cys Arg Pro Leu Gly Gln Ala Phe Leu Asp Cys Cys Cys
            420             425             430

Cys Cys Cys Cys Glu Glu Cys Gly Gly Ala Ser Glu Ala Ser Ala Ala
            435             440             445

Asn Gly Ser Asp Asn Lys Leu Lys Thr Glu Val Ser Ser Ser Ile Tyr
    450             455             460

Phe His Lys Pro Arg Glu Ser Pro Pro Leu Leu Pro Leu Gly Thr Pro
465             470             475             480

Cys
```

```
<210> SEQ ID NO 76
<211> LENGTH: 490
<212> TYPE: PRT
<213> ORGANISM: Artificial Sequence
<220> FEATURE:
<223> OTHER INFORMATION: Synthetic_TEKT3_HUMAN

<400> SEQUENCE: 76
```

```
Met Glu Arg Val Gly Cys Thr Leu Thr Thr Thr Tyr Ala His Pro Arg
1               5               10              15

Pro Thr Pro Thr Asn Phe Leu Pro Ala Ile Ser Thr Met Ala Ser Ser
            20              25              30

Tyr Arg Asp Arg Phe Pro His Ser Asn Leu Thr His Ser Leu Ser Leu
            35              40              45

Pro Trp Arg Pro Ser Thr Tyr Tyr Lys Val Ala Ser Asn Ser Pro Ser
    50              55              60

Val Ala Pro Tyr Cys Thr Arg Ser Gln Arg Val Ser Glu Asn Thr Met
65              70              75              80

Leu Pro Phe Val Ser Asn Arg Thr Thr Phe Phe Thr Arg Tyr Thr Pro
            85              90              95

Asp Asp Trp Tyr Arg Ser Asn Leu Thr Asn Tyr Gln Glu Ser Asn Thr
            100             105             110

Ser Arg His Asn Ser Glu Lys Leu Arg Val Asp Thr Ser Arg Leu Ile
            115             120             125

Gln Asp Lys Tyr Gln Gln Thr Arg Lys Thr Gln Ala Asp Thr Thr Gln
    130             135             140

Asn Leu Gly Glu Arg Val Asn Asp Ile Gly Phe Trp Lys Ser Glu Ile
145             150             155             160

Ile His Glu Leu Asp Glu Met Ile Gly Glu Thr Asn Ala Leu Thr Asp
            165             170             175

Val Lys Lys Arg Leu Glu Arg Ala Leu Met Glu Thr Glu Ala Pro Leu
            180             185             190

Gln Val Ala Arg Glu Cys Leu Phe His Arg Glu Lys Arg Met Gly Ile
```

-continued

```
             195                    200                    205

Asp Leu Val His Asp Glu Val Glu Ala Gln Leu Leu Thr Glu Val Asp
        210                    215                    220

Thr Ile Leu Cys Cys Gln Glu Arg Met Lys Leu His Leu Asp Lys Ala
225                    230                    235                    240

Ile Ala Gln Leu Ala Ala Asn Arg Ala Ser Gln His Glu Leu Glu Lys
                    245                    250                    255

Asp Leu Ser Asp Lys Gln Thr Ala Tyr Arg Ile Asp Asp Lys Cys His
                    260                    265                    270

His Leu Arg Asn Thr Ser Asp Gly Val Gly Tyr Phe Arg Gly Val Glu
                    275                    280                    285

Arg Val Asp Ala Thr Val Ser Val Pro Glu Ser Trp Ala Lys Phe Thr
                    290                    295                    300

Asp Asp Asn Ile Leu Arg Ser Gln Ser Glu Arg Ala Ala Ser Ala Lys
305                    310                    315                    320

Leu Arg Asp Asp Ile Glu Asn Leu Leu Val Val Thr Ala Asn Glu Met
                    325                    330                    335

Trp Asn Gln Phe Asn Lys Val Asn Leu Ser Phe Thr Asn Arg Ile Ala
                    340                    345                    350

Glu Thr Ala Asp Ala Lys Asn Lys Ile Gln Thr His Leu Ala Lys Thr
                    355                    360                    365

Leu Gln Glu Ile Phe Gln Thr Glu Met Thr Ile Glu Ser Ile Lys Lys
                    370                    375                    380

Ala Ile Lys Asp Lys Thr Ala Phe Leu Lys Val Ala Gln Thr Arg Leu
385                    390                    395                    400

Asp Glu Arg Thr Arg Arg Pro Asn Ile Glu Leu Cys Arg Asp Met Ala
                    405                    410                    415

Gln Leu Arg Leu Val Asn Glu Val His Glu Val Asp Asp Thr Ile Gln
                    420                    425                    430

Thr Leu Gln Gln Arg Leu Arg Asp Ala Glu Asp Thr Leu Gln Ser Leu
                    435                    440                    445

Val His Ile Lys Ala Thr Leu Glu Tyr Asp Leu Ala Val Lys Ala Asn
                    450                    455                    460

Ser Leu Tyr Ile Asp Gln Glu Lys Cys Met Ser Met Arg Lys Ser Tyr
465                    470                    475                    480

Pro Asn Thr Leu Arg Leu Val Gly Phe Cys
                    485                    490
```

```
<210> SEQ ID NO 77
<211> LENGTH: 500
<212> TYPE: PRT
<213> ORGANISM: Artificial Sequence
<220> FEATURE:
<223> OTHER INFORMATION: Synthetic_IC1_HUMAN

<400> SEQUENCE: 77

Met Ala Ser Arg Leu Thr Leu Leu Thr Leu Leu Leu Leu Leu Leu Ala
1                    5                    10                    15

Gly Asp Arg Ala Ser Ser Asn Pro Asn Ala Thr Ser Ser Ser Ser Gln
                    20                    25                    30

Asp Pro Glu Ser Leu Gln Asp Arg Gly Glu Gly Lys Val Ala Thr Thr
                    35                    40                    45

Val Ile Ser Lys Met Leu Phe Val Glu Pro Ile Leu Glu Val Ser Ser
        50                    55                    60

Leu Pro Thr Thr Asn Ser Thr Thr Asn Ser Ala Thr Lys Ile Thr Ala
```

```
65              70                 75                80

Asn Thr Thr Asp Glu Pro Thr Thr Gln Pro Thr Thr Glu Pro Thr Thr
                85                 90                 95

Gln Pro Thr Ile Gln Pro Thr Gln Pro Thr Thr Gln Leu Pro Thr Asp
                100                105                110

Ser Pro Thr Gln Pro Thr Thr Gly Ser Phe Cys Pro Gly Pro Val Thr
                115                120                125

Leu Cys Ser Asp Leu Glu Ser His Ser Thr Glu Ala Val Leu Gly Asp
    130                135                140

Ala Leu Val Asp Phe Ser Leu Lys Leu Tyr His Ala Phe Ser Ala Met
145                150                155                160

Lys Lys Val Glu Thr Asn Met Ala Phe Ser Pro Phe Ser Ile Ala Ser
                165                170                175

Leu Leu Thr Gln Val Leu Leu Gly Ala Gly Glu Asn Thr Lys Thr Asn
                180                185                190

Leu Glu Ser Ile Leu Ser Tyr Pro Lys Asp Phe Thr Cys Val His Gln
                195                200                205

Ala Leu Lys Gly Phe Thr Thr Lys Gly Val Thr Ser Val Ser Gln Ile
    210                215                220

Phe His Ser Pro Asp Leu Ala Ile Arg Asp Thr Phe Val Asn Ala Ser
225                230                235                240

Arg Thr Leu Tyr Ser Ser Ser Pro Arg Val Leu Ser Asn Asn Ser Asp
                245                250                255

Ala Asn Leu Glu Leu Ile Asn Thr Trp Val Ala Lys Asn Thr Asn Asn
                260                265                270

Lys Ile Ser Arg Leu Leu Asp Ser Leu Pro Ser Asp Thr Arg Leu Val
                275                280                285

Leu Leu Asn Ala Ile Tyr Leu Ser Ala Lys Trp Lys Thr Thr Phe Asp
    290                295                300

Pro Lys Lys Thr Arg Met Glu Pro Phe His Phe Lys Asn Ser Val Ile
305                310                315                320

Lys Val Pro Met Met Asn Ser Lys Lys Tyr Pro Val Ala His Phe Ile
                325                330                335

Asp Gln Thr Leu Lys Ala Lys Val Gly Gln Leu Gln Leu Ser His Asn
                340                345                350

Leu Ser Leu Val Ile Leu Val Pro Gln Asn Leu Lys His Arg Leu Glu
                355                360                365

Asp Met Glu Gln Ala Leu Ser Pro Ser Val Phe Lys Ala Ile Met Glu
    370                375                380

Lys Leu Glu Met Ser Lys Phe Gln Pro Thr Leu Leu Thr Leu Pro Arg
385                390                395                400

Ile Lys Val Thr Thr Ser Gln Asp Met Leu Ser Ile Met Glu Lys Leu
                405                410                415

Glu Phe Phe Asp Phe Ser Tyr Asp Leu Asn Leu Cys Gly Leu Thr Glu
                420                425                430

Asp Pro Asp Leu Gln Val Ser Ala Met Gln His Gln Thr Val Leu Glu
                435                440                445

Leu Thr Glu Thr Gly Val Glu Ala Ala Ala Ala Ser Ala Ile Ser Val
    450                455                460

Ala Arg Thr Leu Leu Val Phe Glu Val Gln Gln Pro Phe Leu Phe Val
465                470                475                480

Leu Trp Asp Gln Gln His Lys Phe Pro Val Phe Met Gly Arg Val Tyr
                485                490                495
```

Asp Pro Arg Ala
          500

<210> SEQ ID NO 78
<211> LENGTH: 508
<212> TYPE: PRT
<213> ORGANISM: Artificial Sequence
<220> FEATURE:
<223> OTHER INFORMATION: Synthetic_SRF_HUMAN

<400> SEQUENCE: 78

Met Leu Pro Thr Gln Ala Gly Ala Ala Ala Leu Gly Arg Gly Ser
1               5                   10                  15

Ala Leu Gly Gly Ser Leu Asn Arg Thr Pro Thr Gly Arg Pro Gly Gly
            20                  25                  30

Gly Gly Gly Thr Arg Gly Ala Asn Gly Gly Arg Val Pro Gly Asn Gly
            35                  40                  45

Ala Gly Leu Gly Pro Gly Arg Leu Glu Arg Glu Ala Ala Ala Ala
    50                  55                  60

Ala Thr Thr Pro Ala Pro Thr Ala Gly Ala Leu Tyr Ser Gly Ser Glu
65                  70                  75                  80

Gly Asp Ser Glu Ser Gly Glu Glu Glu Leu Gly Ala Glu Arg Arg
                85                  90                  95

Gly Leu Lys Arg Ser Leu Ser Glu Met Glu Ile Gly Met Val Val Gly
            100                 105                 110

Gly Pro Glu Ala Ser Ala Ala Ala Thr Gly Gly Tyr Gly Pro Val Ser
            115                 120                 125

Gly Ala Val Ser Gly Ala Lys Pro Gly Lys Lys Thr Arg Gly Arg Val
    130                 135                 140

Lys Ile Lys Met Glu Phe Ile Asp Asn Lys Leu Arg Arg Tyr Thr Thr
145                 150                 155                 160

Phe Ser Lys Arg Lys Thr Gly Ile Met Lys Lys Ala Tyr Glu Leu Ser
                165                 170                 175

Thr Leu Thr Gly Thr Gln Val Leu Leu Leu Val Ala Ser Glu Thr Gly
                180                 185                 190

His Val Tyr Thr Phe Ala Thr Arg Lys Leu Gln Pro Met Ile Thr Ser
        195                 200                 205

Glu Thr Gly Lys Ala Leu Ile Gln Thr Cys Leu Asn Ser Pro Asp Ser
    210                 215                 220

Pro Pro Arg Ser Asp Pro Thr Thr Asp Gln Arg Met Ser Ala Thr Gly
225                 230                 235                 240

Phe Glu Glu Thr Asp Leu Thr Tyr Gln Val Ser Glu Ser Asp Ser Ser
                245                 250                 255

Gly Glu Thr Lys Asp Thr Leu Lys Pro Ala Phe Thr Val Thr Asn Leu
            260                 265                 270

Pro Gly Thr Thr Ser Thr Ile Gln Thr Ala Pro Ser Thr Ser Thr Thr
            275                 280                 285

Met Gln Val Ser Ser Gly Pro Ser Phe Pro Ile Thr Asn Tyr Leu Ala
    290                 295                 300

Pro Val Ser Ala Ser Val Ser Pro Ser Ala Val Ser Ser Ala Asn Gly
305                 310                 315                 320

Thr Val Leu Lys Ser Thr Gly Ser Gly Pro Val Ser Ser Gly Gly Leu
            325                 330                 335

Met Gln Leu Pro Thr Ser Phe Thr Leu Met Pro Gly Gly Ala Val Ala
            340                 345                 350

-continued

```
Gln Gln Val Pro Val Gln Ala Ile Gln Val His Gln Ala Pro Gln Gln
        355             360             365

Ala Ser Pro Ser Arg Asp Ser Ser Thr Asp Leu Thr Gln Thr Ser Ser
    370             375             380

Ser Gly Thr Val Thr Leu Pro Ala Thr Ile Met Thr Ser Ser Val Pro
385             390             395             400

Thr Thr Val Gly Gly His Met Met Tyr Pro Ser Pro His Ala Val Met
            405             410             415

Tyr Ala Pro Thr Ser Gly Leu Gly Asp Gly Ser Leu Thr Val Leu Asn
            420             425             430

Ala Phe Ser Gln Ala Pro Ser Thr Met Gln Val Ser His Ser Gln Val
        435             440             445

Gln Glu Pro Gly Gly Val Pro Gln Val Phe Leu Thr Ala Ser Ser Gly
    450             455             460

Thr Val Gln Ile Pro Val Ser Ala Val Gln Leu His Gln Met Ala Val
465             470             475             480

Ile Gly Gln Gln Ala Gly Ser Ser Ser Asn Leu Thr Glu Leu Gln Val
            485             490             495

Val Asn Leu Asp Thr Ala His Ser Thr Lys Ser Glu
            500             505
```

<210> SEQ ID NO 79
<211> LENGTH: 512
<212> TYPE: PRT
<213> ORGANISM: Artificial Sequence
<220> FEATURE:
<223> OTHER INFORMATION: Synthetic_IGD_HUMAN

<400> SEQUENCE: 79

```
Arg Leu Gln Leu Gln Glu Ser Gly Pro Gly Leu Val Lys Pro Ser Glu
1               5               10              15

Thr Leu Ser Leu Thr Cys Ile Val Ser Gly Gly Pro Ile Arg Arg Thr
            20              25              30

Gly Tyr Tyr Trp Gly Trp Ile Arg Gln Pro Pro Gly Lys Gly Leu Glu
        35              40              45

Trp Ile Gly Gly Val Tyr Tyr Thr Gly Ser Ile Tyr Tyr Asn Pro Ser
    50              55              60

Leu Arg Gly Arg Val Thr Ile Ser Val Asp Thr Ser Arg Asn Gln Phe
65              70              75              80

Ser Leu Asn Leu Arg Ser Met Ser Ala Ala Asp Thr Ala Met Tyr Tyr
            85              90              95

Cys Ala Arg Gly Asn Pro Pro Tyr Tyr Asp Ile Gly Thr Gly Ser
        100             105             110

Asp Asp Gly Ile Asp Val Trp Gly Gln Gly Thr Thr Val His Val Ser
        115             120             125

Ser Ala Pro Thr Lys Ala Pro Asp Val Phe Pro Ile Ile Ser Gly Cys
    130             135             140

Arg His Pro Lys Asp Asn Ser Pro Val Val Leu Ala Cys Leu Ile Thr
145             150             155             160

Gly Tyr His Pro Thr Ser Val Thr Val Thr Trp Tyr Met Gly Thr Gln
            165             170             175

Ser Gln Pro Gln Arg Thr Phe Pro Glu Ile Gln Arg Arg Asp Ser Tyr
            180             185             190

Tyr Met Thr Ser Ser Gln Leu Ser Thr Pro Leu Gln Gln Trp Arg Gln
            195             200             205
```

```
Gly Glu Tyr Lys Cys Val Val Gln His Thr Ala Ser Lys Ser Lys Lys
    210             215             220

Glu Ile Phe Arg Trp Pro Glu Ser Pro Lys Ala Gln Ala Ser Ser Val
225             230             235             240

Pro Thr Ala Gln Pro Gln Ala Glu Gly Ser Leu Ala Lys Ala Thr Thr
            245             250             255

Ala Pro Ala Thr Thr Arg Asn Thr Gly Arg Gly Gly Glu Glu Lys Lys
            260             265             270

Lys Glu Lys Glu Lys Glu Glu Gln Glu Glu Arg Glu Thr Lys Thr Pro
        275             280             285

Glu Cys Pro Ser His Thr Gln Pro Leu Gly Val Tyr Leu Leu Thr Pro
    290             295             300

Ala Val Gln Asp Leu Trp Leu Arg Asp Lys Ala Thr Phe Thr Cys Phe
305             310             315             320

Val Val Gly Ser Asp Leu Lys Asp Ala His Leu Thr Trp Glu Val Ala
            325             330             335

Gly Lys Val Pro Thr Gly Gly Val Glu Glu Gly Leu Leu Glu Arg His
            340             345             350

Ser Asn Gly Ser Gln Ser Gln His Ser Arg Leu Thr Leu Pro Arg Ser
    355             360             365

Leu Trp Asn Ala Gly Thr Ser Val Thr Cys Thr Leu Asn His Pro Ser
    370             375             380

Leu Pro Pro Gln Arg Leu Met Ala Leu Arg Glu Pro Ala Ala Gln Ala
385             390             395             400

Pro Val Lys Leu Ser Leu Asn Leu Leu Ala Ser Ser Asp Pro Pro Glu
            405             410             415

Ala Ala Ser Trp Leu Leu Cys Glu Val Ser Gly Phe Ser Pro Pro Asn
            420             425             430

Ile Leu Leu Met Trp Leu Glu Asp Gln Arg Glu Val Asn Thr Ser Gly
    435             440             445

Phe Ala Pro Ala Arg Pro Pro Pro Gln Pro Gly Ser Thr Thr Phe Trp
    450             455             460

Ala Trp Ser Val Leu Arg Val Pro Ala Pro Pro Ser Pro Gln Pro Ala
465             470             475             480

Thr Tyr Thr Cys Val Val Ser His Glu Asp Ser Arg Thr Leu Leu Asn
            485             490             495

Ala Ser Arg Ser Leu Glu Val Ser Tyr Val Thr Asp His Gly Pro Met
            500             505             510
```

```
<210> SEQ ID NO 80
<211> LENGTH: 556
<212> TYPE: PRT
<213> ORGANISM: Artificial Sequence
<220> FEATURE:
<223> OTHER INFORMATION: Synthetic_GPC4_HUMAN

<400> SEQUENCE: 80
```

```
Met Ala Arg Phe Gly Leu Pro Ala Leu Leu Cys Thr Leu Ala Val Leu
1               5               10              15

Ser Ala Ala Leu Leu Ala Ala Glu Leu Lys Ser Lys Ser Cys Ser Glu
            20              25              30

Val Arg Arg Leu Tyr Val Ser Lys Gly Phe Asn Lys Asn Asp Ala Pro
        35              40              45

Leu His Glu Ile Asn Gly Asp His Leu Lys Ile Cys Pro Gln Gly Ser
    50              55              60
```

-continued

```
Thr Cys Cys Ser Gln Glu Met Glu Glu Lys Tyr Ser Leu Gln Ser Lys
65                  70                  75                  80

Asp Asp Phe Lys Ser Val Val Ser Glu Gln Cys Asn His Leu Gln Ala
                85                  90                  95

Val Phe Ala Ser Arg Tyr Lys Lys Phe Asp Glu Phe Phe Lys Glu Leu
                100                 105                 110

Leu Glu Asn Ala Glu Lys Ser Leu Asn Asp Met Phe Val Lys Thr Tyr
                115                 120                 125

Gly His Leu Tyr Met Gln Asn Ser Glu Leu Phe Lys Asp Leu Phe Val
        130                 135                 140

Glu Leu Lys Arg Tyr Tyr Val Val Gly Asn Val Asn Leu Glu Glu Met
145                 150                 155                 160

Leu Asn Asp Phe Trp Ala Arg Leu Leu Glu Arg Met Phe Arg Leu Val
                165                 170                 175

Asn Ser Gln Tyr His Phe Thr Asp Glu Tyr Leu Glu Cys Val Ser Lys
                180                 185                 190

Tyr Thr Glu Gln Leu Lys Pro Phe Gly Asp Val Pro Arg Lys Leu Lys
        195                 200                 205

Leu Gln Val Thr Arg Ala Phe Val Ala Ala Arg Thr Phe Ala Gln Gly
        210                 215                 220

Leu Ala Val Ala Gly Asp Val Val Ser Lys Val Ser Val Val Asn Pro
225                 230                 235                 240

Thr Ala Gln Cys Thr His Ala Leu Leu Lys Met Ile Tyr Cys Ser His
                245                 250                 255

Cys Arg Gly Leu Val Thr Val Lys Pro Cys Tyr Asn Tyr Cys Ser Asn
        260                 265                 270

Ile Met Arg Gly Cys Leu Ala Asn Gln Gly Asp Leu Asp Phe Glu Trp
        275                 280                 285

Asn Asn Phe Ile Asp Ala Met Leu Met Val Ala Glu Arg Leu Glu Gly
        290                 295                 300

Pro Phe Asn Ile Glu Ser Val Met Asp Pro Ile Asp Val Lys Ile Ser
305                 310                 315                 320

Asp Ala Ile Met Asn Met Gln Asp Asn Ser Val Gln Val Ser Gln Lys
                325                 330                 335

Val Phe Gln Gly Cys Gly Pro Pro Lys Pro Leu Pro Ala Gly Arg Ile
                340                 345                 350

Ser Arg Ser Ile Ser Glu Ser Ala Phe Ser Ala Arg Phe Arg Pro His
        355                 360                 365

His Pro Glu Glu Arg Pro Thr Thr Ala Ala Gly Thr Ser Leu Asp Arg
        370                 375                 380

Leu Val Thr Asp Val Lys Glu Lys Leu Lys Gln Ala Lys Lys Phe Trp
385                 390                 395                 400

Ser Ser Leu Pro Ser Asn Val Cys Asn Asp Glu Arg Met Ala Ala Gly
                405                 410                 415

Asn Gly Asn Glu Asp Asp Cys Trp Asn Gly Lys Gly Lys Ser Arg Tyr
                420                 425                 430

Leu Phe Ala Val Thr Gly Asn Gly Leu Ala Asn Gln Gly Asn Asn Pro
        435                 440                 445

Glu Val Gln Val Asp Thr Ser Lys Pro Asp Ile Leu Ile Leu Arg Gln
        450                 455                 460

Ile Met Ala Leu Arg Val Met Thr Ser Lys Met Lys Asn Ala Tyr Asn
465                 470                 475                 480
```

```
Gly Asn Asp Val Asp Phe Phe Asp Ile Ser Asp Glu Ser Ser Gly Glu
              485                     490                 495

Gly Ser Gly Ser Gly Cys Glu Tyr Gln Gln Cys Pro Ser Glu Phe Asp
              500                 505                 510

Tyr Asn Ala Thr Asp His Ala Gly Lys Ser Ala Asn Glu Lys Ala Asp
              515                 520                 525

Ser Ala Gly Val Arg Pro Gly Ala Gln Ala Tyr Leu Leu Thr Val Phe
              530                 535                 540

Cys Ile Leu Phe Leu Val Met Gln Arg Glu Trp Arg
545                 550                 555
```

```
<210> SEQ ID NO 81
<211> LENGTH: 558
<212> TYPE: PRT
<213> ORGANISM: Artificial Sequence
<220> FEATURE:
<223> OTHER INFORMATION: Synthetic_GPC1_HUMAN

<400> SEQUENCE: 81
```

```
Met Glu Leu Arg Ala Arg Gly Trp Trp Leu Leu Cys Ala Ala Ala Ala
1                 5                     10                  15

Leu Val Ala Cys Ala Arg Gly Asp Pro Ala Ser Lys Ser Arg Ser Cys
              20                  25                  30

Gly Glu Val Arg Gln Ile Tyr Gly Ala Lys Gly Phe Ser Leu Ser Asp
              35                  40                  45

Val Pro Gln Ala Glu Ile Ser Gly Glu His Leu Arg Ile Cys Pro Gln
              50                  55                  60

Gly Tyr Thr Cys Cys Thr Ser Glu Met Glu Glu Asn Leu Ala Asn Arg
65                  70                  75                  80

Ser His Ala Glu Leu Glu Thr Ala Leu Arg Asp Ser Ser Arg Val Leu
              85                  90                  95

Gln Ala Met Leu Ala Thr Gln Leu Arg Ser Phe Asp Asp His Phe Gln
              100                 105                 110

His Leu Leu Asn Asp Ser Glu Arg Thr Leu Gln Ala Thr Phe Pro Gly
              115                 120                 125

Ala Phe Gly Glu Leu Tyr Thr Gln Asn Ala Arg Ala Phe Arg Asp Leu
              130                 135                 140

Tyr Ser Glu Leu Arg Leu Tyr Tyr Arg Gly Ala Asn Leu His Leu Glu
145                 150                 155                 160

Glu Thr Leu Ala Glu Phe Trp Ala Arg Leu Leu Glu Arg Leu Phe Lys
              165                 170                 175

Gln Leu His Pro Gln Leu Leu Leu Pro Asp Asp Tyr Leu Asp Cys Leu
              180                 185                 190

Gly Lys Gln Ala Glu Ala Leu Arg Pro Phe Gly Glu Ala Pro Arg Glu
              195                 200                 205

Leu Arg Leu Arg Ala Thr Arg Ala Phe Val Ala Ala Arg Ser Phe Val
              210                 215                 220

Gln Gly Leu Gly Val Ala Ser Asp Val Val Arg Lys Val Ala Gln Val
225                 230                 235                 240

Pro Leu Gly Pro Glu Cys Ser Arg Ala Val Met Lys Leu Val Tyr Cys
              245                 250                 255

Ala His Cys Leu Gly Val Pro Gly Ala Arg Pro Cys Pro Asp Tyr Cys
              260                 265                 270

Arg Asn Val Leu Lys Gly Cys Leu Ala Asn Gln Ala Asp Leu Asp Ala
              275                 280                 285
```

-continued

```
Glu Trp Arg Asn Leu Leu Asp Ser Met Val Leu Ile Thr Asp Lys Phe
    290                 295                 300

Trp Gly Thr Ser Gly Val Glu Ser Val Ile Gly Ser Val His Thr Trp
305                 310                 315                 320

Leu Ala Glu Ala Ile Asn Ala Leu Gln Asp Asn Arg Asp Thr Leu Thr
                325                 330                 335

Ala Lys Val Ile Gln Gly Cys Gly Asn Pro Lys Val Asn Pro Gln Gly
            340                 345                 350

Pro Gly Pro Glu Glu Lys Arg Arg Arg Gly Lys Leu Ala Pro Arg Glu
            355                 360                 365

Arg Pro Pro Ser Gly Thr Leu Glu Lys Leu Val Ser Glu Ala Lys Ala
    370                 375                 380

Gln Leu Arg Asp Val Gln Asp Phe Trp Ile Ser Leu Pro Gly Thr Leu
385                 390                 395                 400

Cys Ser Glu Lys Met Ala Leu Ser Thr Ala Ser Asp Asp Arg Cys Trp
                405                 410                 415

Asn Gly Met Ala Arg Gly Arg Tyr Leu Pro Glu Val Met Gly Asp Gly
            420                 425                 430

Leu Ala Asn Gln Ile Asn Asn Pro Glu Val Glu Val Asp Ile Thr Lys
            435                 440                 445

Pro Asp Met Thr Ile Arg Gln Gln Ile Met Gln Leu Lys Ile Met Thr
    450                 455                 460

Asn Arg Leu Arg Ser Ala Tyr Asn Gly Asn Asp Val Asp Phe Gln Asp
465                 470                 475                 480

Ala Ser Asp Asp Gly Ser Gly Ser Gly Ser Gly Asp Gly Cys Leu Asp
                485                 490                 495

Asp Leu Cys Ser Arg Lys Val Ser Arg Lys Ser Ser Ser Arg Thr
            500                 505                 510

Pro Leu Thr His Ala Leu Pro Gly Leu Ser Glu Gln Glu Gly Gln Lys
            515                 520                 525

Thr Ser Ala Ala Ser Cys Pro Gln Pro Pro Thr Phe Leu Leu Pro Leu
    530                 535                 540

Leu Leu Phe Leu Ala Leu Thr Val Ala Arg Pro Arg Trp Arg
545                 550                 555
```

```
<210> SEQ ID NO 82
<211> LENGTH: 572
<212> TYPE: PRT
<213> ORGANISM: Artificial Sequence
<220> FEATURE:
<223> OTHER INFORMATION: Synthetic_GPC5_HUMAN

<400> SEQUENCE: 82

Met Asp Ala Gln Thr Trp Pro Val Gly Phe Arg Cys Leu Leu Leu Leu
1               5                   10                  15

Ala Leu Val Gly Ser Ala Arg Ser Glu Gly Val Gln Thr Cys Glu Glu
            20                  25                  30

Val Arg Lys Leu Phe Gln Trp Arg Leu Leu Gly Ala Val Arg Gly Leu
        35                  40                  45

Pro Asp Ser Pro Arg Ala Gly Pro Asp Leu Gln Val Cys Ile Ser Lys
    50                  55                  60

Lys Pro Thr Cys Cys Thr Arg Lys Met Glu Glu Arg Tyr Gln Ile Ala
65                  70                  75                  80

Ala Arg Gln Asp Met Gln Gln Phe Leu Gln Thr Ser Ser Ser Thr Leu
                85                  90                  95
```

```
Lys Phe Leu Ile Ser Arg Asn Ala Ala Ala Phe Gln Glu Thr Leu Glu
            100                 105                 110

Thr Leu Ile Lys Gln Ala Glu Asn Tyr Thr Ser Ile Leu Phe Cys Ser
            115                 120                 125

Thr Tyr Arg Asn Met Ala Leu Glu Ala Ala Ala Ser Val Gln Glu Phe
        130                 135                 140

Phe Thr Asp Val Gly Leu Tyr Leu Phe Gly Ala Asp Val Asn Pro Glu
145                 150                 155                 160

Glu Phe Val Asn Arg Phe Phe Asp Ser Leu Phe Pro Leu Val Tyr Asn
                165                 170                 175

His Leu Ile Asn Pro Gly Val Thr Asp Ser Ser Leu Glu Tyr Ser Glu
            180                 185                 190

Cys Ile Arg Met Ala Arg Arg Asp Val Ser Pro Phe Gly Asn Ile Pro
        195                 200                 205

Gln Arg Val Met Gly Gln Met Gly Arg Ser Leu Leu Pro Ser Arg Thr
    210                 215                 220

Phe Leu Gln Ala Leu Asn Leu Gly Ile Glu Val Ile Asn Thr Thr Asp
225                 230                 235                 240

Tyr Leu His Phe Ser Lys Glu Cys Ser Arg Ala Leu Leu Lys Met Gln
                245                 250                 255

Tyr Cys Pro His Cys Gln Gly Leu Ala Leu Thr Lys Pro Cys Met Gly
            260                 265                 270

Tyr Cys Leu Asn Val Met Arg Gly Cys Leu Ala His Met Ala Glu Leu
        275                 280                 285

Asn Pro His Trp His Ala Tyr Ile Arg Ser Leu Glu Glu Leu Ser Asp
    290                 295                 300

Ala Met His Gly Thr Tyr Asp Ile Gly His Val Leu Leu Asn Phe His
305                 310                 315                 320

Leu Leu Val Asn Asp Ala Val Leu Gln Ala His Leu Asn Gly Gln Lys
                325                 330                 335

Leu Leu Glu Gln Val Asn Arg Ile Cys Gly Arg Pro Val Arg Thr Pro
            340                 345                 350

Thr Gln Ser Pro Arg Cys Ser Phe Asp Gln Ser Lys Glu Lys His Gly
        355                 360                 365

Met Lys Thr Thr Thr Arg Asn Ser Glu Glu Thr Leu Ala Asn Arg Arg
    370                 375                 380

Lys Glu Phe Ile Asn Ser Leu Arg Leu Tyr Arg Ser Phe Tyr Gly Gly
385                 390                 395                 400

Leu Ala Asp Gln Leu Cys Ala Asn Glu Leu Ala Ala Ala Asp Gly Leu
                405                 410                 415

Pro Cys Trp Asn Gly Glu Asp Ile Val Lys Ser Tyr Thr Gln Arg Val
            420                 425                 430

Val Gly Asn Gly Ile Lys Ala Gln Ser Gly Asn Pro Glu Val Lys Val
        435                 440                 445

Lys Gly Ile Asp Pro Val Ile Asn Gln Ile Ile Asp Lys Leu Lys His
    450                 455                 460

Val Val Gln Leu Leu Gln Gly Arg Ser Pro Lys Pro Asp Lys Trp Glu
465                 470                 475                 480

Leu Leu Gln Leu Gly Ser Gly Gly Met Val Glu Gln Val Ser Gly
                485                 490                 495

Asp Cys Asp Asp Glu Asp Gly Cys Gly Gly Ser Gly Ser Gly Glu Val
            500                 505                 510

Lys Arg Thr Leu Lys Ile Thr Asp Trp Met Pro Asp Asp Met Asn Phe
```

```
              515                 520                 525
Ser Asp Val Lys Gln Ile His Gln Thr Asp Thr Gly Ser Thr Leu Asp
     530                 535                 540

Thr Thr Gly Ala Gly Cys Ala Val Ala Thr Glu Ser Met Thr Phe Thr
545                 550                 555                 560

Leu Ile Ser Val Val Met Leu Leu Pro Gly Ile Trp
              565                 570

<210> SEQ ID NO 83
<211> LENGTH: 579
<212> TYPE: PRT
<213> ORGANISM: Artificial Sequence
<220> FEATURE:
<223> OTHER INFORMATION: Synthetic_GPC2_HUMAN

<400> SEQUENCE: 83

Met Ser Ala Leu Arg Pro Leu Leu Leu Leu Leu Leu Pro Leu Cys Pro
1                 5                  10                 15

Gly Pro Gly Pro Gly Pro Gly Ser Glu Ala Lys Val Thr Arg Ser Cys
              20                 25                 30

Ala Glu Thr Arg Gln Val Leu Gly Ala Arg Gly Tyr Ser Leu Asn Leu
              35                 40                 45

Ile Pro Pro Ala Leu Ile Ser Gly Glu His Leu Arg Val Cys Pro Gln
     50                 55                 60

Glu Tyr Thr Cys Cys Ser Ser Glu Thr Glu Gln Arg Leu Ile Arg Glu
65                 70                 75                 80

Thr Glu Ala Thr Phe Arg Gly Leu Val Glu Asp Ser Gly Ser Phe Leu
              85                 90                 95

Val His Thr Leu Ala Ala Arg His Arg Lys Phe Asp Glu Phe Phe Leu
              100                105                110

Glu Met Leu Ser Val Ala Gln His Ser Leu Thr Gln Leu Phe Ser His
              115                120                125

Ser Tyr Gly Arg Leu Tyr Ala Gln His Ala Leu Ile Phe Asn Gly Leu
     130                135                140

Phe Ser Arg Leu Arg Asp Phe Tyr Gly Glu Ser Gly Glu Gly Leu Asp
145                150                155                160

Asp Thr Leu Ala Asp Phe Trp Ala Gln Leu Leu Glu Arg Val Phe Pro
              165                170                175

Leu Leu His Pro Gln Tyr Ser Phe Pro Pro Asp Tyr Leu Leu Cys Leu
              180                185                190

Ser Arg Leu Ala Ser Ser Thr Asp Gly Ser Leu Gln Pro Phe Gly Asp
              195                200                205

Ser Pro Arg Arg Leu Arg Leu Gln Ile Thr Arg Thr Leu Val Ala Ala
     210                215                220

Arg Ala Phe Val Gln Gly Leu Glu Thr Gly Arg Asn Val Val Ser Glu
225                230                235                240

Ala Leu Lys Val Pro Val Ser Glu Gly Cys Ser Gln Ala Leu Met Arg
              245                250                255

Leu Ile Gly Cys Pro Leu Cys Arg Gly Val Pro Ser Leu Met Pro Cys
              260                265                270

Gln Gly Phe Cys Leu Asn Val Val Arg Gly Cys Leu Ser Ser Arg Gly
              275                280                285

Leu Glu Pro Asp Trp Gly Asn Tyr Leu Asp Gly Leu Leu Ile Leu Ala
     290                295                300

Asp Lys Leu Gln Gly Pro Phe Ser Phe Glu Leu Thr Ala Glu Ser Ile
```

```
305             310             315             320

Gly Val Lys Ile Ser Glu Gly Leu Met Tyr Leu Gln Glu Asn Ser Ala
            325             330             335

Lys Val Ser Ala Gln Val Phe Gln Glu Cys Gly Pro Pro Asp Pro Val
        340             345             350

Pro Ala Arg Asn Arg Arg Ala Pro Pro Arg Glu Glu Ala Gly Arg
        355             360             365

Leu Trp Ser Met Val Thr Glu Glu Glu Arg Pro Thr Thr Ala Ala Gly
    370             375             380

Thr Asn Leu His Arg Leu Val Trp Glu Leu Arg Glu Arg Leu Ala Arg
385             390             395             400

Met Arg Gly Phe Trp Ala Arg Leu Ser Leu Thr Val Cys Gly Asp Ser
            405             410             415

Arg Met Ala Ala Asp Ala Ser Leu Glu Ala Ala Pro Cys Trp Thr Gly
        420             425             430

Ala Gly Arg Gly Arg Tyr Leu Pro Pro Val Val Gly Gly Ser Pro Ala
        435             440             445

Glu Gln Val Asn Asn Pro Glu Leu Lys Val Asp Ala Ser Gly Pro Asp
    450             455             460

Val Pro Thr Arg Arg Arg Arg Leu Gln Leu Arg Ala Ala Thr Ala Arg
465             470             475             480

Met Lys Thr Ala Ala Leu Gly His Asp Leu Asp Gly Gln Asp Ala Asp
            485             490             495

Glu Asp Ala Ser Gly Ser Gly Gly Gln Gln Tyr Ala Asp Asp Trp
        500             505             510

Met Ala Gly Ala Val Ala Pro Pro Ala Arg Pro Pro Arg Pro Pro Tyr
        515             520             525

Pro Pro Arg Arg Asp Gly Ser Gly Gly Lys Gly Gly Gly Gly Ser Ala
    530             535             540

Arg Tyr Asn Gln Gly Arg Ser Arg Ser Gly Gly Ala Ser Ile Gly Phe
545             550             555             560

His Thr Gln Thr Ile Leu Ile Leu Ser Leu Ser Ala Leu Ala Leu Leu
            565             570             575

Gly Pro Arg
```

<210> SEQ ID NO 84
<211> LENGTH: 615
<212> TYPE: PRT
<213> ORGANISM: Artificial Sequence
<220> FEATURE:
<223> OTHER INFORMATION: Synthetic_FA12_HUMAN

<400> SEQUENCE: 84

```
Met Arg Ala Leu Leu Leu Leu Gly Phe Leu Leu Val Ser Leu Glu Ser
1               5               10              15

Thr Leu Ser Ile Pro Pro Trp Glu Ala Pro Lys Glu His Lys Tyr Lys
            20              25              30

Ala Glu Glu His Thr Val Val Leu Thr Val Thr Gly Glu Pro Cys His
        35              40              45

Phe Pro Phe Gln Tyr His Arg Gln Leu Tyr His Lys Cys Thr His Lys
    50              55              60

Gly Arg Pro Gly Pro Gln Pro Trp Cys Ala Thr Thr Pro Asn Phe Asp
65              70              75              80

Gln Asp Gln Arg Trp Gly Tyr Cys Leu Glu Pro Lys Lys Val Lys Asp
            85              90              95
```

```
His Cys Ser Lys His Ser Pro Cys Gln Lys Gly Gly Thr Cys Val Asn
            100                 105                 110

Met Pro Ser Gly Pro His Cys Leu Cys Pro Gln His Leu Thr Gly Asn
            115                 120                 125

His Cys Gln Lys Glu Lys Cys Phe Glu Pro Gln Leu Leu Arg Phe Phe
    130                 135                 140

His Lys Asn Glu Ile Trp Tyr Arg Thr Glu Gln Ala Ala Val Ala Arg
145                 150                 155                 160

Cys Gln Cys Lys Gly Pro Asp Ala His Cys Gln Arg Leu Ala Ser Gln
                165                 170                 175

Ala Cys Arg Thr Asn Pro Cys Leu His Gly Gly Arg Cys Leu Glu Val
            180                 185                 190

Glu Gly His Arg Leu Cys His Cys Pro Val Gly Tyr Thr Gly Ala Phe
            195                 200                 205

Cys Asp Val Asp Thr Lys Ala Ser Cys Tyr Asp Gly Arg Gly Leu Ser
    210                 215                 220

Tyr Arg Gly Leu Ala Arg Thr Thr Leu Ser Gly Ala Pro Cys Gln Pro
225                 230                 235                 240

Trp Ala Ser Glu Ala Thr Tyr Arg Asn Val Thr Ala Glu Gln Ala Arg
            245                 250                 255

Asn Trp Gly Leu Gly Gly His Ala Phe Cys Arg Asn Pro Asp Asn Asp
            260                 265                 270

Ile Arg Pro Trp Cys Phe Val Leu Asn Arg Asp Arg Leu Ser Trp Glu
            275                 280                 285

Tyr Cys Asp Leu Ala Gln Cys Gln Thr Pro Thr Gln Ala Ala Pro Pro
    290                 295                 300

Thr Pro Val Ser Pro Arg Leu His Val Pro Leu Met Pro Ala Gln Pro
305                 310                 315                 320

Ala Pro Pro Lys Pro Gln Pro Thr Thr Arg Thr Pro Pro Gln Ser Gln
            325                 330                 335

Thr Pro Gly Ala Leu Pro Ala Lys Arg Glu Gln Pro Pro Ser Leu Thr
            340                 345                 350

Arg Asn Gly Pro Leu Ser Cys Gly Gln Arg Leu Arg Lys Ser Leu Ser
            355                 360                 365

Ser Met Thr Arg Val Val Gly Gly Leu Val Ala Leu Arg Gly Ala His
    370                 375                 380

Pro Tyr Ile Ala Ala Leu Tyr Trp Gly His Ser Phe Cys Ala Gly Ser
385                 390                 395                 400

Leu Ile Ala Pro Cys Trp Val Leu Thr Ala Ala His Cys Leu Gln Asp
            405                 410                 415

Arg Pro Ala Pro Glu Asp Leu Thr Val Val Leu Gly Gln Glu Arg Arg
            420                 425                 430

Asn His Ser Cys Glu Pro Cys Gln Thr Leu Ala Val Arg Ser Tyr Arg
    435                 440                 445

Leu His Glu Ala Phe Ser Pro Val Ser Tyr Gln His Asp Leu Ala Leu
    450                 455                 460

Leu Arg Leu Gln Glu Asp Ala Asp Gly Ser Cys Ala Leu Leu Ser Pro
465                 470                 475                 480

Tyr Val Gln Pro Val Cys Leu Pro Ser Gly Ala Ala Arg Pro Ser Glu
                485                 490                 495

Thr Thr Leu Cys Gln Val Ala Gly Trp Gly His Gln Phe Glu Gly Ala
            500                 505                 510
```

```
Glu Glu Tyr Ala Ser Phe Leu Gln Glu Ala Gln Val Pro Phe Leu Ser
        515                 520                 525

Leu Glu Arg Cys Ser Ala Pro Asp Val His Gly Ser Ser Ile Leu Pro
        530                 535                 540

Gly Met Leu Cys Ala Gly Phe Leu Glu Gly Gly Thr Asp Ala Cys Gln
545                 550                 555                 560

Gly Asp Ser Gly Gly Pro Leu Val Cys Glu Asp Gln Ala Ala Glu Arg
                565                 570                 575

Arg Leu Thr Leu Gln Gly Ile Ile Ser Trp Gly Ser Gly Cys Gly Asp
                580                 585                 590

Arg Asn Lys Pro Gly Val Tyr Thr Asp Val Ala Tyr Tyr Leu Ala Trp
                595                 600                 605

Ile Arg Glu His Thr Val Ser
        610                 615

<210> SEQ ID NO 85
<211> LENGTH: 644
<212> TYPE: PRT
<213> ORGANISM: Artificial Sequence
<220> FEATURE:
<223> OTHER INFORMATION: Synthetic_KNG1_HUMAN

<400> SEQUENCE: 85

Met Lys Leu Ile Thr Ile Leu Phe Leu Cys Ser Arg Leu Leu Leu Ser
1                 5                  10                  15

Leu Thr Gln Glu Ser Gln Ser Glu Glu Ile Asp Cys Asn Asp Lys Asp
                20                  25                  30

Leu Phe Lys Ala Val Asp Ala Ala Leu Lys Lys Tyr Asn Ser Gln Asn
        35                  40                  45

Gln Ser Asn Asn Gln Phe Val Leu Tyr Arg Ile Thr Glu Ala Thr Lys
        50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
                100                 105                 110

Lys Arg Ser Ser Thr Lys Phe Ser Val Ala Thr Gln Thr Cys Gln Ile
        115                 120                 125

Thr Pro Ala Glu Gly Pro Val Val Thr Ala Gln Tyr Asp Cys Leu Gly
        130                 135                 140

Cys Val His Pro Ile Ser Thr Gln Ser Pro Asp Leu Glu Pro Ile Leu
145                 150                 155                 160

Arg His Gly Ile Gln Tyr Phe Asn Asn Asn Thr Gln His Ser Ser Leu
                165                 170                 175

Phe Met Leu Asn Glu Val Lys Arg Ala Gln Arg Gln Val Val Ala Gly
                180                 185                 190

Leu Asn Phe Arg Ile Thr Tyr Ser Ile Val Gln Thr Asn Cys Ser Lys
        195                 200                 205

Glu Asn Phe Leu Phe Leu Thr Pro Asp Cys Lys Ser Leu Trp Asn Gly
        210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255
```

-continued

```
Val Gln Pro Pro Thr Lys Ile Cys Val Gly Cys Pro Arg Asp Ile Pro
            260                 265                 270

Thr Asn Ser Pro Glu Leu Glu Glu Thr Leu Thr His Thr Ile Thr Lys
            275                 280                 285

Leu Asn Ala Glu Asn Asn Ala Thr Phe Tyr Phe Lys Ile Asp Asn Val
        290                 295                 300

Lys Lys Ala Arg Val Gln Val Val Ala Gly Lys Lys Tyr Phe Ile Asp
305                 310                 315                 320

Phe Val Ala Arg Glu Thr Thr Cys Ser Lys Glu Ser Asn Glu Glu Leu
                325                 330                 335

Thr Glu Ser Cys Glu Thr Lys Lys Leu Gly Gln Ser Leu Asp Cys Asn
            340                 345                 350

Ala Glu Val Tyr Val Val Pro Trp Glu Lys Lys Ile Tyr Pro Thr Val
            355                 360                 365

Asn Cys Gln Pro Leu Gly Met Ile Ser Leu Met Lys Arg Pro Pro Gly
        370                 375                 380

Phe Ser Pro Phe Arg Ser Ser Arg Ile Gly Glu Ile Lys Glu Glu Thr
385                 390                 395                 400

Thr Val Ser Pro Pro His Thr Ser Met Ala Pro Ala Gln Asp Glu Glu
                405                 410                 415

Arg Asp Ser Gly Lys Glu Gln Gly His Thr Arg Arg His Asp Trp Gly
            420                 425                 430

His Glu Lys Gln Arg Lys His Asn Leu Gly His Gly His Lys His Glu
            435                 440                 445

Arg Asp Gln Gly His Gly His Gln Arg Gly His Gly Leu Gly His Gly
        450                 455                 460

His Glu Gln Gln His Gly Leu Gly His Gly His Lys Phe Lys Leu Asp
465                 470                 475                 480

Asp Asp Leu Glu His Gln Gly Gly His Val Leu Asp His Gly His Lys
                485                 490                 495

His Lys His Gly His Gly His Gly Lys His Lys Asn Lys Gly Lys Lys
            500                 505                 510

Asn Gly Lys His Asn Gly Trp Lys Thr Glu His Leu Ala Ser Ser Ser
            515                 520                 525

Glu Asp Ser Thr Thr Pro Ser Ala Gln Thr Gln Glu Lys Thr Glu Gly
        530                 535                 540

Pro Thr Pro Ile Pro Ser Leu Ala Lys Pro Gly Val Thr Val Thr Phe
545                 550                 555                 560

Ser Asp Phe Gln Asp Ser Asp Leu Ile Ala Thr Met Met Pro Pro Ile
                565                 570                 575

Ser Pro Ala Pro Ile Gln Ser Asp Asp Asp Trp Ile Pro Asp Ile Gln
            580                 585                 590

Ile Asp Pro Asn Gly Leu Ser Phe Asn Pro Ile Ser Asp Phe Pro Asp
            595                 600                 605

Thr Thr Ser Pro Lys Cys Pro Gly Arg Pro Trp Lys Ser Val Ser Glu
        610                 615                 620

Ile Asn Pro Thr Thr Gln Met Lys Glu Ser Tyr Tyr Phe Asp Leu Thr
625                 630                 635                 640

Asp Gly Leu Ser
```

```
<210> SEQ ID NO 86
<211> LENGTH: 650
<212> TYPE: PRT
<213> ORGANISM: Artificial Sequence
```

-continued

<220> FEATURE:
<223> OTHER INFORMATION: Synthetic_APLP1_HUMAN

<400> SEQUENCE: 86

```
Met Gly Pro Ala Ser Pro Ala Ala Arg Gly Leu Ser Arg Arg Pro Gly
1               5                   10                  15

Gln Pro Pro Leu Pro Leu Leu Leu Pro Leu Leu Leu Leu Leu Leu Arg
            20                  25                  30

Ala Gln Pro Ala Ile Gly Ser Leu Ala Gly Gly Ser Pro Gly Ala Ala
        35                  40                  45

Glu Ala Pro Gly Ser Ala Gln Val Ala Gly Leu Cys Gly Arg Leu Thr
    50                  55                  60

Leu His Arg Asp Leu Arg Thr Gly Arg Trp Glu Pro Asp Pro Gln Arg
65                  70                  75                  80

Ser Arg Arg Cys Leu Arg Asp Pro Gln Arg Val Leu Glu Tyr Cys Arg
                85                  90                  95

Gln Met Tyr Pro Glu Leu Gln Ile Ala Arg Val Glu Gln Ala Thr Gln
            100                 105                 110

Ala Ile Pro Met Glu Arg Trp Cys Gly Gly Ser Arg Ser Gly Ser Cys
            115                 120                 125

Ala His Pro His His Gln Val Val Pro Phe Arg Cys Leu Pro Gly Glu
        130                 135                 140

Phe Val Ser Glu Ala Leu Leu Val Pro Glu Gly Cys Arg Phe Leu His
145                 150                 155                 160

Gln Glu Arg Met Asp Gln Cys Glu Ser Ser Thr Arg Arg His Gln Glu
                165                 170                 175

Ala Gln Glu Ala Cys Ser Ser Gln Gly Leu Ile Leu His Gly Ser Gly
            180                 185                 190

Met Leu Leu Pro Cys Gly Ser Asp Arg Phe Arg Gly Val Glu Tyr Val
            195                 200                 205

Cys Cys Pro Pro Pro Gly Thr Pro Asp Pro Ser Gly Thr Ala Val Gly
    210                 215                 220

Asp Pro Ser Thr Arg Ser Trp Pro Pro Gly Ser Arg Val Glu Gly Ala
225                 230                 235                 240

Glu Asp Glu Glu Glu Glu Glu Ser Phe Pro Gln Pro Val Asp Asp Tyr
                245                 250                 255

Phe Val Glu Pro Pro Gln Ala Glu Glu Glu Glu Thr Val Pro Pro
            260                 265                 270

Pro Ser Ser His Thr Leu Ala Val Val Gly Lys Val Thr Pro Thr Pro
    275                 280                 285

Arg Pro Thr Asp Gly Val Asp Ile Tyr Phe Gly Met Pro Gly Glu Ile
    290                 295                 300

Ser Glu His Glu Gly Phe Leu Arg Ala Lys Met Asp Leu Glu Glu Arg
305                 310                 315                 320

Arg Met Arg Gln Ile Asn Glu Val Met Arg Glu Trp Ala Met Ala Asp
                325                 330                 335

Asn Gln Ser Lys Asn Leu Pro Lys Ala Asp Arg Gln Ala Leu Asn Glu
            340                 345                 350

His Phe Gln Ser Ile Leu Gln Thr Leu Glu Glu Gln Val Ser Gly Glu
            355                 360                 365

Arg Gln Arg Leu Val Glu Thr His Ala Thr Arg Val Ile Ala Leu Ile
    370                 375                 380

Asn Asp Gln Arg Arg Ala Ala Leu Glu Gly Phe Leu Ala Ala Leu Gln
385                 390                 395                 400
```

-continued

```
Ala Asp Pro Pro Gln Ala Glu Arg Val Leu Leu Ala Leu Arg Arg Tyr
                405                 410                 415

Leu Arg Ala Glu Gln Lys Glu Gln Arg His Thr Leu Arg His Tyr Gln
                420                 425                 430

His Val Ala Ala Val Asp Pro Glu Lys Ala Gln Gln Met Arg Phe Gln
                435                 440                 445

Val His Thr His Leu Gln Val Ile Glu Glu Arg Val Asn Gln Ser Leu
                450                 455                 460

Gly Leu Leu Asp Gln Asn Pro His Leu Ala Gln Glu Leu Arg Pro Gln
465                 470                 475                 480

Ile Gln Glu Leu Leu His Ser Glu His Leu Gly Pro Ser Glu Leu Glu
                485                 490                 495

Ala Pro Ala Pro Gly Gly Ser Ser Glu Asp Lys Gly Gly Leu Gln Pro
                500                 505                 510

Pro Asp Ser Lys Asp Asp Thr Pro Met Thr Leu Pro Lys Gly Ser Thr
                515                 520                 525

Glu Gln Asp Ala Ala Ser Pro Glu Lys Glu Lys Met Asn Pro Leu Glu
                530                 535                 540

Gln Tyr Glu Arg Lys Val Asn Ala Ser Val Pro Arg Gly Phe Pro Phe
545                 550                 555                 560

His Ser Ser Glu Ile Gln Arg Asp Glu Leu Ala Pro Ala Gly Thr Gly
                565                 570                 575

Val Ser Arg Glu Ala Val Ser Gly Leu Leu Ile Met Gly Ala Gly Gly
                580                 585                 590

Gly Ser Leu Ile Val Leu Ser Met Leu Leu Leu Arg Arg Lys Lys Pro
                595                 600                 605

Tyr Gly Ala Ile Ser His Gly Val Val Glu Val Asp Pro Met Leu Thr
                610                 615                 620

Leu Glu Glu Gln Gln Leu Arg Glu Leu Gln Arg His Gly Tyr Glu Asn
625                 630                 635                 640

Pro Thr Tyr Arg Phe Leu Glu Glu Arg Pro
                645                 650
```

```
<210> SEQ ID NO 87
<211> LENGTH: 661
<212> TYPE: PRT
<213> ORGANISM: Artificial Sequence
<220> FEATURE:
<223> OTHER INFORMATION: Synthetic_CRAC1_HUMAN

<400> SEQUENCE: 87
```

```
Met Ala Pro Ser Ala Asp Pro Gly Met Ser Arg Met Leu Pro Phe Leu
1               5                   10                  15

Leu Leu Leu Trp Phe Leu Pro Ile Thr Glu Gly Ser Gln Arg Ala Glu
                20                  25                  30

Pro Met Phe Thr Ala Val Thr Asn Ser Val Leu Pro Pro Asp Tyr Asp
                35                  40                  45

Ser Asn Pro Thr Gln Leu Asn Tyr Gly Val Ala Val Thr Asp Val Asp
                50                  55                  60

His Asp Gly Asp Phe Glu Ile Val Val Ala Gly Tyr Asn Gly Pro Asn
65                  70                  75                  80

Leu Val Leu Lys Tyr Asp Arg Ala Gln Lys Arg Leu Val Asn Ile Ala
                85                  90                  95

Val Asp Glu Arg Ser Ser Pro Tyr Tyr Ala Leu Arg Asp Arg Gln Gly
                100                 105                 110
```

-continued

```
Asn Ala Ile Gly Val Thr Ala Cys Asp Ile Asp Gly Asp Gly Arg Glu
        115                 120             125

Glu Ile Tyr Phe Leu Asn Thr Asn Asn Ala Phe Ser Gly Val Ala Thr
        130                 135             140

Tyr Thr Asp Lys Leu Phe Lys Phe Arg Asn Asn Arg Trp Glu Asp Ile
145                 150                 155             160

Leu Ser Asp Glu Val Asn Val Ala Arg Gly Val Ala Ser Leu Phe Ala
                165                 170             175

Gly Arg Ser Val Ala Cys Val Asp Arg Lys Gly Ser Gly Arg Tyr Ser
                180                 185             190

Ile Tyr Ile Ala Asn Tyr Ala Tyr Gly Asn Val Gly Pro Asp Ala Leu
        195                 200             205

Ile Glu Met Asp Pro Glu Ala Ser Asp Leu Ser Arg Gly Ile Leu Ala
        210                 215             220

Leu Arg Asp Val Ala Ala Glu Ala Gly Val Ser Lys Tyr Thr Gly Gly
225                 230                 235             240

Arg Gly Val Ser Val Gly Pro Ile Leu Ser Ser Ser Ala Ser Asp Ile
                245                 250             255

Phe Cys Asp Asn Glu Asn Gly Pro Asn Phe Leu Phe His Asn Arg Gly
                260                 265             270

Asp Gly Thr Phe Val Asp Ala Ala Ala Ser Ala Gly Val Asp Asp Pro
                275                 280             285

His Gln His Gly Arg Gly Val Ala Leu Ala Asp Phe Asn Arg Asp Gly
        290                 295             300

Lys Val Asp Ile Val Tyr Gly Asn Trp Asn Gly Pro His Arg Leu Tyr
305                 310                 315             320

Leu Gln Met Ser Thr His Gly Lys Val Arg Phe Arg Asp Ile Ala Ser
                325                 330             335

Pro Lys Phe Ser Met Pro Ser Pro Val Arg Thr Val Ile Thr Ala Asp
                340                 345             350

Phe Asp Asn Asp Gln Glu Leu Glu Ile Phe Phe Asn Asn Ile Ala Tyr
                355                 360             365

Arg Ser Ser Ser Ala Asn Arg Leu Phe Arg Val Ile Arg Arg Glu His
        370                 375             380

Gly Asp Pro Leu Ile Glu Glu Leu Asn Pro Gly Asp Ala Leu Glu Pro
385                 390                 395             400

Glu Gly Arg Gly Thr Gly Gly Val Val Thr Asp Phe Asp Gly Asp Gly
                405                 410             415

Met Leu Asp Leu Ile Leu Ser His Gly Glu Ser Met Ala Gln Pro Leu
                420                 425             430

Ser Val Phe Arg Gly Asn Gln Gly Phe Asn Asn Asn Trp Leu Arg Val
        435                 440             445

Val Pro Arg Thr Arg Phe Gly Ala Phe Ala Arg Gly Ala Lys Val Val
        450                 455             460

Leu Tyr Thr Lys Lys Ser Gly Ala His Leu Arg Ile Ile Asp Gly Gly
465                 470                 475             480

Ser Gly Tyr Leu Cys Glu Met Glu Pro Val Ala His Phe Gly Leu Gly
                485                 490             495

Lys Asp Glu Ala Ser Ser Val Glu Val Thr Trp Pro Asp Gly Lys Met
                500                 505             510

Val Ser Arg Asn Val Ala Ser Gly Glu Met Asn Ser Val Leu Glu Ile
        515                 520             525
```

-continued

```
Leu Tyr Pro Arg Asp Glu Asp Thr Leu Gln Asp Pro Ala Pro Leu Glu
    530             535             540

Cys Gly Gln Gly Phe Ser Gln Gln Glu Asn Gly His Cys Met Asp Thr
545             550             555             560

Asn Glu Cys Ile Gln Phe Pro Phe Val Cys Pro Arg Asp Lys Pro Val
            565             570             575

Cys Val Asn Thr Tyr Gly Ser Tyr Arg Cys Arg Thr Asn Lys Lys Cys
            580             585             590

Ser Arg Gly Tyr Glu Pro Asn Glu Asp Gly Thr Ala Cys Val Gly Thr
            595             600             605

Leu Gly Gln Ser Pro Gly Pro Arg Pro Thr Thr Pro Thr Ala Ala Ala
            610             615             620

Ala Thr Ala Ala Ala Ala Ala Ala Ala Gly Ala Ala Thr Ala Ala Pro
625             630             635             640

Val Leu Val Asp Gly Asp Leu Asn Leu Gly Ser Val Val Lys Glu Ser
            645             650             655

Cys Glu Pro Ser Cys
            660
```

```
<210> SEQ ID NO 88
<211> LENGTH: 664
<212> TYPE: PRT
<213> ORGANISM: Artificial Sequence
<220> FEATURE:
<223> OTHER INFORMATION: Synthetic_SPRL1_HUMAN

<400> SEQUENCE: 88

Met Lys Thr Gly Leu Phe Phe Leu Cys Leu Leu Gly Thr Ala Ala Ala
1               5               10              15

Ile Pro Thr Asn Ala Arg Leu Leu Ser Asp His Ser Lys Pro Thr Ala
            20              25              30

Glu Thr Val Ala Pro Asp Asn Thr Ala Ile Pro Ser Leu Arg Ala Glu
            35              40              45

Ala Glu Glu Asn Glu Lys Glu Thr Ala Val Ser Thr Glu Asp Asp Ser
        50              55              60

His His Lys Ala Glu Lys Ser Ser Val Leu Lys Ser Lys Glu Glu Ser
65              70              75              80

His Glu Gln Ser Ala Glu Gln Gly Lys Ser Ser Ser Gln Glu Leu Gly
                85              90              95

Leu Lys Asp Gln Glu Asp Ser Asp Gly His Leu Ser Val Asn Leu Glu
            100             105             110

Tyr Ala Pro Thr Glu Gly Thr Leu Asp Ile Lys Glu Asp Met Ser Glu
            115             120             125

Pro Gln Glu Lys Lys Leu Ser Glu Asn Thr Asp Phe Leu Ala Pro Gly
        130             135             140

Val Ser Ser Phe Thr Asp Ser Asn Gln Gln Glu Ser Ile Thr Lys Arg
145             150             155             160

Glu Glu Asn Gln Glu Gln Pro Arg Asn Tyr Ser His His Gln Leu Asn
                165             170             175

Arg Ser Ser Lys His Ser Gln Gly Leu Arg Asp Gln Gly Asn Gln Glu
                180             185             190

Gln Asp Pro Asn Ile Ser Asn Gly Glu Glu Glu Glu Lys Glu Pro
            195             200             205

Gly Glu Val Gly Thr His Asn Asp Asn Gln Glu Arg Lys Thr Glu Leu
            210             215             220
```

```
Pro Arg Glu His Ala Asn Ser Lys Gln Glu Glu Asp Asn Thr Gln Ser
225             230             235             240

Asp Asp Ile Leu Glu Glu Ser Asp Gln Pro Thr Gln Val Ser Lys Met
            245             250             255

Gln Glu Asp Glu Phe Asp Gln Gly Asn Gln Glu Gln Glu Asp Asn Ser
            260             265             270

Asn Ala Glu Met Glu Glu Glu Asn Ala Ser Asn Val Asn Lys His Ile
            275             280             285

Gln Glu Thr Glu Trp Gln Ser Gln Glu Gly Lys Thr Gly Leu Glu Ala
            290             295             300

Ile Ser Asn His Lys Glu Thr Glu Glu Lys Thr Val Ser Glu Ala Leu
305             310             315             320

Leu Met Glu Pro Thr Asp Asp Gly Asn Thr Thr Pro Arg Asn His Gly
            325             330             335

Val Asp Asp Asp Gly Asp Asp Asp Gly Asp Asp Gly Gly Thr Asp Gly
            340             345             350

Pro Arg His Ser Ala Ser Asp Asp Tyr Phe Ile Pro Ser Gln Ala Phe
            355             360             365

Leu Glu Ala Glu Arg Ala Gln Ser Ile Ala Tyr His Leu Lys Ile Glu
            370             375             380

Glu Gln Arg Glu Lys Val His Glu Asn Glu Asn Ile Gly Thr Thr Glu
385             390             395             400

Pro Gly Glu His Gln Glu Ala Lys Lys Ala Glu Asn Ser Ser Asn Glu
            405             410             415

Glu Glu Thr Ser Ser Glu Gly Asn Met Arg Val His Ala Val Asp Ser
            420             425             430

Cys Met Ser Phe Gln Cys Lys Arg Gly His Ile Cys Lys Ala Asp Gln
            435             440             445

Gln Gly Lys Pro His Cys Val Cys Gln Asp Pro Val Thr Cys Pro Pro
            450             455             460

Thr Lys Pro Leu Asp Gln Val Cys Gly Thr Asp Asn Gln Thr Tyr Ala
465             470             475             480

Ser Ser Cys His Leu Phe Ala Thr Lys Cys Arg Leu Glu Gly Thr Lys
            485             490             495

Lys Gly His Gln Leu Gln Leu Asp Tyr Phe Gly Ala Cys Lys Ser Ile
            500             505             510

Pro Thr Cys Thr Asp Phe Glu Val Ile Gln Phe Pro Leu Arg Met Arg
            515             520             525

Asp Trp Leu Lys Asn Ile Leu Met Gln Leu Tyr Glu Ala Asn Ser Glu
            530             535             540

His Ala Gly Tyr Leu Asn Glu Lys Gln Arg Asn Lys Val Lys Lys Ile
545             550             555             560

Tyr Leu Asp Glu Lys Arg Leu Leu Ala Gly Asp His Pro Ile Asp Leu
            565             570             575

Leu Leu Arg Asp Phe Lys Lys Asn Tyr His Met Tyr Val Tyr Pro Val
            580             585             590

His Trp Gln Phe Ser Glu Leu Asp Gln His Pro Met Asp Arg Val Leu
            595             600             605

Thr His Ser Glu Leu Ala Pro Leu Arg Ala Ser Leu Val Pro Met Glu
            610             615             620

His Cys Ile Thr Arg Phe Phe Glu Glu Cys Asp Pro Asn Lys Asp Lys
625             630             635             640

His Ile Thr Leu Lys Glu Trp Gly His Cys Phe Gly Ile Lys Glu Glu
```

-continued

```
                          645                 650                 655

Asp Ile Asp Glu Asn Leu Leu Phe
                     660

<210> SEQ ID NO 89
<211> LENGTH: 701
<212> TYPE: PRT
<213> ORGANISM: Artificial Sequence
<220> FEATURE:
<223> OTHER INFORMATION: Synthetic_MEP1B_HUMAN

<400> SEQUENCE: 89

Met Asp Leu Trp Asn Leu Ser Trp Phe Leu Phe Leu Asp Ala Leu Leu
1               5                   10                  15

Val Ile Ser Gly Leu Ala Thr Pro Glu Asn Phe Asp Val Asp Gly Gly
                20                  25                  30

Met Asp Gln Asp Ile Phe Asp Ile Asn Glu Gly Leu Gly Leu Asp Leu
            35                  40                  45

Phe Glu Gly Asp Ile Arg Leu Asp Arg Ala Gln Ile Arg Asn Ser Ile
    50                  55                  60

Ile Gly Glu Lys Tyr Arg Trp Pro His Thr Ile Pro Tyr Val Leu Glu
65                  70                  75                  80

Asp Ser Leu Glu Met Asn Ala Lys Gly Val Ile Leu Asn Ala Phe Glu
                85                  90                  95

Arg Tyr Arg Leu Lys Thr Cys Ile Asp Phe Lys Pro Trp Ala Gly Glu
                100                 105                 110

Thr Asn Tyr Ile Ser Val Phe Lys Gly Ser Gly Cys Trp Ser Ser Val
            115                 120                 125

Gly Asn Arg Arg Val Gly Lys Gln Glu Leu Ser Ile Gly Ala Asn Cys
    130                 135                 140

Asp Arg Ile Ala Thr Val Gln His Glu Phe Leu His Ala Leu Gly Phe
145                 150                 155                 160

Trp His Glu Gln Ser Arg Ser Asp Arg Asp Asp Tyr Val Arg Ile Met
                165                 170                 175

Trp Asp Arg Ile Leu Ser Gly Arg Glu His Asn Phe Asn Thr Tyr Ser
            180                 185                 190

Asp Asp Ile Ser Asp Ser Leu Asn Val Pro Tyr Asp Tyr Thr Ser Val
            195                 200                 205

Met His Tyr Ser Lys Thr Ala Phe Gln Asn Gly Thr Glu Pro Thr Ile
    210                 215                 220

Val Thr Arg Ile Ser Asp Phe Glu Asp Val Ile Gly Gln Arg Met Asp
225                 230                 235                 240

Phe Ser Asp Ser Asp Leu Leu Lys Leu Asn Gln Leu Tyr Asn Cys Ser
                245                 250                 255

Ser Ser Leu Ser Phe Met Asp Ser Cys Ser Phe Glu Leu Glu Asn Val
                260                 265                 270

Cys Gly Met Ile Gln Ser Ser Gly Asp Asn Ala Asp Trp Gln Arg Val
            275                 280                 285

Ser Gln Val Pro Arg Gly Pro Glu Ser Asp His Ser Asn Met Gly Gln
    290                 295                 300

Cys Gln Gly Ser Gly Phe Phe Met His Phe Asp Ser Ser Ser Val Asn
305                 310                 315                 320

Val Gly Ala Thr Ala Val Leu Glu Ser Arg Thr Leu Tyr Pro Lys Arg
            325                 330                 335

Gly Phe Gln Cys Leu Gln Phe Tyr Leu Tyr Asn Ser Gly Ser Glu Ser
```

-continued

```
                340                    345                    350

Asp Gln Leu Asn Ile Tyr Ile Arg Glu Tyr Ser Ala Asp Asn Val Asp
        355                    360                    365

Gly Asn Leu Thr Leu Val Glu Glu Ile Lys Glu Ile Pro Thr Gly Ser
        370                    375                    380

Trp Gln Leu Tyr His Val Thr Leu Lys Val Thr Lys Lys Phe Arg Val
385                    390                    395                    400

Val Phe Glu Gly Arg Lys Gly Ser Gly Ala Ser Leu Gly Gly Leu Ser
                405                    410                    415

Ile Asp Asp Ile Asn Leu Ser Glu Thr Arg Cys Pro His His Ile Trp
                420                    425                    430

His Ile Arg Asn Phe Thr Gln Phe Ile Gly Ser Pro Asn Gly Thr Leu
        435                    440                    445

Tyr Ser Pro Pro Phe Tyr Ser Ser Lys Gly Tyr Ala Phe Gln Ile Tyr
        450                    455                    460

Leu Asn Leu Ala His Val Thr Asn Ala Gly Ile Tyr Phe His Leu Ile
465                    470                    475                    480

Ser Gly Ala Asn Asp Asp Gln Leu Gln Trp Pro Cys Pro Trp Gln Gln
                485                    490                    495

Ala Thr Met Thr Leu Leu Asp Gln Asn Pro Asp Ile Arg Gln Arg Met
                500                    505                    510

Ser Asn Gln Arg Ser Ile Thr Thr Asp Pro Phe Met Thr Thr Asp Asn
        515                    520                    525

Gly Asn Tyr Phe Trp Asp Arg Pro Ser Lys Val Gly Thr Val Ala Leu
        530                    535                    540

Phe Ser Asn Gly Thr Gln Phe Arg Arg Gly Gly Gly Tyr Gly Thr Ser
545                    550                    555                    560

Ala Phe Ile Thr His Glu Arg Leu Lys Ser Arg Asp Phe Ile Lys Gly
                565                    570                    575

Asp Asp Val Tyr Ile Leu Leu Thr Val Glu Asp Ile Ser His Leu Asn
                580                    585                    590

Ser Thr Gln Ile Gln Leu Thr Pro Ala Pro Ser Val Gln Asp Leu Cys
        595                    600                    605

Ser Lys Thr Thr Cys Lys Asn Asp Gly Val Cys Thr Val Arg Asp Gly
        610                    615                    620

Lys Ala Glu Cys Arg Cys Gln Ser Gly Glu Asp Trp Trp Tyr Met Gly
625                    630                    635                    640

Glu Arg Cys Glu Lys Arg Gly Ser Thr Arg Asp Thr Ile Val Ile Ala
                645                    650                    655

Val Ser Ser Thr Val Ala Val Phe Ala Leu Met Leu Ile Ile Thr Leu
                660                    665                    670

Val Ser Val Tyr Cys Thr Arg Lys Lys Tyr Arg Glu Arg Met Ser Ser
        675                    680                    685

Asn Arg Pro Asn Leu Thr Pro Gln Asn Gln His Ala Phe
        690                    695                    700
```

<210> SEQ ID NO 90
<211> LENGTH: 705
<212> TYPE: PRT
<213> ORGANISM: Artificial Sequence
<220> FEATURE:
<223> OTHER INFORMATION: Synthetic_SYN1_HUMAN

<400> SEQUENCE: 90

Met Asn Tyr Leu Arg Arg Arg Leu Ser Asp Ser Asn Phe Met Ala Asn

-continued

```
1                5                    10                   15

Leu Pro Asn Gly Tyr Met Thr Asp Leu Gln Arg Pro Gln Pro Pro Pro
            20                  25                  30

Pro Pro Pro Gly Ala His Ser Pro Gly Ala Thr Pro Gly Pro Gly Thr
            35                  40                  45

Ala Thr Ala Glu Arg Ser Ser Gly Val Ala Pro Ala Ala Ser Pro Ala
    50                  55                  60

Ala Pro Ser Pro Gly Ser Ser Gly Gly Gly Phe Phe Ser Ser Leu
65                  70                  75                  80

Ser Asn Ala Val Lys Gln Thr Thr Ala Ala Ala Ala Thr Phe Ser
                85                  90                  95

Glu Gln Val Gly Gly Gly Ser Gly Gly Ala Gly Arg Gly Gly Ala Ala
            100                 105                 110

Ser Arg Val Leu Leu Val Ile Asp Glu Pro His Thr Asp Trp Ala Lys
            115                 120                 125

Tyr Phe Lys Gly Lys Lys Ile His Gly Glu Ile Asp Ile Lys Val Glu
    130                 135                 140

Gln Ala Glu Phe Ser Asp Leu Asn Leu Val Ala His Ala Asn Gly Gly
145                 150                 155                 160

Phe Ser Val Asp Met Glu Val Leu Arg Asn Gly Val Lys Val Val Arg
                165                 170                 175

Ser Leu Lys Pro Asp Phe Val Leu Ile Arg Gln His Ala Phe Ser Met
            180                 185                 190

Ala Arg Asn Gly Asp Tyr Arg Ser Leu Val Ile Gly Leu Gln Tyr Ala
            195                 200                 205

Gly Ile Pro Ser Val Asn Ser Leu His Ser Val Tyr Asn Phe Cys Asp
    210                 215                 220

Lys Pro Trp Val Phe Ala Gln Met Val Arg Leu His Lys Lys Leu Gly
225                 230                 235                 240

Thr Glu Glu Phe Pro Leu Ile Asp Gln Thr Phe Tyr Pro Asn His Lys
                245                 250                 255

Glu Met Leu Ser Ser Thr Thr Tyr Pro Val Val Val Lys Met Gly His
            260                 265                 270

Ala His Ser Gly Met Gly Lys Val Lys Val Asp Asn Gln His Asp Phe
            275                 280                 285

Gln Asp Ile Ala Ser Val Val Ala Leu Thr Lys Thr Tyr Ala Thr Ala
    290                 295                 300

Glu Pro Phe Ile Asp Ala Lys Tyr Asp Val Arg Val Gln Lys Ile Gly
305                 310                 315                 320

Gln Asn Tyr Lys Ala Tyr Met Arg Thr Ser Val Ser Gly Asn Trp Lys
                325                 330                 335

Thr Asn Thr Gly Ser Ala Met Leu Glu Gln Ile Ala Met Ser Asp Arg
            340                 345                 350

Tyr Lys Leu Trp Val Asp Thr Cys Ser Glu Ile Phe Gly Gly Leu Asp
            355                 360                 365

Ile Cys Ala Val Glu Ala Leu His Gly Lys Asp Gly Arg Asp His Ile
    370                 375                 380

Ile Glu Val Val Gly Ser Ser Met Pro Leu Ile Gly Asp His Gln Asp
385                 390                 395                 400

Glu Asp Lys Gln Leu Ile Val Glu Leu Val Val Asn Lys Met Ala Gln
            405                 410                 415

Ala Leu Pro Arg Gln Arg Gln Arg Asp Ala Ser Pro Gly Arg Gly Ser
            420                 425                 430
```

-continued

```
His Gly Gln Thr Pro Ser Pro Gly Ala Leu Pro Leu Gly Arg Gln Thr
        435                 440                 445

Ser Gln Gln Pro Ala Gly Pro Pro Ala Gln Gln Arg Pro Pro Pro Gln
    450                 455                 460

Gly Gly Pro Pro Gln Pro Gly Pro Gly Pro Gln Arg Gln Gly Pro Pro
465                 470                 475                 480

Leu Gln Gln Arg Pro Pro Pro Gln Gly Gln Gln His Leu Ser Gly Leu
                485                 490                 495

Gly Pro Pro Ala Gly Ser Pro Leu Pro Gln Arg Leu Pro Ser Pro Thr
                500                 505                 510

Ser Ala Pro Gln Gln Pro Ala Ser Gln Ala Ala Pro Pro Thr Gln Gly
        515                 520                 525

Gln Gly Arg Gln Ser Arg Pro Val Ala Gly Gly Pro Gly Ala Pro Pro
        530                 535                 540

Ala Ala Arg Pro Pro Ala Ser Pro Ser Pro Gln Arg Gln Ala Gly Pro
545                 550                 555                 560

Pro Gln Ala Thr Arg Gln Thr Ser Val Ser Gly Pro Ala Pro Pro Lys
                565                 570                 575

Ala Ser Gly Ala Pro Pro Gly Gly Gln Gln Arg Gln Gly Pro Pro Gln
        580                 585                 590

Lys Pro Pro Gly Pro Ala Gly Pro Thr Arg Gln Ala Ser Gln Ala Gly
        595                 600                 605

Pro Val Pro Arg Thr Gly Pro Pro Thr Thr Gln Gln Pro Arg Pro Ser
    610                 615                 620

Gly Pro Gly Pro Ala Gly Arg Pro Lys Pro Gln Leu Ala Gln Lys Pro
625                 630                 635                 640

Ser Gln Asp Val Pro Pro Pro Ala Thr Ala Ala Ala Gly Gly Pro Pro
                645                 650                 655

His Pro Gln Leu Asn Lys Ser Gln Ser Leu Thr Asn Ala Phe Asn Leu
        660                 665                 670

Pro Glu Pro Ala Pro Pro Arg Pro Ser Leu Ser Gln Asp Glu Val Lys
        675                 680                 685

Ala Glu Thr Ile Arg Ser Leu Arg Lys Ser Phe Ala Ser Leu Phe Ser
    690                 695                 700

Asp
705
```

```
<210> SEQ ID NO 91
<211> LENGTH: 753
<212> TYPE: PRT
<213> ORGANISM: Artificial Sequence
<220> FEATURE:
<223> OTHER INFORMATION: Synthetic_CEL_HUMAN

<400> SEQUENCE: 91

Met Gly Arg Leu Gln Leu Val Val Leu Gly Leu Thr Cys Cys Trp Ala
1               5                   10                  15

Val Ala Ser Ala Ala Lys Leu Gly Ala Val Tyr Thr Glu Gly Gly Phe
            20                  25                  30

Val Glu Gly Val Asn Lys Lys Leu Gly Leu Leu Gly Asp Ser Val Asp
        35                  40                  45

Ile Phe Lys Gly Ile Pro Phe Ala Ala Pro Thr Lys Ala Leu Glu Asn
    50                  55                  60

Pro Gln Pro His Pro Gly Trp Gln Gly Thr Leu Lys Ala Lys Asn Phe
65                  70                  75                  80
```

-continued

```
Lys Lys Arg Cys Leu Gln Ala Thr Ile Thr Gln Asp Ser Thr Tyr Gly
                85              90              95

Asp Glu Asp Cys Leu Tyr Leu Asn Ile Trp Val Pro Gln Gly Arg Lys
               100             105             110

Gln Val Ser Arg Asp Leu Pro Val Met Ile Trp Ile Tyr Gly Gly Ala
               115             120             125

Phe Leu Met Gly Ser Gly His Gly Ala Asn Phe Leu Asn Asn Tyr Leu
       130             135             140

Tyr Asp Gly Glu Glu Ile Ala Thr Arg Gly Asn Val Ile Val Val Thr
145             150             155             160

Phe Asn Tyr Arg Val Gly Pro Leu Gly Phe Leu Ser Thr Gly Asp Ala
               165             170             175

Asn Leu Pro Gly Asn Tyr Gly Leu Arg Asp Gln His Met Ala Ile Ala
               180             185             190

Trp Val Lys Arg Asn Ile Ala Ala Phe Gly Gly Asp Pro Asn Asn Ile
               195             200             205

Thr Leu Phe Gly Glu Ser Ala Gly Gly Ala Ser Val Ser Leu Gln Thr
       210             215             220

Leu Ser Pro Tyr Asn Lys Gly Leu Ile Arg Arg Ala Ile Ser Gln Ser
225             230             235             240

Gly Val Ala Leu Ser Pro Trp Val Ile Gln Lys Asn Pro Leu Phe Trp
               245             250             255

Ala Lys Lys Val Ala Glu Lys Val Gly Cys Pro Val Gly Asp Ala Ala
               260             265             270

Arg Met Ala Gln Cys Leu Lys Val Thr Asp Pro Arg Ala Leu Thr Leu
       275             280             285

Ala Tyr Lys Val Pro Leu Ala Gly Leu Glu Tyr Pro Met Leu His Tyr
       290             295             300

Val Gly Phe Val Pro Val Ile Asp Gly Asp Phe Ile Pro Ala Asp Pro
305             310             315             320

Ile Asn Leu Tyr Ala Asn Ala Ala Asp Ile Asp Tyr Ile Ala Gly Thr
               325             330             335

Asn Asn Met Asp Gly His Ile Phe Ala Ser Ile Asp Met Pro Ala Ile
       340             345             350

Asn Lys Gly Asn Lys Lys Val Thr Glu Glu Asp Phe Tyr Lys Leu Val
       355             360             365

Ser Glu Phe Thr Ile Thr Lys Gly Leu Arg Gly Ala Lys Thr Thr Phe
       370             375             380

Asp Val Tyr Thr Glu Ser Trp Ala Gln Asp Pro Ser Gln Glu Asn Lys
385             390             395             400

Lys Lys Thr Val Val Asp Phe Glu Thr Asp Val Leu Phe Leu Val Pro
               405             410             415

Thr Glu Ile Ala Leu Ala Gln His Arg Ala Asn Ala Lys Ser Ala Lys
               420             425             430

Thr Tyr Ala Tyr Leu Phe Ser His Pro Ser Arg Met Pro Val Tyr Pro
               435             440             445

Lys Trp Val Gly Ala Asp His Ala Asp Asp Ile Gln Tyr Val Phe Gly
       450             455             460

Lys Pro Phe Ala Thr Pro Thr Gly Tyr Arg Pro Gln Asp Arg Thr Val
465             470             475             480

Ser Lys Ala Met Ile Ala Tyr Trp Thr Asn Phe Ala Lys Thr Gly Asp
               485             490             495
```

Pro Asn Met Gly Asp Ser Ala Val Pro Thr His Trp Glu Pro Tyr Thr
            500                 505                 510

Thr Glu Asn Ser Gly Tyr Leu Glu Ile Thr Lys Lys Met Gly Ser Ser
            515                 520                 525

Ser Met Lys Arg Ser Leu Arg Thr Asn Phe Leu Arg Tyr Trp Thr Leu
            530                 535                 540

Thr Tyr Leu Ala Leu Pro Thr Val Thr Asp Gln Glu Ala Thr Pro Val
545                 550                 555                 560

Pro Pro Thr Gly Asp Ser Glu Ala Thr Pro Val Pro Thr Gly Asp
                565                 570                 575

Ser Glu Thr Ala Pro Val Pro Pro Thr Gly Asp Ser Gly Ala Pro Pro
            580                 585                 590

Val Pro Pro Thr Gly Asp Ser Gly Ala Pro Pro Val Pro Pro Thr Gly
            595                 600                 605

Asp Ser Gly Ala Pro Pro Val Pro Pro Thr Gly Asp Ser Gly Ala Pro
            610                 615                 620

Pro Val Pro Pro Thr Gly Asp Ser Gly Ala Pro Pro Val Pro Pro Thr
625                 630                 635                 640

Gly Asp Ser Gly Ala Pro Pro Val Pro Pro Thr Gly Asp Ser Gly Ala
                645                 650                 655

Pro Pro Val Pro Pro Thr Gly Asp Ser Gly Ala Pro Pro Val Pro Pro
                660                 665                 670

Thr Gly Asp Ala Gly Pro Pro Pro Val Pro Pro Thr Gly Asp Ser Gly
                675                 680                 685

Ala Pro Pro Val Pro Pro Thr Gly Asp Ser Gly Ala Pro Pro Val Thr
            690                 695                 700

Pro Thr Gly Asp Ser Glu Thr Ala Pro Val Pro Pro Thr Gly Asp Ser
705                 710                 715                 720

Gly Ala Pro Pro Val Pro Pro Thr Gly Asp Ser Glu Ala Ala Pro Val
                725                 730                 735

Pro Pro Thr Asp Asp Ser Lys Glu Ala Gln Met Pro Ala Val Ile Arg
            740                 745                 750

Phe

<210> SEQ ID NO 92
<211> LENGTH: 757
<212> TYPE: PRT
<213> ORGANISM: Artificial Sequence
<220> FEATURE:
<223> OTHER INFORMATION: Synthetic_CD248_HUMAN

<400> SEQUENCE: 92

Met Leu Leu Arg Leu Leu Leu Ala Trp Ala Ala Ala Gly Pro Thr Leu
1                   5                   10                  15

Gly Gln Asp Pro Trp Ala Ala Glu Pro Arg Ala Ala Cys Gly Pro Ser
                20                  25                  30

Ser Cys Tyr Ala Leu Phe Pro Arg Arg Arg Thr Phe Leu Glu Ala Trp
            35                  40                  45

Arg Ala Cys Arg Glu Leu Gly Gly Asp Leu Ala Thr Pro Arg Thr Pro
            50                  55                  60

Glu Glu Ala Gln Arg Val Asp Ser Leu Val Gly Ala Gly Pro Ala Ser
65                  70                  75                  80

Arg Leu Leu Trp Ile Gly Leu Gln Arg Gln Ala Arg Gln Cys Gln Leu
                85                  90                  95

Gln Arg Pro Leu Arg Gly Phe Thr Trp Thr Thr Gly Asp Gln Asp Thr

-continued

```
                100                 105                 110

Ala Phe Thr Asn Trp Ala Gln Pro Ala Ser Gly Gly Pro Cys Pro Ala
            115                 120                 125

Gln Arg Cys Val Ala Leu Glu Ala Ser Gly Glu His Arg Trp Leu Glu
        130                 135                 140

Gly Ser Cys Thr Leu Ala Val Asp Gly Tyr Leu Cys Gln Phe Gly Phe
145                 150                 155                 160

Glu Gly Ala Cys Pro Ala Leu Gln Asp Glu Ala Gly Gln Ala Gly Pro
                165                 170                 175

Ala Val Tyr Thr Thr Pro Phe His Leu Val Ser Thr Glu Phe Glu Trp
            180                 185                 190

Leu Pro Phe Gly Ser Val Ala Ala Val Gln Cys Gln Ala Gly Arg Gly
        195                 200                 205

Ala Ser Leu Leu Cys Val Lys Gln Pro Glu Gly Gly Val Gly Trp Ser
    210                 215                 220

Arg Ala Gly Pro Leu Cys Leu Gly Thr Gly Cys Ser Pro Asp Asn Gly
225                 230                 235                 240

Gly Cys Glu His Glu Cys Val Glu Glu Val Asp Gly His Val Ser Cys
                245                 250                 255

Arg Cys Thr Glu Gly Phe Arg Leu Ala Ala Asp Gly Arg Ser Cys Glu
            260                 265                 270

Asp Pro Cys Ala Gln Ala Pro Cys Glu Gln Gln Cys Glu Pro Gly Gly
            275                 280                 285

Pro Gln Gly Tyr Ser Cys His Cys Arg Leu Gly Phe Arg Pro Ala Glu
        290                 295                 300

Asp Asp Pro His Arg Cys Val Asp Thr Asp Glu Cys Gln Ile Ala Gly
305                 310                 315                 320

Val Cys Gln Gln Met Cys Val Asn Tyr Val Gly Gly Phe Glu Cys Tyr
                325                 330                 335

Cys Ser Glu Gly His Glu Leu Glu Ala Asp Gly Ile Ser Cys Ser Pro
            340                 345                 350

Ala Gly Ala Met Gly Ala Gln Ala Ser Gln Asp Leu Gly Asp Glu Leu
        355                 360                 365

Leu Asp Asp Gly Glu Asp Glu Glu Asp Glu Asp Glu Ala Trp Lys Ala
        370                 375                 380

Phe Asn Gly Gly Trp Thr Glu Met Pro Gly Ile Leu Trp Met Glu Pro
385                 390                 395                 400

Thr Gln Pro Pro Asp Phe Ala Leu Ala Tyr Arg Pro Ser Phe Pro Glu
                405                 410                 415

Asp Arg Glu Pro Gln Ile Pro Tyr Pro Glu Pro Thr Trp Pro Pro Pro
            420                 425                 430

Leu Ser Ala Pro Arg Val Pro Tyr His Ser Ser Val Leu Ser Val Thr
        435                 440                 445

Arg Pro Val Val Val Ser Ala Thr His Pro Thr Leu Pro Ser Ala His
    450                 455                 460

Gln Pro Pro Val Ile Pro Ala Thr His Pro Ala Leu Ser Arg Asp His
465                 470                 475                 480

Gln Ile Pro Val Ile Ala Ala Asn Tyr Pro Asp Leu Pro Ser Ala Tyr
                485                 490                 495

Gln Pro Gly Ile Leu Ser Val Ser His Ser Ala Gln Pro Pro Ala His
            500                 505                 510

Gln Pro Pro Met Ile Ser Thr Lys Tyr Pro Glu Leu Phe Pro Ala His
            515                 520                 525
```

-continued

```
Gln Ser Pro Met Phe Pro Asp Thr Arg Val Ala Gly Thr Gln Thr Thr
    530             535             540
```

```
Thr His Leu Pro Gly Ile Pro Pro Asn His Ala Pro Leu Val Thr Thr
545             550             555             560
```

```
Leu Gly Ala Gln Leu Pro Pro Gln Ala Pro Asp Ala Leu Val Leu Arg
            565             570             575
```

```
Thr Gln Ala Thr Gln Leu Pro Ile Ile Pro Thr Ala Gln Pro Ser Leu
            580             585             590
```

```
Thr Thr Thr Ser Arg Ser Pro Val Ser Pro Ala His Gln Ile Ser Val
            595             600             605
```

```
Pro Ala Ala Thr Gln Pro Ala Ala Leu Pro Thr Leu Leu Pro Ser Gln
    610             615             620
```

```
Ser Pro Thr Asn Gln Thr Ser Pro Ile Ser Pro Thr His Pro His Ser
625             630             635             640
```

```
Lys Ala Pro Gln Ile Pro Arg Glu Asp Gly Pro Ser Pro Lys Leu Ala
            645             650             655
```

```
Leu Trp Leu Pro Ser Pro Ala Pro Thr Ala Ala Pro Thr Ala Leu Gly
            660             665             670
```

```
Glu Ala Gly Leu Ala Glu His Ser Gln Arg Asp Asp Arg Trp Leu Leu
            675             680             685
```

```
Val Ala Leu Leu Val Pro Thr Cys Val Phe Leu Val Val Leu Leu Ala
    690             695             700
```

```
Leu Gly Ile Val Tyr Cys Thr Arg Cys Gly Pro His Ala Pro Asn Lys
705             710             715             720
```

```
Arg Ile Thr Asp Cys Tyr Arg Trp Val Ile His Ala Gly Ser Lys Ser
            725             730             735
```

```
Pro Thr Glu Pro Met Pro Pro Arg Gly Ser Leu Thr Gly Val Gln Thr
            740             745             750
```

```
Cys Arg Thr Ser Val
        755
```

```
<210> SEQ ID NO 93
<211> LENGTH: 770
<212> TYPE: PRT
<213> ORGANISM: Artificial Sequence
<220> FEATURE:
<223> OTHER INFORMATION: Synthetic_A4_HUMAN
```

```
<400> SEQUENCE: 93
```

```
Met Leu Pro Gly Leu Ala Leu Leu Leu Leu Ala Ala Trp Thr Ala Arg
1               5               10              15
```

```
Ala Leu Glu Val Pro Thr Asp Gly Asn Ala Gly Leu Leu Ala Glu Pro
            20              25              30
```

```
Gln Ile Ala Met Phe Cys Gly Arg Leu Asn Met His Met Asn Val Gln
        35              40              45
```

```
Asn Gly Lys Trp Asp Ser Asp Pro Ser Gly Thr Lys Thr Cys Ile Asp
    50              55              60
```

```
Thr Lys Glu Gly Ile Leu Gln Tyr Cys Gln Glu Val Tyr Pro Glu Leu
65              70              75              80
```

```
Gln Ile Thr Asn Val Val Glu Ala Asn Gln Pro Val Thr Ile Gln Asn
            85              90              95
```

```
Trp Cys Lys Arg Gly Arg Lys Gln Cys Lys Thr His Pro His Phe Val
            100             105             110
```

```
Ile Pro Tyr Arg Cys Leu Val Gly Glu Phe Val Ser Asp Ala Leu Leu
            115             120             125
```

```
Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
                180                 185                 190

Ser Asp Asn Val Asp Ser Ala Asp Ala Glu Glu Asp Asp Ser Asp Val
                195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
                260                 265                 270

Ala Thr Thr Thr Thr Thr Thr Thr Glu Ser Val Glu Glu Val Val Arg
                275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
                340                 345                 350

Thr Gln Glu Pro Leu Ala Arg Asp Pro Val Lys Leu Pro Thr Thr Ala
                355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
                420                 425                 430

Gln His Phe Gln Glu Lys Val Glu Ser Leu Glu Gln Glu Ala Ala Asn
    435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
                500                 505                 510

Glu His Val Arg Met Val Asp Pro Lys Lys Ala Ala Gln Ile Arg Ser
    515                 520                 525

Gln Val Met Thr His Leu Arg Val Ile Tyr Glu Arg Met Asn Gln Ser
    530                 535                 540
```

```
Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
                580                 585                 590

Leu Met Pro Ser Leu Thr Glu Thr Lys Thr Thr Val Glu Leu Leu Pro
                595                 600                 605

Val Asn Gly Glu Phe Ser Leu Asp Asp Leu Gln Pro Trp His Ser Phe
                610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
                660                 665                 670

Ala Glu Phe Arg His Asp Ser Gly Tyr Glu Val His His Gln Lys Leu
                675                 680                 685

Val Phe Phe Ala Glu Asp Val Gly Ser Asn Lys Gly Ala Ile Ile Gly
                690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
                740                 745                 750

Gln Gln Asn Gly Tyr Glu Asn Pro Thr Tyr Lys Phe Phe Glu Gln Met
                755                 760                 765

Gln Asn
770
```

```
<210> SEQ ID NO 94
<211> LENGTH: 780
<212> TYPE: PRT
<213> ORGANISM: Artificial Sequence
<220> FEATURE:
<223> OTHER INFORMATION: Synthetic_ASAH2_HUMAN

<400> SEQUENCE: 94
```

```
Met Ala Lys Arg Thr Phe Ser Asn Leu Glu Thr Phe Leu Ile Phe Leu
1                 5                   10                  15

Leu Val Met Met Ser Ala Ile Thr Val Ala Leu Leu Ser Leu Leu Phe
                20                  25                  30

Ile Thr Ser Gly Thr Ile Glu Asn His Lys Asp Leu Gly Gly His Phe
                35                  40                  45

Phe Ser Thr Thr Gln Ser Pro Pro Ala Thr Gln Gly Ser Thr Ala Ala
                50                  55                  60

Gln Arg Ser Thr Ala Thr Gln His Ser Thr Ala Thr Gln Ser Ser Thr
65                  70                  75                  80

Ala Thr Gln Thr Ser Pro Val Pro Leu Thr Pro Glu Ser Pro Leu Phe
                85                  90                  95

Gln Asn Phe Ser Gly Tyr His Ile Gly Val Gly Arg Ala Asp Cys Thr
                100                 105                 110

Gly Gln Val Ala Asp Ile Asn Leu Met Gly Tyr Gly Lys Ser Gly Gln
                115                 120                 125
```

-continued

```
Asn Ala Gln Gly Ile Leu Thr Arg Leu Tyr Ser Arg Ala Phe Ile Met
    130                 135                 140

Ala Glu Pro Asp Gly Ser Asn Arg Thr Val Phe Val Ser Ile Asp Ile
145                 150                 155                 160

Gly Met Val Ser Gln Arg Leu Arg Leu Glu Val Leu Asn Arg Leu Gln
                165                 170                 175

Ser Lys Tyr Gly Ser Leu Tyr Arg Arg Asp Asn Val Ile Leu Ser Gly
                180                 185                 190

Thr His Thr His Ser Gly Pro Ala Gly Tyr Phe Gln Tyr Thr Val Phe
                195                 200                 205

Val Ile Ala Ser Glu Gly Phe Ser Asn Gln Thr Phe Gln His Met Val
    210                 215                 220

Thr Gly Ile Leu Lys Ser Ile Asp Ile Ala His Thr Asn Met Lys Pro
225                 230                 235                 240

Gly Lys Ile Phe Ile Asn Lys Gly Asn Val Asp Gly Val Gln Ile Asn
                245                 250                 255

Arg Ser Pro Tyr Ser Tyr Leu Gln Asn Pro Gln Ser Glu Arg Ala Arg
                260                 265                 270

Tyr Ser Ser Asn Thr Asp Lys Glu Met Ile Val Leu Lys Met Val Asp
                275                 280                 285

Leu Asn Gly Asp Asp Leu Gly Leu Ile Ser Trp Phe Ala Ile His Pro
    290                 295                 300

Val Ser Met Asn Asn Ser Asn His Leu Val Asn Ser Asp Asn Val Gly
305                 310                 315                 320

Tyr Ala Ser Tyr Leu Leu Glu Gln Glu Lys Asn Lys Gly Tyr Leu Pro
                325                 330                 335

Gly Gln Gly Pro Phe Val Ala Ala Phe Ala Ser Ser Asn Leu Gly Asp
                340                 345                 350

Val Ser Pro Asn Ile Leu Gly Pro Arg Cys Ile Asn Thr Gly Glu Ser
                355                 360                 365

Cys Asp Asn Ala Asn Ser Thr Cys Pro Ile Gly Gly Pro Ser Met Cys
    370                 375                 380

Ile Ala Lys Gly Pro Gly Gln Asp Met Phe Asp Ser Thr Gln Ile Ile
385                 390                 395                 400

Gly Arg Ala Met Tyr Gln Arg Ala Lys Glu Leu Tyr Ala Ser Ala Ser
                405                 410                 415

Gln Glu Val Thr Gly Pro Leu Ala Ser Ala His Gln Trp Val Asp Met
                420                 425                 430

Thr Asp Val Thr Val Trp Leu Asn Ser Thr His Ala Ser Lys Thr Cys
                435                 440                 445

Lys Pro Ala Leu Gly Tyr Ser Phe Ala Ala Gly Thr Ile Asp Gly Val
    450                 455                 460

Gly Gly Leu Asn Phe Thr Gln Gly Lys Thr Glu Gly Asp Pro Phe Trp
465                 470                 475                 480

Asp Thr Ile Arg Asp Gln Ile Leu Gly Lys Pro Ser Glu Glu Ile Lys
                485                 490                 495

Glu Cys His Lys Pro Lys Pro Ile Leu Leu His Thr Gly Glu Leu Ser
                500                 505                 510

Lys Pro His Pro Trp His Pro Asp Ile Val Asp Val Gln Ile Ile Thr
                515                 520                 525

Leu Gly Ser Leu Ala Ile Thr Ala Ile Pro Gly Glu Phe Thr Thr Met
    530                 535                 540

Ser Gly Arg Arg Leu Arg Glu Ala Val Gln Ala Glu Phe Ala Ser His
```

```
545              550              555              560

Gly Met Gln Asn Met Thr Val Val Ile Ser Gly Leu Cys Asn Val Tyr
            565              570              575

Thr His Tyr Ile Thr Thr Tyr Glu Glu Tyr Gln Ala Gln Arg Tyr Glu
            580              585              590

Ala Ala Ser Thr Ile Tyr Gly Pro His Thr Leu Ser Ala Tyr Ile Gln
            595              600              605

Leu Phe Arg Asn Leu Ala Lys Ala Ile Ala Thr Asp Thr Val Ala Asn
            610              615              620

Leu Ser Arg Gly Pro Glu Pro Pro Phe Phe Lys Gln Leu Ile Val Pro
625              630              635              640

Leu Ile Pro Ser Ile Val Asp Arg Ala Pro Lys Gly Arg Thr Phe Gly
            645              650              655

Asp Val Leu Gln Pro Ala Lys Pro Glu Tyr Arg Val Gly Glu Val Ala
            660              665              670

Glu Val Ile Phe Val Gly Ala Asn Pro Lys Asn Ser Val Gln Asn Gln
            675              680              685

Thr His Gln Thr Phe Leu Thr Val Glu Lys Tyr Glu Ala Thr Ser Thr
            690              695              700

Ser Trp Gln Ile Val Cys Asn Asp Ala Ser Trp Glu Thr Arg Phe Tyr
705              710              715              720

Trp His Lys Gly Leu Leu Gly Leu Ser Asn Ala Thr Val Glu Trp His
            725              730              735

Ile Pro Asp Thr Ala Gln Pro Gly Ile Tyr Arg Ile Arg Tyr Phe Gly
            740              745              750

His Asn Arg Lys Gln Asp Ile Leu Lys Pro Ala Val Ile Leu Ser Phe
            755              760              765

Glu Gly Thr Ser Pro Ala Phe Glu Val Val Thr Ile
            770              775              780

<210> SEQ ID NO 95
<211> LENGTH: 785
<212> TYPE: PRT
<213> ORGANISM: Artificial Sequence
<220> FEATURE:
<223> OTHER INFORMATION: Synthetic_SP1_HUMAN

<400> SEQUENCE: 95

Met Ser Asp Gln Asp His Ser Met Asp Glu Met Thr Ala Val Val Lys
1               5               10              15

Ile Glu Lys Gly Val Gly Gly Asn Asn Gly Gly Asn Gly Asn Gly Gly
            20              25              30

Gly Ala Phe Ser Gln Ala Arg Ser Ser Ser Thr Gly Ser Ser Ser Ser
            35              40              45

Thr Gly Gly Gly Gln Glu Ser Gln Pro Ser Pro Leu Ala Leu Leu
            50              55              60

Ala Ala Thr Cys Ser Arg Ile Glu Ser Pro Asn Glu Asn Ser Asn Asn
65              70              75              80

Ser Gln Gly Pro Ser Gln Ser Gly Gly Thr Gly Glu Leu Asp Leu Thr
            85              90              95

Ala Thr Gln Leu Ser Gln Gly Ala Asn Gly Trp Gln Ile Ile Ser Ser
            100             105             110

Ser Ser Gly Ala Thr Pro Thr Ser Lys Glu Gln Ser Gly Ser Ser Thr
            115             120             125

Asn Gly Ser Asn Gly Ser Glu Ser Ser Lys Asn Arg Thr Val Ser Gly
```

-continued

```
        130                135                140

Gly Gln Tyr Val Val Ala Ala Ala Pro Asn Leu Gln Asn Gln Gln Val
145                150                155                160

Leu Thr Gly Leu Pro Gly Val Met Pro Asn Ile Gln Tyr Gln Val Ile
                165                170                175

Pro Gln Phe Gln Thr Val Asp Gly Gln Gln Leu Gln Phe Ala Ala Thr
                180                185                190

Gly Ala Gln Val Gln Gln Asp Gly Ser Gly Gln Ile Gln Ile Ile Pro
                195                200                205

Gly Ala Asn Gln Gln Ile Ile Thr Asn Arg Gly Ser Gly Gly Asn Ile
        210                215                220

Ile Ala Ala Met Pro Asn Leu Leu Gln Gln Ala Val Pro Leu Gln Gly
225                230                235                240

Leu Ala Asn Asn Val Leu Ser Gly Gln Thr Gln Tyr Val Thr Asn Val
                245                250                255

Pro Val Ala Leu Asn Gly Asn Ile Thr Leu Leu Pro Val Asn Ser Val
                260                265                270

Ser Ala Ala Thr Leu Thr Pro Ser Ser Gln Ala Val Thr Ile Ser Ser
                275                280                285

Ser Gly Ser Gln Glu Ser Gly Ser Gln Pro Val Thr Ser Gly Thr Thr
        290                295                300

Ile Ser Ser Ala Ser Leu Val Ser Ser Gln Ala Ser Ser Ser Ser Phe
305                310                315                320

Phe Thr Asn Ala Asn Ser Tyr Ser Thr Thr Thr Thr Thr Ser Asn Met
                325                330                335

Gly Ile Met Asn Phe Thr Thr Ser Gly Ser Ser Gly Thr Asn Ser Gln
                340                345                350

Gly Gln Thr Pro Gln Arg Val Ser Gly Leu Gln Gly Ser Asp Ala Leu
                355                360                365

Asn Ile Gln Gln Asn Gln Thr Ser Gly Gly Ser Leu Gln Ala Gly Gln
        370                375                380

Gln Lys Glu Gly Glu Gln Asn Gln Gln Thr Gln Gln Gln Gln Ile Leu
385                390                395                400

Ile Gln Pro Gln Leu Val Gln Gly Gly Gln Ala Leu Gln Ala Leu Gln
                405                410                415

Ala Ala Pro Leu Ser Gly Gln Thr Phe Thr Thr Gln Ala Ile Ser Gln
                420                425                430

Glu Thr Leu Gln Asn Leu Gln Leu Gln Ala Val Pro Asn Ser Gly Pro
                435                440                445

Ile Ile Ile Arg Thr Pro Thr Val Gly Pro Asn Gly Gln Val Ser Trp
        450                455                460

Gln Thr Leu Gln Leu Gln Asn Leu Gln Val Gln Asn Pro Gln Ala Gln
465                470                475                480

Thr Ile Thr Leu Ala Pro Met Gln Gly Val Ser Leu Gly Gln Thr Ser
                485                490                495

Ser Ser Asn Thr Thr Leu Thr Pro Ile Ala Ser Ala Ala Ser Ile Pro
                500                505                510

Ala Gly Thr Val Thr Val Asn Ala Ala Gln Leu Ser Ser Met Pro Gly
                515                520                525

Leu Gln Thr Ile Asn Leu Ser Ala Leu Gly Thr Ser Gly Ile Gln Val
        530                535                540

His Pro Ile Gln Gly Leu Pro Leu Ala Ile Ala Asn Ala Pro Gly Asp
545                550                555                560
```

```
His Gly Ala Gln Leu Gly Leu His Gly Ala Gly Gly Asp Gly Ile His
            565             570             575

Asp Asp Thr Ala Gly Gly Glu Glu Gly Glu Asn Ser Pro Asp Ala Gln
            580             585             590

Pro Gln Ala Gly Arg Arg Thr Arg Arg Glu Ala Cys Thr Cys Pro Tyr
            595             600             605

Cys Lys Asp Ser Glu Gly Arg Gly Ser Gly Asp Pro Gly Lys Lys Lys
            610             615             620

Gln His Ile Cys His Ile Gln Gly Cys Gly Lys Val Tyr Gly Lys Thr
625                     630             635                     640

Ser His Leu Arg Ala His Leu Arg Trp His Thr Gly Glu Arg Pro Phe
            645             650             655

Met Cys Thr Trp Ser Tyr Cys Gly Lys Arg Phe Thr Arg Ser Asp Glu
            660             665             670

Leu Gln Arg His Lys Arg Thr His Thr Gly Glu Lys Lys Phe Ala Cys
            675             680             685

Pro Glu Cys Pro Lys Arg Phe Met Arg Ser Asp His Leu Ser Lys His
            690             695             700

Ile Lys Thr His Gln Asn Lys Lys Gly Gly Pro Gly Val Ala Leu Ser
705                     710             715                     720

Val Gly Thr Leu Pro Leu Asp Ser Gly Ala Gly Ser Glu Gly Ser Gly
            725             730             735

Thr Ala Thr Pro Ser Ala Leu Ile Thr Thr Asn Met Val Ala Met Glu
            740             745             750

Ala Ile Cys Pro Glu Gly Ile Ala Arg Leu Ala Asn Ser Gly Ile Asn
            755             760             765

Val Met Gln Val Ala Asp Leu Gln Ser Ile Asn Ile Ser Gly Asn Gly
            770             775             780

Phe
785
```

```
<210> SEQ ID NO 96
<211> LENGTH: 797
<212> TYPE: PRT
<213> ORGANISM: Artificial Sequence
<220> FEATURE:
<223> OTHER INFORMATION: Synthetic_IMPG1_HUMAN

<400> SEQUENCE: 96

Met Tyr Leu Glu Thr Arg Arg Ala Ile Phe Val Phe Trp Ile Phe Leu
1               5               10              15

Gln Val Gln Gly Thr Lys Asp Ile Ser Ile Asn Ile Tyr His Ser Glu
            20              25              30

Thr Lys Asp Ile Asp Asn Pro Pro Arg Asn Glu Thr Thr Glu Ser Thr
            35              40              45

Glu Lys Met Tyr Lys Met Ser Thr Met Arg Arg Ile Phe Asp Leu Ala
            50              55              60

Lys His Arg Thr Lys Arg Ser Ala Phe Phe Pro Thr Gly Val Lys Val
65                      70              75                      80

Cys Pro Gln Glu Ser Met Lys Gln Ile Leu Asp Ser Leu Gln Ala Tyr
                85              90              95

Tyr Arg Leu Arg Val Cys Gln Glu Ala Val Trp Glu Ala Tyr Arg Ile
            100             105             110

Phe Leu Asp Arg Ile Pro Asp Thr Gly Glu Tyr Gln Asp Trp Val Ser
            115             120             125
```

```
Ile Cys Gln Gln Glu Thr Phe Cys Leu Phe Asp Ile Gly Lys Asn Phe
130             135             140

Ser Asn Ser Gln Glu His Leu Asp Leu Leu Gln Gln Arg Ile Lys Gln
145             150             155             160

Arg Ser Phe Pro Asp Arg Lys Asp Glu Ile Ser Ala Glu Lys Thr Leu
            165             170             175

Gly Glu Pro Gly Glu Thr Ile Val Ile Ser Thr Asp Val Ala Asn Val
            180             185             190

Ser Leu Gly Pro Phe Pro Leu Thr Pro Asp Asp Thr Leu Leu Asn Glu
            195             200             205

Ile Leu Asp Asn Thr Leu Asn Asp Thr Lys Met Pro Thr Thr Glu Arg
    210             215             220

Glu Thr Glu Phe Ala Val Leu Glu Glu Gln Arg Val Glu Leu Ser Val
225             230             235             240

Ser Leu Val Asn Gln Lys Phe Lys Ala Glu Leu Ala Asp Ser Gln Ser
            245             250             255

Pro Tyr Tyr Gln Glu Leu Ala Gly Lys Ser Gln Leu Gln Met Gln Lys
            260             265             270

Ile Phe Lys Lys Leu Pro Gly Phe Lys Lys Ile His Val Leu Gly Phe
    275             280             285

Arg Pro Lys Lys Glu Lys Asp Gly Ser Ser Ser Thr Glu Met Gln Leu
    290             295             300

Thr Ala Ile Phe Lys Arg His Ser Ala Glu Ala Lys Ser Pro Ala Ser
305             310             315             320

Asp Leu Leu Ser Phe Asp Ser Asn Lys Ile Glu Ser Glu Glu Val Tyr
            325             330             335

His Gly Thr Met Glu Glu Asp Lys Gln Pro Glu Ile Tyr Leu Thr Ala
            340             345             350

Thr Asp Leu Lys Arg Leu Ile Ser Lys Ala Leu Glu Glu Glu Gln Ser
            355             360             365

Leu Asp Val Gly Thr Ile Gln Phe Thr Asp Glu Ile Ala Gly Ser Leu
    370             375             380

Pro Ala Phe Gly Pro Asp Thr Gln Ser Glu Leu Pro Thr Ser Phe Ala
385             390             395             400

Val Ile Thr Glu Asp Ala Thr Leu Ser Pro Glu Leu Pro Pro Val Glu
            405             410             415

Pro Gln Leu Glu Thr Val Asp Gly Ala Glu His Gly Leu Pro Asp Thr
            420             425             430

Ser Trp Ser Pro Pro Ala Met Ala Ser Thr Ser Leu Ser Glu Ala Pro
            435             440             445

Pro Phe Phe Met Ala Ser Ser Ile Phe Ser Leu Thr Asp Gln Gly Thr
            450             455             460

Thr Asp Thr Met Ala Thr Asp Gln Thr Met Leu Val Pro Gly Leu Thr
465             470             475             480

Ile Pro Thr Ser Asp Tyr Ser Ala Ile Ser Gln Leu Ala Leu Gly Ile
            485             490             495

Ser His Pro Pro Ala Ser Ser Asp Asp Ser Arg Ser Ser Ala Gly Gly
            500             505             510

Glu Asp Met Val Arg His Leu Asp Glu Met Asp Leu Ser Asp Thr Pro
            515             520             525

Ala Pro Ser Glu Val Pro Glu Leu Ser Glu Tyr Val Ser Val Pro Asp
    530             535             540
```

-continued

```
His Phe Leu Glu Asp Thr Thr Pro Val Ser Ala Leu Gln Tyr Ile Thr
545             550             555             560

Thr Ser Ser Met Thr Ile Ala Pro Lys Gly Arg Glu Leu Val Val Phe
                565             570             575

Phe Ser Leu Arg Val Ala Asn Met Ala Phe Ser Asn Asp Leu Phe Asn
            580             585             590

Lys Ser Ser Leu Glu Tyr Arg Ala Leu Glu Gln Gln Phe Thr Gln Leu
            595             600             605

Leu Val Pro Tyr Leu Arg Ser Asn Leu Thr Gly Phe Lys Gln Leu Glu
        610             615             620

Ile Leu Asn Phe Arg Asn Gly Ser Val Ile Val Asn Ser Lys Met Lys
625             630             635             640

Phe Ala Lys Ser Val Pro Tyr Asn Leu Thr Lys Ala Val His Gly Val
                645             650             655

Leu Glu Asp Phe Arg Ser Ala Ala Ala Gln Gln Leu His Leu Glu Ile
                660             665             670

Asp Ser Tyr Ser Leu Asn Ile Glu Pro Ala Asp Gln Ala Asp Pro Cys
            675             680             685

Lys Phe Leu Ala Cys Gly Glu Phe Ala Gln Cys Val Lys Asn Glu Arg
        690             695             700

Thr Glu Glu Ala Glu Cys Arg Cys Lys Pro Gly Tyr Asp Ser Gln Gly
705             710             715             720

Ser Leu Asp Gly Leu Glu Pro Gly Leu Cys Gly Pro Gly Thr Lys Glu
                725             730             735

Cys Glu Val Leu Gln Gly Lys Gly Ala Pro Cys Arg Leu Pro Asp His
            740             745             750

Ser Glu Asn Gln Ala Tyr Lys Thr Ser Val Lys Lys Phe Gln Asn Gln
        755             760             765

Gln Asn Asn Lys Val Ile Ser Lys Arg Asn Ser Glu Leu Leu Thr Val
    770             775             780

Glu Tyr Glu Glu Phe Asn His Gln Asp Trp Glu Gly Asn
785             790             795
```

<210> SEQ ID NO 97
<211> LENGTH: 815
<212> TYPE: PRT
<213> ORGANISM: Artificial Sequence
<220> FEATURE:
<223> OTHER INFORMATION: Synthetic_SL9A1_HUMAN

<400> SEQUENCE: 97

```
Met Val Leu Arg Ser Gly Ile Cys Gly Leu Ser Pro His Arg Ile Phe
1               5               10              15

Pro Ser Leu Leu Val Val Val Ala Leu Val Gly Leu Leu Pro Val Leu
            20              25              30

Arg Ser His Gly Leu Gln Leu Ser Pro Thr Ala Ser Thr Ile Arg Ser
        35              40              45

Ser Glu Pro Pro Arg Glu Arg Ser Ile Gly Asp Val Thr Thr Ala Pro
        50              55              60

Pro Glu Val Thr Pro Glu Ser Arg Pro Val Asn His Ser Val Thr Asp
65              70              75              80

His Gly Met Lys Pro Arg Lys Ala Phe Pro Val Leu Gly Ile Asp Tyr
                85              90              95

Thr His Val Arg Thr Pro Phe Glu Ile Ser Leu Trp Ile Leu Leu Ala
            100             105             110
```

-continued

```
Cys Leu Met Lys Ile Gly Phe His Val Ile Pro Thr Ile Ser Ser Ile
        115             120             125

Val Pro Glu Ser Cys Leu Leu Ile Val Val Gly Leu Leu Val Gly Gly
    130             135             140

Leu Ile Lys Gly Val Gly Glu Thr Pro Pro Phe Leu Gln Ser Asp Val
145             150             155             160

Phe Phe Leu Phe Leu Leu Pro Pro Ile Ile Leu Asp Ala Gly Tyr Phe
                165             170             175

Leu Pro Leu Arg Gln Phe Thr Glu Asn Leu Gly Thr Ile Leu Ile Phe
            180             185             190

Ala Val Val Gly Thr Leu Trp Asn Ala Phe Phe Leu Gly Gly Leu Met
            195             200             205

Tyr Ala Val Cys Leu Val Gly Gly Glu Gln Ile Asn Asn Ile Gly Leu
    210             215             220

Leu Asp Asn Leu Leu Phe Gly Ser Ile Ile Ser Ala Val Asp Pro Val
225             230             235             240

Ala Val Leu Ala Val Phe Glu Glu Ile His Ile Asn Glu Leu Leu His
            245             250             255

Ile Leu Val Phe Gly Glu Ser Leu Leu Asn Asp Ala Val Thr Val Val
            260             265             270

Leu Tyr His Leu Phe Glu Glu Phe Ala Asn Tyr Glu His Val Gly Ile
    275             280             285

Val Asp Ile Phe Leu Gly Phe Leu Ser Phe Phe Val Val Ala Leu Gly
    290             295             300

Gly Val Leu Val Gly Val Val Tyr Gly Val Ile Ala Ala Phe Thr Ser
305             310             315             320

Arg Phe Thr Ser His Ile Arg Val Ile Glu Pro Leu Phe Val Phe Leu
            325             330             335

Tyr Ser Tyr Met Ala Tyr Leu Ser Ala Glu Leu Phe His Leu Ser Gly
            340             345             350

Ile Met Ala Leu Ile Ala Ser Gly Val Val Met Arg Pro Tyr Val Glu
    355             360             365

Ala Asn Ile Ser His Lys Ser His Thr Thr Ile Lys Tyr Phe Leu Lys
    370             375             380

Met Trp Ser Ser Val Ser Glu Thr Leu Ile Phe Ile Phe Leu Gly Val
385             390             395             400

Ser Thr Val Ala Gly Ser His His Trp Asn Trp Thr Phe Val Ile Ser
            405             410             415

Thr Leu Leu Phe Cys Leu Ile Ala Arg Val Leu Gly Val Leu Gly Leu
            420             425             430

Thr Trp Phe Ile Asn Lys Phe Arg Ile Val Lys Leu Thr Pro Lys Asp
        435             440             445

Gln Phe Ile Ile Ala Tyr Gly Gly Leu Arg Gly Ala Ile Ala Phe Ser
    450             455             460

Leu Gly Tyr Leu Leu Asp Lys Lys His Phe Pro Met Cys Asp Leu Phe
465             470             475             480

Leu Thr Ala Ile Ile Thr Val Ile Phe Phe Thr Val Phe Val Gln Gly
            485             490             495

Met Thr Ile Arg Pro Leu Val Asp Leu Leu Ala Val Lys Lys Lys Gln
        500             505             510

Glu Thr Lys Arg Ser Ile Asn Glu Glu Ile His Thr Gln Phe Leu Asp
        515             520             525

His Leu Leu Thr Gly Ile Glu Asp Ile Cys Gly His Tyr Gly His His
```

-continued

```
        530                 535                 540
His Trp Lys Asp Lys Leu Asn Arg Phe Asn Lys Lys Tyr Val Lys Lys
545                 550                 555                 560

Cys Leu Ile Ala Gly Glu Arg Ser Lys Glu Pro Gln Leu Ile Ala Phe
                565                 570                 575

Tyr His Lys Met Glu Met Lys Gln Ala Ile Glu Leu Val Glu Ser Gly
                580                 585                 590

Gly Met Gly Lys Ile Pro Ser Ala Val Ser Thr Val Ser Met Gln Asn
                595                 600                 605

Ile His Pro Lys Ser Leu Pro Ser Glu Arg Ile Leu Pro Ala Leu Ser
                610                 615                 620

Lys Asp Lys Glu Glu Glu Ile Arg Lys Ile Leu Arg Asn Asn Leu Gln
625                 630                 635                 640

Lys Thr Arg Gln Arg Leu Arg Ser Tyr Asn Arg His Thr Leu Val Ala
                645                 650                 655

Asp Pro Tyr Glu Glu Ala Trp Asn Gln Met Leu Leu Arg Arg Gln Lys
                660                 665                 670

Ala Arg Gln Leu Glu Gln Lys Ile Asn Asn Tyr Leu Thr Val Pro Ala
                675                 680                 685

His Lys Leu Asp Ser Pro Thr Met Ser Arg Ala Arg Ile Gly Ser Asp
                690                 695                 700

Pro Leu Ala Tyr Glu Pro Lys Glu Asp Leu Pro Val Ile Thr Ile Asp
705                 710                 715                 720

Pro Ala Ser Pro Gln Ser Pro Glu Ser Val Asp Leu Val Asn Glu Glu
                725                 730                 735

Leu Lys Gly Lys Val Leu Gly Leu Ser Arg Asp Pro Ala Lys Val Ala
                740                 745                 750

Glu Glu Asp Glu Asp Asp Asp Gly Gly Ile Met Met Arg Ser Lys Glu
                755                 760                 765

Thr Ser Ser Pro Gly Thr Asp Asp Val Phe Thr Pro Ala Pro Ser Asp
                770                 775                 780

Ser Pro Ser Ser Gln Arg Ile Gln Arg Cys Leu Ser Asp Pro Gly Pro
785                 790                 795                 800

His Pro Glu Pro Gly Glu Gly Glu Pro Phe Phe Pro Lys Gly Gln
                805                 810                 815
```

<210> SEQ ID NO 98
<211> LENGTH: 882
<212> TYPE: PRT
<213> ORGANISM: Artificial Sequence
<220> FEATURE:
<223> OTHER INFORMATION: Synthetic_CADH1_HUMAN

<400> SEQUENCE: 98

```
Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
                20                  25                  30

Asp Ala Glu Ser Tyr Thr Phe Thr Val Pro Arg Arg His Leu Glu Arg
                35                  40                  45

Gly Arg Val Leu Gly Arg Val Asn Phe Glu Asp Cys Thr Gly Arg Gln
                50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
```

-continued

```
                85                    90                    95

His Phe Leu Val Tyr Ala Trp Asp Ser Thr Tyr Arg Lys Phe Ser Thr
            100                   105                   110

Lys Val Thr Leu Asn Thr Val Gly His His His Arg Pro Pro Pro His
            115                   120                   125

Gln Ala Ser Val Ser Gly Ile Gln Ala Glu Leu Leu Thr Phe Pro Asn
            130                   135                   140

Ser Ser Pro Gly Leu Arg Arg Gln Lys Arg Asp Trp Val Ile Pro Pro
145                   150                   155                   160

Ile Ser Cys Pro Glu Asn Glu Lys Gly Pro Phe Pro Lys Asn Leu Val
                165                   170                   175

Gln Ile Lys Ser Asn Lys Asp Lys Glu Gly Lys Val Phe Tyr Ser Ile
            180                   185                   190

Thr Gly Gln Gly Ala Asp Thr Pro Pro Val Gly Val Phe Ile Ile Glu
            195                   200                   205

Arg Glu Thr Gly Trp Leu Lys Val Thr Glu Pro Leu Asp Arg Glu Arg
            210                   215                   220

Ile Ala Thr Tyr Thr Leu Phe Ser His Ala Val Ser Ser Asn Gly Asn
225                   230                   235                   240

Ala Val Glu Asp Pro Met Glu Ile Leu Ile Thr Val Thr Asp Gln Asn
                245                   250                   255

Asp Asn Lys Pro Glu Phe Thr Gln Glu Val Phe Lys Gly Ser Val Met
                260                   265                   270

Glu Gly Ala Leu Pro Gly Thr Ser Val Met Glu Val Thr Ala Thr Asp
            275                   280                   285

Ala Asp Asp Asp Val Asn Thr Tyr Asn Ala Ala Ile Ala Tyr Thr Ile
            290                   295                   300

Leu Ser Gln Asp Pro Glu Leu Pro Asp Lys Asn Met Phe Thr Ile Asn
305                   310                   315                   320

Arg Asn Thr Gly Val Ile Ser Val Val Thr Thr Gly Leu Asp Arg Glu
                325                   330                   335

Ser Phe Pro Thr Tyr Thr Leu Val Val Gln Ala Ala Asp Leu Gln Gly
            340                   345                   350

Glu Gly Leu Ser Thr Thr Ala Thr Ala Val Ile Thr Val Thr Asp Thr
            355                   360                   365

Asn Asp Asn Pro Pro Ile Phe Asn Pro Thr Thr Tyr Lys Gly Gln Val
            370                   375                   380

Pro Glu Asn Glu Ala Asn Val Val Ile Thr Thr Leu Lys Val Thr Asp
385                   390                   395                   400

Ala Asp Ala Pro Asn Thr Pro Ala Trp Glu Ala Val Tyr Thr Ile Leu
                405                   410                   415

Asn Asp Asp Gly Gly Gln Phe Val Val Thr Thr Asn Pro Val Asn Asn
            420                   425                   430

Asp Gly Ile Leu Lys Thr Ala Lys Gly Leu Asp Phe Glu Ala Lys Gln
            435                   440                   445

Gln Tyr Ile Leu His Val Ala Val Thr Asn Val Val Pro Phe Glu Val
            450                   455                   460

Ser Leu Thr Thr Ser Thr Ala Thr Val Thr Val Asp Val Leu Asp Val
465                   470                   475                   480

Asn Glu Ala Pro Ile Phe Val Pro Pro Glu Lys Arg Val Glu Val Ser
                485                   490                   495

Glu Asp Phe Gly Val Gly Gln Glu Ile Thr Ser Tyr Thr Ala Gln Glu
            500                   505                   510
```

```
Pro Asp Thr Phe Met Glu Gln Lys Ile Thr Tyr Arg Ile Trp Arg Asp
        515                 520                 525

Thr Ala Asn Trp Leu Glu Ile Asn Pro Asp Thr Gly Ala Ile Ser Thr
    530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
            565                 570                 575

Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
        595                 600                 605

Pro Gln Val Ile Asn Ile Ile Asp Ala Asp Leu Pro Pro Asn Thr Ser
        610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
            645                 650                 655

Ala Leu Glu Val Gly Asp Tyr Lys Ile Asn Leu Lys Leu Met Asp Asn
            660                 665                 670

Gln Asn Lys Asp Gln Val Thr Thr Leu Glu Val Ser Val Cys Asp Cys
        675                 680                 685

Glu Gly Ala Ala Gly Val Cys Arg Lys Ala Gln Pro Val Glu Ala Gly
        690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Leu Phe Leu Arg Arg Arg Ala Val
            725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Gly Glu Glu Asp Gln Asp Phe Asp
            755                 760                 765

Leu Ser Gln Leu His Arg Gly Leu Asp Ala Arg Pro Glu Val Thr Arg
        770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
            805                 810                 815

Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
            835                 840                 845

Asn Ser Ser Glu Ser Asp Lys Asp Gln Asp Tyr Asp Tyr Leu Asn Glu
        850                 855                 860

Trp Gly Asn Arg Phe Lys Lys Leu Ala Asp Met Tyr Gly Gly Gly Glu
865                 870                 875                 880

Asp Asp
```

<210> SEQ ID NO 99
<211> LENGTH: 895
<212> TYPE: PRT
<213> ORGANISM: Artificial Sequence
<220> FEATURE:
<223> OTHER INFORMATION: Synthetic_DAG1_HUMAN

```
<400> SEQUENCE: 99

Met Arg Met Ser Val Gly Leu Ser Leu Leu Pro Leu Ser Gly Arg
1               5                   10                  15

Thr Phe Leu Leu Leu Leu Ser Val Val Met Ala Gln Ser His Trp Pro
            20                  25                  30

Ser Glu Pro Ser Glu Ala Val Arg Asp Trp Glu Asn Gln Leu Glu Ala
        35                  40                  45

Ser Met His Ser Val Leu Ser Asp Leu His Glu Ala Val Pro Thr Val
    50                  55                  60

Val Gly Ile Pro Asp Gly Thr Ala Val Val Gly Arg Ser Phe Arg Val
65                  70                  75                  80

Thr Ile Pro Thr Asp Leu Ile Ala Ser Ser Gly Asp Ile Ile Lys Val
            85                  90                  95

Ser Ala Ala Gly Lys Glu Ala Leu Pro Ser Trp Leu His Trp Asp Ser
            100                 105                 110

Gln Ser His Thr Leu Glu Gly Leu Pro Leu Asp Thr Asp Lys Gly Val
        115                 120                 125

His Tyr Ile Ser Val Ser Ala Thr Arg Leu Gly Ala Asn Gly Ser His
    130                 135                 140

Ile Pro Gln Thr Ser Ser Val Phe Ser Ile Glu Val Tyr Pro Glu Asp
145                 150                 155                 160

His Ser Glu Leu Gln Ser Val Arg Thr Ala Ser Pro Asp Pro Gly Glu
                165                 170                 175

Val Val Ser Ser Ala Cys Ala Ala Asp Glu Pro Val Thr Val Leu Thr
            180                 185                 190

Val Ile Leu Asp Ala Asp Leu Thr Lys Met Thr Pro Lys Gln Arg Ile
            195                 200                 205

Asp Leu Leu His Arg Met Arg Ser Phe Ser Glu Val Glu Leu His Asn
    210                 215                 220

Met Lys Leu Val Pro Val Val Asn Asn Arg Leu Phe Asp Met Ser Ala
225                 230                 235                 240

Phe Met Ala Gly Pro Gly Asn Ala Lys Lys Val Val Glu Asn Gly Ala
                245                 250                 255

Leu Leu Ser Trp Lys Leu Gly Cys Ser Leu Asn Gln Asn Ser Val Pro
            260                 265                 270

Asp Ile His Gly Val Glu Ala Pro Ala Arg Glu Gly Ala Met Ser Ala
            275                 280                 285

Gln Leu Gly Tyr Pro Val Val Gly Trp His Ile Ala Asn Lys Lys Pro
    290                 295                 300

Pro Leu Pro Lys Arg Val Arg Arg Gln Ile His Ala Thr Pro Thr Pro
305                 310                 315                 320

Val Thr Ala Ile Gly Pro Pro Thr Thr Ala Ile Gln Glu Pro Pro Ser
            325                 330                 335

Arg Ile Val Pro Thr Pro Thr Ser Pro Ala Ile Ala Pro Pro Thr Glu
            340                 345                 350

Thr Met Ala Pro Pro Val Arg Asp Pro Val Pro Gly Lys Pro Thr Val
            355                 360                 365

Thr Ile Arg Thr Arg Gly Ala Ile Ile Gln Thr Pro Thr Leu Gly Pro
    370                 375                 380

Ile Gln Pro Thr Arg Val Ser Glu Ala Gly Thr Thr Val Pro Gly Gln
385                 390                 395                 400

Ile Arg Pro Thr Met Thr Ile Pro Gly Tyr Val Glu Pro Thr Ala Val
```

-continued

```
                405                 410                 415
Ala Thr Pro Pro Thr Thr Thr Thr Lys Lys Pro Arg Val Ser Thr Pro
            420                 425                 430

Lys Pro Ala Thr Pro Ser Thr Asp Ser Thr Thr Thr Thr Thr Arg Arg
            435                 440                 445

Pro Thr Lys Lys Pro Arg Thr Pro Arg Pro Val Pro Arg Val Thr Thr
    450                 455                 460

Lys Val Ser Ile Thr Arg Leu Glu Thr Ala Ser Pro Pro Thr Arg Ile
465                 470                 475                 480

Arg Thr Thr Thr Ser Gly Val Pro Arg Gly Gly Glu Pro Asn Gln Arg
                485                 490                 495

Pro Glu Leu Lys Asn His Ile Asp Arg Val Asp Ala Trp Val Gly Thr
            500                 505                 510

Tyr Phe Glu Val Lys Ile Pro Ser Asp Thr Phe Tyr Asp His Glu Asp
            515                 520                 525

Thr Thr Thr Asp Lys Leu Lys Leu Thr Leu Lys Leu Arg Glu Gln Gln
    530                 535                 540

Leu Val Gly Glu Lys Ser Trp Val Gln Phe Asn Ser Asn Ser Gln Leu
545                 550                 555                 560

Met Tyr Gly Leu Pro Asp Ser Ser His Val Gly Lys His Glu Tyr Phe
                565                 570                 575

Met His Ala Thr Asp Lys Gly Gly Leu Ser Ala Val Asp Ala Phe Glu
                580                 585                 590

Ile His Val His Arg Arg Pro Gln Gly Asp Arg Ala Pro Ala Arg Phe
            595                 600                 605

Lys Ala Lys Phe Val Gly Asp Pro Ala Leu Val Leu Asn Asp Ile His
    610                 615                 620

Lys Lys Ile Ala Leu Val Lys Lys Leu Ala Phe Ala Phe Gly Asp Arg
625                 630                 635                 640

Asn Cys Ser Thr Ile Thr Leu Gln Asn Ile Thr Arg Gly Ser Ile Val
                645                 650                 655

Val Glu Trp Thr Asn Asn Thr Leu Pro Leu Glu Pro Cys Pro Lys Glu
                660                 665                 670

Gln Ile Ala Gly Leu Ser Arg Arg Ile Ala Glu Asp Asp Gly Lys Pro
            675                 680                 685

Arg Pro Ala Phe Ser Asn Ala Leu Glu Pro Asp Phe Lys Ala Thr Ser
    690                 695                 700

Ile Thr Val Thr Gly Ser Gly Ser Cys Arg His Leu Gln Phe Ile Pro
705                 710                 715                 720

Val Val Pro Pro Arg Arg Val Pro Ser Glu Ala Pro Pro Thr Glu Val
                725                 730                 735

Pro Asp Arg Asp Pro Glu Lys Ser Ser Glu Asp Asp Val Tyr Leu His
            740                 745                 750

Thr Val Ile Pro Ala Val Val Val Ala Ala Ile Leu Leu Ile Ala Gly
            755                 760                 765

Ile Ile Ala Met Ile Cys Tyr Arg Lys Lys Arg Lys Gly Lys Leu Thr
    770                 775                 780

Leu Glu Asp Gln Ala Thr Phe Ile Lys Lys Gly Val Pro Ile Ile Phe
785                 790                 795                 800

Ala Asp Glu Leu Asp Asp Ser Lys Pro Pro Pro Ser Ser Ser Met Pro
                805                 810                 815

Leu Ile Leu Gln Glu Glu Lys Ala Pro Leu Pro Pro Pro Glu Tyr Pro
            820                 825                 830
```

```
Asn Gln Ser Val Pro Glu Thr Thr Pro Leu Asn Gln Asp Thr Met Gly
        835                 840                 845

Glu Tyr Thr Pro Leu Arg Asp Glu Asp Pro Asn Ala Pro Pro Tyr Gln
    850                 855                 860

Pro Pro Pro Pro Phe Thr Ala Pro Met Glu Gly Lys Gly Ser Arg Pro
865                 870                 875                 880

Lys Asn Met Thr Pro Tyr Arg Ser Pro Pro Pro Tyr Val Pro Pro
            885                 890                 895

<210> SEQ ID NO 100
<211> LENGTH: 930
<212> TYPE: PRT
<213> ORGANISM: Artificial Sequence
<220> FEATURE:
<223> OTHER INFORMATION: Synthetic_ITIH4_HUMAN

<400> SEQUENCE: 100

Met Lys Pro Pro Arg Pro Val Arg Thr Cys Ser Lys Val Leu Val Leu
1               5                   10                  15

Leu Ser Leu Leu Ala Ile His Gln Thr Thr Thr Ala Glu Lys Asn Gly
            20                  25                  30

Ile Asp Ile Tyr Ser Leu Thr Val Asp Ser Arg Val Ser Ser Arg Phe
        35                  40                  45

Ala His Thr Val Val Thr Ser Arg Val Val Asn Arg Ala Asn Thr Val
    50                  55                  60

Gln Glu Ala Thr Phe Gln Met Glu Leu Pro Lys Lys Ala Phe Ile Thr
65                  70                  75                  80

Asn Phe Ser Met Ile Ile Asp Gly Met Thr Tyr Pro Gly Ile Ile Lys
            85                  90                  95

Glu Lys Ala Glu Ala Gln Ala Gln Tyr Ser Ala Ala Val Ala Lys Gly
            100                 105                 110

Lys Ser Ala Gly Leu Val Lys Ala Thr Gly Arg Asn Met Glu Gln Phe
            115                 120                 125

Gln Val Ser Val Ser Val Ala Pro Asn Ala Lys Ile Thr Phe Glu Leu
    130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
            165                 170                 175

His Ile Phe Glu Pro Gln Gly Ile Ser Phe Leu Glu Thr Glu Ser Thr
            180                 185                 190

Phe Met Thr Asn Gln Leu Val Asp Ala Leu Thr Thr Trp Gln Asn Lys
            195                 200                 205

Thr Lys Ala His Ile Arg Phe Lys Pro Thr Leu Ser Gln Gln Gln Lys
    210                 215                 220

Ser Pro Glu Gln Gln Glu Thr Val Leu Asp Gly Asn Leu Ile Ile Arg
225                 230                 235                 240

Tyr Asp Val Asp Arg Ala Ile Ser Gly Gly Ser Ile Gln Ile Glu Asn
            245                 250                 255

Gly Tyr Phe Val His Tyr Phe Ala Pro Glu Gly Leu Thr Thr Met Pro
            260                 265                 270

Lys Asn Val Val Phe Val Ile Asp Lys Ser Gly Ser Met Ser Gly Arg
            275                 280                 285

Lys Ile Gln Gln Thr Arg Glu Ala Leu Ile Lys Ile Leu Asp Asp Leu
    290                 295                 300
```

```
Ser Pro Arg Asp Gln Phe Asn Leu Ile Val Phe Ser Thr Glu Ala Thr
305                 310                 315                 320

Gln Trp Arg Pro Ser Leu Val Pro Ala Ser Ala Glu Asn Val Asn Lys
                325                 330                 335

Ala Arg Ser Phe Ala Ala Gly Ile Gln Ala Leu Gly Gly Thr Asn Ile
            340                 345                 350

Asn Asp Ala Met Leu Met Ala Val Gln Leu Leu Asp Ser Ser Asn Gln
            355                 360                 365

Glu Glu Arg Leu Pro Glu Gly Ser Val Ser Leu Ile Ile Leu Leu Thr
        370                 375                 380

Asp Gly Asp Pro Thr Val Gly Glu Thr Asn Pro Arg Ser Ile Gln Asn
385                 390                 395                 400

Asn Val Arg Glu Ala Val Ser Gly Arg Tyr Ser Leu Phe Cys Leu Gly
            405                 410                 415

Phe Gly Phe Asp Val Ser Tyr Ala Phe Leu Glu Lys Leu Ala Leu Asp
            420                 425                 430

Asn Gly Gly Leu Ala Arg Arg Ile His Glu Asp Ser Asp Ser Ala Leu
            435                 440                 445

Gln Leu Gln Asp Phe Tyr Gln Glu Val Ala Asn Pro Leu Leu Thr Ala
    450                 455                 460

Val Thr Phe Glu Tyr Pro Ser Asn Ala Val Glu Glu Val Thr Gln Asn
465                 470                 475                 480

Asn Phe Arg Leu Leu Phe Lys Gly Ser Glu Met Val Val Ala Gly Lys
            485                 490                 495

Leu Gln Asp Arg Gly Pro Asp Val Leu Thr Ala Thr Val Ser Gly Lys
            500                 505                 510

Leu Pro Thr Gln Asn Ile Thr Phe Gln Thr Glu Ser Ser Val Ala Glu
            515                 520                 525

Gln Glu Ala Glu Phe Gln Ser Pro Lys Tyr Ile Phe His Asn Phe Met
    530                 535                 540

Glu Arg Leu Trp Ala Tyr Leu Thr Ile Gln Gln Leu Leu Glu Gln Thr
545                 550                 555                 560

Val Ser Ala Ser Asp Ala Asp Gln Gln Ala Leu Arg Asn Gln Ala Leu
            565                 570                 575

Asn Leu Ser Leu Ala Tyr Ser Phe Val Thr Pro Leu Thr Ser Met Val
            580                 585                 590

Val Thr Lys Pro Asp Asp Gln Glu Gln Ser Gln Val Ala Glu Lys Pro
            595                 600                 605

Met Glu Gly Glu Ser Arg Asn Arg Asn Val His Ser Gly Ser Thr Phe
    610                 615                 620

Phe Lys Tyr Tyr Leu Gln Gly Ala Lys Ile Pro Lys Pro Glu Ala Ser
625                 630                 635                 640

Phe Ser Pro Arg Arg Gly Trp Asn Arg Gln Ala Gly Ala Ala Gly Ser
            645                 650                 655

Arg Met Asn Phe Arg Pro Gly Val Leu Ser Ser Arg Gln Leu Gly Leu
            660                 665                 670

Pro Gly Pro Pro Asp Val Pro Asp His Ala Ala Tyr His Pro Phe Arg
            675                 680                 685

Arg Leu Ala Ile Leu Pro Ala Ser Ala Pro Pro Ala Thr Ser Asn Pro
    690                 695                 700

Asp Pro Ala Val Ser Arg Val Met Asn Met Lys Ile Glu Glu Thr Thr
705                 710                 715                 720
```

```
Met Thr Thr Gln Thr Pro Ala Pro Ile Gln Ala Pro Ser Ala Ile Leu
             725             730             735

Pro Leu Pro Gly Gln Ser Val Glu Arg Leu Cys Val Asp Pro Arg His
             740             745             750

Arg Gln Gly Pro Val Asn Leu Leu Ser Asp Pro Glu Gln Gly Val Glu
             755             760             765

Val Thr Gly Gln Tyr Glu Arg Glu Lys Ala Gly Phe Ser Trp Ile Glu
     770             775             780

Val Thr Phe Lys Asn Pro Leu Val Trp Val His Ala Ser Pro Glu His
785             790             795             800

Val Val Val Thr Arg Asn Arg Arg Ser Ser Ala Tyr Lys Trp Lys Glu
             805             810             815

Thr Leu Phe Ser Val Met Pro Gly Leu Lys Met Thr Met Asp Lys Thr
             820             825             830

Gly Leu Leu Leu Leu Ser Asp Pro Asp Lys Val Thr Ile Gly Leu Leu
             835             840             845

Phe Trp Asp Gly Arg Gly Glu Gly Leu Arg Leu Leu Leu Arg Asp Thr
     850             855             860

Asp Arg Phe Ser Ser His Val Gly Gly Thr Leu Gly Gln Phe Tyr Gln
865             870             875             880

Glu Val Leu Trp Gly Ser Pro Ala Ala Ser Asp Asp Gly Arg Arg Thr
             885             890             895

Leu Arg Val Gln Gly Asn Asp His Ser Ala Thr Arg Glu Arg Arg Leu
             900             905             910

Asp Tyr Gln Glu Gly Pro Pro Gly Val Glu Ile Ser Cys Trp Ser Val
             915             920             925

Glu Leu
     930
```

<210> SEQ ID NO 101
<211> LENGTH: 946
<212> TYPE: PRT
<213> ORGANISM: Artificial Sequence
<220> FEATURE:
<223> OTHER INFORMATION: Synthetic_ITIH2_HUMAN

<400> SEQUENCE: 101

```
Met Lys Arg Leu Thr Cys Phe Phe Ile Cys Phe Phe Leu Ser Glu Val
1               5               10              15

Ser Gly Phe Glu Ile Pro Ile Asn Gly Leu Ser Glu Phe Val Asp Tyr
             20              25              30

Glu Asp Leu Val Glu Leu Ala Pro Gly Lys Phe Gln Leu Val Ala Glu
             35              40              45

Asn Arg Arg Tyr Gln Arg Ser Leu Pro Gly Glu Ser Glu Glu Met Met
     50              55              60

Glu Glu Val Asp Gln Val Thr Leu Tyr Ser Tyr Lys Val Gln Ser Thr
65              70              75              80

Ile Thr Ser Arg Met Ala Thr Thr Met Ile Gln Ser Lys Val Val Asn
             85              90              95

Asn Ser Pro Gln Pro Gln Asn Val Val Phe Asp Val Gln Ile Pro Lys
             100             105             110

Gly Ala Phe Ile Ser Asn Phe Ser Met Thr Val Asp Gly Lys Thr Phe
             115             120             125

Arg Ser Ser Ile Lys Glu Lys Thr Val Gly Arg Ala Leu Tyr Ala Gln
     130             135             140
```

```
Ala Arg Ala Lys Gly Lys Thr Ala Gly Leu Val Arg Ser Ser Ala Leu
145             150             155             160

Asp Met Glu Asn Phe Arg Thr Glu Val Asn Val Leu Pro Gly Ala Lys
            165             170             175

Val Gln Phe Glu Leu His Tyr Gln Glu Val Lys Trp Arg Lys Leu Gly
            180             185             190

Ser Tyr Glu His Arg Ile Tyr Leu Gln Pro Gly Arg Leu Ala Lys His
        195             200             205

Leu Glu Val Asp Val Trp Val Ile Glu Pro Gln Gly Leu Arg Phe Leu
    210             215             220

His Val Pro Asp Thr Phe Glu Gly His Phe Asp Gly Val Pro Val Ile
225             230             235             240

Ser Lys Gly Gln Gln Lys Ala His Val Ser Phe Lys Pro Thr Val Ala
            245             250             255

Gln Gln Arg Ile Cys Pro Asn Cys Arg Glu Thr Ala Val Asp Gly Glu
            260             265             270

Leu Val Val Leu Tyr Asp Val Lys Arg Glu Glu Lys Ala Gly Glu Leu
        275             280             285

Glu Val Phe Asn Gly Tyr Phe Val His Phe Phe Ala Pro Asp Asn Leu
    290             295             300

Asp Pro Ile Pro Lys Asn Ile Leu Phe Val Ile Asp Val Ser Gly Ser
305             310             315             320

Met Trp Gly Val Lys Met Lys Gln Thr Val Glu Ala Met Lys Thr Ile
            325             330             335

Leu Asp Asp Leu Arg Ala Glu Asp His Phe Ser Val Ile Asp Phe Asn
            340             345             350

Gln Asn Ile Arg Thr Trp Arg Asn Asp Leu Ile Ser Ala Thr Lys Thr
        355             360             365

Gln Val Ala Asp Ala Lys Arg Tyr Ile Glu Lys Ile Gln Pro Ser Gly
    370             375             380

Gly Thr Asn Ile Asn Glu Ala Leu Leu Arg Ala Ile Phe Ile Leu Asn
385             390             395             400

Glu Ala Asn Asn Leu Gly Leu Leu Asp Pro Asn Ser Val Ser Leu Ile
            405             410             415

Ile Leu Val Ser Asp Gly Asp Pro Thr Val Gly Glu Leu Lys Leu Ser
            420             425             430

Lys Ile Gln Lys Asn Val Lys Glu Asn Ile Gln Asp Asn Ile Ser Leu
        435             440             445

Phe Ser Leu Gly Met Gly Phe Asp Val Asp Tyr Asp Phe Leu Lys Arg
    450             455             460

Leu Ser Asn Glu Asn His Gly Ile Ala Gln Arg Ile Tyr Gly Asn Gln
465             470             475             480

Asp Thr Ser Ser Gln Leu Lys Lys Phe Tyr Asn Gln Val Ser Thr Pro
            485             490             495

Leu Leu Arg Asn Val Gln Phe Asn Tyr Pro His Thr Ser Val Thr Asp
            500             505             510

Val Thr Gln Asn Asn Phe His Asn Tyr Phe Gly Gly Ser Glu Ile Val
            515             520             525

Val Ala Gly Lys Phe Asp Pro Ala Lys Leu Asp Gln Ile Glu Ser Val
        530             535             540

Ile Thr Ala Thr Ser Ala Asn Thr Gln Leu Val Leu Glu Thr Leu Ala
545             550             555             560

Gln Met Asp Asp Leu Gln Asp Phe Leu Ser Lys Asp Lys His Ala Asp
```

-continued

```
                    565             570             575

Pro Asp Phe Thr Arg Lys Leu Trp Ala Tyr Leu Thr Ile Asn Gln Leu
            580             585             590

Leu Ala Glu Arg Ser Leu Ala Pro Thr Ala Ala Ala Lys Arg Arg Ile
            595             600             605

Thr Arg Ser Ile Leu Gln Met Ser Leu Asp His His Ile Val Thr Pro
        610             615             620

Leu Thr Ser Leu Val Ile Glu Asn Gly Ala Gly Asp Glu Arg Met Leu
    625             630             635             640

Ala Asp Ala Pro Pro Gln Asp Pro Ser Cys Cys Ser Gly Ala Leu Tyr
                645             650             655

Tyr Gly Ser Lys Val Val Pro Asp Ser Thr Pro Ser Trp Ala Asn Pro
            660             665             670

Ser Pro Thr Pro Val Ile Ser Met Leu Ala Gln Gly Ser Gln Val Leu
            675             680             685

Glu Ser Thr Pro Pro Pro His Val Met Arg Val Glu Asn Asp Pro His
    690             695             700

Phe Ile Ile Tyr Leu Pro Lys Ser Gln Lys Asn Ile Cys Phe Asn Ile
705             710             715             720

Asp Ser Glu Pro Gly Lys Ile Leu Asn Leu Val Ser Asp Pro Glu Ser
            725             730             735

Gly Ile Val Val Asn Gly Gln Leu Val Gly Ala Lys Lys Pro Asn Asn
            740             745             750

Gly Lys Leu Ser Thr Tyr Phe Gly Lys Leu Gly Phe Tyr Phe Gln Ser
            755             760             765

Glu Asp Ile Lys Ile Glu Ile Ser Thr Glu Thr Ile Thr Leu Ser His
    770             775             780

Gly Ser Ser Thr Phe Ser Leu Ser Trp Ser Asp Thr Ala Gln Val Thr
785             790             795             800

Asn Gln Arg Val Gln Ile Ser Val Lys Lys Glu Lys Val Val Thr Ile
            805             810             815

Thr Leu Asp Lys Glu Met Ser Phe Ser Val Leu Leu His Arg Val Trp
            820             825             830

Lys Lys His Pro Val Asn Val Asp Phe Leu Gly Ile Tyr Ile Pro Pro
            835             840             845

Thr Asn Lys Phe Ser Pro Lys Ala His Gly Leu Ile Gly Gln Phe Met
    850             855             860

Gln Glu Pro Lys Ile His Ile Phe Asn Glu Arg Pro Gly Lys Asp Pro
865             870             875             880

Glu Lys Pro Glu Ala Ser Met Glu Val Lys Gly Gln Lys Leu Ile Ile
            885             890             895

Thr Arg Gly Leu Gln Lys Asp Tyr Arg Thr Asp Leu Val Phe Gly Thr
            900             905             910

Asp Val Thr Cys Trp Phe Val His Asn Ser Gly Lys Gly Phe Ile Asp
            915             920             925

Gly His Tyr Lys Asp Tyr Phe Val Pro Gln Leu Tyr Ser Phe Leu Lys
    930             935             940

Arg Pro
945
```

<210> SEQ ID NO 102
<211> LENGTH: 953
<212> TYPE: PRT
<213> ORGANISM: Artificial Sequence
<220> FEATURE:
<223> OTHER INFORMATION: Synthetic_TRAK1_HUMAN

<400> SEQUENCE: 102

Met Ala Leu Val Phe Gln Phe Gly Gln Pro Val Arg Ala Gln Pro Leu
1               5                   10                  15

Pro Gly Leu Cys His Gly Lys Leu Ile Arg Thr Asn Ala Cys Asp Val
            20                  25                  30

Cys Asn Ser Thr Asp Leu Pro Glu Val Glu Ile Ile Ser Leu Leu Glu
        35                  40                  45

Glu Gln Leu Pro His Tyr Lys Leu Arg Ala Asp Thr Ile Tyr Gly Tyr
    50                  55                  60

Asp His Asp Asp Trp Leu His Thr Pro Leu Ile Ser Pro Asp Ala Asn
65                  70                  75                  80

Ile Asp Leu Thr Thr Glu Gln Ile Glu Glu Thr Leu Lys Tyr Phe Leu
                85                  90                  95

Leu Cys Ala Glu Arg Val Gly Gln Met Thr Lys Thr Tyr Asn Asp Ile
            100                 105                 110

Asp Ala Val Thr Arg Leu Leu Glu Glu Lys Glu Arg Asp Leu Glu Leu
        115                 120                 125

Ala Ala Arg Ile Gly Gln Ser Leu Leu Lys Lys Asn Lys Thr Leu Thr
    130                 135                 140

Glu Arg Asn Glu Leu Leu Glu Glu Gln Val Glu His Ile Arg Glu Glu
145                 150                 155                 160

Val Ser Gln Leu Arg His Glu Leu Ser Met Lys Asp Glu Leu Leu Gln
            165                 170                 175

Phe Tyr Thr Ser Ala Ala Glu Glu Ser Glu Pro Glu Ser Val Cys Ser
        180                 185                 190

Thr Pro Leu Lys Arg Asn Glu Ser Ser Ser Ser Val Gln Asn Tyr Phe
        195                 200                 205

His Leu Asp Ser Leu Gln Lys Lys Leu Lys Asp Leu Glu Glu Glu Asn
    210                 215                 220

Val Val Leu Arg Ser Glu Ala Ser Gln Leu Lys Thr Glu Thr Ile Thr
225                 230                 235                 240

Tyr Glu Glu Lys Glu Gln Gln Leu Val Asn Asp Cys Val Lys Glu Leu
            245                 250                 255

Arg Asp Ala Asn Val Gln Ile Ala Ser Ile Ser Glu Glu Leu Ala Lys
        260                 265                 270

Lys Thr Glu Asp Ala Ala Arg Gln Gln Glu Glu Ile Thr His Leu Leu
    275                 280                 285

Ser Gln Ile Val Asp Leu Gln Lys Lys Ala Lys Ala Cys Ala Val Glu
    290                 295                 300

Asn Glu Glu Leu Val Gln His Leu Gly Ala Ala Lys Asp Ala Gln Arg
305                 310                 315                 320

Gln Leu Thr Ala Glu Leu Arg Glu Leu Glu Asp Lys Tyr Ala Glu Cys
            325                 330                 335

Met Glu Met Leu His Glu Ala Gln Glu Glu Leu Lys Asn Leu Arg Asn
            340                 345                 350

Lys Thr Met Pro Asn Thr Thr Ser Arg Arg Tyr His Ser Leu Gly Leu
            355                 360                 365

Phe Pro Met Asp Ser Leu Ala Ala Glu Ile Glu Gly Thr Met Arg Lys
    370                 375                 380

Glu Leu Gln Leu Glu Glu Ala Glu Ser Pro Asp Ile Thr His Gln Lys
385                 390                 395                 400

-continued

```
Arg Val Phe Glu Thr Val Arg Asn Ile Asn Gln Val Val Lys Gln Arg
            405             410             415

Ser Leu Thr Pro Ser Pro Met Asn Ile Pro Gly Ser Asn Gln Ser Ser
            420             425             430

Ala Met Asn Ser Leu Leu Ser Ser Cys Val Ser Thr Pro Arg Ser Ser
            435             440             445

Phe Tyr Gly Ser Asp Ile Gly Asn Val Val Leu Asp Asn Lys Thr Asn
    450             455             460

Ser Ile Ile Leu Glu Thr Glu Ala Ala Asp Leu Gly Asn Asp Glu Arg
465             470             475             480

Ser Lys Lys Pro Gly Thr Pro Gly Thr Pro Gly Ser His Asp Leu Glu
            485             490             495

Thr Ala Leu Arg Arg Leu Ser Leu Arg Arg Glu Asn Tyr Leu Ser Glu
            500             505             510

Arg Arg Phe Phe Glu Glu Glu Gln Glu Arg Lys Leu Gln Glu Leu Ala
            515             520             525

Glu Lys Gly Glu Leu Arg Ser Gly Ser Leu Thr Pro Thr Glu Ser Ile
    530             535             540

Met Ser Leu Gly Thr His Ser Arg Phe Ser Glu Phe Thr Gly Phe Ser
545             550             555             560

Gly Met Ser Phe Ser Ser Arg Ser Tyr Leu Pro Glu Lys Leu Gln Ile
            565             570             575

Val Lys Pro Leu Glu Gly Ser Ala Thr Leu His His Trp Gln Gln Leu
            580             585             590

Ala Gln Pro His Leu Gly Gly Ile Leu Asp Pro Arg Pro Gly Val Val
            595             600             605

Thr Lys Gly Phe Arg Thr Leu Asp Val Asp Leu Asp Glu Val Tyr Cys
    610             615             620

Leu Asn Asp Phe Glu Glu Asp Asp Thr Gly Asp His Ile Ser Leu Pro
625             630             635             640

Arg Leu Ala Thr Ser Thr Pro Val Gln His Pro Glu Thr Ser Ala His
            645             650             655

His Pro Gly Lys Cys Met Ser Gln Thr Asn Ser Thr Phe Thr Phe Thr
            660             665             670

Thr Cys Arg Ile Leu His Pro Ser Asp Glu Leu Thr Arg Val Thr Pro
            675             680             685

Ser Leu Asn Ser Ala Pro Thr Pro Ala Cys Gly Ser Thr Ser His Leu
    690             695             700

Lys Ser Thr Pro Val Ala Thr Pro Cys Thr Pro Arg Arg Leu Ser Leu
705             710             715             720

Ala Glu Ser Phe Thr Asn Thr Arg Glu Ser Thr Thr Thr Met Ser Thr
            725             730             735

Ser Leu Gly Leu Val Trp Leu Leu Lys Glu Arg Gly Ile Ser Ala Ala
            740             745             750

Val Tyr Asp Pro Gln Ser Trp Asp Arg Ala Gly Arg Gly Ser Leu Leu
            755             760             765

His Ser Tyr Thr Pro Lys Met Ala Val Ile Pro Ser Thr Pro Pro Asn
    770             775             780

Ser Pro Met Gln Thr Pro Thr Ser Ser Pro Pro Ser Phe Glu Phe Lys
785             790             795             800

Cys Thr Ser Pro Pro Tyr Asp Asn Phe Leu Ala Ser Lys Pro Ala Ser
            805             810             815
```

-continued

```
Ser Ile Leu Arg Glu Val Arg Glu Lys Asn Val Arg Ser Ser Glu Ser
            820             825             830

Gln Thr Asp Val Ser Val Ser Asn Leu Asn Leu Val Asp Lys Val Arg
            835             840             845

Arg Phe Gly Val Ala Lys Val Val Asn Ser Gly Arg Ala His Val Pro
        850             855             860

Thr Leu Thr Glu Glu Gln Gly Pro Leu Leu Cys Gly Pro Pro Gly Pro
865             870             875             880

Ala Pro Ala Leu Val Pro Arg Gly Leu Val Pro Glu Gly Leu Pro Leu
            885             890             895

Arg Cys Pro Thr Val Thr Ser Ala Ile Gly Gly Leu Gln Leu Asn Ser
        900             905             910

Gly Ile Arg Arg Asn Arg Ser Phe Pro Thr Met Val Gly Ser Ser Met
        915             920             925

Gln Met Lys Ala Pro Val Thr Leu Thr Ser Gly Ile Leu Met Gly Ala
    930             935             940

Lys Leu Ser Lys Gln Thr Ser Leu Arg
945             950
```

```
<210> SEQ ID NO 103
<211> LENGTH: 1255
<212> TYPE: PRT
<213> ORGANISM: Artificial Sequence
<220> FEATURE:
<223> OTHER INFORMATION: Synthetic_MUC1_HUMAN

<400> SEQUENCE: 103

Met Thr Pro Gly Thr Gln Ser Pro Phe Phe Leu Leu Leu Leu Leu Thr
1               5               10              15

Val Leu Thr Val Val Thr Gly Ser Gly His Ala Ser Ser Thr Pro Gly
            20              25              30

Gly Glu Lys Glu Thr Ser Ala Thr Gln Arg Ser Ser Val Pro Ser Ser
        35              40              45

Thr Glu Lys Asn Ala Val Ser Met Thr Ser Ser Val Leu Ser Ser His
    50              55              60

Ser Pro Gly Ser Gly Ser Ser Thr Thr Gln Gly Gln Asp Val Thr Leu
65              70              75              80

Ala Pro Ala Thr Glu Pro Ala Ser Gly Ser Ala Ala Thr Trp Gly Gln
            85              90              95

Asp Val Thr Ser Val Pro Val Thr Arg Pro Ala Leu Gly Ser Thr Thr
            100             105             110

Pro Pro Ala His Asp Val Thr Ser Ala Pro Asp Asn Lys Pro Ala Pro
        115             120             125

Gly Ser Thr Ala Pro Pro Ala His Gly Val Thr Ser Ala Pro Asp Thr
    130             135             140

Arg Pro Ala Pro Gly Ser Thr Ala Pro Pro Ala His Gly Val Thr Ser
145             150             155             160

Ala Pro Asp Thr Arg Pro Ala Pro Gly Ser Thr Ala Pro Pro Ala His
            165             170             175

Gly Val Thr Ser Ala Pro Asp Thr Arg Pro Ala Pro Gly Ser Thr Ala
            180             185             190

Pro Pro Ala His Gly Val Thr Ser Ala Pro Asp Thr Arg Pro Ala Pro
    195             200             205

Gly Ser Thr Ala Pro Pro Ala His Gly Val Thr Ser Ala Pro Asp Thr
    210             215             220
```

-continued

```
Arg Pro Ala Pro Gly Ser Thr Ala Pro Pro Ala His Gly Val Thr Ser
225             230             235             240

Ala Pro Asp Thr Arg Pro Ala Pro Gly Ser Thr Ala Pro Pro Ala His
            245             250             255

Gly Val Thr Ser Ala Pro Asp Thr Arg Pro Ala Pro Gly Ser Thr Ala
            260             265             270

Pro Pro Ala His Gly Val Thr Ser Ala Pro Asp Thr Arg Pro Ala Pro
        275             280             285

Gly Ser Thr Ala Pro Pro Ala His Gly Val Thr Ser Ala Pro Asp Thr
    290             295             300

Arg Pro Ala Pro Gly Ser Thr Ala Pro Pro Ala His Gly Val Thr Ser
305             310             315             320

Ala Pro Asp Thr Arg Pro Ala Pro Gly Ser Thr Ala Pro Pro Ala His
            325             330             335

Gly Val Thr Ser Ala Pro Asp Thr Arg Pro Ala Pro Gly Ser Thr Ala
            340             345             350

Pro Pro Ala His Gly Val Thr Ser Ala Pro Asp Thr Arg Pro Ala Pro
        355             360             365

Gly Ser Thr Ala Pro Pro Ala His Gly Val Thr Ser Ala Pro Asp Thr
    370             375             380

Arg Pro Ala Pro Gly Ser Thr Ala Pro Pro Ala His Gly Val Thr Ser
385             390             395             400

Ala Pro Asp Thr Arg Pro Ala Pro Gly Ser Thr Ala Pro Pro Ala His
            405             410             415

Gly Val Thr Ser Ala Pro Asp Thr Arg Pro Ala Pro Gly Ser Thr Ala
            420             425             430

Pro Pro Ala His Gly Val Thr Ser Ala Pro Asp Thr Arg Pro Ala Pro
        435             440             445

Gly Ser Thr Ala Pro Pro Ala His Gly Val Thr Ser Ala Pro Asp Thr
    450             455             460

Arg Pro Ala Pro Gly Ser Thr Ala Pro Pro Ala His Gly Val Thr Ser
465             470             475             480

Ala Pro Asp Thr Arg Pro Ala Pro Gly Ser Thr Ala Pro Pro Ala His
            485             490             495

Gly Val Thr Ser Ala Pro Asp Thr Arg Pro Ala Pro Gly Ser Thr Ala
            500             505             510

Pro Pro Ala His Gly Val Thr Ser Ala Pro Asp Thr Arg Pro Ala Pro
        515             520             525

Gly Ser Thr Ala Pro Pro Ala His Gly Val Thr Ser Ala Pro Asp Thr
    530             535             540

Arg Pro Ala Pro Gly Ser Thr Ala Pro Pro Ala His Gly Val Thr Ser
545             550             555             560

Ala Pro Asp Thr Arg Pro Ala Pro Gly Ser Thr Ala Pro Pro Ala His
            565             570             575

Gly Val Thr Ser Ala Pro Asp Thr Arg Pro Ala Pro Gly Ser Thr Ala
            580             585             590

Pro Pro Ala His Gly Val Thr Ser Ala Pro Asp Thr Arg Pro Ala Pro
        595             600             605

Gly Ser Thr Ala Pro Pro Ala His Gly Val Thr Ser Ala Pro Asp Thr
    610             615             620

Arg Pro Ala Pro Gly Ser Thr Ala Pro Pro Ala His Gly Val Thr Ser
625             630             635             640

Ala Pro Asp Thr Arg Pro Ala Pro Gly Ser Thr Ala Pro Pro Ala His
```

-continued

```
                    645             650             655
Gly Val Thr Ser Ala Pro Asp Thr Arg Pro Ala Pro Gly Ser Thr Ala
                660             665             670

Pro Pro Ala His Gly Val Thr Ser Ala Pro Asp Thr Arg Pro Ala Pro
                675             680             685

Gly Ser Thr Ala Pro Pro Ala His Gly Val Thr Ser Ala Pro Asp Thr
    690             695             700

Arg Pro Ala Pro Gly Ser Thr Ala Pro Pro Ala His Gly Val Thr Ser
705             710             715             720

Ala Pro Asp Thr Arg Pro Ala Pro Gly Ser Thr Ala Pro Pro Ala His
                725             730             735

Gly Val Thr Ser Ala Pro Asp Thr Arg Pro Ala Pro Gly Ser Thr Ala
                740             745             750

Pro Pro Ala His Gly Val Thr Ser Ala Pro Asp Thr Arg Pro Ala Pro
                755             760             765

Gly Ser Thr Ala Pro Pro Ala His Gly Val Thr Ser Ala Pro Asp Thr
    770             775             780

Arg Pro Ala Pro Gly Ser Thr Ala Pro Pro Ala His Gly Val Thr Ser
785             790             795             800

Ala Pro Asp Thr Arg Pro Ala Pro Gly Ser Thr Ala Pro Pro Ala His
                805             810             815

Gly Val Thr Ser Ala Pro Asp Thr Arg Pro Ala Pro Gly Ser Thr Ala
                820             825             830

Pro Pro Ala His Gly Val Thr Ser Ala Pro Asp Thr Arg Pro Ala Pro
                835             840             845

Gly Ser Thr Ala Pro Pro Ala His Gly Val Thr Ser Ala Pro Asp Thr
    850             855             860

Arg Pro Ala Pro Gly Ser Thr Ala Pro Pro Ala His Gly Val Thr Ser
865             870             875             880

Ala Pro Asp Thr Arg Pro Ala Pro Gly Ser Thr Ala Pro Pro Ala His
                885             890             895

Gly Val Thr Ser Ala Pro Asp Thr Arg Pro Ala Pro Gly Ser Thr Ala
                900             905             910

Pro Pro Ala His Gly Val Thr Ser Ala Pro Asp Thr Arg Pro Ala Pro
                915             920             925

Gly Ser Thr Ala Pro Pro Ala His Gly Val Thr Ser Ala Pro Asp Asn
    930             935             940

Arg Pro Ala Leu Gly Ser Thr Ala Pro Pro Val His Asn Val Thr Ser
945             950             955             960

Ala Ser Gly Ser Ala Ser Gly Ser Ala Ser Thr Leu Val His Asn Gly
                965             970             975

Thr Ser Ala Arg Ala Thr Thr Thr Pro Ala Ser Lys Ser Thr Pro Phe
                980             985             990

Ser Ile Pro Ser His His Ser Asp Thr Pro Thr Leu Ala Ser His
        995             1000            1005

Ser Thr Lys Thr Asp Ala Ser Ser Thr His His Ser Ser Val Pro Pro
    1010            1015            1020

Leu Thr Ser Ser Asn His Ser Thr Ser Pro Gln Leu Ser Thr Gly Val
1025            1030            1035            1040

Ser Phe Phe Phe Leu Ser Phe His Ile Ser Asn Leu Gln Phe Asn Ser
                1045            1050            1055

Ser Leu Glu Asp Pro Ser Thr Asp Tyr Tyr Gln Glu Leu Gln Arg Asp
        1060            1065            1070
```

```
Ile Ser Glu Met Phe Leu Gln Ile Tyr Lys Gln Gly Gly Phe Leu Gly
        1075                1080                1085

Leu Ser Asn Ile Lys Phe Arg Pro Gly Ser Val Val Val Gln Leu Thr
        1090                1095                1100

Leu Ala Phe Arg Glu Gly Thr Ile Asn Val His Asp Val Glu Thr Gln
1105                1110                1115                1120

Phe Asn Gln Tyr Lys Thr Glu Ala Ala Ser Arg Tyr Asn Leu Thr Ile
                1125                1130                1135

Ser Asp Val Ser Val Ser Asp Val Pro Phe Pro Phe Ser Ala Gln Ser
                1140                1145                1150

Gly Ala Gly Val Pro Gly Trp Gly Ile Ala Leu Leu Val Leu Val Cys
                1155                1160                1165

Val Leu Val Ala Leu Ala Ile Val Tyr Leu Ile Ala Leu Ala Val Cys
        1170                1175                1180

Gln Cys Arg Arg Lys Asn Tyr Gly Gln Leu Asp Ile Phe Pro Ala Arg
1185                1190                1195                1200

Asp Thr Tyr His Pro Met Ser Glu Tyr Pro Thr Tyr His Thr His Gly
                1205                1210                1215

Arg Tyr Val Pro Pro Ser Ser Thr Asp Arg Ser Pro Tyr Glu Lys Val
                1220                1225                1230

Ser Ala Gly Asn Gly Gly Ser Ser Leu Ser Tyr Thr Asn Pro Ala Val
                1235                1240                1245

Ala Ala Thr Ser Ala Asn Leu
        1250                1255

<210> SEQ ID NO 104
<211> LENGTH: 1322
<212> TYPE: PRT
<213> ORGANISM: Artificial Sequence
<220> FEATURE:
<223> OTHER INFORMATION: Synthetic_EMSY_HUMAN

<400> SEQUENCE: 104

Met Pro Val Val Trp Pro Thr Leu Leu Asp Leu Ser Arg Asp Glu Cys
1               5                   10                  15

Lys Arg Ile Leu Arg Lys Leu Glu Leu Glu Ala Tyr Ala Gly Val Ile
                20                  25                  30

Ser Ala Leu Arg Ala Gln Gly Asp Leu Thr Lys Glu Lys Lys Asp Leu
        35                  40                  45

Leu Gly Glu Leu Ser Lys Val Leu Ser Ile Ser Thr Glu Arg His Arg
        50                  55                  60

Ala Glu Val Arg Arg Ala Val Asn Asp Glu Arg Leu Thr Thr Ile Ala
65                  70                  75                  80

His Asn Met Ser Gly Pro Asn Ser Ser Ser Glu Trp Ser Ile Glu Gly
                85                  90                  95

Arg Arg Leu Val Pro Leu Met Pro Arg Leu Val Pro Gln Thr Ala Phe
                100                 105                 110

Thr Val Thr Ala Asn Ala Val Ala Asn Ala Ala Ile Gln His Asn Ala
        115                 120                 125

Ser Leu Pro Val Pro Ala Glu Thr Gly Ser Lys Glu Val Val Cys Tyr
        130                 135                 140

Ser Tyr Thr Ser Thr Thr Ser Thr Pro Thr Ser Thr Pro Val Pro Ser
145                 150                 155                 160

Gly Ser Ile Ala Thr Val Lys Ser Pro Arg Pro Ala Ser Pro Ala Ser
                165                 170                 175
```

```
Asn Val Val Val Leu Pro Ser Gly Ser Thr Val Tyr Val Lys Ser Val
        180                     185                 190

Ser Cys Ser Asp Glu Asp Glu Lys Pro Arg Lys Arg Arg Arg Thr Asn
        195                     200                 205

Ser Ser Ser Ser Ser Pro Val Val Leu Lys Glu Val Pro Lys Ala Val
        210                     215                 220

Val Pro Val Ser Lys Thr Ile Thr Val Pro Val Ser Gly Ser Pro Lys
225                     230                 235                 240

Met Ser Asn Ile Met Gln Ser Ile Ala Asn Ser Leu Pro Pro His Met
                245                 250                 255

Ser Pro Val Lys Ile Thr Phe Thr Lys Pro Ser Thr Gln Thr Thr Asn
                260                 265                 270

Thr Thr Thr Gln Lys Val Ile Ile Val Thr Thr Ser Pro Ser Ser Thr
        275                     280                 285

Phe Val Pro Asn Ile Leu Ser Lys Ser His Asn Tyr Ala Ala Val Thr
        290                     295                 300

Lys Leu Val Pro Thr Ser Val Ile Ala Ser Thr Thr Gln Lys Pro Pro
305                     310                 315                 320

Val Val Ile Thr Ala Ser Gln Ser Ser Leu Val Ser Asn Ser Ser Ser
                325                     330                 335

Gly Ser Ser Ser Ser Thr Pro Ser Pro Ile Pro Asn Thr Val Ala Val
                340                     345                 350

Thr Ala Val Val Ser Ser Thr Pro Ser Val Val Met Ser Thr Val Ala
                355                     360                 365

Gln Gly Val Ser Thr Ser Ala Ile Lys Met Ala Ser Thr Arg Leu Pro
        370                     375                 380

Ser Pro Lys Ser Leu Val Ser Ala Pro Thr Gln Ile Leu Ala Gln Phe
385                     390                 395                 400

Pro Lys Gln His Gln Gln Ser Pro Lys Gln Gln Leu Tyr Gln Val Gln
                405                     410                 415

Gln Gln Thr Gln Gln Gln Val Ala Gln Pro Ser Pro Val Ser His Gln
                420                     425                 430

Gln Gln Pro Gln Gln Ser Pro Leu Pro Pro Gly Ile Lys Pro Thr Ile
                435                     440                 445

Gln Ile Lys Gln Glu Ser Gly Val Lys Ile Ile Thr Gln Gln Val Gln
        450                     455                 460

Pro Ser Lys Ile Leu Pro Lys Pro Val Thr Ala Thr Leu Pro Thr Ser
465                     470                 475                 480

Ser Asn Ser Pro Ile Met Val Val Ser Ser Asn Gly Ala Ile Met Thr
                485                     490                 495

Thr Lys Leu Val Thr Thr Pro Thr Gly Thr Gln Ala Thr Tyr Thr Arg
                500                     505                 510

Pro Thr Val Ser Pro Ser Ile Gly Arg Met Ala Ala Thr Pro Gly Ala
        515                     520                 525

Ala Thr Tyr Val Lys Thr Thr Ser Gly Ser Ile Ile Thr Val Val Pro
        530                     535                 540

Lys Ser Leu Ala Thr Leu Gly Gly Lys Ile Ile Ser Ser Asn Ile Val
545                     550                 555                 560

Ser Gly Thr Thr Thr Lys Ile Thr Thr Ile Pro Met Thr Ser Lys Pro
                565                     570                 575

Asn Val Ile Val Val Gln Lys Thr Thr Gly Lys Gly Thr Thr Ile Gln
        580                     585                 590
```

-continued

```
Gly Leu Pro Gly Lys Asn Val Val Thr Thr Leu Leu Asn Ala Gly Gly
        595                 600                 605

Glu Lys Thr Ile Gln Thr Val Pro Thr Gly Ala Lys Pro Ala Ile Leu
    610                 615                 620

Thr Ala Thr Arg Pro Ile Thr Lys Met Ile Val Thr Gln Pro Lys Gly
625                 630                 635                 640

Ile Gly Ser Thr Val Gln Pro Ala Ala Lys Ile Ile Pro Thr Lys Ile
                645                 650                 655

Val Tyr Gly Gln Gln Gly Lys Thr Gln Val Leu Ile Lys Pro Lys Pro
                660                 665                 670

Val Thr Phe Gln Ala Thr Val Val Ser Glu Gln Thr Arg Gln Leu Val
                675                 680                 685

Thr Glu Thr Leu Gln Gln Ala Ser Arg Val Ala Glu Ala Gly Asn Ser
        690                 695                 700

Ser Ile Gln Glu Gly Lys Glu Glu Pro Gln Asn Tyr Thr Asp Ser Ser
705                 710                 715                 720

Ser Ser Ser Thr Glu Ser Ser Gln Ser Ser Gln Asp Ser Gln Pro Val
                725                 730                 735

Val His Val Ile Ala Ser Arg Arg Gln Asp Trp Ser Glu His Glu Ile
                740                 745                 750

Ala Met Glu Thr Ser Pro Thr Ile Ile Tyr Gln Asp Val Ser Ser Glu
        755                 760                 765

Ser Gln Ser Ala Thr Ser Thr Ile Lys Ala Leu Leu Glu Leu Gln Gln
        770                 775                 780

Thr Thr Val Lys Glu Lys Leu Glu Ser Lys Pro Arg Gln Pro Thr Ile
785                 790                 795                 800

Asp Leu Ser Gln Met Ala Val Pro Ile Gln Met Thr Gln Glu Lys Arg
                805                 810                 815

His Ser Pro Glu Ser Pro Ser Ile Ala Val Val Glu Ser Glu Leu Val
                820                 825                 830

Ala Glu Tyr Ile Thr Thr Glu Arg Thr Asp Glu Gly Thr Glu Val Ala
        835                 840                 845

Phe Pro Leu Leu Val Ser His Arg Ser Gln Pro Gln Gln Pro Ser Gln
    850                 855                 860

Pro Gln Arg Thr Leu Leu Gln His Val Ala Gln Ser Gln Thr Ala Thr
865                 870                 875                 880

Gln Thr Ser Val Val Val Lys Ser Ile Pro Ala Ser Ser Pro Gly Ala
                885                 890                 895

Ile Thr His Ile Met Gln Gln Ala Leu Ser Ser His Thr Ala Phe Thr
                900                 905                 910

Lys His Ser Glu Glu Leu Gly Thr Glu Glu Gly Glu Val Glu Glu Met
        915                 920                 925

Asp Thr Leu Asp Pro Gln Thr Gly Leu Phe Tyr Arg Ser Ala Leu Thr
    930                 935                 940

Gln Ser Gln Ser Ala Lys Gln Gln Lys Leu Ser Gln Pro Pro Leu Glu
945                 950                 955                 960

Gln Thr Gln Leu Gln Val Lys Thr Leu Gln Cys Phe Gln Thr Lys Gln
                965                 970                 975

Lys Gln Thr Ile His Leu Gln Ala Asp Gln Leu Gln His Lys Leu Pro
                980                 985                 990

Gln Met Pro Gln Leu Ser Ile Arg His Gln Lys Leu Thr Pro Leu Gln
        995                 1000                1005

Gln Glu Gln Ala Gln Pro Lys Pro Asp Val Gln His Thr Gln His Pro
```

-continued

```
        1010            1015            1020

Met Val Ala Lys Asp Arg Gln Leu Pro Thr Leu Met Ala Gln Pro Pro
1025            1030            1035            1040

Gln Thr Val Val Gln Val Leu Ala Val Lys Thr Thr Gln Gln Leu Pro
            1045            1050            1055

Lys Leu Gln Gln Ala Pro Asn Gln Pro Lys Ile Tyr Val Gln Pro Gln
            1060            1065            1070

Thr Pro Gln Ser Gln Met Ser Leu Pro Ala Ser Ser Glu Lys Gln Thr
        1075            1080            1085

Ala Ser Gln Val Glu Gln Pro Ile Ile Thr Gln Gly Ser Ser Val Thr
    1090            1095            1100

Lys Ile Thr Phe Glu Gly Arg Gln Pro Pro Thr Val Thr Lys Ile Thr
1105            1110            1115            1120

Gly Gly Ser Ser Val Pro Lys Leu Thr Ser Pro Val Thr Ser Ile Ser
            1125            1130            1135

Pro Ile Gln Ala Ser Glu Lys Thr Ala Val Ser Asp Ile Leu Lys Met
        1140            1145            1150

Ser Leu Met Glu Ala Gln Ile Asp Thr Asn Val Glu His Met Ile Val
    1155            1160            1165

Asp Pro Pro Lys Lys Ala Leu Ala Thr Ser Met Leu Thr Gly Glu Ala
    1170            1175            1180

Gly Ser Leu Pro Ser Thr His Met Val Val Ala Gly Met Ala Asn Ser
1185            1190            1195            1200

Thr Pro Gln Gln Gln Lys Cys Arg Glu Ser Cys Ser Ser Pro Ser Thr
            1205            1210            1215

Val Gly Ser Ser Leu Thr Thr Arg Lys Ile Asp Pro Pro Ala Val Pro
            1220            1225            1230

Ala Thr Gly Gln Phe Met Arg Ile Gln Asn Val Gly Gln Lys Lys Ala
        1235            1240            1245

Glu Glu Ser Pro Ala Glu Ile Ile Ile Gln Ala Ile Pro Gln Tyr Ala
    1250            1255            1260

Ile Pro Cys His Ser Ser Ser Asn Val Val Val Glu Pro Ser Gly Leu
1265            1270            1275            1280

Leu Glu Leu Asn Asn Phe Thr Ser Gln Gln Leu Asp Asp Glu Glu Thr
            1285            1290            1295

Ala Met Glu Gln Asp Ile Asp Ser Ser Thr Glu Asp Gly Thr Glu Pro
        1300            1305            1310

Ser Pro Ser Gln Ser Ser Ala Glu Arg Ser
        1315            1320
```

```
<210> SEQ ID NO 105
<211> LENGTH: 1404
<212> TYPE: PRT
<213> ORGANISM: Artificial Sequence
<220> FEATURE:
<223> OTHER INFORMATION: Synthetic_PRG4_HUMAN

<400> SEQUENCE: 105

Met Ala Trp Lys Thr Leu Pro Ile Tyr Leu Leu Leu Leu Leu Ser Val
1               5               10              15

Phe Val Ile Gln Gln Val Ser Ser Gln Asp Leu Ser Ser Cys Ala Gly
            20              25              30

Arg Cys Gly Glu Gly Tyr Ser Arg Asp Ala Thr Cys Asn Cys Asp Tyr
        35              40              45

Asn Cys Gln His Tyr Met Glu Cys Cys Pro Asp Phe Lys Arg Val Cys
```

```
        50              55              60

Thr Ala Glu Leu Ser Cys Lys Gly Arg Cys Phe Glu Ser Phe Glu Arg
65              70              75              80

Gly Arg Glu Cys Asp Cys Asp Ala Gln Cys Lys Lys Tyr Asp Lys Cys
            85              90              95

Cys Pro Asp Tyr Glu Ser Phe Cys Ala Glu Val His Asn Pro Thr Ser
            100             105             110

Pro Pro Ser Ser Lys Lys Ala Pro Pro Pro Ser Gly Ala Ser Gln Thr
            115             120             125

Ile Lys Ser Thr Thr Lys Arg Ser Pro Lys Pro Asn Lys Lys Lys
            130             135             140

Thr Lys Lys Val Ile Glu Ser Glu Glu Ile Thr Glu Glu His Ser Val
145             150             155             160

Ser Glu Asn Gln Glu Ser Ser Ser Ser Ser Ser Ser Ser Ser Ser
            165             170             175

Ser Thr Ile Arg Lys Ile Lys Ser Ser Lys Asn Ser Ala Ala Asn Arg
            180             185             190

Glu Leu Gln Lys Lys Leu Lys Val Lys Asp Asn Lys Lys Asn Arg Thr
            195             200             205

Lys Lys Lys Pro Thr Pro Lys Pro Pro Val Val Asp Glu Ala Gly Ser
            210             215             220

Gly Leu Asp Asn Gly Asp Phe Lys Val Thr Thr Pro Asp Thr Ser Thr
225             230             235             240

Thr Gln His Asn Lys Val Ser Thr Ser Pro Lys Ile Thr Thr Ala Lys
            245             250             255

Pro Ile Asn Pro Arg Pro Ser Leu Pro Pro Asn Ser Asp Thr Ser Lys
            260             265             270

Glu Thr Ser Leu Thr Val Asn Lys Glu Thr Thr Val Glu Thr Lys Glu
            275             280             285

Thr Thr Thr Thr Asn Lys Gln Thr Ser Thr Asp Gly Lys Glu Lys Thr
            290             295             300

Thr Ser Ala Lys Glu Thr Gln Ser Ile Glu Lys Thr Ser Ala Lys Asp
305             310             315             320

Leu Ala Pro Thr Ser Lys Val Leu Ala Lys Pro Thr Pro Lys Ala Glu
            325             330             335

Thr Thr Thr Lys Gly Pro Ala Leu Thr Thr Pro Lys Glu Pro Thr Pro
            340             345             350

Thr Thr Pro Lys Glu Pro Ala Ser Thr Thr Pro Lys Glu Pro Thr Pro
            355             360             365

Thr Thr Ile Lys Ser Ala Pro Thr Thr Pro Lys Glu Pro Ala Pro Thr
            370             375             380

Thr Thr Lys Ser Ala Pro Thr Thr Pro Lys Glu Pro Ala Pro Thr Thr
385             390             395             400

Thr Lys Glu Pro Ala Pro Thr Thr Pro Lys Glu Pro Ala Pro Thr Thr
            405             410             415

Thr Lys Glu Pro Ala Pro Thr Thr Thr Lys Ser Ala Pro Thr Thr Pro
            420             425             430

Lys Glu Pro Ala Pro Thr Thr Pro Lys Lys Pro Ala Pro Thr Thr Pro
            435             440             445

Lys Glu Pro Ala Pro Thr Thr Pro Lys Glu Pro Thr Pro Thr Thr Pro
            450             455             460

Lys Glu Pro Ala Pro Thr Thr Lys Glu Pro Ala Pro Thr Thr Pro Lys
465             470             475             480
```

```
Glu Pro Ala Pro Thr Ala Pro Lys Lys Pro Ala Pro Thr Thr Pro Lys
                485             490             495

Glu Pro Ala Pro Thr Thr Pro Lys Glu Pro Ala Pro Thr Thr Thr Lys
                500             505             510

Glu Pro Ser Pro Thr Thr Pro Lys Glu Pro Ala Pro Thr Thr Thr Lys
                515             520             525

Ser Ala Pro Thr Thr Thr Lys Glu Pro Ala Pro Thr Thr Thr Lys Ser
    530             535             540

Ala Pro Thr Thr Pro Lys Glu Pro Ser Pro Thr Thr Thr Lys Glu Pro
545             550             555             560

Ala Pro Thr Thr Pro Lys Glu Pro Ala Pro Thr Thr Pro Lys Lys Pro
                565             570             575

Ala Pro Thr Thr Pro Lys Glu Pro Ala Pro Thr Thr Pro Lys Glu Pro
                580             585             590

Ala Pro Thr Thr Thr Lys Lys Pro Ala Pro Thr Thr Pro Lys Glu Pro
                595             600             605

Ala Pro Thr Thr Pro Lys Glu Thr Ala Pro Thr Thr Pro Lys Lys Leu
    610             615             620

Thr Pro Thr Thr Pro Glu Lys Leu Ala Pro Thr Thr Pro Glu Lys Pro
625             630             635             640

Ala Pro Thr Thr Pro Glu Glu Leu Ala Pro Thr Thr Pro Glu Glu Pro
                645             650             655

Thr Pro Thr Thr Pro Glu Glu Pro Ala Pro Thr Thr Pro Lys Ala Ala
                660             665             670

Ala Pro Asn Thr Pro Lys Glu Pro Ala Pro Thr Thr Pro Lys Glu Pro
                675             680             685

Ala Pro Thr Thr Pro Lys Glu Pro Ala Pro Thr Thr Pro Lys Glu Thr
    690             695             700

Ala Pro Thr Thr Pro Lys Gly Thr Ala Pro Thr Thr Leu Lys Glu Pro
705             710             715             720

Ala Pro Thr Thr Pro Lys Lys Pro Ala Pro Lys Glu Leu Ala Pro Thr
                725             730             735

Thr Thr Lys Glu Pro Thr Ser Thr Thr Ser Asp Lys Pro Ala Pro Thr
                740             745             750

Thr Pro Lys Gly Thr Ala Pro Thr Thr Pro Lys Glu Pro Ala Pro Thr
                755             760             765

Thr Pro Lys Glu Pro Ala Pro Thr Thr Pro Lys Gly Thr Ala Pro Thr
    770             775             780

Thr Leu Lys Glu Pro Ala Pro Thr Thr Pro Lys Lys Pro Ala Pro Lys
785             790             795             800

Glu Leu Ala Pro Thr Thr Thr Lys Gly Pro Thr Ser Thr Thr Ser Asp
                805             810             815

Lys Pro Ala Pro Thr Thr Pro Lys Glu Thr Ala Pro Thr Thr Pro Lys
                820             825             830

Glu Pro Ala Pro Thr Thr Pro Lys Lys Pro Ala Pro Thr Thr Pro Glu
    835             840             845

Thr Pro Pro Pro Thr Thr Ser Glu Val Ser Thr Pro Thr Thr Thr Lys
    850             855             860

Glu Pro Thr Thr Ile His Lys Ser Pro Asp Glu Ser Thr Pro Glu Leu
865             870             875             880

Ser Ala Glu Pro Thr Pro Lys Ala Leu Glu Asn Ser Pro Lys Glu Pro
                885             890             895
```

-continued

```
Gly Val Pro Thr Thr Lys Thr Pro Ala Ala Thr Lys Pro Glu Met Thr
            900             905             910

Thr Thr Ala Lys Asp Lys Thr Thr Glu Arg Asp Leu Arg Thr Thr Pro
            915             920             925

Glu Thr Thr Thr Ala Ala Pro Lys Met Thr Lys Glu Thr Ala Thr Thr
            930             935             940

Thr Glu Lys Thr Thr Glu Ser Lys Ile Thr Ala Thr Thr Thr Gln Val
945             950             955             960

Thr Ser Thr Thr Thr Gln Asp Thr Thr Pro Phe Lys Ile Thr Thr Leu
            965             970             975

Lys Thr Thr Thr Leu Ala Pro Lys Val Thr Thr Thr Lys Lys Thr Ile
            980             985             990

Thr Thr Thr Glu Ile Met Asn Lys Pro Glu Glu Thr Ala Lys Pro Lys
            995             1000            1005

Asp Arg Ala Thr Asn Ser Lys Ala Thr Thr Pro Lys Pro Gln Lys Pro
        1010            1015            1020

Thr Lys Ala Pro Lys Lys Pro Thr Ser Thr Lys Lys Pro Lys Thr Met
1025            1030            1035            1040

Pro Arg Val Arg Lys Pro Lys Thr Thr Pro Thr Pro Arg Lys Met Thr
            1045            1050            1055

Ser Thr Met Pro Glu Leu Asn Pro Thr Ser Arg Ile Ala Glu Ala Met
            1060            1065            1070

Leu Gln Thr Thr Thr Arg Pro Asn Gln Thr Pro Asn Ser Lys Leu Val
        1075            1080            1085

Glu Val Asn Pro Lys Ser Glu Asp Ala Gly Gly Ala Glu Gly Glu Thr
        1090            1095            1100

Pro His Met Leu Leu Arg Pro His Val Phe Met Pro Glu Val Thr Pro
1105            1110            1115            1120

Asp Met Asp Tyr Leu Pro Arg Val Pro Asn Gln Gly Ile Ile Ile Asn
            1125            1130            1135

Pro Met Leu Ser Asp Glu Thr Asn Ile Cys Asn Gly Lys Pro Val Asp
            1140            1145            1150

Gly Leu Thr Thr Leu Arg Asn Gly Thr Leu Val Ala Phe Arg Gly His
            1155            1160            1165

Tyr Phe Trp Met Leu Ser Pro Phe Ser Pro Pro Ser Pro Ala Arg Arg
        1170            1175            1180

Ile Thr Glu Val Trp Gly Ile Pro Ser Pro Ile Asp Thr Val Phe Thr
1185            1190            1195            1200

Arg Cys Asn Cys Glu Gly Lys Thr Phe Phe Phe Lys Asp Ser Gln Tyr
            1205            1210            1215

Trp Arg Phe Thr Asn Asp Ile Lys Asp Ala Gly Tyr Pro Lys Pro Ile
            1220            1225            1230

Phe Lys Gly Phe Gly Gly Leu Thr Gly Gln Ile Val Ala Ala Leu Ser
        1235            1240            1245

Thr Ala Lys Tyr Lys Asn Trp Pro Glu Ser Val Tyr Phe Phe Lys Arg
        1250            1255            1260

Gly Gly Ser Ile Gln Gln Tyr Ile Tyr Lys Gln Glu Pro Val Gln Lys
1265            1270            1275            1280

Cys Pro Gly Arg Arg Pro Ala Leu Asn Tyr Pro Val Tyr Gly Glu Thr
            1285            1290            1295

Thr Gln Val Arg Arg Arg Arg Phe Glu Arg Ala Ile Gly Pro Ser Gln
            1300            1305            1310

Thr His Thr Ile Arg Ile Gln Tyr Ser Pro Ala Arg Leu Ala Tyr Gln
```

-continued

```
                    1315                 1320                 1325

Asp Lys Gly Val Leu His Asn Glu Val Lys Val Ser Ile Leu Trp Arg
    1330                 1335                 1340

Gly Leu Pro Asn Val Val Thr Ser Ala Ile Ser Leu Pro Asn Ile Arg
1345                 1350                 1355                 1360

Lys Pro Asp Gly Tyr Asp Tyr Tyr Ala Phe Ser Lys Asp Gln Tyr Tyr
                1365                 1370                 1375

Asn Ile Asp Val Pro Ser Arg Thr Ala Arg Ala Ile Thr Thr Arg Ser
            1380                 1385                 1390

Gly Gln Thr Leu Ser Lys Val Trp Tyr Asn Cys Pro
        1395                 1400
```

```
<210> SEQ ID NO 106
<211> LENGTH: 1427
<212> TYPE: PRT
<213> ORGANISM: Artificial Sequence
<220> FEATURE:
<223> OTHER INFORMATION: Synthetic_ATS13_HUMAN

<400> SEQUENCE: 106

Met His Gln Arg His Pro Arg Ala Arg Cys Pro Pro Leu Cys Val Ala
1               5                   10                  15

Gly Ile Leu Ala Cys Gly Phe Leu Leu Gly Cys Trp Gly Pro Ser His
                20                  25                  30

Phe Gln Gln Ser Cys Leu Gln Ala Leu Glu Pro Gln Ala Val Ser Ser
            35                  40                  45

Tyr Leu Ser Pro Gly Ala Pro Leu Lys Gly Arg Pro Pro Ser Pro Gly
    50                  55                  60

Phe Gln Arg Gln Arg Gln Arg Gln Arg Arg Ala Ala Gly Gly Ile Leu
65                  70                  75                  80

His Leu Glu Leu Leu Val Ala Val Gly Pro Asp Val Phe Gln Ala His
                85                  90                  95

Gln Glu Asp Thr Glu Arg Tyr Val Leu Thr Asn Leu Asn Ile Gly Ala
                100                 105                 110

Glu Leu Leu Arg Asp Pro Ser Leu Gly Ala Gln Phe Arg Val His Leu
            115                 120                 125

Val Lys Met Val Ile Leu Thr Glu Pro Glu Gly Ala Pro Asn Ile Thr
    130                 135                 140

Ala Asn Leu Thr Ser Ser Leu Leu Ser Val Cys Gly Trp Ser Gln Thr
145                 150                 155                 160

Ile Asn Pro Glu Asp Asp Thr Asp Pro Gly His Ala Asp Leu Val Leu
                165                 170                 175

Tyr Ile Thr Arg Phe Asp Leu Glu Leu Pro Asp Gly Asn Arg Gln Val
                180                 185                 190

Arg Gly Val Thr Gln Leu Gly Gly Ala Cys Ser Pro Thr Trp Ser Cys
            195                 200                 205

Leu Ile Thr Glu Asp Thr Gly Phe Asp Leu Gly Val Thr Ile Ala His
    210                 215                 220

Glu Ile Gly His Ser Phe Gly Leu Glu His Asp Gly Ala Pro Gly Ser
225                 230                 235                 240

Gly Cys Gly Pro Ser Gly His Val Met Ala Ser Asp Gly Ala Ala Pro
                245                 250                 255

Arg Ala Gly Leu Ala Trp Ser Pro Cys Ser Arg Arg Gln Leu Leu Ser
            260                 265                 270

Leu Leu Ser Ala Gly Arg Ala Arg Cys Val Trp Asp Pro Pro Arg Pro
```

-continued

```
              275                 280                 285
Gln Pro Gly Ser Ala Gly His Pro Pro Asp Ala Gln Pro Gly Leu Tyr
    290                 295                 300

Tyr Ser Ala Asn Glu Gln Cys Arg Val Ala Phe Gly Pro Lys Ala Val
305                 310                 315                 320

Ala Cys Thr Phe Ala Arg Glu His Leu Asp Met Cys Gln Ala Leu Ser
                325                 330                 335

Cys His Thr Asp Pro Leu Asp Gln Ser Ser Cys Ser Arg Leu Leu Val
                340                 345                 350

Pro Leu Leu Asp Gly Thr Glu Cys Gly Val Glu Lys Trp Cys Ser Lys
                355                 360                 365

Gly Arg Cys Arg Ser Leu Val Glu Leu Thr Pro Ile Ala Ala Val His
    370                 375                 380

Gly Arg Trp Ser Ser Trp Gly Pro Arg Ser Pro Cys Ser Arg Ser Cys
385                 390                 395                 400

Gly Gly Gly Val Val Thr Arg Arg Arg Gln Cys Asn Asn Pro Arg Pro
                405                 410                 415

Ala Phe Gly Gly Arg Ala Cys Val Gly Ala Asp Leu Gln Ala Glu Met
                420                 425                 430

Cys Asn Thr Gln Ala Cys Glu Lys Thr Gln Leu Glu Phe Met Ser Gln
    435                 440                 445

Gln Cys Ala Arg Thr Asp Gly Gln Pro Leu Arg Ser Ser Pro Gly Gly
    450                 455                 460

Ala Ser Phe Tyr His Trp Gly Ala Ala Val Pro His Ser Gln Gly Asp
465                 470                 475                 480

Ala Leu Cys Arg His Met Cys Arg Ala Ile Gly Glu Ser Phe Ile Met
                485                 490                 495

Lys Arg Gly Asp Ser Phe Leu Asp Gly Thr Arg Cys Met Pro Ser Gly
                500                 505                 510

Pro Arg Glu Asp Gly Thr Leu Ser Leu Cys Val Ser Gly Ser Cys Arg
                515                 520                 525

Thr Phe Gly Cys Asp Gly Arg Met Asp Ser Gln Gln Val Trp Asp Arg
    530                 535                 540

Cys Gln Val Cys Gly Gly Asp Asn Ser Thr Cys Ser Pro Arg Lys Gly
545                 550                 555                 560

Ser Phe Thr Ala Gly Arg Ala Arg Glu Tyr Val Thr Phe Leu Thr Val
                565                 570                 575

Thr Pro Asn Leu Thr Ser Val Tyr Ile Ala Asn His Arg Pro Leu Phe
                580                 585                 590

Thr His Leu Ala Val Arg Ile Gly Gly Arg Tyr Val Val Ala Gly Lys
    595                 600                 605

Met Ser Ile Ser Pro Asn Thr Thr Tyr Pro Ser Leu Leu Glu Asp Gly
    610                 615                 620

Arg Val Glu Tyr Arg Val Ala Leu Thr Glu Asp Arg Leu Pro Arg Leu
625                 630                 635                 640

Glu Glu Ile Arg Ile Trp Gly Pro Leu Gln Glu Asp Ala Asp Ile Gln
                645                 650                 655

Val Tyr Arg Arg Tyr Gly Glu Glu Tyr Gly Asn Leu Thr Arg Pro Asp
                660                 665                 670

Ile Thr Phe Thr Tyr Phe Gln Pro Lys Pro Arg Gln Ala Trp Val Trp
                675                 680                 685

Ala Ala Val Arg Gly Pro Cys Ser Val Ser Cys Gly Ala Gly Leu Arg
    690                 695                 700
```

-continued

```
Trp Val Asn Tyr Ser Cys Leu Asp Gln Ala Arg Lys Glu Leu Val Glu
705             710             715             720

Thr Val Gln Cys Gln Gly Ser Gln Gln Pro Pro Ala Trp Pro Glu Ala
            725             730             735

Cys Val Leu Glu Pro Cys Pro Pro Tyr Trp Ala Val Gly Asp Phe Gly
            740             745             750

Pro Cys Ser Ala Ser Cys Gly Gly Gly Leu Arg Glu Arg Pro Val Arg
            755             760             765

Cys Val Glu Ala Gln Gly Ser Leu Leu Lys Thr Leu Pro Pro Ala Arg
            770             775             780

Cys Arg Ala Gly Ala Gln Gln Pro Ala Val Ala Leu Glu Thr Cys Asn
785             790             795             800

Pro Gln Pro Cys Pro Ala Arg Trp Glu Val Ser Glu Pro Ser Ser Cys
            805             810             815

Thr Ser Ala Gly Gly Ala Gly Leu Ala Leu Glu Asn Glu Thr Cys Val
            820             825             830

Pro Gly Ala Asp Gly Leu Glu Ala Pro Val Thr Glu Gly Pro Gly Ser
            835             840             845

Val Asp Glu Lys Leu Pro Ala Pro Glu Pro Cys Val Gly Met Ser Cys
    850             855             860

Pro Pro Gly Trp Gly His Leu Asp Ala Thr Ser Ala Gly Glu Lys Ala
865             870             875             880

Pro Ser Pro Trp Gly Ser Ile Arg Thr Gly Ala Gln Ala Ala His Val
            885             890             895

Trp Thr Pro Ala Ala Gly Ser Cys Ser Val Ser Cys Gly Arg Gly Leu
            900             905             910

Met Glu Leu Arg Phe Leu Cys Met Asp Ser Ala Leu Arg Val Pro Val
            915             920             925

Gln Glu Glu Leu Cys Gly Leu Ala Ser Lys Pro Gly Ser Arg Arg Glu
    930             935             940

Val Cys Gln Ala Val Pro Cys Pro Ala Arg Trp Gln Tyr Lys Leu Ala
945             950             955             960

Ala Cys Ser Val Ser Cys Gly Arg Gly Val Val Arg Arg Ile Leu Tyr
            965             970             975

Cys Ala Arg Ala His Gly Glu Asp Asp Gly Glu Glu Ile Leu Leu Asp
            980             985             990

Thr Gln Cys Gln Gly Leu Pro Arg Pro Glu Pro Gln Glu Ala Cys Ser
            995             1000            1005

Leu Glu Pro Cys Pro Pro Arg Trp Lys Val Met Ser Leu Gly Pro Cys
    1010            1015            1020

Ser Ala Ser Cys Gly Leu Gly Thr Ala Arg Arg Ser Val Ala Cys Val
1025            1030            1035            1040

Gln Leu Asp Gln Gly Gln Asp Val Glu Val Asp Glu Ala Ala Cys Ala
            1045            1050            1055

Ala Leu Val Arg Pro Glu Ala Ser Val Pro Cys Leu Ile Ala Asp Cys
            1060            1065            1070

Thr Tyr Arg Trp His Val Gly Thr Trp Met Glu Cys Ser Val Ser Cys
            1075            1080            1085

Gly Asp Gly Ile Gln Arg Arg Arg Asp Thr Cys Leu Gly Pro Gln Ala
    1090            1095            1100

Gln Ala Pro Val Pro Ala Asp Phe Cys Gln His Leu Pro Lys Pro Val
1105            1110            1115            1120
```

-continued

```
Thr Val Arg Gly Cys Trp Ala Gly Pro Cys Val Gly Gln Gly Thr Pro
              1125                1130                1135

Ser Leu Val Pro His Glu Glu Ala Ala Ala Pro Gly Arg Thr Thr Ala
              1140                1145                1150

Thr Pro Ala Gly Ala Ser Leu Glu Trp Ser Gln Ala Arg Gly Leu Leu
              1155                1160                1165

Phe Ser Pro Ala Pro Gln Pro Arg Arg Leu Leu Pro Gly Pro Gln Glu
         1170                1175                1180

Asn Ser Val Gln Ser Ser Ala Cys Gly Arg Gln His Leu Glu Pro Thr
1185                1190                1195                1200

Gly Thr Ile Asp Met Arg Gly Pro Gly Gln Ala Asp Cys Ala Val Ala
              1205                1210                1215

Ile Gly Arg Pro Leu Gly Glu Val Val Thr Leu Arg Val Leu Glu Ser
              1220                1225                1230

Ser Leu Asn Cys Ser Ala Gly Asp Met Leu Leu Leu Trp Gly Arg Leu
              1235                1240                1245

Thr Trp Arg Lys Met Cys Arg Lys Leu Leu Asp Met Thr Phe Ser Ser
         1250                1255                1260

Lys Thr Asn Thr Leu Val Val Arg Gln Arg Cys Gly Arg Pro Gly Gly
1265                1270                1275                1280

Gly Val Leu Leu Arg Tyr Gly Ser Gln Leu Ala Pro Glu Thr Phe Tyr
              1285                1290                1295

Arg Glu Cys Asp Met Gln Leu Phe Gly Pro Trp Gly Glu Ile Val Ser
              1300                1305                1310

Pro Ser Leu Ser Pro Ala Thr Ser Asn Ala Gly Gly Cys Arg Leu Phe
              1315                1320                1325

Ile Asn Val Ala Pro His Ala Arg Ile Ala Ile His Ala Leu Ala Thr
         1330                1335                1340

Asn Met Gly Ala Gly Thr Glu Gly Ala Asn Ala Ser Tyr Ile Leu Ile
1345                1350                1355                1360

Arg Asp Thr His Ser Leu Arg Thr Thr Ala Phe His Gly Gln Gln Val
              1365                1370                1375

Leu Tyr Trp Glu Ser Glu Ser Ser Gln Ala Glu Met Glu Phe Ser Glu
              1380                1385                1390

Gly Phe Leu Lys Ala Gln Ala Ser Leu Arg Gly Gln Tyr Trp Thr Leu
              1395                1400                1405

Gln Ser Trp Val Pro Glu Met Gln Asp Pro Gln Ser Trp Lys Gly Lys
         1410                1415                1420

Glu Gly Thr
1425
```

```
<210> SEQ ID NO 107
<211> LENGTH: 1475
<212> TYPE: PRT
<213> ORGANISM: Artificial Sequence
<220> FEATURE:
<223> OTHER INFORMATION: Synthetic_NU153_HUMAN

<400> SEQUENCE: 107

Met Ala Ser Gly Ala Gly Gly Val Gly Gly Gly Gly Gly Gly Lys Ile
1               5                   10                  15

Arg Thr Arg Arg Cys His Gln Gly Pro Ile Lys Pro Tyr Gln Gln Gly
              20                  25                  30

Arg Gln Gln His Gln Gly Ile Leu Ser Arg Val Thr Glu Ser Val Lys
         35                  40                  45
```

-continued

```
Asn Ile Val Pro Gly Trp Leu Gln Arg Tyr Phe Asn Lys Asn Glu Asp
    50                  55                  60

Val Cys Ser Cys Ser Thr Asp Thr Ser Glu Val Pro Arg Trp Pro Glu
65                  70                  75                  80

Asn Lys Glu Asp His Leu Val Tyr Ala Asp Glu Glu Ser Ser Asn Ile
                85                  90                  95

Thr Asp Gly Arg Ile Thr Pro Glu Pro Ala Val Ser Asn Thr Glu Glu
            100                 105                 110

Pro Ser Thr Thr Ser Thr Ala Ser Asn Tyr Pro Asp Val Leu Thr Arg
            115                 120                 125

Pro Ser Leu His Arg Ser His Leu Asn Phe Ser Met Leu Glu Ser Pro
    130                 135                 140

Ala Leu His Cys Gln Pro Ser Thr Ser Ser Ala Phe Pro Ile Gly Ser
145                 150                 155                 160

Ser Gly Phe Ser Leu Val Lys Glu Ile Lys Asp Ser Thr Ser Gln His
            165                 170                 175

Asp Asp Asp Asn Ile Ser Thr Thr Ser Gly Phe Ser Ser Arg Ala Ser
            180                 185                 190

Asp Lys Asp Ile Thr Val Ser Lys Asn Thr Ser Leu Pro Pro Leu Trp
            195                 200                 205

Ser Pro Glu Ala Glu Arg Ser His Ser Leu Ser Gln His Thr Ala Thr
    210                 215                 220

Ser Ser Lys Lys Pro Ala Phe Asn Leu Ser Ala Phe Gly Thr Leu Ser
225                 230                 235                 240

Pro Ser Leu Gly Asn Ser Ser Ile Leu Lys Thr Ser Gln Leu Gly Asp
            245                 250                 255

Ser Pro Phe Tyr Pro Gly Lys Thr Thr Tyr Gly Gly Ala Ala Ala Ala
            260                 265                 270

Val Arg Gln Ser Lys Leu Arg Asn Thr Pro Tyr Gln Ala Pro Val Arg
    275                 280                 285

Arg Gln Met Lys Ala Lys Gln Leu Ser Ala Gln Ser Tyr Gly Val Thr
    290                 295                 300

Ser Ser Thr Ala Arg Arg Ile Leu Gln Ser Leu Glu Lys Met Ser Ser
305                 310                 315                 320

Pro Leu Ala Asp Ala Lys Arg Ile Pro Ser Ile Val Ser Ser Pro Leu
            325                 330                 335

Asn Ser Pro Leu Asp Arg Ser Gly Ile Asp Ile Thr Asp Phe Gln Ala
            340                 345                 350

Lys Arg Glu Lys Val Asp Ser Gln Tyr Pro Pro Val Gln Arg Leu Met
            355                 360                 365

Thr Pro Lys Pro Val Ser Ile Ala Thr Asn Arg Ser Val Tyr Phe Lys
    370                 375                 380

Pro Ser Leu Thr Pro Ser Gly Glu Phe Arg Lys Thr Asn Gln Arg Ile
385                 390                 395                 400

Asp Asn Lys Cys Ser Thr Gly Tyr Glu Lys Asn Met Thr Pro Gly Gln
            405                 410                 415

Asn Arg Glu Gln Arg Glu Ser Gly Phe Ser Tyr Pro Asn Phe Ser Leu
            420                 425                 430

Pro Ala Ala Asn Gly Leu Ser Ser Gly Val Gly Gly Gly Gly Gly Lys
            435                 440                 445

Met Arg Arg Glu Arg Thr Arg Phe Val Ala Ser Lys Pro Leu Glu Glu
    450                 455                 460

Glu Glu Met Glu Val Pro Val Leu Pro Lys Ile Ser Leu Pro Ile Thr
```

-continued

```
465                 470                 475                 480

Ser Ser Ser Leu Pro Thr Phe Asn Phe Ser Ser Pro Glu Ile Thr Thr
                485                 490                 495

Ser Ser Pro Ser Pro Ile Asn Ser Ser Gln Ala Leu Thr Asn Lys Val
                500                 505                 510

Gln Met Thr Ser Pro Ser Ser Thr Gly Ser Pro Met Phe Lys Phe Ser
                515                 520                 525

Ser Pro Ile Val Lys Ser Thr Glu Ala Asn Val Leu Pro Pro Ser Ser
                530                 535                 540

Ile Gly Phe Thr Phe Ser Val Pro Val Ala Lys Thr Ala Glu Leu Ser
545                 550                 555                 560

Gly Ser Ser Ser Thr Leu Glu Pro Ile Ile Ser Ser Ser Ala His His
                565                 570                 575

Val Thr Thr Val Asn Ser Thr Asn Cys Lys Lys Thr Pro Pro Glu Asp
                580                 585                 590

Cys Glu Gly Pro Phe Arg Pro Ala Glu Ile Leu Lys Glu Gly Ser Val
                595                 600                 605

Leu Asp Ile Leu Lys Ser Pro Gly Phe Ala Ser Pro Lys Ile Asp Ser
                610                 615                 620

Val Ala Ala Gln Pro Thr Ala Thr Ser Pro Val Val Tyr Thr Arg Pro
625                 630                 635                 640

Ala Ile Ser Ser Phe Ser Ser Ser Gly Ile Gly Phe Gly Glu Ser Leu
                645                 650                 655

Lys Ala Gly Ser Ser Trp Gln Cys Asp Thr Cys Leu Leu Gln Asn Lys
                660                 665                 670

Val Thr Asp Asn Lys Cys Ile Ala Cys Gln Ala Ala Lys Leu Ser Pro
                675                 680                 685

Arg Asp Thr Ala Lys Gln Thr Gly Ile Glu Thr Pro Asn Lys Ser Gly
                690                 695                 700

Lys Thr Thr Leu Ser Ala Ser Gly Thr Gly Phe Gly Asp Lys Phe Lys
705                 710                 715                 720

Pro Val Ile Gly Thr Trp Asp Cys Asp Thr Cys Leu Val Gln Asn Lys
                725                 730                 735

Pro Glu Ala Ile Lys Cys Val Ala Cys Glu Thr Pro Lys Pro Gly Thr
                740                 745                 750

Cys Val Lys Arg Ala Leu Thr Leu Thr Val Val Ser Glu Ser Ala Glu
                755                 760                 765

Thr Met Thr Ala Ser Ser Ser Ser Cys Thr Val Thr Thr Gly Thr Leu
                770                 775                 780

Gly Phe Gly Asp Lys Phe Lys Arg Pro Ile Gly Ser Trp Glu Cys Ser
785                 790                 795                 800

Val Cys Cys Val Ser Asn Asn Ala Glu Asp Asn Lys Cys Val Ser Cys
                805                 810                 815

Met Ser Glu Lys Pro Gly Ser Ser Val Pro Ala Ser Ser Ser Ser Thr
                820                 825                 830

Val Pro Val Ser Leu Pro Ser Gly Gly Ser Leu Gly Leu Glu Lys Phe
                835                 840                 845

Lys Lys Pro Glu Gly Ser Trp Asp Cys Glu Leu Cys Leu Val Gln Asn
                850                 855                 860

Lys Ala Asp Ser Thr Lys Cys Leu Ala Cys Glu Ser Ala Lys Pro Gly
865                 870                 875                 880

Thr Lys Ser Gly Phe Lys Gly Phe Asp Thr Ser Ser Ser Ser Ser Asn
                885                 890                 895
```

```
Ser Ala Ala Ser Ser Ser Phe Lys Phe Gly Val Ser Ser Ser Ser Ser
        900                 905                 910

Gly Pro Ser Gln Thr Leu Thr Ser Thr Gly Asn Phe Lys Phe Gly Asp
        915                 920                 925

Gln Gly Gly Phe Lys Ile Gly Val Ser Ser Asp Ser Gly Ser Ile Asn
        930                 935                 940

Pro Met Ser Glu Gly Phe Lys Phe Ser Lys Pro Ile Gly Asp Phe Lys
945                 950                 955                 960

Phe Gly Val Ser Ser Glu Ser Lys Pro Glu Glu Val Lys Lys Asp Ser
                965                 970                 975

Lys Asn Asp Asn Phe Lys Phe Gly Leu Ser Ser Gly Leu Ser Asn Pro
                980                 985                 990

Val Ser Leu Thr Pro Phe Gln Phe Gly Val Ser Asn Leu Gly Gln Glu
        995                 1000                1005

Glu Lys Lys Glu Glu Leu Pro Lys Ser Ser Ser Ala Gly Phe Ser Phe
    1010                1015                1020

Gly Thr Gly Val Ile Asn Ser Thr Pro Ala Pro Ala Asn Thr Ile Val
1025                1030                1035                1040

Thr Ser Glu Asn Lys Ser Ser Phe Asn Leu Gly Thr Ile Glu Thr Lys
                1045                1050                1055

Ser Ala Ser Val Ala Pro Phe Thr Cys Lys Thr Ser Glu Ala Lys Lys
                1060                1065                1070

Glu Glu Met Pro Ala Thr Lys Gly Gly Phe Ser Phe Gly Asn Val Glu
        1075                1080                1085

Pro Ala Ser Leu Pro Ser Ala Ser Val Phe Val Leu Gly Arg Thr Glu
    1090                1095                1100

Glu Lys Gln Gln Glu Pro Val Thr Ser Thr Ser Leu Val Phe Gly Lys
1105                1110                1115                1120

Lys Ala Asp Asn Glu Glu Pro Lys Cys Gln Pro Val Phe Ser Phe Gly
                1125                1130                1135

Asn Ser Glu Gln Thr Lys Asp Glu Asn Ser Ser Lys Ser Thr Phe Ser
        1140                1145                1150

Phe Ser Met Thr Lys Pro Ser Glu Lys Glu Ser Glu Gln Pro Ala Lys
        1155                1160                1165

Ala Thr Phe Ala Phe Gly Ala Gln Thr Ser Thr Thr Ala Asp Gln Gly
    1170                1175                1180

Ala Ala Lys Pro Val Phe Ser Phe Leu Asn Asn Ser Ser Ser Ser Ser
1185                1190                1195                1200

Ser Thr Pro Ala Thr Ser Ala Gly Gly Gly Ile Phe Gly Ser Ser Thr
        1205                1210                1215

Ser Ser Ser Asn Pro Pro Val Ala Thr Phe Val Phe Gly Gln Ser Ser
        1220                1225                1230

Asn Pro Val Ser Ser Ser Ala Phe Gly Asn Thr Ala Glu Ser Ser Thr
        1235                1240                1245

Ser Gln Ser Leu Leu Phe Ser Gln Asp Ser Lys Leu Ala Thr Thr Ser
    1250                1255                1260

Ser Thr Gly Thr Ala Val Thr Pro Phe Val Phe Gly Pro Gly Ala Ser
1265                1270                1275                1280

Ser Asn Asn Thr Thr Thr Ser Gly Phe Gly Phe Gly Ala Thr Thr Thr
        1285                1290                1295

Ser Ser Ser Ala Gly Ser Ser Phe Val Phe Gly Thr Gly Pro Ser Ala
        1300                1305                1310
```

-continued

```
Pro Ser Ala Ser Pro Ala Phe Gly Ala Asn Gln Thr Pro Thr Phe Gly
        1315            1320            1325

Gln Ser Gln Gly Ala Ser Gln Pro Asn Pro Pro Gly Phe Gly Ser Ile
        1330            1335            1340

Ser Ser Ser Thr Ala Leu Phe Pro Thr Gly Ser Gln Pro Ala Pro Pro
1345            1350            1355            1360

Thr Phe Gly Thr Val Ser Ser Ser Gln Pro Pro Val Phe Gly Gln
            1365            1370            1375

Gln Pro Ser Gln Ser Ala Phe Gly Ser Gly Thr Thr Pro Asn Ser Ser
        1380            1385            1390

Ser Ala Phe Gln Phe Gly Ser Ser Thr Thr Asn Phe Asn Phe Thr Asn
        1395            1400            1405

Asn Ser Pro Ser Gly Val Phe Thr Phe Gly Ala Asn Ser Ser Thr Pro
        1410            1415            1420

Ala Ala Ser Ala Gln Pro Ser Gly Ser Gly Gly Phe Pro Phe Asn Gln
1425            1430            1435            1440

Ser Pro Ala Ala Phe Thr Val Gly Ser Asn Gly Lys Asn Val Phe Ser
            1445            1450            1455

Ser Ser Gly Thr Ser Phe Ser Gly Arg Lys Ile Lys Thr Ala Val Arg
            1460            1465            1470

Arg Arg Lys
        1475

<210> SEQ ID NO 108
<211> LENGTH: 1500
<212> TYPE: PRT
<213> ORGANISM: Artificial Sequence
<220> FEATURE:
<223> OTHER INFORMATION: Synthetic_CPSM_HUMAN

<400> SEQUENCE: 108

Met Thr Arg Ile Leu Thr Ala Phe Lys Val Val Arg Thr Leu Lys Thr
1               5               10              15

Gly Phe Gly Phe Thr Asn Val Thr Ala His Gln Lys Trp Lys Phe Ser
            20              25              30

Arg Pro Gly Ile Arg Leu Leu Ser Val Lys Ala Gln Thr Ala His Ile
        35              40              45

Val Leu Glu Asp Gly Thr Lys Met Lys Gly Tyr Ser Phe Gly His Pro
    50              55              60

Ser Ser Val Ala Gly Glu Val Val Phe Asn Thr Gly Leu Gly Gly Tyr
65              70              75              80

Pro Glu Ala Ile Thr Asp Pro Ala Tyr Lys Gly Gln Ile Leu Thr Met
            85              90              95

Ala Asn Pro Ile Ile Gly Asn Gly Gly Ala Pro Asp Thr Thr Ala Leu
            100             105             110

Asp Glu Leu Gly Leu Ser Lys Tyr Leu Glu Ser Asn Gly Ile Lys Val
        115             120             125

Ser Gly Leu Leu Val Leu Asp Tyr Ser Lys Asp Tyr Asn His Trp Leu
        130             135             140

Ala Thr Lys Ser Leu Gly Gln Trp Leu Gln Glu Glu Lys Val Pro Ala
145             150             155             160

Ile Tyr Gly Val Asp Thr Arg Met Leu Thr Lys Ile Ile Arg Asp Lys
            165             170             175

Gly Thr Met Leu Gly Lys Ile Glu Phe Glu Gly Gln Pro Val Asp Phe
            180             185             190
```

-continued

```
Val Asp Pro Asn Lys Gln Asn Leu Ile Ala Glu Val Ser Thr Lys Asp
        195                 200                 205

Val Lys Val Tyr Gly Lys Gly Asn Pro Thr Lys Val Val Ala Val Asp
        210                 215                 220

Cys Gly Ile Lys Asn Asn Val Ile Arg Leu Leu Val Lys Arg Gly Ala
225                 230                 235                 240

Glu Val His Leu Val Pro Trp Asn His Asp Phe Thr Lys Met Glu Tyr
                245                 250                 255

Asp Gly Ile Leu Ile Ala Gly Gly Pro Gly Asn Pro Ala Leu Ala Glu
                260                 265                 270

Pro Leu Ile Gln Asn Val Arg Lys Ile Leu Glu Ser Asp Arg Lys Glu
        275                 280                 285

Pro Leu Phe Gly Ile Ser Thr Gly Asn Leu Ile Thr Gly Leu Ala Ala
        290                 295                 300

Gly Ala Lys Thr Tyr Lys Met Ser Met Ala Asn Arg Gly Gln Asn Gln
305                 310                 315                 320

Pro Val Leu Asn Ile Thr Asn Lys Gln Ala Phe Ile Thr Ala Gln Asn
                325                 330                 335

His Gly Tyr Ala Leu Asp Asn Thr Leu Pro Ala Gly Trp Lys Pro Leu
                340                 345                 350

Phe Val Asn Val Asn Asp Gln Thr Asn Glu Gly Ile Met His Glu Ser
                355                 360                 365

Lys Pro Phe Phe Ala Val Gln Phe His Pro Glu Val Thr Pro Gly Pro
        370                 375                 380

Ile Asp Thr Glu Tyr Leu Phe Asp Ser Phe Phe Ser Leu Ile Lys Lys
385                 390                 395                 400

Gly Lys Ala Thr Thr Ile Thr Ser Val Leu Pro Lys Pro Ala Leu Val
                405                 410                 415

Ala Ser Arg Val Glu Val Ser Lys Val Leu Ile Leu Gly Ser Gly Gly
                420                 425                 430

Leu Ser Ile Gly Gln Ala Gly Glu Phe Asp Tyr Ser Gly Ser Gln Ala
        435                 440                 445

Val Lys Ala Met Lys Glu Glu Asn Val Lys Thr Val Leu Met Asn Pro
        450                 455                 460

Asn Ile Ala Ser Val Gln Thr Asn Glu Val Gly Leu Lys Gln Ala Asp
465                 470                 475                 480

Thr Val Tyr Phe Leu Pro Ile Thr Pro Gln Phe Val Thr Glu Val Ile
                485                 490                 495

Lys Ala Glu Gln Pro Asp Gly Leu Ile Leu Gly Met Gly Gly Gln Thr
                500                 505                 510

Ala Leu Asn Cys Gly Val Glu Leu Phe Lys Arg Gly Val Leu Lys Glu
        515                 520                 525

Tyr Gly Val Lys Val Leu Gly Thr Ser Val Glu Ser Ile Met Ala Thr
        530                 535                 540

Glu Asp Arg Gln Leu Phe Ser Asp Lys Leu Asn Glu Ile Asn Glu Lys
545                 550                 555                 560

Ile Ala Pro Ser Phe Ala Val Glu Ser Ile Glu Asp Ala Leu Lys Ala
                565                 570                 575

Ala Asp Thr Ile Gly Tyr Pro Val Met Ile Arg Ser Ala Tyr Ala Leu
                580                 585                 590

Gly Gly Leu Gly Ser Gly Ile Cys Pro Asn Arg Glu Thr Leu Met Asp
        595                 600                 605

Leu Ser Thr Lys Ala Phe Ala Met Thr Asn Gln Ile Leu Val Glu Lys
```

-continued

```
              610             615             620

Ser Val Thr Gly Trp Lys Glu Ile Glu Tyr Glu Val Val Arg Asp Ala
625             630             635             640

Asp Asp Asn Cys Val Thr Val Cys Asn Met Glu Asn Val Asp Ala Met
                645             650             655

Gly Val His Thr Gly Asp Ser Val Val Val Ala Pro Ala Gln Thr Leu
            660             665             670

Ser Asn Ala Glu Phe Gln Met Leu Arg Arg Thr Ser Ile Asn Val Val
            675             680             685

Arg His Leu Gly Ile Val Gly Glu Cys Asn Ile Gln Phe Ala Leu His
        690             695             700

Pro Thr Ser Met Glu Tyr Cys Ile Ile Glu Val Asn Ala Arg Leu Ser
705             710             715             720

Arg Ser Ser Ala Leu Ala Ser Lys Ala Thr Gly Tyr Pro Leu Ala Phe
            725             730             735

Ile Ala Ala Lys Ile Ala Leu Gly Ile Pro Leu Pro Glu Ile Lys Asn
            740             745             750

Val Val Ser Gly Lys Thr Ser Ala Cys Phe Glu Pro Ser Leu Asp Tyr
        755             760             765

Met Val Thr Lys Ile Pro Arg Trp Asp Leu Asp Arg Phe His Gly Thr
    770             775             780

Ser Ser Arg Ile Gly Ser Ser Met Lys Ser Val Gly Glu Val Met Ala
785             790             795             800

Ile Gly Arg Thr Phe Glu Glu Ser Phe Gln Lys Ala Leu Arg Met Cys
            805             810             815

His Pro Ser Ile Glu Gly Phe Thr Pro Arg Leu Pro Met Asn Lys Glu
            820             825             830

Trp Pro Ser Asn Leu Asp Leu Arg Lys Glu Leu Ser Glu Pro Ser Ser
        835             840             845

Thr Arg Ile Tyr Ala Ile Ala Lys Ala Ile Asp Asp Asn Met Ser Leu
    850             855             860

Asp Glu Ile Glu Lys Leu Thr Tyr Ile Asp Lys Trp Phe Leu Tyr Lys
865             870             875             880

Met Arg Asp Ile Leu Asn Met Glu Lys Thr Leu Lys Gly Leu Asn Ser
            885             890             895

Glu Ser Met Thr Glu Glu Thr Leu Lys Arg Ala Lys Glu Ile Gly Phe
            900             905             910

Ser Asp Lys Gln Ile Ser Lys Cys Leu Gly Leu Thr Glu Ala Gln Thr
        915             920             925

Arg Glu Leu Arg Leu Lys Lys Asn Ile His Pro Trp Val Lys Gln Ile
    930             935             940

Asp Thr Leu Ala Ala Glu Tyr Pro Ser Val Thr Asn Tyr Leu Tyr Val
945             950             955             960

Thr Tyr Asn Gly Gln Glu His Asp Val Asn Phe Asp Asp His Gly Met
            965             970             975

Met Val Leu Gly Cys Gly Pro Tyr His Ile Gly Ser Ser Val Glu Phe
            980             985             990

Asp Trp Cys Ala Val Ser Ser Ile Arg Thr Leu Arg Gln Leu Gly Lys
        995             1000            1005

Lys Thr Val Val Val Asn Cys Asn Pro Glu Thr Val Ser Thr Asp Phe
    1010            1015            1020

Asp Glu Cys Asp Lys Leu Tyr Phe Glu Glu Leu Ser Leu Glu Arg Ile
1025            1030            1035            1040
```

-continued

```
Leu Asp Ile Tyr His Gln Glu Ala Cys Gly Gly Cys Ile Ile Ser Val
            1045                1050                1055

Gly Gly Gln Ile Pro Asn Asn Leu Ala Val Pro Leu Tyr Lys Asn Gly
            1060                1065                1070

Val Lys Ile Met Gly Thr Ser Pro Leu Gln Ile Asp Arg Ala Glu Asp
        1075                1080                1085

Arg Ser Ile Phe Ser Ala Val Leu Asp Glu Leu Lys Val Ala Gln Ala
        1090                1095                1100

Pro Trp Lys Ala Val Asn Thr Leu Asn Glu Ala Leu Glu Phe Ala Lys
1105                1110                1115                1120

Ser Val Asp Tyr Pro Cys Leu Leu Arg Pro Ser Tyr Val Leu Ser Gly
            1125                1130                1135

Ser Ala Met Asn Val Val Phe Ser Glu Asp Glu Met Lys Lys Phe Leu
            1140                1145                1150

Glu Glu Ala Thr Arg Val Ser Gln Glu His Pro Val Val Leu Thr Lys
            1155                1160                1165

Phe Val Glu Gly Ala Arg Glu Val Glu Met Asp Ala Val Gly Lys Asp
        1170                1175                1180

Gly Arg Val Ile Ser His Ala Ile Ser Glu His Val Glu Asp Ala Gly
1185                1190                1195                1200

Val His Ser Gly Asp Ala Thr Leu Met Leu Pro Thr Gln Thr Ile Ser
            1205                1210                1215

Gln Gly Ala Ile Glu Lys Val Lys Asp Ala Thr Arg Lys Ile Ala Lys
            1220                1225                1230

Ala Phe Ala Ile Ser Gly Pro Phe Asn Val Gln Phe Leu Val Lys Gly
            1235                1240                1245

Asn Asp Val Leu Val Ile Glu Cys Asn Leu Arg Ala Ser Arg Ser Phe
        1250                1255                1260

Pro Phe Val Ser Lys Thr Leu Gly Val Asp Phe Ile Asp Val Ala Thr
1265                1270                1275                1280

Lys Val Met Ile Gly Glu Asn Val Asp Glu Lys His Leu Pro Thr Leu
            1285                1290                1295

Asp His Pro Ile Ile Pro Ala Asp Tyr Val Ala Ile Lys Ala Pro Met
            1300                1305                1310

Phe Ser Trp Pro Arg Leu Arg Asp Ala Asp Pro Ile Leu Arg Cys Glu
            1315                1320                1325

Met Ala Ser Thr Gly Glu Val Ala Cys Phe Gly Glu Gly Ile His Thr
            1330                1335                1340

Ala Phe Leu Lys Ala Met Leu Ser Thr Gly Phe Lys Ile Pro Gln Lys
1345                1350                1355                1360

Gly Ile Leu Ile Gly Ile Gln Gln Ser Phe Arg Pro Arg Phe Leu Gly
            1365                1370                1375

Val Ala Glu Gln Leu His Asn Glu Gly Phe Lys Leu Phe Ala Thr Glu
            1380                1385                1390

Ala Thr Ser Asp Trp Leu Asn Ala Asn Asn Val Pro Ala Thr Pro Val
        1395                1400                1405

Ala Trp Pro Ser Gln Glu Gly Gln Asn Pro Ser Leu Ser Ser Ile Arg
        1410                1415                1420

Lys Leu Ile Arg Asp Gly Ser Ile Asp Leu Val Ile Asn Leu Pro Asn
1425                1430                1435                1440

Asn Asn Thr Lys Phe Val His Asp Asn Tyr Val Ile Arg Arg Thr Ala
            1445                1450                1455
```

-continued

```
Val Asp Ser Gly Ile Pro Leu Leu Thr Asn Phe Gln Val Thr Lys Leu
            1460                    1465                    1470

Phe Ala Glu Ala Val Gln Lys Ser Arg Lys Val Asp Ser Lys Ser Leu
        1475                    1480                    1485

Phe His Tyr Arg Gln Tyr Ser Ala Gly Lys Ala Ala
        1490                    1495                    1500

<210> SEQ ID NO 109
<211> LENGTH: 1762
<212> TYPE: PRT
<213> ORGANISM: Artificial Sequence
<220> FEATURE:
<223> OTHER INFORMATION: Synthetic_ATL1_HUMAN

<400> SEQUENCE: 109

Met Glu Cys Cys Arg Arg Ala Thr Pro Gly Thr Leu Leu Leu Phe Leu
1                   5                   10                  15

Ala Phe Leu Leu Leu Ser Ser Arg Thr Ala Arg Ser Glu Glu Asp Arg
            20                  25                  30

Asp Gly Leu Trp Asp Ala Trp Gly Pro Trp Ser Glu Cys Ser Arg Thr
        35                  40                  45

Cys Gly Gly Gly Ala Ser Tyr Ser Leu Arg Arg Cys Leu Ser Ser Lys
        50                  55                  60

Ser Cys Glu Gly Arg Asn Ile Arg Tyr Arg Thr Cys Ser Asn Val Asp
65                  70                  75                  80

Cys Pro Pro Glu Ala Gly Asp Phe Arg Ala Gln Gln Cys Ser Ala His
                85                  90                  95

Asn Asp Val Lys His His Gly Gln Phe Tyr Glu Trp Leu Pro Val Ser
            100                 105                 110

Asn Asp Pro Asp Asn Pro Cys Ser Leu Lys Cys Gln Ala Lys Gly Thr
        115                 120                 125

Thr Leu Val Val Glu Leu Ala Pro Lys Val Leu Asp Gly Thr Arg Cys
        130                 135                 140

Tyr Thr Glu Ser Leu Asp Met Cys Ile Ser Gly Leu Cys Gln Ile Val
145                 150                 155                 160

Gly Cys Asp His Gln Leu Gly Ser Thr Val Lys Glu Asp Asn Cys Gly
                165                 170                 175

Val Cys Asn Gly Asp Gly Ser Thr Cys Arg Leu Val Arg Gly Gln Tyr
            180                 185                 190

Lys Ser Gln Leu Ser Ala Thr Lys Ser Asp Asp Thr Val Val Ala Ile
        195                 200                 205

Pro Tyr Gly Ser Arg His Ile Arg Leu Val Leu Lys Gly Pro Asp His
        210                 215                 220

Leu Tyr Leu Glu Thr Lys Thr Leu Gln Gly Thr Lys Gly Glu Asn Ser
225                 230                 235                 240

Leu Ser Ser Thr Gly Thr Phe Leu Val Asp Asn Ser Ser Val Asp Phe
                245                 250                 255

Gln Lys Phe Pro Asp Lys Glu Ile Leu Arg Met Ala Gly Pro Leu Thr
            260                 265                 270

Ala Asp Phe Ile Val Lys Ile Arg Asn Ser Gly Ser Ala Asp Ser Thr
        275                 280                 285

Val Gln Phe Ile Phe Tyr Gln Pro Ile Ile His Arg Trp Arg Glu Thr
        290                 295                 300

Asp Phe Phe Pro Cys Ser Ala Thr Cys Gly Gly Gly Tyr Gln Leu Thr
305                 310                 315                 320
```

-continued

```
Ser Ala Glu Cys Tyr Asp Leu Arg Ser Asn Arg Val Val Ala Asp Gln
                325                 330                 335

Tyr Cys His Tyr Tyr Pro Glu Asn Ile Lys Pro Lys Pro Lys Leu Gln
            340                 345                 350

Glu Cys Asn Leu Asp Pro Cys Pro Ala Ser Asp Gly Tyr Lys Gln Ile
        355                 360                 365

Met Pro Tyr Asp Leu Tyr His Pro Leu Pro Arg Trp Glu Ala Thr Pro
    370                 375                 380

Trp Thr Ala Cys Ser Ser Ser Cys Gly Gly Gly Ile Gln Ser Arg Ala
385                 390                 395                 400

Val Ser Cys Val Glu Glu Asp Ile Gln Gly His Val Thr Ser Val Glu
                405                 410                 415

Glu Trp Lys Cys Met Tyr Thr Pro Lys Met Pro Ile Ala Gln Pro Cys
            420                 425                 430

Asn Ile Phe Asp Cys Pro Lys Trp Leu Ala Gln Glu Trp Ser Pro Cys
        435                 440                 445

Thr Val Thr Cys Gly Gln Gly Leu Arg Tyr Arg Val Val Leu Cys Ile
    450                 455                 460

Asp His Arg Gly Met His Thr Gly Gly Cys Ser Pro Lys Thr Lys Pro
465                 470                 475                 480

His Ile Lys Glu Glu Cys Ile Val Pro Thr Pro Cys Tyr Lys Pro Lys
                485                 490                 495

Glu Lys Leu Pro Val Glu Ala Lys Leu Pro Trp Phe Lys Gln Ala Gln
            500                 505                 510

Glu Leu Glu Glu Gly Ala Ala Val Ser Glu Glu Pro Ser Phe Ile Pro
        515                 520                 525

Glu Ala Trp Ser Ala Cys Thr Val Thr Cys Gly Val Gly Thr Gln Val
    530                 535                 540

Arg Ile Val Arg Cys Gln Val Leu Leu Ser Phe Ser Gln Ser Val Ala
545                 550                 555                 560

Asp Leu Pro Ile Asp Glu Cys Glu Gly Pro Lys Pro Ala Ser Gln Arg
                565                 570                 575

Ala Cys Tyr Ala Gly Pro Cys Ser Gly Glu Ile Pro Glu Phe Asn Pro
            580                 585                 590

Asp Glu Thr Asp Gly Leu Phe Gly Gly Leu Gln Asp Phe Asp Glu Leu
        595                 600                 605

Tyr Asp Trp Glu Tyr Glu Gly Phe Thr Lys Cys Ser Glu Ser Cys Gly
    610                 615                 620

Gly Gly Val Gln Glu Ala Val Val Ser Cys Leu Asn Lys Gln Thr Arg
625                 630                 635                 640

Glu Pro Ala Glu Glu Asn Leu Cys Val Thr Ser Arg Arg Pro Pro Gln
                645                 650                 655

Leu Leu Lys Ser Cys Asn Leu Asp Pro Cys Pro Ala Arg Trp Glu Ile
            660                 665                 670

Gly Lys Trp Ser Pro Cys Ser Leu Thr Cys Gly Val Gly Leu Gln Thr
        675                 680                 685

Arg Asp Val Phe Cys Ser His Leu Leu Ser Arg Glu Met Asn Glu Thr
    690                 695                 700

Val Ile Leu Ala Asp Glu Leu Cys Arg Gln Pro Lys Pro Ser Thr Val
705                 710                 715                 720

Gln Ala Cys Asn Arg Phe Asn Cys Pro Pro Ala Trp Tyr Pro Ala Gln
                725                 730                 735

Trp Gln Pro Cys Ser Arg Thr Cys Gly Gly Gly Val Gln Lys Arg Glu
```

-continued

```
              740              745              750

Val Leu Cys Lys Gln Arg Met Ala Asp Gly Ser Phe Leu Glu Leu Pro
      755              760              765

Glu Thr Phe Cys Ser Ala Ser Lys Pro Ala Cys Gln Gln Ala Cys Lys
      770              775              780

Lys Asp Asp Cys Pro Ser Glu Trp Leu Leu Ser Asp Trp Thr Glu Cys
785              790              795              800

Ser Thr Ser Cys Gly Glu Gly Thr Gln Thr Arg Ser Ala Ile Cys Arg
              805              810              815

Lys Met Leu Lys Thr Gly Leu Ser Thr Val Val Asn Ser Thr Leu Cys
              820              825              830

Pro Pro Leu Pro Phe Ser Ser Ser Ile Arg Pro Cys Met Leu Ala Thr
      835              840              845

Cys Ala Arg Pro Gly Arg Pro Ser Thr Lys His Ser Pro His Ile Ala
      850              855              860

Ala Ala Arg Lys Val Tyr Ile Gln Thr Arg Arg Gln Arg Lys Leu His
865              870              875              880

Phe Val Val Gly Gly Phe Ala Tyr Leu Leu Pro Lys Thr Ala Val Val
              885              890              895

Leu Arg Cys Pro Ala Arg Arg Val Arg Lys Pro Leu Ile Thr Trp Glu
              900              905              910

Lys Asp Gly Gln His Leu Ile Ser Ser Thr His Val Thr Val Ala Pro
      915              920              925

Phe Gly Tyr Leu Lys Ile His Arg Leu Lys Pro Ser Asp Ala Gly Val
      930              935              940

Tyr Thr Cys Ser Ala Gly Pro Ala Arg Glu His Phe Val Ile Lys Leu
945              950              955              960

Ile Gly Gly Asn Arg Lys Leu Val Ala Arg Pro Leu Ser Pro Arg Ser
              965              970              975

Glu Glu Glu Val Leu Ala Gly Arg Lys Gly Gly Pro Lys Glu Ala Leu
              980              985              990

Gln Thr His Lys His Gln Asn Gly Ile Phe Ser Asn Gly Ser Lys Ala
      995              1000              1005

Glu Lys Arg Gly Leu Ala Ala Asn Pro Gly Ser Arg Tyr Asp Asp Leu
      1010              1015              1020

Val Ser Arg Leu Leu Glu Gln Gly Gly Trp Pro Gly Glu Leu Leu Ala
1025              1030              1035              1040

Ser Trp Glu Ala Gln Asp Ser Ala Glu Arg Asn Thr Thr Ser Glu Glu
              1045              1050              1055

Asp Pro Gly Ala Glu Gln Val Leu Leu His Leu Pro Phe Thr Met Val
              1060              1065              1070

Thr Glu Gln Arg Arg Leu Asp Asp Ile Leu Gly Asn Leu Ser Gln Gln
      1075              1080              1085

Pro Glu Glu Leu Arg Asp Leu Tyr Ser Lys His Leu Val Ala Gln Leu
      1090              1095              1100

Ala Gln Glu Ile Phe Arg Ser His Leu Glu His Gln Asp Thr Leu Leu
1105              1110              1115              1120

Lys Pro Ser Glu Arg Arg Thr Ser Pro Val Thr Leu Ser Pro His Lys
              1125              1130              1135

His Val Ser Gly Phe Ser Ser Ser Leu Arg Thr Ser Ser Thr Gly Asp
              1140              1145              1150

Ala Gly Gly Gly Ser Arg Arg Pro His Arg Lys Pro Thr Ile Leu Arg
              1155              1160              1165
```

```
Lys Ile Ser Ala Ala Gln Gln Leu Ser Ala Ser Glu Val Val Thr His
    1170                1175                1180

Leu Gly Gln Thr Val Ala Leu Ala Ser Gly Thr Leu Ser Val Leu Leu
1185                1190                1195                1200

His Cys Glu Ala Ile Gly His Pro Arg Pro Thr Ile Ser Trp Ala Arg
                1205                1210                1215

Asn Gly Glu Glu Val Gln Phe Ser Asp Arg Ile Leu Leu Gln Pro Asp
                1220                1225                1230

Asp Ser Leu Gln Ile Leu Ala Pro Val Glu Ala Asp Val Gly Phe Tyr
            1235                1240                1245

Thr Cys Asn Ala Thr Asn Ala Leu Gly Tyr Asp Ser Val Ser Ile Ala
    1250                1255                1260

Val Thr Leu Ala Gly Lys Pro Leu Val Lys Thr Ser Arg Met Thr Val
1265                1270                1275                1280

Ile Asn Thr Glu Lys Pro Ala Val Thr Val Asp Ile Gly Ser Thr Ile
                1285                1290                1295

Lys Thr Val Gln Gly Val Asn Val Thr Ile Asn Cys Gln Val Ala Gly
            1300                1305                1310

Val Pro Glu Ala Glu Val Thr Trp Phe Arg Asn Lys Ser Lys Leu Gly
            1315                1320                1325

Ser Pro His His Leu His Glu Gly Ser Leu Leu Leu Thr Asn Val Ser
    1330                1335                1340

Ser Ser Asp Gln Gly Leu Tyr Ser Cys Arg Ala Ala Asn Leu His Gly
1345                1350                1355                1360

Glu Leu Thr Glu Ser Thr Gln Leu Leu Ile Leu Asp Pro Pro Gln Val
                1365                1370                1375

Pro Thr Gln Leu Glu Asp Ile Arg Ala Leu Leu Ala Ala Thr Gly Pro
            1380                1385                1390

Asn Leu Pro Ser Val Leu Thr Ser Pro Leu Gly Thr Gln Leu Val Leu
    1395                1400                1405

Asp Pro Gly Asn Ser Ala Leu Leu Gly Cys Pro Ile Lys Gly His Pro
    1410                1415                1420

Val Pro Asn Ile Thr Trp Phe His Gly Gly Gln Pro Ile Val Thr Ala
1425                1430                1435                1440

Thr Gly Leu Thr His His Ile Leu Ala Ala Gly Gln Ile Leu Gln Val
            1445                1450                1455

Ala Asn Leu Ser Gly Gly Ser Gln Gly Glu Phe Ser Cys Leu Ala Gln
            1460                1465                1470

Asn Glu Ala Gly Val Leu Met Gln Lys Ala Ser Leu Val Ile Gln Asp
        1475                1480                1485

Tyr Trp Trp Ser Val Asp Arg Leu Ala Thr Cys Ser Ala Ser Cys Gly
    1490                1495                1500

Asn Arg Gly Val Gln Gln Pro Arg Leu Arg Cys Leu Leu Asn Ser Thr
1505                1510                1515                1520

Glu Val Asn Pro Ala His Cys Ala Gly Lys Val Arg Pro Ala Val Gln
                1525                1530                1535

Pro Ile Ala Cys Asn Arg Arg Asp Cys Pro Ser Arg Trp Met Val Thr
            1540                1545                1550

Ser Trp Ser Ala Cys Thr Arg Ser Cys Gly Gly Gly Val Gln Thr Arg
        1555                1560                1565

Arg Val Thr Cys Gln Lys Leu Lys Ala Ser Gly Ile Ser Thr Pro Val
    1570                1575                1580
```

-continued

```
Ser Asn Asp Met Cys Thr Gln Val Ala Lys Arg Pro Val Asp Thr Gln
1585                1590                1595                1600

Ala Cys Asn Gln Gln Leu Cys Val Glu Trp Ala Phe Ser Ser Trp Gly
                1605                1610                1615

Gln Cys Asn Gly Pro Cys Ile Gly Pro His Leu Ala Val Gln His Arg
                1620                1625                1630

Gln Val Phe Cys Gln Thr Arg Asp Gly Ile Thr Leu Pro Ser Glu Gln
        1635                1640                1645

Cys Ser Ala Leu Pro Arg Pro Val Ser Thr Gln Asn Cys Trp Ser Glu
    1650                1655                1660

Ala Cys Ser Val His Trp Arg Val Ser Leu Trp Thr Leu Cys Thr Ala
1665                1670                1675                1680

Thr Cys Gly Asn Tyr Gly Phe Gln Ser Arg Arg Val Glu Cys Val His
                1685                1690                1695

Ala Arg Thr Asn Lys Ala Val Pro Glu His Leu Cys Ser Trp Gly Pro
                1700                1705                1710

Arg Pro Ala Asn Trp Gln Arg Cys Asn Ile Thr Pro Cys Glu Asn Met
                1715                1720                1725

Glu Cys Arg Asp Thr Thr Arg Tyr Cys Glu Lys Val Lys Gln Leu Lys
        1730                1735                1740

Leu Cys Gln Leu Ser Gln Phe Lys Ser Arg Cys Cys Gly Thr Cys Gly
1745                1750                1755                1760

Lys Ala
```

```
<210> SEQ ID NO 110
<211> LENGTH: 2555
<212> TYPE: PRT
<213> ORGANISM: Artificial Sequence
<220> FEATURE:
<223> OTHER INFORMATION: Synthetic_NOTC1_HUMAN

<400> SEQUENCE: 110
```

```
Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
                20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
                100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
```

-continued

```
                180             185             190
Gly Thr Cys His Asn Glu Val Gly Ser Tyr Arg Cys Val Cys Arg Ala
        195             200             205

Thr His Thr Gly Pro Asn Cys Glu Arg Pro Tyr Val Pro Cys Ser Pro
    210             215             220

Ser Pro Cys Gln Asn Gly Gly Thr Cys Arg Pro Thr Gly Asp Val Thr
225             230             235             240

His Glu Cys Ala Cys Leu Pro Gly Phe Thr Gly Gln Asn Cys Glu Glu
            245             250             255

Asn Ile Asp Asp Cys Pro Gly Asn Asn Cys Lys Asn Gly Gly Ala Cys
            260             265             270

Val Asp Gly Val Asn Thr Tyr Asn Cys Arg Cys Pro Pro Glu Trp Thr
        275             280             285

Gly Gln Tyr Cys Thr Glu Asp Val Asp Glu Cys Gln Leu Met Pro Asn
    290             295             300

Ala Cys Gln Asn Gly Gly Thr Cys His Asn Thr His Gly Gly Tyr Asn
305             310             315             320

Cys Val Cys Val Asn Gly Trp Thr Gly Glu Asp Cys Ser Glu Asn Ile
            325             330             335

Asp Asp Cys Ala Ser Ala Ala Cys Phe His Gly Ala Thr Cys His Asp
            340             345             350

Arg Val Ala Ser Phe Tyr Cys Glu Cys Pro His Gly Arg Thr Gly Leu
        355             360             365

Leu Cys His Leu Asn Asp Ala Cys Ile Ser Asn Pro Cys Asn Glu Gly
    370             375             380

Ser Asn Cys Asp Thr Asn Pro Val Asn Gly Lys Ala Ile Cys Thr Cys
385             390             395             400

Pro Ser Gly Tyr Thr Gly Pro Ala Cys Ser Gln Asp Val Asp Glu Cys
            405             410             415

Ser Leu Gly Ala Asn Pro Cys Glu His Ala Gly Lys Cys Ile Asn Thr
            420             425             430

Leu Gly Ser Phe Glu Cys Gln Cys Leu Gln Gly Tyr Thr Gly Pro Arg
        435             440             445

Cys Glu Ile Asp Val Asn Glu Cys Val Ser Asn Pro Cys Gln Asn Asp
    450             455             460

Ala Thr Cys Leu Asp Gln Ile Gly Glu Phe Gln Cys Ile Cys Met Pro
465             470             475             480

Gly Tyr Glu Gly Val His Cys Glu Val Asn Thr Asp Glu Cys Ala Ser
            485             490             495

Ser Pro Cys Leu His Asn Gly Arg Cys Leu Asp Lys Ile Asn Glu Phe
            500             505             510

Gln Cys Glu Cys Pro Thr Gly Phe Thr Gly His Leu Cys Gln Tyr Asp
        515             520             525

Val Asp Glu Cys Ala Ser Thr Pro Cys Lys Asn Gly Ala Lys Cys Leu
    530             535             540

Asp Gly Pro Asn Thr Tyr Thr Cys Val Cys Thr Glu Gly Tyr Thr Gly
545             550             555             560

Thr His Cys Glu Val Asp Ile Asp Glu Cys Asp Pro Asp Pro Cys His
            565             570             575

Tyr Gly Ser Cys Lys Asp Gly Val Ala Thr Phe Thr Cys Leu Cys Arg
        580             585             590

Pro Gly Tyr Thr Gly His His Cys Glu Thr Asn Ile Asn Glu Cys Ser
        595             600             605
```

-continued

```
Ser Gln Pro Cys Arg His Gly Gly Thr Cys Gln Asp Arg Asp Asn Ala
    610             615             620

Tyr Leu Cys Phe Cys Leu Lys Gly Thr Thr Gly Pro Asn Cys Glu Ile
625             630             635             640

Asn Leu Asp Asp Cys Ala Ser Ser Pro Cys Asp Ser Gly Thr Cys Leu
            645             650             655

Asp Lys Ile Asp Gly Tyr Glu Cys Ala Cys Glu Pro Gly Tyr Thr Gly
            660             665             670

Ser Met Cys Asn Ile Asn Ile Asp Glu Cys Ala Gly Asn Pro Cys His
        675             680             685

Asn Gly Gly Thr Cys Glu Asp Gly Ile Asn Gly Phe Thr Cys Arg Cys
    690             695             700

Pro Glu Gly Tyr His Asp Pro Thr Cys Leu Ser Glu Val Asn Glu Cys
705             710             715             720

Asn Ser Asn Pro Cys Val His Gly Ala Cys Arg Asp Ser Leu Asn Gly
            725             730             735

Tyr Lys Cys Asp Cys Asp Pro Gly Trp Ser Gly Thr Asn Cys Asp Ile
            740             745             750

Asn Asn Asn Glu Cys Glu Ser Asn Pro Cys Val Asn Gly Gly Thr Cys
        755             760             765

Lys Asp Met Thr Ser Gly Tyr Val Cys Thr Cys Arg Glu Gly Phe Ser
    770             775             780

Gly Pro Asn Cys Gln Thr Asn Ile Asn Glu Cys Ala Ser Asn Pro Cys
785             790             795             800

Leu Asn Gln Gly Thr Cys Ile Asp Asp Val Ala Gly Tyr Lys Cys Asn
            805             810             815

Cys Leu Leu Pro Tyr Thr Gly Ala Thr Cys Glu Val Val Leu Ala Pro
            820             825             830

Cys Ala Pro Ser Pro Cys Arg Asn Gly Gly Glu Cys Arg Gln Ser Glu
        835             840             845

Asp Tyr Glu Ser Phe Ser Cys Val Cys Pro Thr Gly Trp Gln Gly Gln
    850             855             860

Thr Cys Glu Val Asp Ile Asn Glu Cys Val Leu Ser Pro Cys Arg His
865             870             875             880

Gly Ala Ser Cys Gln Asn Thr His Gly Gly Tyr Arg Cys His Cys Gln
            885             890             895

Ala Gly Tyr Ser Gly Arg Asn Cys Glu Thr Asp Ile Asp Asp Cys Arg
            900             905             910

Pro Asn Pro Cys His Asn Gly Gly Ser Cys Thr Asp Gly Ile Asn Thr
        915             920             925

Ala Phe Cys Asp Cys Leu Pro Gly Phe Arg Gly Thr Phe Cys Glu Glu
    930             935             940

Asp Ile Asn Glu Cys Ala Ser Asp Pro Cys Arg Asn Gly Ala Asn Cys
945             950             955             960

Thr Asp Cys Val Asp Ser Tyr Thr Cys Thr Cys Pro Ala Gly Phe Ser
            965             970             975

Gly Ile His Cys Glu Asn Asn Thr Pro Asp Cys Thr Glu Ser Ser Cys
        980             985             990

Phe Asn Gly Gly Thr Cys Val Asp Gly Ile Asn Ser Phe Thr Cys Leu
    995             1000             1005

Cys Pro Pro Gly Phe Thr Gly Ser Tyr Cys Gln His Asp Val Asn Glu
    1010             1015             1020
```

```
Cys Asp Ser Gln Pro Cys Leu His Gly Gly Thr Cys Gln Asp Gly Cys
1025            1030                1035                1040

Gly Ser Tyr Arg Cys Thr Cys Pro Gln Gly Tyr Thr Gly Pro Asn Cys
                1045                1050                1055

Gln Asn Leu Val His Trp Cys Asp Ser Ser Pro Cys Lys Asn Gly Gly
            1060                1065                1070

Lys Cys Trp Gln Thr His Thr Gln Tyr Arg Cys Glu Cys Pro Ser Gly
        1075                1080                1085

Trp Thr Gly Leu Tyr Cys Asp Val Pro Ser Val Ser Cys Glu Val Ala
    1090                1095                1100

Ala Gln Arg Gln Gly Val Asp Val Ala Arg Leu Cys Gln His Gly Gly
1105                1110                1115                1120

Leu Cys Val Asp Ala Gly Asn Thr His His Cys Arg Cys Gln Ala Gly
            1125                1130                1135

Tyr Thr Gly Ser Tyr Cys Glu Asp Leu Val Asp Glu Cys Ser Pro Ser
            1140                1145                1150

Pro Cys Gln Asn Gly Ala Thr Cys Thr Asp Tyr Leu Gly Gly Tyr Ser
        1155                1160                1165

Cys Lys Cys Val Ala Gly Tyr His Gly Val Asn Cys Ser Glu Glu Ile
    1170                1175                1180

Asp Glu Cys Leu Ser His Pro Cys Gln Asn Gly Gly Thr Cys Leu Asp
1185                1190                1195                1200

Leu Pro Asn Thr Tyr Lys Cys Ser Cys Pro Arg Gly Thr Gln Gly Val
                1205                1210                1215

His Cys Glu Ile Asn Val Asp Asp Cys Asn Pro Pro Val Asp Pro Val
            1220                1225                1230

Ser Arg Ser Pro Lys Cys Phe Asn Asn Gly Thr Cys Val Asp Gln Val
        1235                1240                1245

Gly Gly Tyr Ser Cys Thr Cys Pro Pro Gly Phe Val Gly Glu Arg Cys
    1250                1255                1260

Glu Gly Asp Val Asn Glu Cys Leu Ser Asn Pro Cys Asp Ala Arg Gly
1265                1270                1275                1280

Thr Gln Asn Cys Val Gln Arg Val Asn Asp Phe His Cys Glu Cys Arg
            1285                1290                1295

Ala Gly His Thr Gly Arg Arg Cys Glu Ser Val Ile Asn Gly Cys Lys
        1300                1305                1310

Gly Lys Pro Cys Lys Asn Gly Gly Thr Cys Ala Val Ala Ser Asn Thr
        1315                1320                1325

Ala Arg Gly Phe Ile Cys Lys Cys Pro Ala Gly Phe Glu Gly Ala Thr
    1330                1335                1340

Cys Glu Asn Asp Ala Arg Thr Cys Gly Ser Leu Arg Cys Leu Asn Gly
1345                1350                1355                1360

Gly Thr Cys Ile Ser Gly Pro Arg Ser Pro Thr Cys Leu Cys Leu Gly
            1365                1370                1375

Pro Phe Thr Gly Pro Glu Cys Gln Phe Pro Ala Ser Ser Pro Cys Leu
        1380                1385                1390

Gly Gly Asn Pro Cys Tyr Asn Gln Gly Thr Cys Glu Pro Thr Ser Glu
        1395                1400                1405

Ser Pro Phe Tyr Arg Cys Leu Cys Pro Ala Lys Phe Asn Gly Leu Leu
    1410                1415                1420

Cys His Ile Leu Asp Tyr Ser Phe Gly Gly Gly Ala Gly Arg Asp Ile
1425                1430                1435                1440

Pro Pro Pro Leu Ile Glu Glu Ala Cys Glu Leu Pro Glu Cys Gln Glu
```

-continued

```
                    1445           1450           1455

Asp Ala Gly Asn Lys Val Cys Ser Leu Gln Cys Asn Asn His Ala Cys
          1460           1465           1470

Gly Trp Asp Gly Gly Asp Cys Ser Leu Asn Phe Asn Asp Pro Trp Lys
          1475           1480           1485

Asn Cys Thr Gln Ser Leu Gln Cys Trp Lys Tyr Phe Ser Asp Gly His
          1490           1495           1500

Cys Asp Ser Gln Cys Asn Ser Ala Gly Cys Leu Phe Asp Gly Phe Asp
1505           1510           1515           1520

Cys Gln Arg Ala Glu Gly Gln Cys Asn Pro Leu Tyr Asp Gln Tyr Cys
          1525           1530           1535

Lys Asp His Phe Ser Asp Gly His Cys Asp Gln Gly Cys Asn Ser Ala
          1540           1545           1550

Glu Cys Glu Trp Asp Gly Leu Asp Cys Ala Glu His Val Pro Glu Arg
          1555           1560           1565

Leu Ala Ala Gly Thr Leu Val Val Val Val Leu Met Pro Pro Glu Gln
          1570           1575           1580

Leu Arg Asn Ser Ser Phe His Phe Leu Arg Glu Leu Ser Arg Val Leu
1585           1590           1595           1600

His Thr Asn Val Val Phe Lys Arg Asp Ala His Gly Gln Gln Met Ile
          1605           1610           1615

Phe Pro Tyr Tyr Gly Arg Glu Glu Glu Leu Arg Lys His Pro Ile Lys
          1620           1625           1630

Arg Ala Ala Glu Gly Trp Ala Ala Pro Asp Ala Leu Leu Gly Gln Val
          1635           1640           1645

Lys Ala Ser Leu Leu Pro Gly Gly Ser Glu Gly Gly Arg Arg Arg Arg
          1650           1655           1660

Glu Leu Asp Pro Met Asp Val Arg Gly Ser Ile Val Tyr Leu Glu Ile
1665           1670           1675           1680

Asp Asn Arg Gln Cys Val Gln Ala Ser Ser Gln Cys Phe Gln Ser Ala
          1685           1690           1695

Thr Asp Val Ala Ala Phe Leu Gly Ala Leu Ala Ser Leu Gly Ser Leu
          1700           1705           1710

Asn Ile Pro Tyr Lys Ile Glu Ala Val Gln Ser Glu Thr Val Glu Pro
          1715           1720           1725

Pro Pro Pro Ala Gln Leu His Phe Met Tyr Val Ala Ala Ala Ala Phe
          1730           1735           1740

Val Leu Leu Phe Phe Val Gly Cys Gly Val Leu Leu Ser Arg Lys Arg
1745           1750           1755           1760

Arg Arg Gln His Gly Gln Leu Trp Phe Pro Glu Gly Phe Lys Val Ser
          1765           1770           1775

Glu Ala Ser Lys Lys Lys Arg Arg Glu Pro Leu Gly Glu Asp Ser Val
          1780           1785           1790

Gly Leu Lys Pro Leu Lys Asn Ala Ser Asp Gly Ala Leu Met Asp Asp
          1795           1800           1805

Asn Gln Asn Glu Trp Gly Asp Glu Asp Leu Glu Thr Lys Lys Phe Arg
          1810           1815           1820

Phe Glu Glu Pro Val Val Leu Pro Asp Leu Asp Asp Gln Thr Asp His
1825           1830           1835           1840

Arg Gln Trp Thr Gln Gln His Leu Asp Ala Ala Asp Leu Arg Met Ser
          1845           1850           1855

Ala Met Ala Pro Thr Pro Pro Gln Gly Glu Val Asp Ala Asp Cys Met
          1860           1865           1870
```

```
Asp Val Asn Val Arg Gly Pro Asp Gly Phe Thr Pro Leu Met Ile Ala
        1875                1880                1885

Ser Cys Ser Gly Gly Gly Leu Glu Thr Gly Asn Ser Glu Glu Glu Glu
        1890                1895                1900

Asp Ala Pro Ala Val Ile Ser Asp Phe Ile Tyr Gln Gly Ala Ser Leu
1905                1910                1915                1920

His Asn Gln Thr Asp Arg Thr Gly Glu Thr Ala Leu His Leu Ala Ala
            1925                1930                1935

Arg Tyr Ser Arg Ser Asp Ala Ala Lys Arg Leu Leu Glu Ala Ser Ala
            1940                1945                1950

Asp Ala Asn Ile Gln Asp Asn Met Gly Arg Thr Pro Leu His Ala Ala
        1955                1960                1965

Val Ser Ala Asp Ala Gln Gly Val Phe Gln Ile Leu Ile Arg Asn Arg
        1970                1975                1980

Ala Thr Asp Leu Asp Ala Arg Met His Asp Gly Thr Thr Pro Leu Ile
1985                1990                1995                2000

Leu Ala Ala Arg Leu Ala Val Glu Gly Met Leu Glu Asp Leu Ile Asn
            2005                2010                2015

Ser His Ala Asp Val Asn Ala Val Asp Asp Leu Gly Lys Ser Ala Leu
            2020                2025                2030

His Trp Ala Ala Ala Val Asn Asn Val Asp Ala Ala Val Val Leu Leu
        2035                2040                2045

Lys Asn Gly Ala Asn Lys Asp Met Gln Asn Asn Arg Glu Glu Thr Pro
        2050                2055                2060

Leu Phe Leu Ala Ala Arg Glu Gly Ser Tyr Glu Thr Ala Lys Val Leu
2065                2070                2075                2080

Leu Asp His Phe Ala Asn Arg Asp Ile Thr Asp His Met Asp Arg Leu
            2085                2090                2095

Pro Arg Asp Ile Ala Gln Glu Arg Met His His Asp Ile Val Arg Leu
            2100                2105                2110

Leu Asp Glu Tyr Asn Leu Val Arg Ser Pro Gln Leu His Gly Ala Pro
        2115                2120                2125

Leu Gly Gly Thr Pro Thr Leu Ser Pro Pro Leu Cys Ser Pro Asn Gly
        2130                2135                2140

Tyr Leu Gly Ser Leu Lys Pro Gly Val Gln Gly Lys Lys Val Arg Lys
2145                2150                2155                2160

Pro Ser Ser Lys Gly Leu Ala Cys Gly Ser Lys Glu Ala Lys Asp Leu
            2165                2170                2175

Lys Ala Arg Arg Lys Lys Ser Gln Asp Gly Lys Gly Cys Leu Leu Asp
            2180                2185                2190

Ser Ser Gly Met Leu Ser Pro Val Asp Ser Leu Glu Ser Pro His Gly
            2195                2200                2205

Tyr Leu Ser Asp Val Ala Ser Pro Pro Leu Leu Pro Ser Pro Phe Gln
        2210                2215                2220

Gln Ser Pro Ser Val Pro Leu Asn His Leu Pro Gly Met Pro Asp Thr
2225                2230                2235                2240

His Leu Gly Ile Gly His Leu Asn Val Ala Ala Lys Pro Glu Met Ala
            2245                2250                2255

Ala Leu Gly Gly Gly Gly Arg Leu Ala Phe Glu Thr Gly Pro Pro Arg
            2260                2265                2270

Leu Ser His Leu Pro Val Ala Ser Gly Thr Ser Thr Val Leu Gly Ser
        2275                2280                2285
```

```
Ser Ser Gly Gly Ala Leu Asn Phe Thr Val Gly Gly Ser Thr Ser Leu
    2290              2295              2300

Asn Gly Gln Cys Glu Trp Leu Ser Arg Leu Gln Ser Gly Met Val Pro
2305              2310              2315              2320

Asn Gln Tyr Asn Pro Leu Arg Gly Ser Val Ala Pro Gly Pro Leu Ser
            2325              2330              2335

Thr Gln Ala Pro Ser Leu Gln His Gly Met Val Gly Pro Leu His Ser
            2340              2345              2350

Ser Leu Ala Ala Ser Ala Leu Ser Gln Met Met Ser Tyr Gln Gly Leu
            2355              2360              2365

Pro Ser Thr Arg Leu Ala Thr Gln Pro His Leu Val Gln Thr Gln Gln
    2370              2375              2380

Val Gln Pro Gln Asn Leu Gln Met Gln Gln Gln Asn Leu Gln Pro Ala
2385              2390              2395              2400

Asn Ile Gln Gln Gln Gln Ser Leu Gln Pro Pro Pro Pro Pro Pro Gln
            2405              2410              2415

Pro His Leu Gly Val Ser Ser Ala Ala Ser Gly His Leu Gly Arg Ser
            2420              2425              2430

Phe Leu Ser Gly Glu Pro Ser Gln Ala Asp Val Gln Pro Leu Gly Pro
            2435              2440              2445

Ser Ser Leu Ala Val His Thr Ile Leu Pro Gln Glu Ser Pro Ala Leu
    2450              2455              2460

Pro Thr Ser Leu Pro Ser Ser Leu Val Pro Pro Val Thr Ala Ala Gln
2465              2470              2475              2480

Phe Leu Thr Pro Pro Ser Gln His Ser Tyr Ser Ser Pro Val Asp Asn
            2485              2490              2495

Thr Pro Ser His Gln Leu Gln Val Pro Glu His Pro Phe Leu Thr Pro
            2500              2505              2510

Ser Pro Glu Ser Pro Asp Gln Trp Ser Ser Ser Ser Pro His Ser Asn
            2515              2520              2525

Val Ser Asp Trp Ser Glu Gly Val Ser Ser Pro Pro Thr Ser Met Gln
    2530              2535              2540

Ser Gln Ile Ala Arg Ile Pro Glu Ala Phe Lys
2545              2550              2555

<210> SEQ ID NO 111
<211> LENGTH: 2813
<212> TYPE: PRT
<213> ORGANISM: Artificial Sequence
<220> FEATURE:
<223> OTHER INFORMATION: Synthetic_VWF_HUMAN

<400> SEQUENCE: 111

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95
```

-continued

```
Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
        130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
            195                 200                 205

Ser Cys Asn Ile Ser Ser Gly Glu Met Gln Lys Gly Leu Trp Glu Gln
        210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
            245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
            275                 280                 285

Ser Ala Cys Ser Pro Val Cys Pro Ala Gly Met Glu Tyr Arg Gln Cys
        290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
        370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
        450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
```

-continued

```
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
            645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
            725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
            805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Gln Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
            915                 920                 925

Val Glu Gly Gly Glu Ile Glu Leu Phe Asp Gly Glu Val Asn Val Lys
        930                 935                 940
```

-continued

```
Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp Gly Ile Gln Asn Asn Asp Leu Thr
        995                 1000                1005

Ser Ser Asn Leu Gln Val Glu Glu Asp Pro Val Asp Phe Gly Asn Ser
    1010                1015                1020

Trp Lys Val Ser Ser Gln Cys Ala Asp Thr Arg Lys Val Pro Leu Asp
1025                1030                1035                1040

Ser Ser Pro Ala Thr Cys His Asn Asn Ile Met Lys Gln Thr Met Val
                1045                1050                1055

Asp Ser Ser Cys Arg Ile Leu Thr Ser Asp Val Phe Gln Asp Cys Asn
                1060                1065                1070

Lys Leu Val Asp Pro Glu Pro Tyr Leu Asp Val Cys Ile Tyr Asp Thr
            1075                1080                1085

Cys Ser Cys Glu Ser Ile Gly Asp Cys Ala Cys Phe Cys Asp Thr Ile
    1090                1095                1100

Ala Ala Tyr Ala His Val Cys Ala Gln His Gly Lys Val Val Thr Trp
1105                1110                1115                1120

Arg Thr Ala Thr Leu Cys Pro Gln Ser Cys Glu Glu Arg Asn Leu Arg
                1125                1130                1135

Glu Asn Gly Tyr Glu Cys Glu Trp Arg Tyr Asn Ser Cys Ala Pro Ala
            1140                1145                1150

Cys Gln Val Thr Cys Gln His Pro Glu Pro Leu Ala Cys Pro Val Gln
    1155                1160                1165

Cys Val Glu Gly Cys His Ala His Cys Pro Pro Gly Lys Ile Leu Asp
    1170                1175                1180

Glu Leu Leu Gln Thr Cys Val Asp Pro Glu Asp Cys Pro Val Cys Glu
1185                1190                1195                1200

Val Ala Gly Arg Arg Phe Ala Ser Gly Lys Lys Val Thr Leu Asn Pro
                1205                1210                1215

Ser Asp Pro Glu His Cys Gln Ile Cys His Cys Asp Val Val Asn Leu
            1220                1225                1230

Thr Cys Glu Ala Cys Gln Glu Pro Gly Gly Leu Val Val Pro Pro Thr
        1235                1240                1245

Asp Ala Pro Val Ser Pro Thr Thr Leu Tyr Val Glu Asp Ile Ser Glu
    1250                1255                1260

Pro Pro Leu His Asp Phe Tyr Cys Ser Arg Leu Leu Asp Leu Val Phe
1265                1270                1275                1280

Leu Leu Asp Gly Ser Ser Arg Leu Ser Glu Ala Glu Phe Glu Val Leu
                1285                1290                1295

Lys Ala Phe Val Val Asp Met Met Glu Arg Leu Arg Ile Ser Gln Lys
            1300                1305                1310

Trp Val Arg Val Ala Val Val Glu Tyr His Asp Gly Ser His Ala Tyr
            1315                1320                1325

Ile Gly Leu Lys Asp Arg Lys Arg Pro Ser Glu Leu Arg Arg Ile Ala
    1330                1335                1340

Ser Gln Val Lys Tyr Ala Gly Ser Gln Val Ala Ser Thr Ser Glu Val
1345                1350                1355                1360
```

-continued

```
Leu Lys Tyr Thr Leu Phe Gln Ile Phe Ser Lys Ile Asp Arg Pro Glu
                1365                1370                1375

Ala Ser Arg Ile Thr Leu Leu Leu Met Ala Ser Gln Glu Pro Gln Arg
                1380                1385                1390

Met Ser Arg Asn Phe Val Arg Tyr Val Gln Gly Leu Lys Lys Lys Lys
                1395                1400                1405

Val Ile Val Ile Pro Val Gly Ile Gly Pro His Ala Asn Leu Lys Gln
        1410                1415                1420

Ile Arg Leu Ile Glu Lys Gln Ala Pro Glu Asn Lys Ala Phe Val Leu
1425                1430                1435                1440

Ser Ser Val Asp Glu Leu Glu Gln Gln Arg Asp Glu Ile Val Ser Tyr
                1445                1450                1455

Leu Cys Asp Leu Ala Pro Glu Ala Pro Pro Pro Thr Leu Pro Pro Asp
                1460                1465                1470

Met Ala Gln Val Thr Val Gly Pro Gly Leu Leu Gly Val Ser Thr Leu
                1475                1480                1485

Gly Pro Lys Arg Asn Ser Met Val Leu Asp Val Ala Phe Val Leu Glu
        1490                1495                1500

Gly Ser Asp Lys Ile Gly Glu Ala Asp Phe Asn Arg Ser Lys Glu Phe
1505                1510                1515                1520

Met Glu Glu Val Ile Gln Arg Met Asp Val Gly Gln Asp Ser Ile His
                1525                1530                1535

Val Thr Val Leu Gln Tyr Ser Tyr Met Val Thr Val Glu Tyr Pro Phe
                1540                1545                1550

Ser Glu Ala Gln Ser Lys Gly Asp Ile Leu Gln Arg Val Arg Glu Ile
        1555                1560                1565

Arg Tyr Gln Gly Gly Asn Arg Thr Asn Thr Gly Leu Ala Leu Arg Tyr
        1570                1575                1580

Leu Ser Asp His Ser Phe Leu Val Ser Gln Gly Asp Arg Glu Gln Ala
1585                1590                1595                1600

Pro Asn Leu Val Tyr Met Val Thr Gly Asn Pro Ala Ser Asp Glu Ile
                1605                1610                1615

Lys Arg Leu Pro Gly Asp Ile Gln Val Val Pro Ile Gly Val Gly Pro
        1620                1625                1630

Asn Ala Asn Val Gln Glu Leu Glu Arg Ile Gly Trp Pro Asn Ala Pro
        1635                1640                1645

Ile Leu Ile Gln Asp Phe Glu Thr Leu Pro Arg Glu Ala Pro Asp Leu
        1650                1655                1660

Val Leu Gln Arg Cys Cys Ser Gly Glu Gly Leu Gln Ile Pro Thr Leu
1665                1670                1675                1680

Ser Pro Ala Pro Asp Cys Ser Gln Pro Leu Asp Val Ile Leu Leu Leu
                1685                1690                1695

Asp Gly Ser Ser Ser Phe Pro Ala Ser Tyr Phe Asp Glu Met Lys Ser
                1700                1705                1710

Phe Ala Lys Ala Phe Ile Ser Lys Ala Asn Ile Gly Pro Arg Leu Thr
                1715                1720                1725

Gln Val Ser Val Leu Gln Tyr Gly Ser Ile Thr Thr Ile Asp Val Pro
        1730                1735                1740

Trp Asn Val Val Pro Glu Lys Ala His Leu Leu Ser Leu Val Asp Val
1745                1750                1755                1760

Met Gln Arg Glu Gly Gly Pro Ser Gln Ile Gly Asp Ala Leu Gly Phe
                1765                1770                1775

Ala Val Arg Tyr Leu Thr Ser Glu Met His Gly Ala Arg Pro Gly Ala
```

-continued

```
             1780               1785               1790

Ser Lys Ala Val Val Ile Leu Val Thr Asp Val Ser Val Asp Ser Val
        1795               1800               1805

Asp Ala Ala Ala Asp Ala Ala Arg Ser Asn Arg Val Thr Val Phe Pro
    1810               1815               1820

Ile Gly Ile Gly Asp Arg Tyr Asp Ala Ala Gln Leu Arg Ile Leu Ala
1825               1830               1835               1840

Gly Pro Ala Gly Asp Ser Asn Val Val Lys Leu Gln Arg Ile Glu Asp
            1845               1850               1855

Leu Pro Thr Met Val Thr Leu Gly Asn Ser Phe Leu His Lys Leu Cys
        1860               1865               1870

Ser Gly Phe Val Arg Ile Cys Met Asp Glu Asp Gly Asn Glu Lys Arg
        1875               1880               1885

Pro Gly Asp Val Trp Thr Leu Pro Asp Gln Cys His Thr Val Thr Cys
    1890               1895               1900

Gln Pro Asp Gly Gln Thr Leu Leu Lys Ser His Arg Val Asn Cys Asp
1905               1910               1915               1920

Arg Gly Leu Arg Pro Ser Cys Pro Asn Ser Gln Ser Pro Val Lys Val
            1925               1930               1935

Glu Glu Thr Cys Gly Cys Arg Trp Thr Cys Pro Cys Val Cys Thr Gly
        1940               1945               1950

Ser Ser Thr Arg His Ile Val Thr Phe Asp Gly Gln Asn Phe Lys Leu
        1955               1960               1965

Thr Gly Ser Cys Ser Tyr Val Leu Phe Gln Asn Lys Glu Gln Asp Leu
    1970               1975               1980

Glu Val Ile Leu His Asn Gly Ala Cys Ser Pro Gly Ala Arg Gln Gly
1985               1990               1995               2000

Cys Met Lys Ser Ile Glu Val Lys His Ser Ala Leu Ser Val Glu Leu
            2005               2010               2015

His Ser Asp Met Glu Val Thr Val Asn Gly Arg Leu Val Ser Val Pro
            2020               2025               2030

Tyr Val Gly Gly Asn Met Glu Val Asn Val Tyr Gly Ala Ile Met His
        2035               2040               2045

Glu Val Arg Phe Asn His Leu Gly His Ile Phe Thr Phe Thr Pro Gln
    2050               2055               2060

Asn Asn Glu Phe Gln Leu Gln Leu Ser Pro Lys Thr Phe Ala Ser Lys
2065               2070               2075               2080

Thr Tyr Gly Leu Cys Gly Ile Cys Asp Glu Asn Gly Ala Asn Asp Phe
            2085               2090               2095

Met Leu Arg Asp Gly Thr Val Thr Thr Asp Trp Lys Thr Leu Val Gln
        2100               2105               2110

Glu Trp Thr Val Gln Arg Pro Gly Gln Thr Cys Gln Pro Ile Leu Glu
        2115               2120               2125

Glu Gln Cys Leu Val Pro Asp Ser Ser His Cys Gln Val Leu Leu Leu
    2130               2135               2140

Pro Leu Phe Ala Glu Cys His Lys Val Leu Ala Pro Ala Thr Phe Tyr
2145               2150               2155               2160

Ala Ile Cys Gln Gln Asp Ser Cys His Gln Glu Gln Val Cys Glu Val
            2165               2170               2175

Ile Ala Ser Tyr Ala His Leu Cys Arg Thr Asn Gly Val Cys Val Asp
        2180               2185               2190

Trp Arg Thr Pro Asp Phe Cys Ala Met Ser Cys Pro Pro Ser Leu Val
        2195               2200               2205
```

-continued

```
Tyr Asn His Cys Glu His Gly Cys Pro Arg His Cys Asp Gly Asn Val
    2210             2215             2220

Ser Ser Cys Gly Asp His Pro Ser Glu Gly Cys Phe Cys Pro Pro Asp
2225             2230             2235             2240

Lys Val Met Leu Glu Gly Ser Cys Val Pro Glu Glu Ala Cys Thr Gln
            2245             2250             2255

Cys Ile Gly Glu Asp Gly Val Gln His Gln Phe Leu Glu Ala Trp Val
            2260             2265             2270

Pro Asp His Gln Pro Cys Gln Ile Cys Thr Cys Leu Ser Gly Arg Lys
            2275             2280             2285

Val Asn Cys Thr Thr Gln Pro Cys Pro Thr Ala Lys Ala Pro Thr Cys
    2290             2295             2300

Gly Leu Cys Glu Val Ala Arg Leu Arg Gln Asn Ala Asp Gln Cys Cys
2305             2310             2315             2320

Pro Glu Tyr Glu Cys Val Cys Asp Pro Val Ser Cys Asp Leu Pro Pro
            2325             2330             2335

Val Pro His Cys Glu Arg Gly Leu Gln Pro Thr Leu Thr Asn Pro Gly
            2340             2345             2350

Glu Cys Arg Pro Asn Phe Thr Cys Ala Cys Arg Lys Glu Glu Cys Lys
            2355             2360             2365

Arg Val Ser Pro Pro Ser Cys Pro Pro His Arg Leu Pro Thr Leu Arg
            2370             2375             2380

Lys Thr Gln Cys Cys Asp Glu Tyr Glu Cys Ala Cys Asn Cys Val Asn
2385             2390             2395             2400

Ser Thr Val Ser Cys Pro Leu Gly Tyr Leu Ala Ser Thr Ala Thr Asn
            2405             2410             2415

Asp Cys Gly Cys Thr Thr Thr Thr Cys Leu Pro Asp Lys Val Cys Val
            2420             2425             2430

His Arg Ser Thr Ile Tyr Pro Val Gly Gln Phe Trp Glu Glu Gly Cys
            2435             2440             2445

Asp Val Cys Thr Cys Thr Asp Met Glu Asp Ala Val Met Gly Leu Arg
    2450             2455             2460

Val Ala Gln Cys Ser Gln Lys Pro Cys Glu Asp Ser Cys Arg Ser Gly
2465             2470             2475             2480

Phe Thr Tyr Val Leu His Glu Gly Glu Cys Cys Gly Arg Cys Leu Pro
            2485             2490             2495

Ser Ala Cys Glu Val Val Thr Gly Ser Pro Arg Gly Asp Ser Gln Ser
            2500             2505             2510

Ser Trp Lys Ser Val Gly Ser Gln Trp Ala Ser Pro Glu Asn Pro Cys
            2515             2520             2525

Leu Ile Asn Glu Cys Val Arg Val Lys Glu Glu Val Phe Ile Gln Gln
            2530             2535             2540

Arg Asn Val Ser Cys Pro Gln Leu Glu Val Pro Val Cys Pro Ser Gly
2545             2550             2555             2560

Phe Gln Leu Ser Cys Lys Thr Ser Ala Cys Cys Pro Ser Cys Arg Cys
            2565             2570             2575

Glu Arg Met Glu Ala Cys Met Leu Asn Gly Thr Val Ile Gly Pro Gly
            2580             2585             2590

Lys Thr Val Met Ile Asp Val Cys Thr Thr Cys Arg Cys Met Val Gln
            2595             2600             2605

Val Gly Val Ile Ser Gly Phe Lys Leu Glu Cys Arg Lys Thr Thr Cys
    2610             2615             2620
```

```
Asn Pro Cys Pro Leu Gly Tyr Lys Glu Glu Asn Asn Thr Gly Glu Cys
2625                2630                2635                2640

Cys Gly Arg Cys Leu Pro Thr Ala Cys Thr Ile Gln Leu Arg Gly Gly
                2645                2650                2655

Gln Ile Met Thr Leu Lys Arg Asp Glu Thr Leu Gln Asp Gly Cys Asp
                2660                2665                2670

Thr His Phe Cys Lys Val Asn Glu Arg Gly Glu Tyr Phe Trp Glu Lys
            2675                2680                2685

Arg Val Thr Gly Cys Pro Pro Phe Asp Glu His Lys Cys Leu Ala Glu
            2690                2695                2700

Gly Gly Lys Ile Met Lys Ile Pro Gly Thr Cys Cys Asp Thr Cys Glu
2705                2710                2715                2720

Glu Pro Glu Cys Asn Asp Ile Thr Ala Arg Leu Gln Tyr Val Lys Val
                2725                2730                2735

Gly Ser Cys Lys Ser Glu Val Glu Val Asp Ile His Tyr Cys Gln Gly
                2740                2745                2750

Lys Cys Ala Ser Lys Ala Met Tyr Ser Ile Asp Ile Asn Asp Val Gln
            2755                2760                2765

Asp Gln Cys Ser Cys Cys Ser Pro Thr Arg Thr Glu Pro Met Gln Val
            2770                2775                2780

Ala Leu His Cys Thr Asn Gly Ser Val Val Tyr His Glu Val Leu Asn
2785                2790                2795                2800

Ala Met Glu Cys Lys Cys Ser Pro Arg Lys Cys Ser Lys
                2805                2810
```

```
<210> SEQ ID NO 112
<211> LENGTH: 3926
<212> TYPE: PRT
<213> ORGANISM: Artificial Sequence
<220> FEATURE:
<223> OTHER INFORMATION: Synthetic_BSN_HUMAN

<400> SEQUENCE: 112

Met Gly Asn Glu Val Ser Leu Glu Gly Gly Ala Gly Asp Gly Pro Leu
1               5                   10                  15

Pro Pro Gly Gly Ala Gly Pro Gly Pro Gly Pro Gly Pro Gly Pro Gly
                20                  25                  30

Ala Gly Lys Pro Pro Ser Ala Pro Ala Gly Gly Gln Leu Pro Ala
            35                  40                  45

Ala Gly Ala Ala Arg Ser Thr Ala Val Pro Pro Val Pro Gly Pro Gly
        50                  55                  60

Pro Gly Pro Gly Pro Gly Pro Gly Pro Gly Ser Thr Ser Arg Arg Leu
65                  70                  75                  80

Asp Pro Lys Glu Pro Leu Gly Asn Gln Arg Ala Ala Ser Pro Thr Pro
                85                  90                  95

Lys Gln Ala Ser Ala Thr Thr Pro Gly His Glu Ser Pro Arg Glu Thr
                100                 105                 110

Arg Ala Gln Gly Pro Ala Gly Gln Glu Ala Asp Gly Pro Arg Arg Thr
            115                 120                 125

Leu Gln Val Asp Ser Arg Thr Gln Arg Ser Gly Arg Ser Pro Ser Val
        130                 135                 140

Ser Pro Asp Arg Gly Ser Thr Pro Thr Ser Pro Tyr Ser Val Pro Gln
145                 150                 155                 160

Ile Ala Pro Leu Pro Ser Ser Thr Leu Cys Pro Ile Cys Lys Thr Ser
                165                 170                 175
```

-continued

```
Asp Leu Thr Ser Thr Pro Ser Gln Pro Asn Phe Asn Thr Cys Thr Gln
            180             185             190

Cys His Asn Lys Val Cys Asn Gln Cys Gly Phe Asn Pro Asn Pro His
            195             200             205

Leu Thr Gln Val Lys Glu Trp Leu Cys Leu Asn Cys Gln Met Gln Arg
        210             215             220

Ala Leu Gly Met Asp Met Thr Thr Ala Pro Arg Ser Lys Ser Gln Gln
225             230             235             240

Gln Leu His Ser Pro Ala Leu Ser Pro Ala His Ser Pro Ala Lys Gln
            245             250             255

Pro Leu Gly Lys Pro Asp Gln Glu Arg Ser Arg Gly Pro Gly Gly Pro
            260             265             270

Gln Pro Gly Ser Arg Gln Ala Glu Thr Ala Arg Ala Thr Ser Val Pro
            275             280             285

Gly Pro Ala Gln Ala Ala Ala Pro Pro Glu Val Gly Arg Val Ser Pro
        290             295             300

Gln Pro Pro Gln Pro Thr Lys Pro Ser Thr Ala Glu Pro Arg Pro Pro
305             310             315             320

Ala Gly Glu Ala Pro Ala Lys Ser Ala Thr Ala Val Pro Ala Gly Leu
            325             330             335

Gly Ala Thr Glu Gln Thr Gln Glu Gly Leu Thr Gly Lys Leu Phe Gly
            340             345             350

Leu Gly Ala Ser Leu Leu Thr Gln Ala Ser Thr Leu Met Ser Val Gln
            355             360             365

Pro Glu Ala Asp Thr Gln Gly Gln Pro Ala Pro Ser Lys Gly Thr Pro
        370             375             380

Lys Ile Val Phe Asn Asp Ala Ser Lys Glu Ala Gly Pro Lys Pro Leu
385             390             395             400

Gly Ser Gly Pro Gly Pro Gly Pro Ala Pro Gly Ala Lys Thr Glu Pro
            405             410             415

Gly Ala Arg Met Gly Pro Gly Ser Gly Pro Gly Ala Leu Pro Lys Thr
            420             425             430

Gly Gly Thr Thr Ser Pro Lys His Gly Arg Ala Glu His Gln Ala Ala
            435             440             445

Ser Lys Ala Ala Ala Lys Pro Lys Thr Met Pro Lys Glu Arg Ala Ile
        450             455             460

Cys Pro Leu Cys Gln Ala Glu Leu Asn Val Gly Ser Lys Ser Pro Ala
465             470             475             480

Asn Tyr Asn Thr Cys Thr Thr Cys Arg Leu Gln Val Cys Asn Leu Cys
            485             490             495

Gly Phe Asn Pro Thr Pro His Leu Val Glu Lys Thr Glu Trp Leu Cys
            500             505             510

Leu Asn Cys Gln Thr Lys Arg Leu Leu Glu Gly Ser Leu Gly Glu Pro
            515             520             525

Thr Pro Leu Pro Pro Pro Thr Ser Gln Gln Pro Pro Val Gly Ala Pro
        530             535             540

His Arg Ala Ser Gly Thr Ser Pro Leu Lys Gln Lys Gly Pro Gln Gly
545             550             555             560

Leu Gly Gln Pro Ser Gly Pro Leu Pro Ala Lys Ala Ser Pro Leu Ser
            565             570             575

Thr Lys Ala Ser Pro Leu Pro Ser Lys Ala Ser Pro Gln Ala Lys Pro
            580             585             590

Leu Arg Ala Ser Glu Pro Ser Lys Thr Pro Ser Ser Val Gln Glu Lys
```

```
            595                 600                 605

Lys Thr Arg Val Pro Thr Lys Ala Glu Pro Met Pro Lys Pro Pro Pro
    610                 615                 620

Glu Thr Thr Pro Thr Pro Ala Thr Pro Lys Val Lys Ser Gly Val Arg
625                 630                 635                 640

Arg Ala Glu Pro Ala Thr Pro Val Val Lys Ala Val Pro Glu Ala Pro
                645                 650                 655

Lys Gly Gly Glu Ala Glu Asp Leu Val Gly Lys Pro Tyr Ser Gln Asp
                660                 665                 670

Ala Ser Arg Ser Pro Gln Ser Leu Ser Asp Thr Gly Tyr Ser Ser Asp
                675                 680                 685

Gly Ile Ser Ser Ser Gln Ser Glu Ile Thr Gly Val Val Gln Gln Glu
    690                 695                 700

Val Glu Gln Leu Asp Ser Ala Gly Val Thr Gly Pro His Pro Pro Ser
705                 710                 715                 720

Pro Ser Glu Ile His Lys Val Gly Ser Ser Met Arg Pro Leu Leu Gln
                725                 730                 735

Ala Gln Gly Leu Ala Pro Ser Glu Arg Ser Lys Pro Leu Ser Ser Gly
                740                 745                 750

Thr Gly Glu Glu Gln Lys Gln Arg Pro His Ser Leu Ser Ile Thr Pro
                755                 760                 765

Glu Ala Phe Asp Ser Asp Glu Glu Leu Glu Asp Ile Leu Glu Glu Asp
    770                 775                 780

Glu Asp Ser Ala Glu Trp Arg Arg Arg Glu Gln Gln Asp Thr Ala
785                 790                 795                 800

Glu Ser Ser Asp Asp Phe Gly Ser Gln Leu Arg His Asp Tyr Val Glu
                805                 810                 815

Asp Ser Ser Glu Gly Gly Leu Ser Pro Leu Pro Pro Gln Pro Pro Ala
                820                 825                 830

Arg Ala Ala Glu Leu Thr Asp Glu Asp Phe Met Arg Arg Gln Ile Leu
                835                 840                 845

Glu Met Ser Ala Glu Glu Asp Asn Leu Glu Glu Asp Asp Thr Ala Thr
    850                 855                 860

Ser Gly Arg Gly Leu Ala Lys His Gly Thr Gln Lys Gly Gly Pro Arg
865                 870                 875                 880

Pro Arg Pro Glu Pro Ser Gln Glu Pro Ala Ala Leu Pro Lys Arg Arg
                885                 890                 895

Leu Pro His Asn Ala Thr Thr Gly Tyr Glu Glu Leu Leu Pro Glu Gly
                900                 905                 910

Gly Ser Ala Glu Ala Thr Asp Gly Ser Gly Thr Leu Gln Gly Gly Leu
                915                 920                 925

Arg Arg Phe Lys Thr Ile Glu Leu Asn Ser Thr Gly Ser Tyr Gly His
    930                 935                 940

Glu Leu Asp Leu Gly Gln Gly Pro Asp Pro Ser Leu Asp Arg Glu Pro
945                 950                 955                 960

Glu Leu Glu Met Glu Ser Leu Thr Gly Ser Pro Glu Asp Arg Ser Arg
                965                 970                 975

Gly Glu His Ser Ser Thr Leu Pro Ala Ser Thr Pro Ser Tyr Thr Ser
                980                 985                 990

Gly Thr Ser Pro Thr Ser Leu Ser Ser Leu Glu Glu Asp Ser Asp Ser
                995                 1000                1005

Ser Pro Ser Arg Arg Gln Arg Leu Glu Glu Ala Lys Gln Gln Arg Lys
    1010                1015                1020
```

```
Ala Arg His Arg Ser His Gly Pro Leu Leu Pro Thr Ile Glu Asp Ser
1025                1030                1035                1040

Ser Glu Glu Glu Glu Leu Arg Glu Glu Glu Glu Leu Leu Arg Glu Gln
                    1045                1050                1055

Glu Lys Met Arg Glu Val Glu Gln Gln Arg Ile Arg Ser Thr Ala Arg
                1060                1065                1070

Lys Thr Arg Arg Asp Lys Glu Glu Leu Arg Ala Gln Arg Arg Arg Glu
                1075                1080                1085

Arg Ser Lys Thr Pro Pro Ser Asn Leu Ser Pro Ile Glu Asp Ala Ser
    1090                1095                1100

Pro Thr Glu Glu Leu Arg Gln Ala Ala Glu Met Glu Glu Leu His Arg
1105                1110                1115                1120

Ser Ser Cys Ser Glu Tyr Ser Pro Ser Pro Ser Leu Asp Ser Glu Ala
                1125                1130                1135

Glu Ala Leu Asp Gly Gly Pro Ser Arg Leu Tyr Lys Ser Gly Ser Glu
                1140                1145                1150

Tyr Asn Leu Pro Thr Phe Met Ser Leu Tyr Ser Pro Thr Glu Thr Pro
    1155                1160                1165

Ser Gly Ser Ser Thr Thr Pro Ser Ser Gly Arg Pro Leu Lys Ser Ala
    1170                1175                1180

Glu Glu Ala Tyr Glu Glu Met Met Arg Lys Ala Glu Leu Leu Gln Arg
1185                1190                1195                1200

Gln Gln Gly Gln Ala Ala Gly Ala Arg Gly Pro His Gly Gly Pro Ser
                1205                1210                1215

Gln Pro Thr Gly Pro Arg Gly Leu Gly Ser Phe Glu Tyr Gln Asp Thr
                1220                1225                1230

Thr Asp Arg Glu Tyr Gly Gln Ala Ala Gln Pro Ala Ala Glu Gly Thr
    1235                1240                1245

Pro Ala Ser Leu Gly Ala Ala Val Tyr Glu Glu Ile Leu Gln Thr Ser
    1250                1255                1260

Gln Ser Ile Val Arg Met Arg Gln Ala Ser Ser Arg Asp Leu Ala Phe
1265                1270                1275                1280

Ala Glu Asp Lys Lys Lys Glu Lys Gln Phe Leu Asn Ala Glu Ser Ala
                1285                1290                1295

Tyr Met Asp Pro Met Lys Gln Asn Gly Gly Pro Leu Thr Pro Gly Thr
                1300                1305                1310

Ser Pro Thr Gln Leu Ala Ala Pro Val Ser Phe Ser Thr Pro Thr Ser
    1315                1320                1325

Ser Asp Ser Ser Gly Gly Arg Val Ile Pro Asp Val Arg Val Thr Gln
    1330                1335                1340

His Phe Ala Lys Glu Thr Gln Asp Pro Leu Lys Leu His Ser Ser Pro
1345                1350                1355                1360

Ala Ser Pro Ser Ser Ala Ser Lys Glu Ile Gly Met Pro Phe Ser Gln
                1365                1370                1375

Gly Pro Gly Thr Pro Ala Thr Thr Ala Val Ala Pro Cys Pro Ala Gly
                1380                1385                1390

Leu Pro Arg Gly Tyr Met Thr Pro Ala Ser Pro Ala Gly Ser Glu Arg
    1395                1400                1405

Ser Pro Ser Pro Ser Ser Thr Ala His Ser Tyr Gly His Ser Pro Thr
    1410                1415                1420

Thr Ala Asn Tyr Gly Ser Gln Thr Glu Asp Leu Pro Gln Ala Pro Ser
1425                1430                1435                1440
```

-continued

```
Gly Leu Ala Ala Ala Gly Arg Ala Ala Arg Glu Lys Pro Leu Ser Ala
              1445                1450                1455

Ser Asp Gly Glu Gly Gly Thr Pro Gln Pro Ser Arg Ala Tyr Ser Tyr
              1460                1465                1470

Phe Ala Ser Ser Ser Pro Pro Leu Ser Pro Ser Ser Pro Ser Glu Ser
              1475                1480                1485

Pro Thr Phe Ser Pro Gly Lys Met Gly Pro Arg Ala Thr Ala Glu Phe
              1490                1495                1500

Ser Thr Gln Thr Pro Ser Pro Ala Pro Ala Ser Asp Met Pro Arg Ser
         1505                1510                1515                1520

Pro Gly Ala Pro Thr Pro Ser Pro Met Val Ala Gln Gly Thr Gln Thr
                   1525                1530                1535

Pro His Arg Pro Ser Thr Pro Arg Leu Val Trp Gln Glu Ser Ser Gln
              1540                1545                1550

Glu Ala Pro Phe Met Val Ile Thr Leu Ala Ser Asp Ala Ser Ser Gln
              1555                1560                1565

Thr Arg Met Val His Ala Ser Ala Ser Thr Ser Pro Leu Cys Ser Pro
         1570                1575                1580

Thr Glu Thr Gln Pro Thr Thr His Gly Tyr Ser Gln Thr Thr Pro Pro
         1585                1590                1595                1600

Ser Val Ser Gln Leu Pro Pro Glu Pro Pro Gly Pro Pro Gly Phe Pro
                   1605                1610                1615

Arg Val Pro Ser Ala Gly Ala Asp Gly Pro Leu Ala Leu Tyr Gly Trp
              1620                1625                1630

Gly Ala Leu Pro Ala Glu Asn Ile Ser Leu Cys Arg Ile Ser Ser Val
              1635                1640                1645

Pro Gly Thr Ser Arg Val Glu Pro Gly Pro Arg Thr Pro Gly Thr Ala
         1650                1655                1660

Val Val Asp Leu Arg Thr Ala Val Lys Pro Thr Pro Ile Ile Leu Thr
    1665                1670                1675                1680

Asp Gln Gly Met Asp Leu Thr Ser Leu Ala Val Glu Ala Arg Lys Tyr
              1685                1690                1695

Gly Leu Ala Leu Asp Pro Ile Pro Gly Arg Gln Ser Thr Ala Val Gln
              1700                1705                1710

Pro Leu Val Ile Asn Leu Asn Ala Gln Glu His Thr Phe Leu Ala Thr
         1715                1720                1725

Ala Thr Thr Val Ser Ile Thr Met Ala Ser Ser Val Phe Met Ala Gln
         1730                1735                1740

Gln Lys Gln Pro Val Val Tyr Gly Asp Pro Tyr Gln Ser Arg Leu Asp
    1745                1750                1755                1760

Phe Gly Gln Gly Gly Gly Ser Pro Val Cys Leu Ala Gln Val Lys Gln
              1765                1770                1775

Val Glu Gln Ala Val Gln Thr Ala Pro Tyr Arg Ser Gly Pro Arg Gly
              1780                1785                1790

Arg Pro Arg Glu Ala Lys Phe Ala Arg Tyr Asn Leu Pro Asn Gln Val
              1795                1800                1805

Ala Pro Leu Ala Arg Arg Asp Val Leu Ile Thr Gln Met Gly Thr Ala
         1810                1815                1820

Gln Ser Ile Gly Leu Lys Pro Gly Pro Val Pro Glu Pro Gly Ala Glu
    1825                1830                1835                1840

Pro His Arg Ala Thr Pro Ala Glu Leu Arg Ser His Ala Leu Pro Gly
              1845                1850                1855

Ala Arg Lys Pro His Thr Val Val Val Gln Met Gly Glu Gly Thr Ala
```

-continued

```
              1860              1865              1870

Gly Thr Val Thr Thr Leu Leu Pro Glu Glu Pro Ala Gly Ala Leu Asp
        1875              1880              1885

Leu Thr Gly Met Arg Pro Glu Ser Gln Leu Ala Cys Cys Asp Met Val
        1890              1895              1900

Tyr Lys Leu Pro Phe Gly Ser Ser Cys Thr Gly Thr Phe His Pro Ala
1905              1910              1915              1920

Pro Ser Val Pro Glu Lys Ser Met Ala Asp Ala Ala Pro Pro Gly Gln
              1925              1930              1935

Ser Ser Ser Pro Phe Tyr Gly Pro Arg Asp Pro Glu Pro Pro Glu Pro
              1940              1945              1950

Pro Thr Tyr Arg Ala Gln Gly Val Val Gly Pro Gly Pro His Glu Glu
        1955              1960              1965

Gln Arg Pro Tyr Pro Gln Gly Leu Pro Gly Arg Leu Tyr Ser Ser Met
        1970              1975              1980

Ser Asp Thr Asn Leu Ala Glu Ala Gly Leu Asn Tyr His Ala Gln Arg
1985              1990              1995              2000

Ile Gly Gln Leu Phe Gln Gly Pro Gly Arg Asp Ser Ala Met Asp Leu
              2005              2010              2015

Ser Ser Leu Lys His Ser Tyr Ser Leu Gly Phe Ala Asp Gly Arg Tyr
              2020              2025              2030

Leu Gly Gln Gly Leu Gln Tyr Gly Ser Val Thr Asp Leu Arg His Pro
        2035              2040              2045

Thr Asp Leu Leu Ala His Pro Leu Pro Met Arg Arg Tyr Ser Ser Val
        2050              2055              2060

Ser Asn Ile Tyr Ser Asp His Arg Tyr Gly Pro Arg Gly Asp Ala Val
2065              2070              2075              2080

Gly Phe Gln Glu Ala Ser Leu Ala Gln Tyr Ser Ala Thr Thr Ala Arg
              2085              2090              2095

Glu Ile Ser Arg Met Cys Ala Ala Leu Asn Ser Met Asp Gln Tyr Gly
              2100              2105              2110

Gly Arg His Gly Ser Gly Gly Gly Pro Asp Leu Val Gln Tyr Gln
        2115              2120              2125

Pro Gln His Gly Pro Gly Leu Ser Ala Pro Gln Ser Leu Val Pro Leu
        2130              2135              2140

Arg Pro Gly Leu Leu Gly Asn Pro Thr Phe Pro Glu Gly His Pro Ser
2145              2150              2155              2160

Pro Gly Asn Leu Ala Gln Tyr Gly Pro Ala Ala Gly Gln Gly Thr Ala
              2165              2170              2175

Val Arg Gln Leu Leu Pro Ser Thr Ala Thr Val Arg Ala Ala Asp Gly
              2180              2185              2190

Met Ile Tyr Ser Thr Ile Asn Thr Pro Ile Ala Ala Thr Leu Pro Ile
        2195              2200              2205

Thr Thr Gln Pro Ala Ser Val Leu Arg Pro Met Val Arg Gly Gly Met
        2210              2215              2220

Tyr Arg Pro Tyr Ala Ser Gly Gly Ile Thr Ala Val Pro Leu Thr Ser
2225              2230              2235              2240

Leu Thr Arg Val Pro Met Ile Ala Pro Arg Val Pro Leu Gly Pro Thr
              2245              2250              2255

Gly Leu Tyr Arg Tyr Pro Ala Pro Ser Arg Phe Pro Ile Ala Ser Ser
              2260              2265              2270

Val Pro Pro Ala Glu Gly Pro Val Tyr Leu Gly Lys Pro Ala Ala Ala
              2275              2280              2285
```

```
Lys Ala Pro Gly Ala Gly Gly Pro Ser Arg Pro Glu Met Pro Val Gly
    2290                2295                2300

Ala Ala Arg Glu Glu Pro Leu Pro Thr Thr Thr Pro Ala Ala Ile Lys
2305                2310                2315                2320

Glu Ala Ala Gly Ala Pro Ala Pro Ala Pro Leu Ala Gly Gln Lys Pro
                2325                2330                2335

Pro Ala Asp Ala Ala Pro Gly Gly Gly Ser Gly Ala Leu Ser Arg Pro
                2340                2345                2350

Gly Phe Glu Lys Glu Glu Ala Ser Gln Glu Glu Arg Gln Arg Lys Gln
                2355                2360                2365

Gln Glu Gln Leu Leu Gln Leu Glu Arg Glu Arg Val Glu Leu Glu Lys
    2370                2375                2380

Leu Arg Gln Leu Arg Leu Gln Glu Glu Leu Glu Arg Glu Arg Val Glu
2385                2390                2395                2400

Leu Gln Arg His Arg Glu Glu Glu Gln Leu Leu Val Gln Arg Glu Leu
                2405                2410                2415

Gln Glu Leu Gln Thr Ile Lys His His Val Leu Gln Gln Gln Gln Glu
                2420                2425                2430

Glu Arg Gln Ala Gln Phe Ala Leu Gln Arg Glu Gln Leu Ala Gln Gln
                2435                2440                2445

Arg Leu Gln Leu Glu Gln Ile Gln Gln Leu Gln Gln Gln Leu Gln Gln
    2450                2455                2460

Gln Leu Glu Glu Gln Lys Gln Arg Gln Lys Ala Pro Phe Pro Ala Ala
2465                2470                2475                2480

Cys Glu Ala Pro Gly Arg Gly Pro Pro Leu Ala Ala Ala Glu Leu Ala
                2485                2490                2495

Gln Asn Gly Gln Tyr Trp Pro Pro Leu Thr His Ala Ala Phe Ile Ala
                2500                2505                2510

Met Ala Gly Pro Glu Gly Leu Gly Gln Pro Arg Glu Pro Val Leu His
                2515                2520                2525

Arg Gly Leu Pro Ser Ser Ala Ser Asp Met Ser Leu Gln Thr Glu Glu
    2530                2535                2540

Gln Trp Glu Ala Ser Arg Ser Gly Ile Lys Lys Arg His Ser Met Pro
2545                2550                2555                2560

Arg Leu Arg Asp Ala Cys Glu Leu Glu Ser Gly Thr Glu Pro Cys Val
                2565                2570                2575

Val Arg Arg Ile Ala Asp Ser Ser Val Gln Thr Asp Asp Glu Asp Gly
                2580                2585                2590

Glu Ser Arg Tyr Leu Leu Ser Arg Arg Arg Ala Arg Arg Ser Ala
    2595                2600                2605

Asp Cys Ser Val Gln Thr Asp Asp Glu Asp Ser Ala Glu Trp Glu Gln
    2610                2615                2620

Pro Val Arg Arg Arg Arg Ser Arg Leu Pro Arg His Ser Asp Ser Gly
2625                2630                2635                2640

Ser Asp Ser Lys His Asp Ala Thr Ala Ser Ser Ser Ser Ala Ala Ala
                2645                2650                2655

Thr Val Arg Ala Met Ser Ser Val Gly Ile Gln Thr Ile Ser Asp Cys
                2660                2665                2670

Ser Val Gln Thr Glu Pro Asp Gln Leu Pro Arg Val Ser Pro Ala Ile
        2675                2680                2685

His Ile Thr Ala Ala Thr Asp Pro Lys Val Glu Ile Val Arg Tyr Ile
    2690                2695                2700
```

-continued

```
Ser Ala Pro Glu Lys Thr Gly Arg Gly Glu Ser Leu Ala Cys Gln Thr
2705              2710              2715              2720

Glu Pro Asp Gly Gln Ala Gln Gly Val Ala Gly Pro Gln Leu Val Gly
              2725              2730              2735

Pro Thr Ala Ile Ser Pro Tyr Leu Pro Gly Ile Gln Ile Val Thr Pro
              2740              2745              2750

Gly Pro Leu Gly Arg Phe Glu Lys Lys Lys Pro Asp Pro Leu Glu Ile
              2755              2760              2765

Gly Tyr Gln Ala His Leu Pro Pro Glu Ser Leu Ser Gln Leu Val Ser
2770              2775              2780

Arg Gln Pro Pro Lys Ser Pro Gln Val Leu Tyr Ser Pro Val Ser Pro
2785              2790              2795              2800

Leu Ser Pro His Arg Leu Leu Asp Thr Ser Phe Ala Ser Ser Glu Arg
              2805              2810              2815

Leu Asn Lys Ala His Val Ser Pro Gln Lys His Phe Thr Ala Asp Ser
              2820              2825              2830

Ala Leu Arg Gln Gln Thr Leu Pro Arg Pro Met Lys Thr Leu Gln Arg
              2835              2840              2845

Ser Leu Ser Asp Pro Lys Pro Leu Ser Pro Thr Ala Glu Glu Ser Ala
2850              2855              2860

Lys Glu Arg Phe Ser Leu Tyr Gln His Gln Gly Gly Leu Gly Ser Gln
2865              2870              2875              2880

Val Ser Ala Leu Pro Pro Asn Ser Leu Val Arg Lys Val Lys Arg Thr
              2885              2890              2895

Leu Pro Ser Pro Pro Pro Glu Glu Ala His Leu Pro Leu Ala Gly Gln
              2900              2905              2910

Ala Ser Pro Gln Leu Tyr Ala Ala Ser Leu Leu Gln Arg Gly Leu Thr
              2915              2920              2925

Gly Pro Thr Thr Val Pro Ala Thr Lys Ala Ser Leu Leu Arg Glu Leu
              2930              2935              2940

Asp Arg Asp Leu Arg Leu Val Glu His Glu Ser Thr Lys Leu Arg Lys
2945              2950              2955              2960

Lys Gln Ala Glu Leu Asp Glu Glu Glu Lys Glu Ile Asp Ala Lys Leu
              2965              2970              2975

Lys Tyr Leu Glu Leu Gly Ile Thr Gln Arg Lys Glu Ser Leu Ala Lys
              2980              2985              2990

Asp Arg Gly Gly Arg Asp Tyr Pro Pro Leu Arg Gly Leu Gly Glu His
              2995              3000              3005

Arg Asp Tyr Leu Ser Asp Ser Glu Leu Asn Gln Leu Arg Leu Gln Gly
              3010              3015              3020

Cys Thr Thr Pro Ala Gly Gln Phe Val Asp Phe Pro Ala Thr Ala Ala
3025              3030              3035              3040

Ala Pro Ala Thr Pro Ser Gly Pro Thr Ala Phe Gln Gln Pro Arg Phe
              3045              3050              3055

Gln Pro Pro Ala Pro Gln Tyr Ser Ala Gly Ser Gly Gly Pro Thr Gln
              3060              3065              3070

Asn Gly Phe Pro Ala His Gln Ala Pro Thr Tyr Pro Gly Pro Ser Thr
              3075              3080              3085

Tyr Pro Ala Pro Ala Phe Pro Pro Gly Ala Ser Tyr Pro Ala Glu Pro
              3090              3095              3100

Gly Leu Pro Asn Gln Gln Ala Phe Arg Pro Thr Gly His Tyr Ala Gly
3105              3110              3115              3120

Gln Thr Pro Met Pro Thr Thr Gln Ser Thr Leu Phe Pro Val Pro Ala
```

-continued

```
                     3125            3130            3135

Asp Ser Arg Ala Pro Leu Gln Lys Pro Arg Gln Thr Ser Leu Ala Asp
            3140            3145            3150

Leu Glu Gln Lys Val Pro Thr Asn Tyr Glu Val Ile Ala Ser Pro Val
            3155            3160            3165

Val Pro Met Ser Ser Ala Pro Ser Glu Thr Ser Tyr Ser Gly Pro Ala
            3170            3175            3180

Val Ser Ser Gly Tyr Glu Gln Gly Lys Val Pro Glu Val Pro Arg Ala
3185            3190            3195            3200

Gly Asp Arg Gly Ser Val Ser Gln Ser Pro Ala Pro Thr Tyr Pro Ser
            3205            3210            3215

Asp Ser His Tyr Thr Ser Leu Glu Gln Asn Val Pro Arg Asn Tyr Val
            3220            3225            3230

Met Ile Asp Asp Ile Ser Glu Leu Thr Lys Asp Ser Thr Ser Thr Ala
            3235            3240            3245

Pro Asp Ser Gln Arg Leu Glu Pro Leu Gly Pro Gly Ser Ser Gly Arg
            3250            3255            3260

Pro Gly Lys Glu Pro Gly Glu Pro Gly Val Leu Asp Gly Pro Thr Leu
3265            3270            3275            3280

Pro Cys Cys Tyr Ala Arg Gly Glu Glu Glu Ser Glu Glu Asp Ser Tyr
            3285            3290            3295

Asp Pro Arg Gly Lys Gly Gly His Leu Arg Ser Met Glu Ser Asn Gly
            3300            3305            3310

Arg Pro Ala Ser Thr His Tyr Tyr Gly Asp Ser Asp Tyr Arg His Gly
            3315            3320            3325

Ala Arg Val Glu Lys Tyr Gly Pro Gly Pro Met Gly Pro Lys His Pro
            3330            3335            3340

Ser Lys Ser Leu Ala Pro Ala Ala Ile Ser Ser Lys Arg Ser Lys His
3345            3350            3355            3360

Arg Lys Gln Gly Met Glu Gln Lys Ile Ser Lys Phe Ser Pro Ile Glu
            3365            3370            3375

Glu Ala Lys Asp Val Glu Ser Asp Leu Ala Ser Tyr Pro Pro Pro Ala
            3380            3385            3390

Val Ser Ser Ser Leu Val Ser Arg Gly Arg Lys Phe Gln Asp Glu Ile
            3395            3400            3405

Thr Tyr Gly Leu Lys Lys Asn Val Tyr Glu Gln Gln Lys Tyr Tyr Gly
            3410            3415            3420

Met Ser Ser Arg Asp Ala Val Glu Asp Asp Arg Ile Tyr Gly Gly Ser
3425            3430            3435            3440

Ser Arg Ser Arg Ala Pro Ser Ala Tyr Ser Gly Glu Lys Leu Ser Ser
            3445            3450            3455

His Asp Phe Ser Gly Trp Gly Lys Gly Tyr Glu Arg Glu Arg Glu Ala
            3460            3465            3470

Val Glu Arg Leu Gln Lys Ala Gly Pro Lys Pro Ser Ser Leu Ser Met
            3475            3480            3485

Ala His Ser Arg Val Arg Pro Pro Met Arg Ser Gln Ala Ser Glu Glu
            3490            3495            3500

Glu Ser Pro Val Ser Pro Leu Gly Arg Pro Arg Pro Ala Gly Gly Pro
3505            3510            3515            3520

Leu Pro Pro Gly Gly Asp Thr Cys Pro Gln Phe Cys Ser Ser His Ser
            3525            3530            3535

Met Pro Asp Val Gln Glu His Val Lys Asp Gly Pro Arg Ala His Ala
            3540            3545            3550
```

```
Tyr Lys Arg Glu Glu Gly Tyr Ile Leu Asp Asp Ser His Cys Val Val
        3555                3560                3565

Ser Asp Ser Glu Ala Tyr His Leu Gly Gln Glu Glu Thr Asp Trp Phe
    3570                3575                3580

Asp Lys Pro Arg Asp Ala Arg Ser Asp Arg Phe Arg His His Gly Gly
3585                3590                3595                3600

His Ala Val Ser Ser Ser Ser Gln Lys Arg Gly Pro Ala Arg His Ser
            3605                3610                3615

Tyr His Asp Tyr Asp Glu Pro Pro Glu Glu Gly Leu Trp Pro His Asp
            3620                3625                3630

Glu Gly Gly Pro Gly Arg His Ala Ser Ala Lys Glu His Arg His Gly
        3635                3640                3645

Asp His Gly Arg His Ser Gly Arg His Thr Gly Glu Glu Pro Gly Arg
    3650                3655                3660

Arg Ala Ala Lys Pro His Ala Arg Asp Leu Gly Arg His Glu Ala Arg
3665                3670                3675                3680

Pro His Ser Gln Pro Ser Ser Ala Pro Ala Met Pro Lys Lys Gly Gln
            3685                3690                3695

Pro Gly Tyr Pro Ser Ser Ala Glu Tyr Ser Gln Pro Ser Arg Ala Ser
            3700                3705                3710

Ser Ala Tyr His His Ala Ser Asp Ser Lys Lys Gly Ser Arg Gln Ala
        3715                3720                3725

His Ser Gly Pro Ala Ala Leu Gln Ser Lys Ala Glu Pro Gln Ala Gln
    3730                3735                3740

Pro Gln Leu Gln Gly Arg Gln Ala Ala Pro Gly Pro Gln Gln Ser Gln
3745                3750                3755                3760

Ser Pro Ser Ser Arg Gln Ile Pro Ser Gly Ala Ala Ser Arg Gln Pro
            3765                3770                3775

Gln Thr Gln Gln Gln Gln Gly Leu Gly Leu Gln Pro Pro Gln Gln
            3780                3785                3790

Ala Leu Thr Gln Ala Arg Leu Gln Gln Gln Ser Gln Pro Thr Thr Arg
        3795                3800                3805

Gly Ser Ala Pro Ala Ala Ser Gln Pro Ala Gly Lys Pro Gln Pro Gly
    3810                3815                3820

Pro Ser Thr Ala Thr Gly Pro Gln Pro Ala Gly Pro Pro Arg Ala Glu
3825                3830                3835                3840

Gln Thr Asn Gly Ser Lys Gly Thr Ala Lys Ala Pro Gln Gln Gly Arg
            3845                3850                3855

Ala Pro Gln Ala Gln Pro Ala Pro Gly Pro Gly Pro Ala Gly Val Lys
            3860                3865                3870

Ala Gly Ala Arg Pro Gly Gly Thr Pro Gly Ala Pro Ala Gly Gln Pro
        3875                3880                3885

Gly Ala Asp Gly Glu Ser Val Phe Ser Lys Ile Leu Pro Gly Gly Ala
    3890                3895                3900

Ala Glu Gln Ala Gly Lys Leu Thr Glu Ala Val Ser Ala Phe Gly Lys
3905                3910                3915                3920

Lys Phe Ser Ser Phe Trp
            3925

<210> SEQ ID NO 113
<211> LENGTH: 4243
<212> TYPE: PRT
<213> ORGANISM: Artificial Sequence
<220> FEATURE:
```

<223> OTHER INFORMATION: Synthetic_PKHL1_HUMAN

<400> SEQUENCE: 113

```
Met Gly His Leu Trp Leu Leu Gly Ile Trp Gly Leu Cys Gly Leu Leu
1               5                   10                  15

Leu Cys Ala Ala Asp Pro Ser Thr Asp Gly Ser Gln Ile Ile Pro Lys
            20                  25                  30

Val Thr Glu Ile Ile Pro Lys Tyr Gly Ser Ile Asn Gly Ala Thr Arg
            35                  40                  45

Leu Thr Ile Arg Gly Glu Gly Phe Ser Gln Ala Asn Gln Phe Asn Tyr
        50                  55                  60

Gly Val Asp Asn Ala Glu Leu Gly Asn Ser Val Gln Leu Ile Ser Ser
65                  70                  75                  80

Phe Gln Ser Ile Thr Cys Asp Val Glu Lys Asp Ala Ser His Ser Thr
                85                  90                  95

Gln Ile Thr Cys Tyr Thr Arg Ala Met Pro Glu Asp Ser Tyr Thr Val
            100                 105                 110

Arg Val Ser Val Asp Gly Val Pro Val Thr Glu Asn Asn Thr Cys Lys
            115                 120                 125

Gly His Ile Asn Ser Trp Glu Cys Thr Phe Asn Ala Lys Ser Phe Arg
        130                 135                 140

Thr Pro Thr Ile Arg Ser Ile Thr Pro Leu Ser Gly Thr Pro Gly Thr
145                 150                 155                 160

Leu Ile Thr Ile Gln Gly Arg Ile Phe Thr Asp Val Tyr Gly Ser Asn
                165                 170                 175

Ile Ala Leu Ser Ser Asn Gly Lys Asn Val Arg Ile Leu Arg Val Tyr
            180                 185                 190

Ile Gly Gly Met Pro Cys Glu Leu Leu Ile Pro Gln Ser Asp Asn Leu
            195                 200                 205

Tyr Gly Leu Lys Leu Asp His Pro Asn Gly Asp Met Gly Ser Met Val
        210                 215                 220

Cys Lys Thr Thr Gly Thr Phe Ile Gly His His Asn Val Ser Phe Ile
225                 230                 235                 240

Leu Asp Asn Asp Tyr Gly Arg Ser Phe Pro Gln Lys Met Ala Tyr Phe
                245                 250                 255

Val Ser Ser Leu Asn Lys Ile Ala Met Phe Gln Thr Tyr Ala Glu Val
            260                 265                 270

Thr Met Ile Phe Pro Ser Gln Gly Ser Ile Arg Gly Gly Thr Thr Leu
            275                 280                 285

Thr Ile Ser Gly Arg Phe Phe Asp Gln Thr Asp Phe Pro Val Arg Val
        290                 295                 300

Leu Val Gly Gly Glu Pro Cys Asp Ile Leu Asn Val Thr Glu Asn Ser
305                 310                 315                 320

Ile Cys Cys Lys Thr Pro Pro Lys Pro His Ile Leu Lys Thr Val Tyr
                325                 330                 335

Pro Gly Gly Arg Gly Leu Lys Leu Glu Val Trp Asn Asn Ser Arg Pro
            340                 345                 350

Ile Arg Leu Glu Glu Ile Leu Glu Tyr Asn Glu Lys Thr Pro Gly Tyr
            355                 360                 365

Met Gly Ala Ser Trp Val Asp Ser Ala Ser Tyr Ile Trp Leu Met Glu
        370                 375                 380

Gln Asp Thr Phe Val Ala Arg Phe Ser Gly Phe Leu Val Ala Pro Asp
385                 390                 395                 400
```

-continued

```
Ser Asp Val Tyr Arg Phe Tyr Ile Lys Gly Asp Asp Arg Tyr Ala Ile
                405                 410                 415

Tyr Phe Ser Gln Thr Gly Leu Pro Glu Asp Lys Val Arg Ile Ala Tyr
            420                 425                 430

His Ser Ala Asn Ala Asn Ser Tyr Phe Ser Ser Pro Thr Gln Arg Ser
        435                 440                 445

Asp Asp Ile His Leu Gln Lys Gly Lys Glu Tyr Tyr Ile Glu Ile Leu
    450                 455                 460

Leu Gln Glu Tyr Arg Leu Ser Ala Phe Val Asp Val Gly Leu Tyr Gln
465                 470                 475                 480

Tyr Arg Asn Val Tyr Thr Glu Gln Gln Thr Gly Asp Ala Val Asn Glu
                485                 490                 495

Glu Gln Val Ile Lys Ser Gln Ser Thr Ile Leu Gln Glu Val Gln Val
            500                 505                 510

Ile Thr Leu Glu Asn Trp Glu Thr Thr Asn Ala Ile Asn Glu Val Gln
        515                 520                 525

Lys Ile Lys Val Thr Ser Pro Cys Val Glu Ala Asn Ser Cys Ser Leu
    530                 535                 540

Tyr Gln Tyr Arg Leu Ile Tyr Asn Met Glu Lys Thr Val Phe Leu Pro
545                 550                 555                 560

Ala Asp Ala Ser Glu Phe Ile Leu Gln Ser Ala Leu Asn Asp Leu Trp
                565                 570                 575

Ser Ile Lys Pro Asp Thr Val Gln Val Ile Arg Thr Gln Asn Pro Gln
                580                 585                 590

Ser Tyr Val Tyr Met Val Thr Phe Ile Ser Thr Arg Gly Asp Phe Asp
                595                 600                 605

Leu Leu Gly Tyr Glu Val Val Glu Gly Asn Asn Val Thr Leu Asp Ile
    610                 615                 620

Thr Glu Gln Thr Lys Gly Lys Pro Asn Leu Glu Thr Phe Thr Leu Asn
625                 630                 635                 640

Trp Asp Gly Ile Ala Ser Lys Pro Leu Thr Leu Trp Ser Ser Glu Ala
                645                 650                 655

Glu Phe Gln Gly Ala Val Glu Glu Met Val Ser Thr Lys Cys Pro Pro
            660                 665                 670

Gln Ile Ala Asn Phe Glu Glu Gly Phe Val Val Lys Tyr Phe Arg Asp
        675                 680                 685

Tyr Glu Thr Asp Phe Asn Leu Glu His Ile Asn Arg Gly Gln Lys Thr
    690                 695                 700

Ala Glu Thr Asp Ala Tyr Cys Gly Arg Tyr Ser Leu Lys Asn Pro Ala
705                 710                 715                 720

Val Leu Phe Asp Ser Ala Asp Val Lys Pro Asn Arg Arg Pro Tyr Gly
                725                 730                 735

Asp Ile Leu Leu Phe Pro Tyr Asn Gln Leu Cys Leu Ala Tyr Lys Gly
                740                 745                 750

Phe Leu Ala Asn Tyr Ile Gly Leu Lys Phe Gln Tyr Gln Asp Asn Ser
        755                 760                 765

Lys Ile Thr Arg Ser Thr Asp Thr Gln Phe Thr Tyr Asn Phe Ala Tyr
    770                 775                 780

Gly Asn Asn Trp Thr Tyr Thr Cys Ile Asp Leu Leu Asp Leu Val Arg
785                 790                 795                 800

Thr Lys Tyr Thr Gly Thr Asn Val Ser Leu Gln Arg Ile Ser Leu His
                805                 810                 815

Lys Ala Ser Glu Ser Gln Ser Phe Tyr Val Asp Val Val Tyr Ile Gly
```

339 340

-continued

```
              820              825              830

His Thr Ser Thr Ile Ser Thr Leu Asp Glu Met Pro Lys Arg Arg Leu
        835              840              845

Pro Ala Leu Ala Asn Lys Gly Ile Phe Leu Glu His Phe Gln Val Asn
    850              855              860

Gln Thr Lys Thr Asn Gly Pro Thr Met Thr Asn Gln Tyr Ser Val Thr
865              870              875              880

Met Thr Ser Tyr Asn Cys Ser Tyr Asn Ile Pro Met Met Ala Val Ser
            885              890              895

Phe Gly Gln Ile Ile Thr His Glu Thr Glu Asn Glu Phe Val Tyr Arg
            900              905              910

Gly Asn Asn Trp Pro Gly Glu Ser Lys Ile His Ile Gln Arg Ile Gln
        915              920              925

Ala Ala Ser Pro Pro Leu Ser Gly Ser Phe Asp Ile Gln Ala Tyr Gly
    930              935              940

His Ile Leu Lys Gly Leu Pro Ala Ala Val Ser Ala Ala Asp Leu Gln
945              950              955              960

Phe Ala Leu Gln Ser Leu Glu Gly Met Gly Arg Ile Ser Val Thr Arg
            965              970              975

Glu Gly Thr Cys Ala Gly Tyr Ala Trp Asn Ile Lys Trp Arg Ser Thr
        980              985              990

Cys Gly Lys Gln Asn Leu Leu Gln Ile Asn Asp Ser Asn Ile Ile Gly
        995              1000              1005

Glu Lys Ala Asn Met Thr Val Thr Arg Ile Lys Glu Gly Gly Leu Phe
    1010              1015              1020

Arg Gln His Val Leu Gly Asp Leu Leu Arg Thr Pro Ser Gln Gln Pro
1025              1030              1035              1040

Gln Val Glu Val Tyr Val Asn Gly Ile Pro Ala Lys Cys Ser Gly Asp
            1045              1050              1055

Cys Gly Phe Thr Trp Asp Ser Asn Ile Thr Pro Leu Val Leu Ala Ile
        1060              1065              1070

Ser Pro Ser Gln Gly Ser Tyr Glu Glu Gly Thr Ile Leu Thr Ile Val
        1075              1080              1085

Gly Ser Gly Phe Ser Pro Ser Ser Ala Val Thr Val Ser Val Gly Pro
    1090              1095              1100

Val Gly Cys Ser Leu Leu Ser Val Asp Glu Lys Glu Leu Lys Cys Gln
1105              1110              1115              1120

Ile Leu Asn Gly Ser Ala Gly His Ala Pro Val Ala Val Ser Met Ala
            1125              1130              1135

Asp Val Gly Leu Ala Gln Asn Val Gly Gly Glu Glu Phe Tyr Phe Val
            1140              1145              1150

Tyr Gln Ser Gln Ile Ser His Ile Trp Pro Asp Ser Gly Ser Ile Ala
        1155              1160              1165

Gly Gly Thr Leu Leu Thr Leu Ser Gly Phe Gly Phe Asn Glu Asn Ser
    1170              1175              1180

Lys Val Leu Val Gly Asn Glu Thr Cys Asn Val Ile Glu Gly Asp Leu
1185              1190              1195              1200

Asn Arg Ile Thr Cys Arg Thr Pro Lys Lys Thr Glu Gly Thr Val Asp
            1205              1210              1215

Ile Ser Val Thr Thr Asn Gly Phe Gln Ala Thr Ala Arg Asp Ala Phe
            1220              1225              1230

Ser Tyr Asn Cys Leu Gln Thr Pro Ile Ile Thr Asp Phe Ser Pro Lys
        1235              1240              1245
```

-continued

```
Val Arg Thr Ile Leu Gly Glu Val Asn Leu Thr Ile Lys Gly Tyr Asn
    1250            1255            1260

Phe Gly Asn Glu Leu Thr Gln Asn Met Ala Val Tyr Val Gly Gly Lys
1265            1270            1275            1280

Thr Cys Gln Ile Leu His Trp Asn Phe Thr Asp Ile Arg Cys Leu Leu
            1285            1290            1295

Pro Lys Leu Ser Pro Gly Lys His Asp Ile Tyr Val Glu Val Arg Asn
            1300            1305            1310

Trp Gly Phe Ala Ser Thr Arg Asp Lys Leu Asn Ser Ser Ile Gln Tyr
            1315            1320            1325

Val Leu Glu Val Thr Ser Met Phe Pro Gln Arg Gly Ser Leu Phe Gly
    1330            1335            1340

Gly Thr Glu Ile Thr Ile Arg Gly Phe Gly Phe Ser Thr Ile Pro Ala
1345            1350            1355            1360

Glu Asn Thr Val Leu Leu Gly Ser Ile Pro Cys Asn Val Thr Ser Ser
            1365            1370            1375

Ser Glu Asn Val Ile Lys Cys Ile Leu His Ser Thr Gly Asn Ile Phe
            1380            1385            1390

Arg Ile Thr Asn Asn Gly Lys Asp Ser Val His Gly Leu Gly Tyr Ala
    1395            1400            1405

Trp Ser Pro Pro Val Leu Asn Val Ser Val Gly Asp Thr Val Ala Trp
    1410            1415            1420

His Trp Gln Thr His Pro Phe Leu Arg Gly Ile Gly Tyr Arg Ile Phe
1425            1430            1435            1440

Ser Val Ser Ser Pro Gly Ser Val Ile Tyr Asp Gly Lys Gly Phe Thr
            1445            1450            1455

Ser Gly Arg Gln Lys Ser Thr Ser Gly Ser Phe Ser Tyr Gln Phe Thr
            1460            1465            1470

Ser Pro Gly Ile His Tyr Tyr Ser Ser Gly Tyr Val Asp Glu Ala His
    1475            1480            1485

Ser Ile Phe Leu Gln Gly Val Ile Asn Val Leu Pro Ala Glu Thr Arg
    1490            1495            1500

His Ile Pro Leu His Leu Phe Val Gly Arg Ser Glu Ala Thr Tyr Ala
1505            1510            1515            1520

Tyr Gly Gly Pro Glu Asn Leu His Leu Gly Ser Ser Val Ala Gly Cys
            1525            1530            1535

Leu Ala Thr Glu Pro Leu Cys Ser Leu Asn Asn Thr Arg Val Lys Asn
            1540            1545            1550

Ser Lys Arg Leu Leu Phe Glu Val Ser Ser Cys Phe Ser Pro Ser Ile
            1555            1560            1565

Ser Asn Ile Thr Pro Ser Thr Gly Thr Val Asn Glu Leu Ile Thr Ile
    1570            1575            1580

Ile Gly His Gly Phe Ser Asn Leu Pro Trp Ala Asn Lys Val Thr Ile
1585            1590            1595            1600

Gly Ser Tyr Pro Cys Val Val Glu Glu Ser Ser Glu Asp Ser Ile Thr
            1605            1610            1615

Cys His Ile Asp Pro Gln Asn Ser Met Asp Val Gly Ile Arg Glu Thr
            1620            1625            1630

Val Thr Leu Thr Val Tyr Asn Leu Gly Thr Ala Ile Asn Thr Leu Ser
    1635            1640            1645

Asn Glu Phe Asp Arg Arg Phe Val Leu Leu Pro Asn Ile Asp Leu Val
    1650            1655            1660
```

-continued

```
Leu Pro Asn Ala Gly Ser Thr Thr Gly Met Thr Ser Val Thr Ile Lys
1665                1670                1675                1680

Gly Ser Gly Phe Ala Val Ser Ser Ala Gly Val Lys Val Leu Met Gly
                1685                1690                1695

His Phe Pro Cys Lys Val Leu Ser Val Asn Tyr Thr Ala Ile Glu Cys
            1700                1705                1710

Glu Thr Ser Pro Ala Ala Gln Gln Leu Val Asp Val Asp Leu Leu Ile
        1715                1720                1725

His Gly Val Pro Ala Gln Cys Gln Gly Asn Cys Thr Phe Ser Tyr Leu
        1730                1735                1740

Glu Ser Ile Thr Pro Tyr Ile Thr Gly Val Phe Pro Asn Ser Val Ile
1745                1750                1755                1760

Gly Ser Val Lys Val Leu Ile Glu Gly Glu Gly Leu Gly Thr Val Leu
                1765                1770                1775

Glu Asp Ile Ala Val Phe Ile Gly Asn Gln Gln Phe Arg Ala Ile Glu
                1780                1785                1790

Val Asn Glu Asn Asn Ile Thr Ala Leu Val Thr Pro Leu Pro Val Gly
        1795                1800                1805

His His Ser Val Ser Val Val Val Gly Ser Lys Gly Leu Ala Leu Gly
        1810                1815                1820

Asn Leu Thr Val Ser Ser Pro Pro Val Ala Ser Leu Ser Pro Thr Ser
1825                1830                1835                1840

Gly Ser Ile Gly Gly Gly Thr Thr Leu Val Ile Thr Gly Asn Gly Phe
                1845                1850                1855

Tyr Pro Gly Asn Thr Thr Val Thr Ile Gly Asp Glu Pro Cys Gln Ile
                1860                1865                1870

Ile Ser Ile Asn Pro Asn Glu Val Tyr Cys Arg Thr Pro Ala Gly Thr
        1875                1880                1885

Thr Gly Met Val Asp Val Lys Ile Phe Val Asn Thr Ile Ala Tyr Pro
        1890                1895                1900

Pro Leu Leu Phe Thr Tyr Ala Leu Glu Asp Thr Pro Phe Leu Arg Gly
1905                1910                1915                1920

Ile Ile Pro Ser Arg Gly Pro Pro Gly Thr Glu Ile Glu Ile Thr Gly
                1925                1930                1935

Ser Asn Phe Gly Phe Glu Ile Leu Glu Ile Ser Val Met Ile Asn Asn
                1940                1945                1950

Ile Gln Cys Asn Val Thr Met Ala Asn Asp Ser Val Val Gln Cys Ile
        1955                1960                1965

Val Gly Asp His Ala Gly Gly Thr Phe Pro Val Met Met His His Lys
        1970                1975                1980

Thr Lys Gly Ser Ala Met Ser Thr Val Val Phe Glu Tyr Pro Leu Asn
1985                1990                1995                2000

Ile Gln Asn Ile Asn Pro Ser Gln Gly Ser Phe Gly Gly Gly Gln Thr
                2005                2010                2015

Met Thr Val Thr Gly Thr Gly Phe Asn Pro Gln Asn Ser Ile Ile Leu
                2020                2025                2030

Val Cys Gly Ser Glu Cys Ala Ile Asp Arg Leu Arg Ser Asp Tyr Thr
        2035                2040                2045

Thr Leu Leu Cys Glu Ile Pro Ser Asn Asn Gly Thr Gly Ala Glu Gln
        2050                2055                2060

Ala Cys Glu Val Ser Val Val Asn Gly Lys Asp Leu Ser Gln Ser Met
2065                2070                2075                2080

Thr Pro Phe Thr Tyr Ala Val Ser Leu Thr Pro Leu Ile Thr Ala Val
```

-continued

```
                2085              2090              2095

Ser Pro Lys Arg Gly Ser Thr Ala Gly Gly Thr Arg Leu Thr Val Val
            2100              2105              2110

Gly Ser Gly Phe Ser Glu Asn Met Glu Asp Val His Ile Thr Ile Ala
            2115              2120              2125

Glu Ala Lys Cys Asp Val Glu Tyr Ser Asn Lys Thr His Ile Ile Cys
        2130              2135              2140

Met Thr Asp Ala His Thr Leu Ser Gly Trp Ala Pro Val Cys Val His
2145              2150              2155              2160

Ile Arg Gly Val Gly Met Ala Lys Leu Asp Asn Ala Asp Phe Leu Tyr
                2165              2170              2175

Val Asp Ala Trp Ser Ser Asn Phe Ser Trp Gly Gly Lys Ser Pro Pro
            2180              2185              2190

Glu Glu Gly Ser Leu Val Val Ile Thr Lys Gly Gln Thr Ile Leu Leu
            2195              2200              2205

Asp Gln Ser Thr Pro Ile Leu Lys Met Leu Leu Ile Gln Gly Gly Thr
        2210              2215              2220

Leu Ile Phe Asp Glu Ala Asp Ile Glu Leu Gln Ala Glu Asn Ile Leu
2225              2230              2235              2240

Ile Thr Asp Gly Gly Val Leu Gln Ile Gly Thr Glu Thr Ser Pro Phe
                2245              2250              2255

Gln His Lys Ala Val Ile Thr Leu His Gly His Leu Arg Ser Pro Glu
            2260              2265              2270

Leu Pro Val Tyr Gly Ala Lys Thr Leu Ala Val Arg Glu Gly Ile Leu
            2275              2280              2285

Asp Leu His Gly Val Pro Val Pro Val Thr Trp Thr Arg Leu Ala His
        2290              2295              2300

Thr Ala Lys Ala Gly Glu Arg Ile Leu Ile Leu Gln Glu Ala Val Thr
2305              2310              2315              2320

Trp Lys Pro Gly Asp Asn Ile Val Ile Ala Ser Thr Gly His Arg His
                2325              2330              2335

Ser Gln Gly Glu Asn Glu Lys Met Thr Ile Ala Ser Val Ser Ala Asp
            2340              2345              2350

Gly Ile Asn Ile Thr Leu Ser Asn Pro Leu Asn Tyr Thr His Leu Gly
            2355              2360              2365

Ile Thr Val Thr Leu Pro Asp Gly Thr Leu Phe Glu Ala Arg Ala Glu
        2370              2375              2380

Val Gly Ile Leu Thr Arg Asn Ile Leu Ile Arg Gly Ser Asp Asn Val
2385              2390              2395              2400

Glu Trp Asn Asn Lys Ile Pro Ala Cys Pro Asp Gly Phe Asp Thr Gly
                2405              2410              2415

Glu Phe Ala Thr Gln Thr Cys Leu Gln Gly Lys Phe Gly Glu Glu Ile
            2420              2425              2430

Gly Ser Asp Gln Phe Gly Gly Cys Val Met Phe His Ala Pro Val Pro
            2435              2440              2445

Gly Ala Asn Met Val Thr Gly Arg Ile Glu Tyr Val Glu Val Phe His
        2450              2455              2460

Ala Gly Gln Ala Phe Arg Leu Gly Arg Tyr Pro Ile His Trp His Leu
2465              2470              2475              2480

Leu Gly Asp Leu Gln Phe Lys Ser Tyr Val Arg Gly Cys Ala Ile His
                2485              2490              2495

Gln Ala Tyr Asn Arg Ala Val Thr Ile His Asn Thr His His Leu Leu
            2500              2505              2510
```

-continued

```
Val Glu Arg Asn Ile Ile Tyr Asp Ile Lys Gly Gly Ala Phe Phe Ile
        2515                2520                2525

Glu Asp Gly Ile Glu His Gly Asn Ile Leu Gln Tyr Asn Leu Ala Val
    2530                2535                2540

Phe Val Gln Gln Ser Thr Ser Leu Leu Asn Asp Asp Val Thr Pro Ala
2545                2550                2555                2560

Ala Phe Trp Val Thr Asn Pro Asn Asn Thr Ile Arg His Asn Ala Val
                2565                2570                2575

Ala Gly Gly Thr His Phe Gly Phe Trp Tyr Arg Met Asn Asn His Pro
                2580                2585                2590

Asp Gly Pro Ser Tyr Asp Arg Asn Ile Cys Gln Lys Arg Val Pro Leu
                2595                2600                2605

Gly Glu Phe Phe Asn Asn Thr Val His Ser Gln Gly Trp Phe Gly Met
    2610                2615                2620

Trp Ile Phe Glu Glu Tyr Phe Pro Met Gln Thr Gly Ser Cys Thr Ser
2625                2630                2635                2640

Thr Val Pro Ala Pro Ala Ile Phe Asn Ser Leu Thr Thr Trp Asn Cys
                2645                2650                2655

Gln Lys Gly Ala Glu Trp Val Asn Gly Gly Ala Leu Gln Phe His Asn
                2660                2665                2670

Phe Val Met Val Asn Asn Tyr Glu Ala Gly Ile Glu Thr Lys Arg Ile
                2675                2680                2685

Leu Ala Pro Tyr Val Gly Gly Trp Gly Glu Thr Asn Gly Ala Val Ile
    2690                2695                2700

Lys Asn Ala Lys Ile Val Gly His Leu Asp Glu Leu Gly Met Gly Ser
2705                2710                2715                2720

Ala Phe Cys Thr Ala Lys Gly Leu Val Leu Pro Phe Ser Glu Gly Leu
                2725                2730                2735

Thr Val Ser Ser Val His Phe Met Asn Phe Asp Arg Pro Asn Cys Val
                2740                2745                2750

Ala Leu Gly Val Thr Ser Ile Ser Gly Val Cys Asn Asp Arg Cys Gly
    2755                2760                2765

Gly Trp Ser Ala Lys Phe Val Asp Val Gln Tyr Ser His Thr Pro Asn
    2770                2775                2780

Lys Ala Gly Phe Arg Trp Glu His Glu Met Val Met Ile Asp Val Asp
2785                2790                2795                2800

Gly Ser Leu Thr Gly His Lys Gly His Thr Val Ile Pro His Ser Ser
                2805                2810                2815

Leu Leu Asp Pro Ser His Cys Thr Gln Glu Ala Glu Trp Ser Ile Gly
                2820                2825                2830

Phe Pro Gly Ser Val Cys Asp Ala Ser Val Ser Phe His Arg Leu Ala
    2835                2840                2845

Phe Asn Gln Pro Ser Pro Val Ser Leu Leu Glu Lys Asp Val Val Leu
    2850                2855                2860

Ser Asp Ser Phe Gly Thr Ser Ile Ile Pro Phe Gln Lys Lys Arg Leu
2865                2870                2875                2880

Thr His Met Ser Gly Trp Met Ala Leu Ile Pro Asn Ala Asn His Ile
                2885                2890                2895

Asn Trp Tyr Phe Lys Gly Val Asp His Ile Thr Asn Ile Ser Tyr Thr
                2900                2905                2910

Ser Thr Phe Tyr Gly Phe Lys Glu Glu Asp Tyr Val Ile Ile Ser His
    2915                2920                2925
```

-continued

```
Asn Phe Thr Gln Asn Pro Asp Met Phe Asn Ile Ile Asp Met Arg Asn
    2930                    2935                2940

Gly Ser Ser Asn Pro Leu Asn Trp Asn Thr Ser Lys Asn Gly Asp Trp
2945                    2950                2955                2960

His Leu Glu Ala Asn Thr Ser Thr Leu Tyr Tyr Leu Val Ser Gly Arg
                    2965                2970                2975

Asn Asp Leu His Gln Ser Gln Leu Ile Ser Gly Asn Leu Asp Pro Asp
                2980                2985                2990

Val Lys Asp Val Val Ile Asn Phe Gln Ala Tyr Cys Cys Ile Leu Gln
            2995                3000                3005

Asp Cys Phe Pro Val His Pro Pro Ser Arg Lys Pro Ile Pro Lys Lys
    3010                    3015                3020

Arg Pro Ala Thr Tyr Asn Leu Trp Ser Asn Asp Ser Phe Trp Gln Ser
3025                    3030                3035                3040

Ser Arg Glu Asn Asn Tyr Thr Val Pro His Pro Gly Ala Asn Val Ile
                    3045                3050                3055

Ile Pro Glu Gly Thr Trp Ile Val Ala Asp Ile Asp Met Pro Ser Met
                3060                3065                3070

Glu Arg Leu Ile Ile Trp Gly Val Leu Glu Leu Glu Asp Lys Tyr Asn
                3075                3080                3085

Val Gly Ala Ala Glu Ser Ser Tyr Arg Glu Val Val Leu Asn Ala Thr
            3090                3095                3100

Tyr Ile Ser Leu Gln Gly Gly Arg Leu Ile Gly Gly Trp Glu Asp Asn
3105                    3110                3115                3120

Pro Phe Lys Gly Asp Leu Lys Ile Val Leu Arg Gly Asn His Thr Thr
                3125                3130                3135

Gln Asp Trp Ala Leu Pro Glu Gly Pro Asn Gln Gly Ala Lys Val Leu
                3140                3145                3150

Gly Val Phe Gly Glu Leu Asp Leu His Gly Ile Pro His Ser Ile Tyr
            3155                3160                3165

Lys Thr Lys Leu Ser Glu Thr Ala Phe Ala Gly Ser Lys Val Leu Ser
    3170                    3175                3180

Leu Met Asp Ala Val Asp Trp Gln Glu Gly Glu Glu Ile Val Ile Thr
3185                    3190                3195                3200

Thr Thr Ser Tyr Asp Phe His Gln Thr Glu Thr Arg Ser Ile Val Lys
                3205                3210                3215

Ile Leu His Asp His Lys Ile Leu Ile Leu Asn Asp Ser Leu Ser Tyr
                3220                3225                3230

Thr His Phe Ala Glu Lys Tyr His Val Pro Gly Thr Gly Glu Ser Tyr
            3235                3240                3245

Thr Leu Ala Ala Asp Val Gly Ile Leu Ser Arg Asn Ile Lys Ile Val
    3250                    3255                3260

Gly Glu Asp Tyr Pro Gly Trp Ser Glu Asp Ser Phe Gly Ala Arg Val
3265                    3270                3275                3280

Leu Val Gly Ser Phe Thr Glu Asn Met Met Thr Phe Lys Gly Asn Ala
                3285                3290                3295

Arg Ile Ser Asn Val Glu Phe Tyr His Ser Gly Gln Glu Gly Phe Arg
                3300                3305                3310

Asp Ser Thr Asp Pro Arg Tyr Ala Val Thr Phe Leu Asn Leu Gly Gln
            3315                3320                3325

Ile Gln Glu His Gly Ser Ser Tyr Ile Arg Gly Cys Ala Phe His His
    3330                    3335                3340

Gly Phe Ser Pro Ala Ile Gly Val Phe Gly Thr Asp Gly Leu Asp Ile
```

-continued

```
3345            3350            3355            3360

Asp Asp Asn Ile Ile His Phe Thr Val Gly Glu Gly Ile Arg Ile Trp
            3365            3370            3375

Gly Asn Ala Asn Arg Val Arg Gly Asn Leu Ile Ala Leu Ser Val Trp
            3380            3385            3390

Pro Gly Thr Tyr Gln Asn Arg Lys Asp Leu Ser Ser Thr Leu Trp His
            3395            3400            3405

Ala Ala Ile Glu Ile Asn Arg Gly Thr Asn Thr Val Leu Gln Asn Asn
            3410            3415            3420

Val Val Ala Gly Phe Gly Arg Ala Gly Tyr Arg Ile Asp Gly Glu Pro
3425            3430            3435            3440

Cys Pro Gly Gln Phe Asn Pro Val Glu Lys Trp Phe Asp Asn Glu Ala
            3445            3450            3455

His Gly Gly Leu Tyr Gly Ile Tyr Met Asn Gln Asp Gly Leu Pro Gly
            3460            3465            3470

Cys Ser Leu Ile Gln Gly Phe Thr Ile Trp Thr Cys Trp Asp Tyr Gly
            3475            3480            3485

Ile Tyr Phe Gln Thr Thr Glu Ser Val His Ile Tyr Asn Val Thr Leu
            3490            3495            3500

Val Asp Asn Gly Met Ala Ile Phe Pro Met Ile Tyr Met Pro Ala Ala
3505            3510            3515            3520

Ile Ser His Lys Ile Ser Ser Lys Asn Val Gln Ile Lys Ser Ser Leu
            3525            3530            3535

Ile Val Gly Ser Ser Pro Gly Phe Asn Cys Ser Asp Val Leu Thr Asn
            3540            3545            3550

Asp Asp Pro Asn Ile Glu Leu Thr Ala Ala His Arg Ser Pro Arg Ser
            3555            3560            3565

Pro Ser Gly Gly Arg Ser Gly Ile Cys Trp Pro Thr Phe Ala Ser Ala
            3570            3575            3580

His Asn Met Ala Pro Arg Lys Pro His Ala Gly Ile Met Ser Tyr Asn
3585            3590            3595            3600

Ala Ile Ser Gly Leu Leu Asp Ile Ser Gly Ser Thr Phe Val Gly Phe
            3605            3610            3615

Lys Asn Val Cys Ser Gly Glu Thr Asn Val Ile Phe Ile Thr Asn Pro
            3620            3625            3630

Leu Asn Glu Asp Leu Gln His Pro Ile His Val Lys Asn Ile Lys Leu
            3635            3640            3645

Val Asp Thr Thr Glu Gln Ser Lys Ile Phe Ile His Arg Pro Asp Ile
            3650            3655            3660

Ser Lys Val Asn Pro Ser Asp Cys Val Asp Met Val Cys Asp Ala Lys
3665            3670            3675            3680

Arg Lys Ser Phe Leu Arg Asp Ile Asp Gly Ser Phe Leu Gly Asn Ala
            3685            3690            3695

Gly Ser Val Ile Pro Gln Ala Glu Tyr Glu Trp Asp Gly Asn Ser Gln
            3700            3705            3710

Val Gly Ile Gly Asp Tyr Arg Ile Pro Lys Ala Met Leu Thr Phe Leu
            3715            3720            3725

Asn Gly Ser Arg Ile Pro Val Thr Glu Lys Ala Pro His Lys Gly Ile
            3730            3735            3740

Ile Arg Asp Ser Thr Cys Lys Tyr Leu Pro Glu Trp Gln Ser Tyr Gln
3745            3750            3755            3760

Cys Phe Gly Met Glu Tyr Ala Met Met Val Ile Glu Ser Leu Asp Pro
            3765            3770            3775
```

-continued

```
Asp Thr Glu Thr Arg Arg Leu Ser Pro Val Ala Ile Met Gly Asn Gly
        3780                3785                3790

Tyr Val Asp Leu Ile Asn Gly Pro Gln Asp His Gly Trp Cys Ala Gly
        3795                3800                3805

Tyr Thr Cys Gln Arg Arg Leu Ser Leu Phe His Ser Ile Val Ala Leu
        3810                3815                3820

Asn Lys Ser Tyr Glu Val Tyr Phe Thr Gly Thr Ser Pro Gln Asn Leu
3825                3830                3835                3840

Arg Leu Met Leu Leu Asn Val Asp His Asn Lys Ala Val Leu Val Gly
                3845                3850                3855

Ile Phe Phe Ser Thr Leu Gln Arg Leu Asp Val Tyr Val Asn Asn Leu
                3860                3865                3870

Leu Val Cys Pro Lys Thr Thr Ile Trp Asn Ala Gln Gln Lys His Cys
        3875                3880                3885

Glu Leu Asn Asn His Leu Tyr Lys Asp Gln Phe Leu Pro Asn Leu Asp
        3890                3895                3900

Ser Thr Val Leu Gly Glu Asn Tyr Phe Asp Gly Thr Tyr Gln Met Leu
3905                3910                3915                3920

Tyr Leu Leu Val Lys Gly Thr Ile Pro Val Glu Ile His Thr Ala Thr
                3925                3930                3935

Val Ile Phe Val Ser Phe Gln Leu Ser Val Ala Thr Glu Asp Asp Phe
        3940                3945                3950

Tyr Thr Ser His Asn Leu Val Lys Asn Leu Ala Leu Phe Leu Lys Ile
        3955                3960                3965

Pro Ser Asp Lys Ile Arg Ile Ser Lys Ile Arg Gly Lys Ser Leu Arg
        3970                3975                3980

Arg Lys Arg Ser Met Gly Phe Ile Ile Glu Ile Glu Ile Gly Asp Pro
3985                3990                3995                4000

Pro Ile Gln Phe Ile Ser Asn Gly Thr Thr Gly Gln Met Gln Leu Ser
                4005                4010                4015

Glu Leu Gln Glu Ile Ala Gly Ser Leu Gly Gln Ala Val Ile Leu Gly
        4020                4025                4030

Asn Ile Ser Ser Ile Leu Gly Phe Asn Ile Ser Ser Met Ser Ile Thr
        4035                4040                4045

Asn Pro Leu Pro Ser Pro Ser Asp Ser Gly Trp Ile Lys Val Thr Ala
        4050                4055                4060

Gln Pro Val Glu Arg Ser Ala Phe Pro Val His His Val Ala Phe Val
4065                4070                4075                4080

Ser Ser Leu Leu Val Ile Thr Gln Pro Val Ala Ala Gln Pro Gly Gln
                4085                4090                4095

Pro Phe Pro Gln Gln Pro Ser Val Lys Ala Thr Asp Ser Asp Gly Asn
        4100                4105                4110

Cys Val Ser Val Gly Ile Thr Ala Leu Thr Leu Arg Ala Ile Leu Lys
        4115                4120                4125

Asp Ser Asn Asn Asn Gln Val Asn Gly Leu Ser Gly Asn Thr Thr Ile
        4130                4135                4140

Pro Phe Ser Ser Cys Trp Ala Asn Tyr Thr Asp Leu Thr Pro Leu Arg
4145                4150                4155                4160

Thr Gly Lys Asn Tyr Lys Ile Glu Phe Ile Leu Asp Asn Val Val Gly
                4165                4170                4175

Val Glu Ser Arg Thr Phe Ser Leu Leu Ala Glu Ser Val Ser Ser Ser
        4180                4185                4190
```

-continued

```
Gly Ser Ser Ser Ser Ser Asn Ser Lys Ala Ser Thr Val Gly Thr Tyr
        4195                4200                4205

Ala Gln Ile Met Thr Val Val Ile Ser Cys Leu Val Gly Arg Met Trp
    4210                4215                4220

Leu Leu Glu Ile Phe Met Ala Ala Val Ser Thr Leu Asn Ile Thr Leu
4225                4230                4235                4240

Arg Ser Tyr

<210> SEQ ID NO 114
<211> LENGTH: 5
<212> TYPE: PRT
<213> ORGANISM: Artificial Sequence
<220> FEATURE:
<223> OTHER INFORMATION: peptide linker

<400> SEQUENCE: 114

Gly Gly Gly Gly Ser
1               5
```

FUSION POLYPEPTIDE COMPRISING POLYPEPTIDE REGION THAT CAN BE O-GLYCOSYLATED

CROSS-REFERENCE TO RELATED APPLICATION

This application is a 35 U.S.C. 371 National Phase Entry Application from PCT/KR2019/011409, filed on Sep. 4, 2019 and, designating the United States, which claims the benefit of Korean Patent Application No. 10-2018-0105741 filed on September 5, with the Korean Intellectual Property Office, the disclosures of which are herein incorporated by reference in their entirety.

The present application includes a Sequence Listing filed in electronic format. The Sequence Listing is entitled "US17_273591_SEQ_revised_20240903.txt" created on Sep. 20, 2024 and is 492,514 bytes in size. The information in the electronic format of the Sequence Listing is part of the present application and is incorporated herein by reference in its entirety.

TECHNICAL FIELD

The present disclosure relates to a fusion polypeptide including a target polypeptide and an O-glycosylatable polypeptide region, a pharmaceutical composition containing the fusion polypeptide; and a method for increasing the in vivo sustained period of a target polypeptide, including a step of fusing an O-glycosylatable polypeptide region.

BACKGROUND OF THE INVENTION

Most protein or peptide drugs shorten the period of maintaining the in vivo activity, and has a low absorption rate when administered by methods other than intravenous administration. When long-term drug treatment is required, there is an inconvenience that these drugs must be repeatedly and continuously injected at short dosage intervals. In order to eliminate such inconvenience, there is a need to develop a technique that continuously releases the drug in a single administration. In an attempt to meet these needs, sustained-release formulations for continuous release are being developed.

For example, research on sustained-release dosage forms is being actively conducted in which fine particles in the form of enclosing a protein or peptide drug with a biodegradable polymer matrix are prepared, and the drug is gradually released at the time of administration while the matrix substance is gradually decomposed and removed in the body.

For example, U.S. Pat. No. 5,416,017 discloses a sustained-release injection of erythropoietin using a gel with a hyaluronic acid concentration of 0.01 to 3%, Japanese Unexamined Patent Publication No. (Hei) 1-287041 discloses a sustained-release injection containing insulin in a gel with a hyaluronic acid concentration of 1%, and Japanese Unexamined Patent Publication No. (Hei) 2-213 discloses a sustained-release formulation containing calcitonin, elkatonin, or a human target polypeptide in 5% concentration of hyaluronic acid. In such a formulation, the protein drug dissolved in the hyaluronic acid gel passes at a low speed through the gel matrix having a high viscosity, and thus can exhibit a sustained release effect. However, there is a disadvantage that it is not easy to administer the drug by injection due to the high viscosity, the gel is easily diluted or decomposed by body fluids after injection, so that it is difficult to sustainably release the drug longer than a day.

Meanwhile, there are examples in which solid microparticles are prepared by an emulsion solvent extraction method using a hyaluronic acid derivative (e.g., hyaluronic acid-benzyl ester) having hydrophobicity (N. S. Nightlinger, et al., Proceed. Intern. Symp. Control. Rel. Bioact. Mater., 22nd, Paper No. 3205 (1995); L. Ilum, et al., J. Controlled Rel., 29, 133(1994)). When the drug release formulation particles are produced using a hydrophobic hyaluronic acid derivative, an organic solvent must be used, and thus, the protein drug may come into contact with the organic solvent to be denatured, and there is a high possibility of denaturing proteins due to the hydrophobicity of the hyaluronic acid derivative.

Therefore, in order to improve the in vivo sustained period of protein or peptide drugs, approach to aspects different from existing studies is required.

DETAILED DESCRIPTION OF THE INVENTION

Provided herein is a technique in which an O-glycosylatable polypeptide (e.g., a hinge region of immunoglobulin, or the like) is linked to a target polypeptide to form a fusion polypeptide, thereby increasing the in vivo half-life of a target polypeptide and thus enhancing the in vivo sustained period, and increasing the dosage interval, as compared with the case that is not fused with an O-glycosylatable polypeptide region.

One example provides a fusion polypeptide comprising a target polypeptide and an 0-glycosylatable polypeptide region.

In the fusion polypeptide, the O-glycosylatable polypeptide region may be included at the N-terminus, C-terminus, or both the N- and C-termini of the target polypeptide.

The total number of O-glycosylatable polypeptide regions contained in the fusion polypeptide may be 1 or more, for example, 1 to 10, 1 to 8, 1 to 6, 1 to 4, 2 to 10, 2 to 8, 2 to 6, 2 to 4 (e.g., 1, 2, 3, 4, 5, 6, 7, 8, 9 or 10).

In one embodiment, the fusion polypeptide may be represented by the following general formula:

$$N'—(Z)n\text{-}Y—(Z)m—C' \qquad \text{[General Formula]}$$

in the above formula,

N' is the N-terminus of the fusion polypeptide, C' is the C-terminus of the fusion polypeptide, Y is the target polypeptide, Z is an O-glycosylatable polypeptide region, n is the number of O-glycosylatable polypeptide regions (bound to the N-terminus of the target polypeptide) located at the N-terminus of the fusion polypeptide, and is an integer of 0 to 10 (i.e., 0, 1, 2, 3, 4, 5, 6, 7, 8, 9, 10), 0 to 7, 0 to 5, 1 to 10, 1 to 7, 1 to 5, or 1 to 3, m is the number of O-glycosylatable polypeptide regions (bound to the C-terminus of the target polypeptide) located at the C-terminus of the fusion polypeptide, and is an integer of 0 to 10 (i.e., 0, 1, 2, 3, 4, 5, 6, 7, 8, 9, 10), 0 to 7, 0 to 5, 1 to 10, 1 to 7, 1 to 5, or 1 to 3, at least one of n and m is not zero, and n+m is the total number of O-glycosylatable polypeptide regions contained in the fusion polypeptide, and is an integer of 1 to 10, 1 to 8, 1 to 6, 1 to 4, 2 to 10, 2 to 8, 2 to 6, or 2 to 4.

The n+m O-glycosylatable polypeptide regions contained in the fusion polypeptide may each independently be selected from polypeptide moieties including O-glycosylatable amino acid residues. For example, the polypeptide moiety comprising O-glycosylatable amino acid residues may be a hinge region of immunoglobulin. In one embodiment, the O-glycosylatable polypeptide region may each independently be selected from a group consisting of a hinge region of immunoglobulin D (IgD) and a hinge region of immunoglobulin A (IgA, such as IgA1) (That is, the hinge regions of n+m immunoglobulins may be the same or different from each other).

In the fusion polypeptide, the stability (sustained period) in the body (or blood) of the target polypeptide fused with an O-glycosylatable polypeptide region is increased as compared with a target polypeptide not fused with an O-glycosylatable polypeptide region (for example, increase of the half-life in the body or blood).

Another embodiment provides a nucleic acid molecule encoding the fusion polypeptide.

Another embodiment provides a recombinant vector comprising the nucleic acid molecule.

Another embodiment provides a recombinant cell comprising the recombinant vector.

Another embodiment provides a method for producing a target polypeptide having an increased half-life in the body (or blood), comprising the step of expressing the recombinant vector in cells, or a method for producing a fusion polypeptide containing the target polypeptide having an increased half-life in the body (or blood).

Another embodiment provides a method of increasing the in vivo sustained period of a target polypeptide including the step of fusing (or linking or binding) a target polypeptide with an O-glycosylatable polypeptide region, or a method of increasing the in vivo (or blood) stability and/or increasing the in vivo (or blood) half-life of the target polypeptide (protein or peptide) drug. In one embodiment, the fusing step may include a step of fusing (or linking or binding) one or more O-glycosylatable polypeptide regions to the N-terminus, C-terminus, or both the N- and C-termini of the target polypeptide via a linker or without through the linker. The fusing (or linking or binding) step may be performed in vitro.

Another embodiment provides a pharmaceutical composition comprising at least one selected from the group consisting of the fusion polypeptide, a nucleic acid molecule encoding the fusion polypeptide, a recombinant vector containing the nucleic acid molecule, and a recombinant cell containing the recombinant vector.

Another embodiment provides a method for producing a pharmaceutical composition using at least one selected from the group consisting of the fusion polypeptide, a nucleic acid molecule encoding the fusion polypeptide, a recombinant vector containing the nucleic acid molecule, and a recombinant cell containing the recombinant vector.

Another embodiment provides an application thereof for use in the manufacture of a pharmaceutical composition comprising at least one selected from the group consisting of the fusion polypeptide, a nucleic acid molecule encoding the fusion polypeptide, a recombinant vector containing the nucleic acid molecule, and a recombinant cell containing the recombinant vector.

Another embodiment provides a use of the O-glycosylatable polypeptide region for promoting the in vivo (or blood) stability and/or increasing the in vivo (or blood) half-life of the target polypeptide (protein or peptide) drug. Specifically, one embodiment provides a composition for enhancing the in vivo (or blood) stability and/or increasing the vivo (or blood) half-life of the target polypeptide (protein or peptide) drug comprising an O-glycosylatable polypeptide region.

The present disclosure provides the form of a fusion polypeptide in which an O-glycosylatable polypeptide region, such as an immunoglobulin hinge region, is fused to a target polypeptide, and thereby, provides a technique capable of enhancing the stability in the body (or blood) and/or the sustained period in the body (or blood) and increasing the dosage interval, when the target polypeptide is applied in vivo.

One embodiment provides a fusion polypeptide comprising a target polypeptide and an O-glycosylatable polypeptide region.

In the fusion polypeptide, the O-glycosylatable polypeptide region may be included at the N-terminus, C-terminus, or both the N- and C-termini of the target polypeptide.

The total number of O-glycosylatable polypeptide regions contained in the fusion polypeptide may be 1 or more, for example, 1 to 10, 1 to 8, 1 to 6, 1 to 4, 2 to 10, 2 to 8, 2 to 6, 2 to 4 (e.g., 1, 2, 3, 4, 5, 6, 7, 8, 9 or 10).

In one embodiment, the fusion polypeptide may be represented by the following general formula:

$$N'\text{—}(Z)n\text{-}Y\text{—}(Z)m\text{-}C' \qquad \text{[General Formula]}$$

in the above formula,

N' is the N-terminus of the fusion polypeptide, C' is the C-terminus of the fusion polypeptide, Y is the target polypeptide, Z is an O-glycosylatable polypeptide region, n is the number of O-glycosylatable polypeptide regions (bound to the N-terminus of the target polypeptide) located at the N-terminus of the fusion polypeptide, and is an integer of 0 to 10 (i.e., 0, 1, 2, 3, 4, 5, 6, 7, 8, 9, 10), 0 to 7, 0 to 5, 1 to 10, 1 to 7, 1 to 5, or 1 to 3, m is the number of O-glycosylatable polypeptide regions (bound to the C-terminus of the target polypeptide) located at the C-terminus of the fusion polypeptide, and is an integer of 0 to 10 (i.e., 0, 1, 2, 3, 4, 5, 6, 7, 8, 9, 10), 0 to 7, 0 to 5, 1 to 10, 1 to 7, 1 to 5, or 1 to 3, at least one of n and m is not zero (for example, if n is 0, m is not 0, and if m is 0, n is not 0), and n+m is the total number of O-glycosylatable polypeptide regions contained in the fusion polypeptide, and is an integer of 1 to 10, 1 to 8, 1 to 6, 1 to 4, 2 to 10, 2 to 8, 2 to 6, or 2 to 4.

In one embodiment, when the active site of the target polypeptide is located at the N-terminus, the O-glycosylatable polypeptide region may be fused to the C-terminus (i.e., n is 0, and m is not 0), and when the active site is located at the C-terminus, the O-glycosylatable polypeptide region can be fused to the N-terminus (i.e., n is not 0, and m is 0).

The n+m O-glycosylatable polypeptide regions contained in the fusion polypeptide may each independently be selected from polypeptides containing O-glycosylatable amino acid residues. For example, the polypeptide moiety containing O-glycosylatable amino acid residues may be a hinge region of immunoglobulin. In one embodiment, the O-glycosylatable polypeptide region may each independently be selected from a group consisting of a hinge region of immunoglobulin D (IgD) and a hinge region of immunoglobulin A (IgA, such as IgA1). The hinge regions of n+m immunoglobulins may be the same or different from each other.

In one embodiment, when the n+m O-glycosylatable polypeptide regions contained in the fusion polypeptide are located at both the N-terminus and C-terminus of the fusion polypeptide (that is, when one or more O-glycosylatable polypeptide regions each independently exist at the N-terminus and C-terminus of the fusion polypeptide), the type and number of the O-glycosylatable polypeptide region located at the N-terminus and the 0-glycosylatable polypeptide region located at the C-terminus may be the same or different from each other. In one embodiment, one or more (e.g., 1, 2, 3, 4, 5, 6, 7, 8, 9, or 10) 0-glycosylatable polypeptide regions located at the N-terminus all are hinge regions of IgD or hinge regions of IgA (e.g., IgA1), or one or more (e.g., 1, 2, 3, 4, 5, 6, 7, 8, 9, or 10) hinge regions of IgD and one or more (e.g., 1, 2, 3, 4, 5, 6, 7, 8, 9, or 10) hinge regions of IgA (e.g., IgA1) may be included in various orders. The one or more hinge regions of immunoglobulins located at the C-terminus all are hinge regions of IgD or hinge regions of IgA (e.g., IgA1), or one or more hinge regions of IgD and one or more hinge regions of IgA (e.g., IgA1) may be included in various orders.

In another embodiment, when all the n+m O-glycosylatable polypeptide regions contained in the fusion polypeptide are located only at the N-terminus of the fusion polypeptide (i.e., when one or more O-glycosylatable polypeptide regions exist only at the N-terminus of the fusion polypeptide), the one or more (e.g., 1, 2, 3, 4, 5, 6, 7, 8, 9, or 10) O-glycosylatable polypeptide regions all are hinge regions of IgD or hinge regions of IgA, or one or more (e.g., 1, 2, 3, 4, 5, 6, 7, 8, 9, or 10) hinge regions of IgD and one or more (e.g., 1, 2, 3, 4, 5, 6, 7, 8, 9, or 10) hinge regions of IgA may be included in various orders.

In another embodiment, when all the n+m O-glycosylatable polypeptide regions contained in the fusion polypeptide are located only at the C-terminus (i.e., when one or more O-glycosylatable polypeptide regions exist only at the C-terminus of the fusion polypeptide), the one or more (e.g., 1, 2, 3, 4, 5, 6, 7, 8, 9, or 10) O-glycosylatable polypeptide regions all are hinge regions of IgD or hinge regions of IgA (e.g., IgA1), or one or more (e.g., 1, 2, 3, 4, 5, 6, 7, 8, 9, or 10) hinge regions of IgD and one or more (e.g., 1, 2, 3, 4, 5, 6, 7, 8, 9, or 10) hinge regions of IgA (e.g., IgA1) may be included in various orders.

The O-glycosylatable polypeptide region (each region when there are two or more 0-glycosylatable polypeptide regions) may include 1 or more, 2 or more, 3 or more, 4 or more, 5 or more, 6 or more, or 7 or more (the upper limit is 100, 50, 25, 20, 19, 18, 17, 16, 15, 14, 13, 12, 11, 10, 9, or 8) (e.g., 1, 2, 3, 4, 5, 6, 7, or 8) O-glycosylatable polypeptide residues (0-glycosylatable amino acid residues). For example, the O-glycosylatable polypeptide region (each region when there are two or more O-glycosylatable polypeptide regions) may include 1 to 10 or 3 to 10 O-glycosylated residues (O-glycosylatable amino acid residues).

In one embodiment, the O-glycosylatable polypeptide region may be selected from one or more hinge regions of immunoglobulins (e.g., human immunoglobulins), and for example, it may be an IgD hinge region, an IgA hinge region, or a combination thereof.

The IgD may be human IgD (e.g., UniProKB P01880 (constant region; SEQ ID NO: 7), etc.), and the hinge region of IgD may be at least one selected from the group consisting of:
  a polypeptide ("IgD hinge") comprising an amino acid sequence of "N'-ESPKAQASSVPTAQPQAE-GSLAKATTAPATTRNT-C' (SEQ ID NO: 1); the amino acid residues shown in bold are O-glycosylated residues (7 in total)", or consisting essentially of the amino acid sequence,
  a polypeptide comprising 5 or more, 7 or more, 10 or more, 15 or more, 20 or more, 22 or more, or 24 or more (the upper limit is 34 or 33) consecutive amino acids containing 1 or more, 2 or more, 3 or more, 4 or more, 5 or more, 6 or more, or 7 O-glycosylated residues in the amino acid sequences of SEQ ID NO: 1, or consisting essentially of the amino acids ("a part of IgD hinge"; for example, a polypeptide comprising 5 or more consecutive amino acids containing "SSVPT" (SEQ ID NO: 9) in SEQ ID NO: 1 or a polypeptide comprising 7 or more consecutive amino acids containing "TTAPATT" (SEQ ID NO: 10)), and
  a polypeptide comprising 34 or more or 35 or more consecutive amino acids containing an amino acid sequence of SEQ ID NO: 1 (IgD hinge) in IgD (e.g., SEQ ID NO: 7), or 7 or more, 10 or more, 15 or more, 20 or more, 22 or more, or 24 or more consecutive amino acids containing a part of the IgD hinge, or consisting essentially of the amino acids ("extension of IgD hinge"; for example, SEQ ID NO: 1 in "ESPKAQASS VPTAQPQAEG SLAKATTAPA TTRNTGRGGE EKKKEKEKEE QEERETKTP" (SEQ ID NO: 11) among IgD (SEQ ID NO: 7) or comprising 34 or more or 35 or more consecutive amino acids containing a part of the IgD hinge.

The IgA may be human IgA (e.g., IgA1 (UniProKB P01876, constant region; SEQ ID NO: 8), etc.), and the hinge region of the IgA may be at least one selected from the group consisting of:
  a polypeptide ("IgA hinge") comprising an amino acid sequence of "N'-VPSTPPTPSPSTPPTPSPS-C' (SEQ ID NO: 2); the amino acid residues shown in bold are O-glycosylated residues (8 in total)", or consisting essentially of the amino acid sequence,
  a polypeptide comprising 5 or more, 6 or more, 7 or more, 8 or more, 9 or more, 10 or more, 12 or more, 15 or more, 17 or more, or 18 consecutive amino acids containing 1 or more, 2 or more, 3 or more, 4 or more, 5 or more, 6 or more, 7 or more, or 8 O-glycosylated residues in the amino acid sequence of SEQ ID NO: 2, or consisting essentially of the amino acids ("a part of IgA hinge"; for example, a polypeptide comprising 8 or more or 9 or more consecutive amino acids containing "STPPTPSP" (SEQ ID NO: 12) in SEQ ID NO: 2, and
  a polypeptide ("extension of IgA hinge") comprising 19 or more or 20 or more consecutive amino acids containing the amino acid sequence of SEQ ID NO: 2 in IgA (e.g., IgA1) hinge) in IgA (e.g., IgA1 (SEQ ID NO: 8)), or 7 or more, 10 or more, 12 or more, 15 or more, 17 or more, or 18 consecutive amino acids containing a part of IgA (e.g., IgA1) hinge, or consisting essentially of the amino acid sequence.

In another embodiment, the O-glycosylatable polypeptide region may be a polypeptide region comprising 5 or more, 7 or more, 10 or more, 12 or more, 15 or more, 17 or more, 20 or more, 22 or more, 25 or more, 27 or more, 30 or more, 32 or more or 35 or more consecutive amino acids (the upper limit is 40, 50, 60, 70, 80, 90, 100, 150, 200, 250, 300, or the total number of amino acids in each protein) containing 1 or more, 2 or more, 5 or more, 7 or more, 10 or more, 12 or more, 15 or more, 17 or more, 20 or more, or 22 or more (e.g., 1 to 10, 3 to 10; or 1, 2, 3, 4, 5, 6, 7, 8, 9, 10, 11, 12, 13, 14, 15, 16, 17, 18, 15, 16, 17, 18, 19, 20, 21, 22, 23, 24 or 25) M-glycosylatable amino acid residues (3-glycosylation site) in the proteins exemplified in Table 1 below (for example, a protein comprising an amino acid sequence selected from the group consisting of SEQ ID NOs: 23 to 113), or consisting essentially of the amino acid sequences. It is preferable that the O-glycosylatable polypeptide region as used herein does not affect the function of the target polypeptide. The O-glycosylatable polypeptide region of the proteins exemplified in Table 1 below may be selected from regions that are not involved in the intrinsic function of the full-length protein. This allows the O-glycosylatable polypeptide region to serve only to increase the half-life without affecting the function of the target polypeptide:

TABLE 1

| UniProtKB Entry No. | UniProtKB Entry name | Protein names | Gene names | Length | O-Glycosylation (site) | SEQ ID NO |
|---|---|---|---|---|---|---|
| Q96DR8 | MUCL1_HUMAN | Mucin-like protein 1 | MUCL1 SBEM UNQ590/ PRO1160 | 90 | 23T, 24T, 30T, 34T, 46T, 47T, 51T, 52T, 54T, 55T, 59T, 60T, 62T, 63T, 66S, 67T, 68T | 23 |
| Q0VAQ4 | SMAGP_HUMAN | Small cell adhesion glycoprotein | SMAGP | 97 | 2T, 3S, 6T, 7T, 9S, 16T, 17T, 23T | 24 |
| P04921 | GLPC_HUMAN | Glycophorin-C | GYPC GLPC GPC | 128 | 3S, 4T, 6S, 9S, 10T, 15S, 24S, 26S, 27T, 28T, 31T, 32T, 33T, 42S | 25 |
| P16860 | ANFB_HUMAN | Natriuretic peptides B | NPPB | 134 | 62T, 63S, 70S, 74T, 79S, 84T, 97T | 26 |
| P04141 | CSF2_HUMAN | Granulocyte-macrophage colony-stimulating factor | CSF2 GMCSF | 144 | 22S, 24S, 26S, 27T | 27 |
| P02724 | GLPA_HUMAN | Glycophorin-A | GYPA GPA | 150 | 21S, 22T, 23T, 29T, 30S, 31T, 32S, 36T, 38S, 41S, 44T, 52T, 56T, 63S, 66S, 69T | 28 |
| P10124 | SRGN_HUMAN | Serglycin | SRGN PRG PRG1 | 158 | 94S, 96S, 100S, 102S, 104S, 106S, 108S, 110S | 29 |
| Q86YL7 | PDPN_HUMAN | Podoplanin | PDPN GP36 PSEC0003 PSEC0025 | 162 | 25T, 32T, 34T, 35T, 52T, 55T, 65T, 66T, 76T, 85T, 86S, 88S, 89T, 96S, 98S, 100T, 102S, 106T, 107S, 109S, 110T, 117T, 119T, 120T | 30 |
| P0DN87 | CGB7_HUMAN | Choriogonadotropin subunit beta 7 | CGB7 | 165 | 139S, 141S, 147S, 150S, 152S, 158S | 31 |
| P0DN86 | CGB3_HUMAN | Choriogonadotropin subunit beta 3 | CGB3 CGB; CGB5; CGB8 | 165 | 139S, 141S, 147S, 150S, 152S, 158S | 32 |
| P01344 | IGF2_HUMAN | Insulin-like growth factor II | IGF2 PP1446 | 180 | 96T, 99T, 163T | 33 |
| P07498 | CASK_HUMAN | Kappa-casein | CSN3 CASK CSN10 CSNK | 182 | 133T, 143T, 148T, 151T, 157T, 167T, 169T, 178T | 34 |
| P31431 | SDC4_HUMAN | Syndecan-4 | SDC4 | 198 | 39S, 61S, 63S | 35 |
| P34741 | SDC2_HUMAN | Syndecan-2 | SDC2 HSPG1 | 201 | 41S, 55S, 57S, 101T | 36 |
| Q99075 | HBEGF_HUMAN | Proheparin-binding EGF-like growth factor | HBEGF DTR DTS HEGFL | 208 | 37T, 38S, 44T, 47T, 75T, 85T | 37 |
| P13727 | PRG2_HUMAN | Bone marrow proteoglycan (BMPG) | PRG2 MBP | 222 | 23T, 24S, 25T, 34T, 62S | 38 |
| P24592 | IBP6_HUMAN | Insulin-like growth factor-binding protein 6 (IBP-6) | IGFBP6 IBP6 | 240 | 126T, 144S, 145T, 146T, 152S | 39 |
| Q9UHG2 | PCSK1_HUMAN | ProSAAS (Proprotein convertase subtilisin/kexin type 1 inhibitor) | PCSK1N | 260 | 53T, 228S, 247T | 40 |
| P01589 | IL2RA_HUMAN | Interleukin-2 receptor subunit alpha (IL-2 receptor subunit alpha) | IL2RA | 272 | 218T, 224T, 229T, 237T | 41 |
| P21583 | SCF_HUMAN | Kit ligand (Mast cell growth factor) (MGF) | KITLG MGF SCF | 273 | 167S, 168T, 180T | 42 |
| A1E959 | ODAM_HUMAN | Odontogenic ameloblast-associated protein (Apin) | ODAM APIN | 279 | 115T, 119T, 244T, 249S, 250T, 251T, 255T, 256S, 261T, 263T, 273T, 275S | 43 |
| P10451 | OSTP_HUMAN | Osteopontin | SPP1 BNSP OPN PSEC0156 | 314 | 134T, 138T, 143T, 147T, 152T | 44 |

TABLE 1-continued

| UniProtKB Entry No. | UniProtKB Entry name | Protein names | Gene names | Length | O-Glycosylation (site) | SEQ ID NO |
|---|---|---|---|---|---|---|
| P21815 | SIAL_HUMAN | Bone sialoprotein 2 (Bone sialoprotein II) (BSP II) | IBSP BNSP | 317 | 119T, 122T, 227T, 228T, 229T, 238T, 239T | 45 |
| P02649 | APOE_HUMAN | Apolipoprotein E (Apo-E) | APOE | 317 | 26T, 36T, 212T, 307T, 308S, 314S | 46 |
| Q99645 | EPYC_HUMAN | Epiphycan (Dermatan sulfate proteoglycan 3) | EPYC DSPG3 PGLB SLRR3B | 322 | 60T, 64S, 96S | 47 |
| Q6UXG3 | CLM9_HUMAN | CMRF35-like molecule 9 (CLM-9) | CD300L G CLM9 TREM4 UNQ422/ PRO846 | 332 | 137T, 143T, 144T, 155T, 161T, 170T, 171T, 177T, 187T, 195T, 196S, 199T, 201T, 202S, 207T, 208S, 213S, 214S, 222S, 223T, 224S, 228T, 229S, 237S | 48 |
| Q9GZM5 | YIPF3_HUMAN | Protein YIPF3 (Killer lineage protein 1) | YIPF3 C6orf109 KLIP1 | 350 | 333T, 334T, 339T, 346T | 49 |
| P51681 | CCR5_HUMAN | C-C chemokine receptor type 5 (C-C CKR-5) | CCR5 CMKBR5 | 352 | 6S, 7S, 16T, 17S | 50 |
| P40225 | TPO_HUMAN | Thrombopoietin (C-mpl ligand) (ML) | THPO MGDF | 353 | 22S, 58T, 131T, 179T, 180T, 184S, 213T, 265S | 51 |
| P01876 | IGHA1_HUMAN | Immunoglobulin heavy constant alpha 1 (Ig alpha-1 chain C region) | IGHA1 | 353 | 105S, 106T, 109T, 111S, 113S, 117T, 119S, 121S | 8 |
| P02765 | FETUA_HUMAN | Alpha-2-HS-glycoprotein (Alpha-2-Z-globulin) | AHSG FETUA PRO2743 | 367 | 270T, 280S, 293S, 339T, 341T, 346S | 52 |
| P21810 | PGS1_HUMAN | Biglycan | BGN SLRR1A | 368 | 42S, 47S, 180S, 198S | 53 |
| P01860 | IGHG3_HUMAN | Immunoglobulin heavy constant gamma 3 (HDC) | IGHG3 | 377 | 122T, 137T, 152T | 54 |
| P80370 | DLK1_HUMAN | Protein delta homolog 1 (DLK-1) | DLK1 DLK | 383 | 94S, 143T, 163S, 214S, 222T 251S 256T, 260S | 55 |
| P01880 | IGHD_HUMAN | Immunoglobulin heavy constant delta (Ig delta chain C region) | IGHD | 384 | 109S, 110S, 113T, 126T, 127T, 131T, 132T | 7 |
| P15529 | MCP_HUMAN | Membrane cofactor protein (TLX) | CD46 MCP MIC10 | 392 | 290S, 291S, 292T, 298S, 300S, 302S, 303T, 304S, 305S, 306T, 307T, 309S, 312S, 313S, 315S, 320T, 326S | 56 |
| P04280 | PRP1_HUMAN | Basic salivary proline-rich protein 1 | PRB1 | 392 | 40S, 87S, 150S, 330S | 57 |
| P78423 | X3CL1_HUMAN | Fractalkine (C-X3-C motif chemokine 1) | CX3CL1 FKN NTT SCYD1 A-152E5.2 | 397 | 183T, 253S, 329T | 58 |
| P16150 | LEUK_HUMAN | Leukosialin (GPL115) | SPN CD43 | 400 | 21T, 22T, 26T, 28T, 29S, 35S, 36T, 37S, 41S, 42S, 46T, 47T, 48S, 50T, 58T, 69T, 99S, 103S, 109T, 113T, 114S, 136T, 137T, 173T, 178T | 59 |
| P13473 | LAMP2_HUMAN | Lysosome-associated membrane glycoprotein 2 (LAMP-2) | LAMP2 | 410 | 195S, 196T, 200T, 203T, 204T, 207S, 209T, 210T, 211T, 213T | 60 |
| P11279 | LAMP1_HUMAN | Lysosome-associated membrane glycoprotein 1 (LAMP-1) | LAMP1 | 417 | 197S, 199T, 200T, 207S, 209S, 211S, | 61 |

TABLE 1-continued

| UniProtKB Entry No. | UniProtKB Entry name | Protein names | Gene names | Length | O-Glycosylation (site) | SEQ ID NO |
|---|---|---|---|---|---|---|
| P21754 | ZP3_HUMAN | Zona pellucida sperm-binding protein 3 (Sperm receptor) | ZP3 ZP3A ZP3B ZPC | 424 | 156T, 162T, 163T | 62 |
| P05783 | K1C18_HUMAN | Keratin, type I cytoskeletal 18 | KRT18 CYK18 PIG46 | 430 | 30S, 31S, 49S | 63 |
| Q08629 | TICN1_HUMAN | Testican-1 (Protein SPOCK) | SPOCK1 SPOCK TIC1 TICN1 | 439 | 228T, 383S, 388S | 64 |
| O75056 | SDC3_HUMAN | Syndecan-3 (SYND3) | SDC3 KIAA0468 | 442 | 80S, 82S, 84S, 91S, 314S, 367S | 65 |
| P10645 | CMGA_HUMAN | Chromogranin-A (CgA) | CHGA | 457 | 181T, 183T, 251T | 66 |
| P15169 | CBPN_HUMAN | Carboxypeptidase N catalytic chain (CPN) | CPN1 ACBP | 458 | 400T, 402T, 409T | 67 |
| P00740 | FA9_HUMAN | Coagulation factor IX (EC 3.4.21.22) | F9 | 461 | 85T, 99S, 107S | 68 |
| P20333 | TNR1B_HUMAN | Tumor necrosis factor receptor superfamily member 1B | TNFRSF1B TNFBR TNFR2 | 461 | 30T, 206T, 221S, 222T, 224S, 230T, 234S, 235T, 239T, 240S, 248S | 69 |
| P08670 | VIME_HUMAN | Vimentin | VIM | 466 | 7S, 33T, 34S | 70 |
| Q8WXD2 | SCG3_HUMAN | Secretogranin-3 (Secretogranin III) (SgIII) | SCG3 UNQ2502/ PRO5990 | 468 | 216T, 231T, 359S | 71 |
| Q16566 | KCC4_HUMAN | Calcium/calmodulin-dependent protein kinase type IV (CaMK IV) (EC 2.7.11.17) | CAMK4 CAMK CAMK-GR CAMKIV | 473 | 57T, 58S, 137S, 189S, 344S, 345S, 356S | 72 |
| P31749 | AKT1_HUMAN | RAC-alpha serine/threonine-protein kinase (EC 2.7.11.1) | AKT1 PKB RAC | 480 | 126S, 129S, 305T, 312T, 473S | 73 |
| P31751 | AKT2_HUMAN | RAC-beta serine/threonine-protein kinase (EC 2.7.11.1) | AKT2 | 481 | 128S, 131S, 306T, 313T | 74 |
| O60883 | G37L1_HUMAN | G-protein coupled receptor 37-like 1 | GPR37L1 ETBRLP2 | 481 | 79T, 85T, 86S, 95T, 107T | 75 |
| Q9BXF9 | TEKT3_HUMAN | Tektin-3 | TEKT3 | 490 | 7T, 9T, 10T | 76 |
| P05155 | IC1_HUMAN | Plasma protease C1 inhibitor (C1 Inh) | SERPING1 C1IN C1NH | 500 | 47T, 48T, 64S, 71T, 83T, 88T, 92T, 96T | 77 |
| P11831 | SRF_HUMAN | Serum response factor (SRF) | SRF | 508 | 277S, 307S, 309S, 316S, 383S | 78 |
| P0DOX3 | IGD_HUMAN | Immunoglobulin delta heavy chain | | 512 | 238S, 255T, 256T, 260T, 261T, | 79 |
| O75487 | GPC4_HUMAN | Glypican-4 (K-glypican) | GPC4 UNQ474/ PRO937 | 556 | 494S, 498S, 500S | 80 |
| P35052 | GPC1_HUMAN | Glypican-1 | GPC1 | 558 | 486S, 488S, 490S | 81 |
| P78333 | GPC5_HUMAN | Glypican-5 | GPC5 | 572 | 441S, 486S, 495S, 507S, 509S | 82 |
| Q8N158 | GPC2_HUMAN | Glypican-2 | GPC2 | 579 | 55S, 92S, 155S, 500S, 502S | 83 |
| P00748 | FA12_HUMAN | Coagulation factor XII (EC 3.4.21.38) | F12 | 615 | 109T, 299T, 305T, 308S, 328T, 329T, 337T | 84 |
| P01042 | KNG1_HUMAN | Kininogen-1 (Alpha-2-thiol proteinase inhibitor) | KNG1 BDK KNG | 644 | 401T, 533T, 542T, 546T, 557T, 571T, 577S, 628T | 85 |
| P51693 | APLP1_HUMAN | Amyloid-like protein 1 (APLP) (APLP-1) | APLP1 | 650 | 215T, 227S, 228T | 86 |
| Q9NQ79 | CRAC1_HUMAN | Cartilage acidic protein 1 (68 kDa chondrocyte-expressed protein) (CEP-68) (ASPIC) | CRTAC1 ASPIC1 CEP68 | 661 | 608T, 618T, 619T, 621T, 626T | 87 |
| Q14515 | SPRL1_HUMAN | SPARC-like protein 1 (High endothelial venule protein) (Hevin) (MAST 9) | SPARCL1 | 664 | 31T, 40T, 44S, 116T | 88 |

TABLE 1-continued

| UniProtKB Entry No. | UniProtKB Entry name | Protein names | Gene names | Length | O-Glycosylation (site) | SEQ ID NO |
|---|---|---|---|---|---|---|
| Q16820 | MEP1B_HUMAN | Meprin A subunit beta (EC 3.4.24.63) | MEP1B | 701 | 593S, 594T, 599T, 603S | 89 |
| P17600 | SYN1_HUMAN | Synapsin-1 (Brain protein 4.1) (Synapsin I) | SYN1 | 705 | 55S, 87T, 96S, 103S, 261S, 432S, 526T, 564T, 578S | 90 |
| P19835 | CEL_HUMAN | Bile salt-activated lipase (BAL) (EC 3.1.1.13) (EC 3.1.1.3) | CEL BAL | 753 | 558T, 569T, 579T, 607T, 618T, 629T, 640T, 651T, 662T, 673T | 91 |
| Q9HCU0 | CD248_HUMAN | Endosialin (Tumor endothelial marker 1) (CD antigen CD248) | CD248 CD164L1 TEM1 | 757 | 60T, 401T, 428T, 448T, 456T, 459T, 472T, 519T, 541T, 543T, 544T, 545T, 587T, 593T, 594T, 595T, 598S, 601S, 612T, 619T, 623S, 625S, 627T, 630T, 631S, 636T, 640S, 633T, 651T, 652T, 656S, 659T, 663T, 667S, | 92 |
| P05067 | A4_HUMAN | Amyloid-beta precursor protein (APP) | APP A4 AD1 | 770 | | 93 |
| Q9NR71 | ASAH2_HUMAN | Neutral ceramidase (N-CDase) (NCDase) (EC 3.5.1.—) (EC 3.5.1.23) | ASAH2 HNAC1 | 780 | 62T, 67S, 68T, 70T, 73S, 74T, 76T, 78S, 79S, 80T, 82T, 84T | 94 |
| P08047 | SP1_HUMAN | Transcription factor Sp1 | SP1 TSFP1 | 785 | 491S, 612S, 640T, 641S, 698S, 702S | 95 |
| Q17R60 | IMPG1_HUMAN | Interphotoreceptor matrix proteoglycan 1 | IMPG1 IPM150 SPACR | 797 | 403T, 421T, 432T, 442T | 96 |
| P19634 | SL9A1_HUMAN | Sodium/hydrogen exchanger 1 (APNH) | SLC9A1 APNH1 NHE1 | 815 | 42T, 56S, 61T, 62T, 68T | 97 |
| P12830 | CADH1_HUMAN | Cadherin-1 (CAM 120/80) | CDH1 CDHE UVO | 882 | 280S, 285T, 358T, 470T, 472T, 509T, 576T, 578T, 580T | 98 |
| Q14118 | DAG1_HUMAN | Dystroglycan (Dystrophin-associated glycoprotein 1) | DAG1 | 895 | 63T, 317T, 319T, 367T, 369T, 372T, 379T, 388T, 455T | 99 |
| Q14624 | ITIH4_HUMAN | Inter-alpha-trypsin inhibitor heavy chain H4 (ITI heavy chain H4) (ITI-HC4) | ITIH4 IHRP ITIHL1 PK120 PRO1851 | 930 | 719T, 720T, 722T | 100 |
| P19823 | ITIH2_HUMAN | Inter-alpha-trypsin inhibitor heavy chain H2 (ITI heavy chain H2) (ITI-HC2) | ITIH2 IGHEP2 | 946 | 666T, 673S, 675T, 691T | 101 |
| Q9UPV9 | TRAK1_HUMAN | Trafficking kinesin-binding protein 1 | TRAK1 KIAA1042 OIP106 | 953 | 447S, 680S, 719S, 935T | 102 |
| P15941 | MUC1_HUMAN | Mucin-1 (MUC-1) | MUC1 PUM | 1255 | 131T, 139T, 140S, 144T | 103 |
| Q7Z589 | EMSY_HUMAN | BRCA2-interacting transcriptional repressor EMSY | EMSY C11orf30 GL002 | 1322 | 228S, 236S, 271T, 501T, 506T, 557S, 1120T | 104 |
| Q92954 | PRG4_HUMAN | Proteoglycan 4 (Lubricin) | PRG4 MSF SZP | 1404 | 123S, 136S, 240T, 253T, 277T, 291T, 305T, 306S, 310T, 317S, 324T, 332T, 338T, 367T, 373S, 376T, 384T, 385T, 388S, 391T, 399T, 400T, 407T, 408T, 415T, 423T, 427S, 430T, 438T, 439T, 446T, 447T, 454T, 455T, 477T, 478T, 485T, 493T, 494T, 501T, 502T, 509T, 525T, 529S, 532T, 540T, 541T, 553S, 555T, 563T, 564T, 571T, 572T, 579T, | 105 |

TABLE 1-continued

| UniProtKB Entry No. | UniProtKB Entry name | Protein names | Gene names | Length | O-Glycosylation (site) | SEQ ID NO |
|---|---|---|---|---|---|---|
| | | | | | 580T, 587T, 588T, 595T, 603T, 604T, 611T, 612T, 616T, 619T, 627T, 676T, 683T, 684T, 691T, 692T, 699T, 700T, 704T, 707T, 723T, 724T, 736T, 768T, 769T, 776T, 777T, 792T, 793T, 805T, 812S, 829T, 837T, 838T, 892S, 900T, 930T, 931T, 962S, 963T, 968T, 975T, 978T, 979T, 980T, 1039T, 1161T | |
| Q76LX8 | ATS13_HUMAN | A disintegrin and metalloproteinase with thrombospondin motifs 13 (ADAM-TS 13) | ADAMTS13 C9orf8 UNQ6102/ PRO20085 | 1427 | 399S, 698S, 757S, 907S, 965S, 1027S, 1087S | 106 |
| P49790 | NU153_HUMAN | Nuclear pore complex protein Nup153 (153 kDa nucleoporin) (Nucleoporin Nup153) | NUP153 | 1475 | 534S, 544S, 908S, 909S, 1113S, 1156T | 107 |
| P31327 | CPSM_HUMAN | Carbamoyl-phosphate synthase [ammonia], mitochondrial (EC 6.3.4.16) | CPS1 | 1500 | 537S, 1331S, 1332T | 108 |
| Q8N6G6 | ATL1_HUMAN | ADAMTS-like protein 1 (ADAMTSL-1) (Punctin-1) | ADAMTSL1 ADAMTSR1 C9orf94 UNQ528/ PRO1071 | 1762 | 48T, 312T, 391S, 451T | 109 |
| P46531 | NOTC1_HUMAN | Neurogenic locus notch homolog protein 1 (Notch 1) (hN1) | NOTCH1 TAN1 | 2555 | 65S, 73T, 116T, 146S, 194T, 232T, 311T, 341S, 349T, 378S, 435S, 458S, 466T, 496S, 534S, 609S, 617T, 647S, 692T, 722S, 759S, 767T, 784S, 797S, 805T, 921S, 951S, 997T, 1027S, 1035T, 1065S, 1159T, 1189S, 1197T, 1273S, 1362T, 1379T, 1402T, | 110 |
| P04275 | VWF_HUMAN | von Willebrand factor (vWF) | VWF F8VWF | 2813 | 1248T, 1255T, 1256T, 1263S, 1468T, 1477T, 1486S, 1487T, | 111 |
| Q9UPA5 | BSN_HUMAN | Protein bassoon (Zinc finger protein 231) | BSN KIAA0434 ZNF231 | 3926 | 1343T, 1384T, 2314T, 2691T, 2936T | 112 |
| Q86WI1 | PKHL1_HUMAN | Fibrocystin-L (Polycystic kidney and hepatic disease 1-like protein 1) (PKHD1-like protein 1) | PKHD1L1 | 4243 | 122T, 445T, 1803T, 1839T, 2320T, 3736T | 113 |

In the fusion polypeptide, the total number of O-glycans actually contained may be 13 or more, 14 or more, 15 or more, 16 or more, 17 or more, 18 or more, 19 or more, 20 or more, or 21 or more (the maximum value is determined by the number of O-glycosylatable polypeptide regions described above and the number of O-glycosylated residues contained in respective O-glycosylatable polypeptide regions), or the total number of O-glycans contained theo-retically may be 20 or more, 21 or more, 23, or 24 or more (the maximum value is determined by the number of O-gly-cosylatable polypeptide regions described above and the number of O-glycosylated residues contained in respective O-glycosylatable polypeptide regions). Further, the total number of O-glycans actually contained in the fusion poly-peptide may be associated with the stability when adminis-tered in vivo (e.g., in blood). Specifically, as the total number of O-glycans actually contained in the fusion polypeptide increases, the in vivo stability of the fusion polypeptide or the target polypeptide contained in the fusion polypeptide may increase (that is, increased half-life in the body (in blood) and/or increased concentration in the body (blood) and/or decreased degradation rate in the body (in blood), etc.).

The fusion polypeptide may further comprise a peptide linker between the target polypeptide and the O-glycosylatable polypeptide region, and/or between O-glycosylatable polypeptide regions when the fusion polypeptide includes two or more O-glycosylatable polypeptide regions. In one embodiment, the peptide linker may be a GS linker that repeatedly contains one or more Gly (G) and one or more Ser (S), and for example, it may be (GGGGS) n (where n is an integer of 1 to 10 or 1 to 5 as the number of repetitions of GGGGS (SEQ ID NO: 13) (e.g., 1, 2, 3, 4, or 5)), without being limited thereto.

In the fusion polypeptide, the stability (sustained period) in the body (or blood) of the target polypeptide fused with an O-glycosylatable polypeptide region is increased as compared with a target polypeptide not fused with an O-glycosylatable polypeptide region (for example, increase of the half-life in the body or blood).

Another embodiment provides a nucleic acid molecule encoding the fusion polypeptide.

Another embodiment provides a recombinant vector comprising the nucleic acid molecule.

Another embodiment provides a recombinant cell comprising the recombinant vector.

Another embodiment provides a method for producing a target polypeptide having an increased half-life in the body (or blood), comprising the step of expressing the recombinant vector in cells, or a method for producing a fusion polypeptide containing the target polypeptide having an increased half-life in the body (or blood).

Another embodiment provides a method of increasing the in vivo sustained period of a target polypeptide including the step of fusing (or linking or binding) a target polypeptide with an O-glycosylatable polypeptide region. In one embodiment, the fusing step may include a step of fusing (or linking or binding) one or more O-glycosylated polypeptide regions to the N-terminus, C-terminus, or both the N- and C-termini of the target polypeptide via a linker or without through the linker. The fusing (or linking or binding) step may be performed in vitro.

Another embodiment provides a pharmaceutical composition comprising at least one selected from the group consisting of the fusion polypeptide, a nucleic acid molecule encoding the fusion polypeptide, a recombinant vector comprising the nucleic acid molecule, and a recombinant cell containing the recombinant vector.

Another embodiment provides an application thereof for use in the manufacture of a pharmaceutical composition containing at least one selected from the group consisting of the fusion polypeptide, a nucleic acid molecule encoding the fusion polypeptide, a recombinant vector containing the nucleic acid molecule, and a recombinant cell containing the recombinant vector.

Another embodiment provides the use of the O-glycosylatable polypeptide region for enhancing the in vivo (or blood) stability and/or increasing the in vivo (or blood) half-life of the target polypeptide (protein or peptide) drug. Specifically, one embodiment provides a composition for enhancing the in vivo (or blood) stability and/or increasing the in vivo (or blood) half-life of the polypeptide (protein or peptide) drug comprising an O-glycosylatable polypeptide region. As used herein, enhancing the stability and/or increasing the half-life means that the stability is improved and/or the half-life is increased as compared with a polypeptide (protein or peptide) that does not contain an O-glycosylatable polypeptide region.

Hereinafter, the present disclosure will be described in more detail: The target polypeptide (Y) may be at least one selected from all soluble proteins. In one embodiment, the target polypeptide is a protein and/or peptide having a desired in vivo activity (for example, preventive, alleviating, and/or therapeutic activity of a particular disease or condition, and/or activity as a marker, or activity of replacing substances necessary for living organisms) (for example, including about 100 or less or about 50 or less amino acids). For example, it may be at least one selected from the group consisting of an enzymatically active protein or peptide (e.g., proteases, kinases, phosphatases, etc.), a receptor protein or peptide, a transporter protein or peptide, a sterile and/or endotoxin-binding polypeptide, a structural protein or peptide, an immunogenic polypeptide, an antibody-mimetic protein (e.g., protein scaffolds, fc-fusion protein, etc.), toxins, antibiotics, hormones, growth factors, vaccines, and the like.

In one embodiment, the target polypeptide may be at least one selected from the group consisting of hormone, cytokine, tissue plasminogen activator, immunoglobulin, and the like (for example, antibodies or antigen binding fragments or variants thereof), antibody-mimetic protein (e.g., protein scaffold, fc-fusion protein, etc.).

In another embodiment, the target polypeptide may include at least one selected from the group consisting of: growth hormone (e.g., human growth hormone (hGH)), p40, BMP-1 (bone morphogenetic protein-1), growth hormone-releasing hormone, growth hormone-releasing peptide, interferons (e.g., interferon-alpha, -beta, -gamma, etc.), interferon receptors (e.g., water-soluble type I interferon receptors, etc.), G-CSF (granulocyte colony stimulating factor), GM-CSF (granulocyte-macrophage colony stimulating factor), glucagon-like peptides (e.g., GLP-1, etc.), insulin-like growth factor (IGF), G-protein-coupled receptor, interleukins (e.g., interleukin-1, -2, -3, -4, -5, -6, -7, -8, -9, -10, -11, -12, -13, -14, -15, -16, -17, -18, -19, -20, -21, -22, -23, -24, -25, -26, -27, 28, -29, -30, etc.), interleukin receptors (e.g., IL-1 receptor, IL-4 receptor, etc.), enzymes (e.g. glucocerebrosidase), iduronate-2-sulfatase, alpha-galactosidase-A, agalsidase alpha and beta, alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin or cytokine binding protein (e.g., IL-18 bp, TNF-binding protein, etc.), macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins; hemoglobin, thrombin, thrombin receptor activating peptide, thrombomodulin, blood factor VII, blood factor VIIa, blood factor IX, blood factor IX, blood factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factor (e.g., nerve growth factor, ciliary neurotrophic factor, AF-1 (axogenesis factor-1), brain-natriuretic peptide, glial derived neurotrophic factor, netrin, neutrophil inhibitor factor, neurotrophic factor, nuturin, etc.), parathyroid hormone, relaxin, secretin, somatomedin, adrenocortical hormone, glucagon, cholecystokinin, pancreatic polypeptide, gastrin releasing peptide, corticotropin releasing factor, thyroid stimulating hormone, autotaxin, lactoferrin, myostatin, receptor (e.g., TNF receptor (e.g., TNFR(p75), TNFR(p55), etc.)), IL-1 receptor, VEGF receptor, EGF receptor, B cell activating factor receptor, etc.), receptor antagonists (IL1-Ra, etc.), cell surface antigen (e.g., CD2, 3, 4, 5, 7, 11a, 11b, 18, 19, 20, 23, 25, 33, 38, 40, 45, 69, etc.), virus vaccine antigen, antibody (e.g., monoclonal antibody, polyclonal antibody), antibody fragment (e.g. scFv, Fab, Fab', F(ab')2 and Fd), virus-derived vaccine antigen, and variants/fragments thereof (e.g., variants/fragments that maintain the desired function and/or structure), antibody-mimetic protein (e.g., protein scaffold, fc-fusion protein, etc.), and the like, without being limited thereto.

The antibody may be of any isotype (e.g., IgA (IgA1, IgA2, etc.), IgD, IgG (IgG1, IgG2, IgG3, IgG4, etc.), IgM or IgE), and the antibody fragment is an antigen-binding fragment that retains the antigen-binding ability of the original antibody, and may be any fragment of an antibody comprising at least about 20 amino acids, such as at least about 100 amino acids (e.g., CDR, Fab, Fab', F(ab)2, Fd, Fv, scFv, scFv-Fc, etc.). The Fab fragment includes a variable domain (VL) and a constant domain (CL) of the light chain and a variable domain (VH) and a first constant domain (CH1) of the heavy chain. The Fab' fragment differs from Fab fragments in that an amino acid residue containing at least one cysteine residue has been added from the hinge region to the carboxyl terminal of the CH1 domain. The Fd fragment includes only the VH and CH1 domains, and the F(ab')2 fragment is produced by pairing the Fab' fragments via disulfide bonds or chemical reactions. The scFv (single-chain Fv) fragment exists as a single polypeptide chain since it contains VL and VH domains linked by a peptide linker. The antibody-mimetic protein may mean any protein including a site capable of binding to a specific antigen other than an antibody. For example, it may be at least one selected from the group consisting of antibody-mimetic protein scaffold, such as a repebody, Fc-fusion proteins such as nanobody and peptibody (fusion protein of Fc and antigen-binding polypeptide), without being limited thereto.

In another embodiment, the target polypeptide may be at least one selected from the group consisting of all secretory proteins.

The above-mentioned target polypeptide may be a mammalian-derived (isolated from mammals) polypeptide, including primates such as humans and monkeys, and rodents such as mice and rats, and may be, for example, a human-derived (isolated from human) polypeptide.

In the fusion polypeptide comprising the target polypeptide and an O-glycosylatable polypeptide region provided herein, a target polypeptide and an O-glycosylatable polypeptide region, and/or two or more O-glycosylatable polypeptide regions may be covalently or non-covalently linked directly (e.g., without a linker), or may be linked through a suitable linker (e.g., a peptide linker). The peptide linker may be a polypeptide consisting of 1 to 20, 1 to 15, 1 to 10, 2 to 20, 2 to 15, or 2 to 10 arbitrary amino acids, and the type of amino acid contained therein is not limited. The peptide linker may include, for example, Gly, Asn and/or Ser residues, and may also include neutral amino acids such as Thr and/or Ala, without being limited thereto, and amino acid sequences suitable for peptide linkers are known in the art. In one embodiment, the peptide linker may be a GS linker that repeatedly includes one or more Gly(G) and one or more Ser(S), and for example, it may be (GGGGS)n (where n is the number of repetitions of GGGGS (SEQ ID NO: 13) and may be an integer of 1 to 10 or an integer of 1 to 5 (1, 2, 3, 4, or 5)), without being limited thereto.

In addition, the fusion polypeptide may contain a total of 1 or more or a total of 2 or more (e.g., 2 to 10, 2 to 8, 2 to 6, 2 to 5, 2 to 4, 2 or 3) O-glycosylatable polypeptide regions. When the fusion polypeptide contains two or more O-glycosylatable polypeptide regions, the fusion polypeptide may be those in which two or more O-glycosylatable polypeptide regions are bound to the N-terminus or C-terminus of the target polypeptide, or one or more O-glycosylatable polypeptide regions are each independently bound to the N-terminus and C-terminus of the target polypeptide (in this case, the type and number of hinge regions bound to the N-terminus and C-terminus of the target polypeptide may be the same or different). In this case, the above-mentioned peptide linker may be further contained between the O-glycosylatable polypeptide regions and/or between the O-glycosylatable polypeptide region and the human target polypeptide.

The fusion polypeptide provided herein may be recombinantly or synthetically produced, and may not be naturally occurring.

The in vivo (or blood) half-life in mammals of the target polypeptide contained in the fusion polypeptide provided herein may increase by about 1.5 times or more, about 2 times or more, about 2.5 times or more, about 3 times or more, about 3.5 times or more, about 4 times or more, about 5 times or more, about 6 times or more, about 7 times or more, about 8 times or more, about 9 times or more, or about 10 times or more, as compared with the target polypeptide not fused with an O-glycosylated polypeptide region.

Due to the increased half-life of the target polypeptide in this way, the target polypeptide in the form of a fusion polypeptide in which the O-glycosylatable polypeptide region is bound has the advantage that the dosage interval can be extended as compared with the target polypeptide in the form in which the O-glycosylatable polypeptide region is not linked.

The fusion polypeptide including a target polypeptide and an O-glycosylatable polypeptide region can be produced by a conventional chemical synthesis method or a recombinant method.

As used herein, the term "vector" refers to an expression means for expressing a target gene in a host cell, and may be selected, for example, from the group consisting of plasmid vectors, cosmids vector, and bacteriophage vectors, viral vectors such as adenovirus vectors, retroviral vectors and adeno-associated virus vectors, and the like. In one embodiment, the vector that can be used in the recombinant vector may be prepared based on a plasmid (e.g., pcDNA series, pSC101, pGV1106, pACYC177, ColEl, pKT230, pME290, pBR322, pUC8/9, pUC6, pBD9, pHC79, pIJ61, pLAFRI, pHV14, pGEX series, pET series, pUC19, etc.), phage (e.g., kgt4 kB, k-Charon, kAz1, M13, etc.) or virus (e.g., SV40, etc.), without being limited thereto.

In the recombinant vector, the nucleic acid molecule encoding the fusion polypeptide may be operably linked to a promoter. The term "operatively linked" refers to a functional linkage between a nucleic acid expression regulatory sequence (e.g., a promoter sequence) and a different nucleic acid sequence. The regulatory sequences can be "operatively linked" to regulate transcription and/or translation of the different nucleic acid sequence.

The recombinant vector can be typically constructed as a vector for cloning or an expression vector for expression. As the expression vector, a conventional one used for expressing a foreign protein in plants, animals or microorganisms in the art can be used. The recombinant vector can be constructed via various methods known in the art.

The recombinant vector can be expressed using eukaryotic cells as a host. When a eukaryotic cell is expressed as a host, the recombinant vector may include a nucleic acid molecule to be expressed and the above-mentioned promoter, ribosome binding site, and secretory signal sequence (see Korean Unexamined Patent Publication No. 2015-0125402) and/or the transcription/translation termination sequence. In addition, the replication origin that operates in eukaryotic cells may include an f1 origin of replication, a SV40 origin of replication, a pMB1 origin of replication, an adeno origin of replication, a AAV origin of replication, and/or a BBV origin of replication, and the like, without being limited thereto. Further, promoters derived from the genome of mammalian cells (e.g., metallotionein promoter) or promoter derived from mammalian virus (e.g., adenovirus late promoter, vaccinia virus 7.5K promoter, SV40 promoter, cytomegalovirus promoter and tk promoter of HSV) can be used, and all secretory signal sequences commonly available as secretory signal sequences can be used. For example, the secretory signal sequence described in Korean Unexamined Patent Publication No. 2015-0125402 may be used, without being limited thereto, and a polyadenylation sequence may be included as a transcription termination sequence.

The recombinant cell may be obtained by introducing (transforming or transfecting) the recombinant vector into an appropriate host cell. The host cell may be selected from all eukaryotic cells capable of stably and continuously cloning or expressing the recombinant vector. The eukaryotic cells that can be used as hosts include yeast (*Saccharomyces cerevisiae*), insect cells, plant cells, animal cells, and the like, and examples thereof include cells derived from mouse (e.g., COP, L, C127, Sp2/0, NS-0, NS-1, At20, or NIH3T3), rat (e.g., PC12, PC12h, GH3, or MtT), hamster (e.g., BHK, CHO, GS gene-deficient CHO, or DHFR gene-deficient CHO), monkey (e.g., COS (COS1, COS3, COS7, etc.), CV1 or Vero), human (e.g., HeLa, HEK-293, retinal-derived PER-C6, diploid fibroblasts, myeloma cells or HepG2), or other animal cells (e.g., MDCK, etc.), insect cells (e.g., Sf9 cells, Sf21 cells, Tn-368 cells, BTI-TN-5B1-4 cells, etc.), hybridoma, and the like, without being limited thereto.

The nucleic acid molecule encoding the fusion polypeptide provided herein can expressed in the appropriate host cell described above to thereby produce a target polypeptide having improved in vivo stability as compared with a non-fused form, or a fusion polypeptide comprising the same. The method for producing the fusion polypeptide may include a step of culturing the recombinant cell containing the nucleic acid molecule. The culturing step may be performed under normal culturing conditions. Further, the production method may further include a step of isolating and/or purifying the fusion polypeptide from the culture after the culturing step.

Transport (introduction) of the nucleic acid molecule or a recombinant vector containing the same into a host cell may use a transport method widely known in the art. The usable transport method may, when the host cell is a eukaryotic cell, include microinjection, calcium phosphate precipitation, electroporation, liposome-mediated transfection, gene bombardment, and the like, without being limited thereto.

The method of selecting the transformed (recombinant vector-introduced) host cells can be easily carried out according to a method widely known in the art by using a phenotype expressed by the selection label. For example, if the selection label is a specific antibiotic resistance gene, the recombinant cells having an introduced recombinant vector can be easily selected by culturing in a medium containing the antibiotic.

The fusion polypeptide may be used for the prevention and/or treatment of any disease that is associated with a deficiency and/or functional abnormality of the target polypeptide, or enables treatment, alleviation or amelioration by the activity of the target polypeptide. Therefore, in one embodiment, there is provided a pharmaceutical composition comprising at least one selected from the group consisting of the fusion polypeptide, a nucleic acid molecule encoding the fusion polypeptide, a recombinant vector containing the nucleic acid molecule, and a recombinant cell containing the recombinant vector. The pharmaceutical composition may be a pharmaceutical composition for the prevention and/or treatment of a disease associated with a deficiency and/or functional abnormality of the target polypeptide, or a disease in which the target polypeptide has therapeutic and/or prophylactic effects. Another embodiment provides a method for preventing and/or treating a disease associated with a deficiency and/or functional abnormality of the target polypeptide contained in the fusion protein or a disease in which the target polypeptide has therapeutic and/or prophylactic effects, the method comprising the step of administering at least one selected from the group consisting of the fusion polypeptide, a nucleic acid molecule encoding the fusion polypeptide, a recombinant vector containing the nucleic acid molecule, and a recombinant cell containing the recombinant vector, to a patient in need of prevention and/or treatment of diseases associated with a deficiency and/or functional abnormality of the target polypeptide contained in the fusion protein or diseases in which the target polypeptide has therapeutic and/or prophylactic effects. The method may further include, prior to the administering step, a step of identifying a patient in need of prevention and/or treatment of diseases associated with a deficiency and/or functional abnormality of the target polypeptide contained in the fusion protein or diseases in which the target polypeptide has therapeutic and/or prophylactic effects.

The pharmaceutical composition may contain a pharmaceutically effective amount of one or more active ingredients selected from the group consisting of the fusion polypeptide, the nucleic acid molecule, the recombinant vector, and the recombinant cell. The pharmaceutically effective amount refers to the content or dose of an active ingredient capable of obtaining the intended effects. The content or dose of the active ingredient in the pharmaceutical composition may vary depending on factors, such as formulation method, administration method, age, body weight, sex or disease condition of the patient, diet, administration time, dosage interval, administration route, excretion speed, and response sensitivity. For example, a single dose of the active ingredient may be within a range of 0.001 to 1000 mg/kg, 0.01 to 100 mg/kg, 0.01 to 50 mg/kg, 0.01 to 20 mg/kg, or 0.01 to 1 mg/kg, without being limited thereto.

In addition, the pharmaceutical composition may further include a pharmaceutically acceptable carrier in addition to the active ingredient. The carrier is commonly used during formulation of a drug containing a protein, a nucleic acid, or a cell, and may be at least one selected from the group consisting of lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like, without being limited thereto. The pharmaceutical composition may further include at least one selected from the group consisting of a diluent, an excipient, a lubricant, a wetting agent, a sweetening agent, a flavoring agent, an emulsifying agent, a suspending agent, a preservative, and the like, which are commonly used in the manufacture of pharmaceutical compositions.

The object for administering the pharmaceutical composition may be mammals, including primates such as humans and monkeys, and rodents such as mice, rats, and the like, or cells, tissues, cell cultures or tissue cultures derived therefrom.

The pharmaceutical composition may be administered by oral administration or parenteral administration, or may be administered by contacting cells, tissues, or body fluids. Specifically, in the case of parenteral administration, it can may be administered by intravenous injection, subcutaneous injection, intramuscular injection, intraperitoneal injection, endothelial administration, topical administration, intranasal administration, intrapulmonary administration, rectal administration and the like. Since the protein or peptide is digested upon oral administration, the oral composition should be formulated so as to coat with an active agent or to be protected from degradation in the stomach.

In addition, the pharmaceutical composition may be in the form of a solution, suspension, syrup or emulsion in an oil or aqueous medium, or may be formulated in the form of an extract, powder, granule, tablet or capsule, and a dispersing agent or a stabilizer may be further included for formulation.

Advantageous Effects

The target polypeptide fused with an O-glycosylatable polypeptide region provided herein has a long sustained period when administered to the body and thus can prolong the dosing interval and reduce the dosage, which has an advantageous effect in terms of ease of administration and/or economic aspects, and can be usefully applied to a field where treatment of the target polypeptide is required.

BRIEF DESCRIPTION OF THE DRAWINGS

FIG. 1 is a diagram schematically showing the structure of the fusion polypeptide IgD-hGH-His (DHDD-8His), IgD-hGH (DHDD), IgA-hGH (AHAA), IgD-hGH-IgA (DHAA), and IgA-hGH-IgD (AHDD) according to one embodiment.

FIG. 2 is a graph showing the results of the analysis of the fusion polypeptide IgD-hGH according to one embodiment by Q-TOF Mass Spectrometry.

FIG. 3 is a result showing the isomer distribution of the fusion polypeptide IgD-hGH-His analyzed by IEF (Isoelectric focusing).

FIG. 4 is a graph showing the results of the analysis of the fusion polypeptide IgD-hGH-His according to one embodiment by Q-TOF Mass Spectrometry.

FIG. 5 is a diagram schematically showing the structure of the fusion polypeptide Dulaglutide-ID and Dulaglutide-ID2 according to one embodiment.

FIG. 6 is the results showing the isomer distribution of the fusion polypeptide Dulaglutide-ID2 analyzed by IEF (Isoelectric focusing).

FIG. 7 is a graph showing the change in blood concentration with time after administration of the fusion polypeptide IgD-hGH compared to when hGH is administered.

FIG. 8 is a graph showing the change in blood concentration with time after administration of the fusion polypeptide IgD-hGH-His compared to when hGH is administered.

FIG. 9 is a graph showing the change in blood concentration with time after administration of the fusion polypeptides IgA-hGH F3, IgA-hGH F4, and IgA-hGH F5.

FIG. 10 is a graph showing the change in blood concentration with time after administration of the fusion polypeptide Dulaglutide-ID2 (pGIgG4DD) compared to when Dulaglutide (Trulicity) is administered.

DETAILED DESCRIPTION OF THE EMBODIMENTS

Hereinafter, the present disclosure will be described in detail with reference to the following examples. However, these examples are for illustration purposes only, and the scope of the disclosure is not limited by these examples.

Example 1: Production of Fusion Polypeptide 1.1. Production of Fusion Polypeptide Containing Human Growth Hormone (hGH) as Target Polypeptide A fusion polypeptide IgD-hGH-His (DHDD-8His), IgD-hGH (DHDD), IgA-hGH (AHAA), IgD-hGH-IgA (DHAA), and IgA-hGH-IgD (AHDD) (see FIG. 1; the underlined part of the sequences of IgD and IgA1 is the part capable of performing O-Glycosylation) was produced in which IgD hinge (ESPKAQASSVPTAQPQAEGSLAKATTAPATTRNT; SEQ ID NO: 1), IgA1 hinge (VPSTPPTPSP-STPPTPSPS; SEQ ID NO: 2), or a combination of the hinge of IgD and the hinge of IgA1 was fused with the target polypeptide (human growth hormone: hGH; SEQ ID NO: 3). The amino acid sequences of each part contained in the fusion polypeptide were summarized in Table 2 below.

TABLE 2

| | Amino acid sequence (N-terminus→C-terminus) | | | SEQ ID NO |
|---|---|---|---|---|
| Signal Peptide (SP7.2) | MHRPEAMLLL | LTLALLGGPT | WA | 4 |
| Target polypeptide (hGH) | FPTIPLSRLF FLEAYIPKEQ PSNREETQQK QFLRSVFANS IQTLMGRLED HNDDALLKNY QCRSVEGSCG | DNAMLRAHRL KYSFLQNPQT SNLELLRISL LVYGASDSNV GSPRTGQIFK GLLYCFRKDM F | HQLAFDTYQE SLCFSESIPT LLIQSWLEPV YDLLKDLEEG QTYSKFDTNS DKVETFLRIV | 3 |
| Hinge region of Immunoglobulin IgD (ID) | ESPKAQASSV TRNT | PTAQPQAEGS | LAKATTAPAT | 1 |
| Hinge region of Immunoglobulin IgA1 (IA) | VPSTPPTPSP | STPPTPSPS | | 2 |
| His-Tag | HHHHHHHH | | | 5 |

1.1.1. IgD-hGH (DHDD)

Plasmid pAF-D1G1 (including the promoter of Korean Patent No. 10-1868139B1), which is a variant of pcDNA3.1 (+) (Invitrogen, Cat. No. V790-20), was treated with BamHI (restriction site: GGATCC) and NotI (restriction site: GCGGCCGC), into which the gene encoding the fusion polypeptide of '(N-terminus)-[BamHI restriction site-signal peptide (SEQ ID NO: 4)-IgD hinge (IgDH1; SEQ ID NO: 1)-human growth hormone (hGH; SEQ ID NO: 3)-IgD hinge (IgDH1; SEQ ID NO: 1)-IgD hinge (IgDH1; SEQ ID NO: 1)-NotI restriction site]-(C-terminus)' was inserted to prepare a recombinant vector pDHDD-D1G1 for the production of a fusion polypeptide containing the target polypeptide (human growth hormone) and the hinge region of immunoglobulin (IgD) (293 aa in total (excluding signal peptide); the number of O-Glycosylatable sites: a total of 21); hereinafter, referred to as 'IgD-hGH').

The prepared recombinant vector pDHDD-D1G1 was introduced into ExpiCHO-S™ cells (Thermo Fisher Scientific), and cultured in ExpiCHO Expression Medium (Thermo Fisher Scientific; 400 mL) for 12 days (Fed-Batch Culture; Day 1 & Day 5 Feeding) to produce the fusion polypeptide IgD-hGH. The fusion polypeptide IgD-hGH theoretically has a molecular weight of 32.2 kDa (excluding O-Glycans) and 21 O-Glycans.

The fusion polypeptide IgD-hGH produced through the expression of the recombinant vector was purified and O-Glyan site Occupancy was analyzed using Q-TOF Mass Spectrometry.

Specifically, the first purification process was performed by mounting a column made by CaptureSelect™ Human Growth Hormone Affinity Matrix (Life Technologies) having Binding Specificity to hGH on an AKTA™ Purifier (GE Healthcare Life Sciences), and loading a sample. The primary washing was performed with an equilibration buffer, and eluted with 20 mM citric acid pH 3.0 or 0.1M Acetic acid pH 3.0. Immediately after completion of the process, the elution solution was adjusted to pH 7.0 using 2M Tris Buffer and left in a frozen state until before the next purification process.

The second purification process was performed by applying Anion Exchange Chromatography and using TMAE as a resin. After the frozen sample obtained through the first process was dissolved, the conductivity was measured and the sample was diluted with water for injection so as to have a conductivity suitable for loading, and subjected to a pretreatment with a 0.22 um PES Filtration System (Corning, USA). Columns were mounted on AKTA Avant (GE Healthcare Life Sciences) and the sample was loaded. Elution was made in gradient form for isolation according to the conductivity, and fractions were divided and pooled with reference to elution peak.

Concentration or buffer exchange was performed to prepare an analytical sample and an animal experimental sample during the purification process. The sample was placed in Amicon Ultra System (Millipore), centrifuged at low temperature and subjected to concentration or diafiltration. 25 mM Sodium Phosphate pH 7.0 was used as a buffer for analysis, and PBS Buffer was used to prepare animal experimental samples.

The concentration of samples was measured after the purification process, concentration process, or diafiltration, in which the Extinction Coefficient of the substance was calculated using the amino acid sequence, and absorbances at 280 nm and 340 nm were measured with a UV Spectrophotometer (G1103A, Agilent Technologies) and calculated using the following Equation.

$$\frac{(A_{280\ nm} - A_{340\ nm})}{(\text{Extinction Coefficient})} \times (\text{Dilution Factor})$$

In the case of animal experimental samples, they were diluted to a predetermined concentration using PBS Buffer, and filtered with 0.22 um Syringe Filter (Millex-GV, 0.22 um, Millipore) in a Biosafety Cabinet before administration, and then stored in a frozen state until subsequent administration.

The results of analyzing IgD-hGH by Q-TOF Mass Spectrometry are shown in FIG. 2 (Y-axis: %; X-axis: mass; the numbers 7 to 21 shown above the peak are O-Glycan numbers). As shown in FIG. 2, O-Glycans were distributed from 7 to 21 in IgD-hGH, and the average number of O-Glycans was 13.5.

1.1.2. IgD-hGH-His

Primers in Table 3 were synthesized to add 8His-tag to the C-terminus of IgD-hGH (Example 1.1.1) for convenience of purification.

TABLE 3

| Primer Name | DNA Sequence (5'→3') | SEQ ID NO |
|---|---|---|
| hGH-Pst_F | AAGTATTCCTTC*CTGCAG*AACCCCCAG | 14 |
| DD_R | CCTGTGCCTTTGGAGACTCTGTGTTACGGG | 15 |
| DD_F | GAGTCTCCAAAGGCACAGGCCTCCTCCGTG | 16 |
| DHis_R | GTGGTGATGATGGTGTGTGTTACGGGTGGTGGC | 17 |
| His-Not_R | *GCGGCCGC*TTTAGTGATGGTGGTGGTGATGATGGTG | 18 |

PCR was performed using each primer, and then overlapping PCR was performed again with an appropriate combination of primers to finally obtain a PCR product of 693 bp ('(N-terminus)-[PstI restriction site-signal peptide (SEQ ID NO:4)—IgD hinge (IgDH1; SEQ ID NO:1)—human growth hormone (hGH; SEQ ID NO: 3)—IgD hinge (IgDH1; SEQ ID NO: 1)—IgD hinge (IgDH1; SEQ ID NO: 1)—8His-NotI restriction site]-gene encoding (C-terminus)'). Then, the pDHDD-D1G1 and PCR products were treated with PstI and NotI, respectively, and then ligated to finally prepare the recombinant vector pDHDD-8His-D1G1 for the preparation of a fusion polypeptide (total 301 aa (excluding signal peptide); O-Glycosylatable sites—total 21); hereinafter, referred to as 'IgD-hGH-His') including the target polypeptide (human growth hormone) and the hinge region of immunoglobulin (IgD) and 8His Tag.

The fusion polypeptide IgD-hGH-His produced through the expression of the recombinant vector was purified and O-Glycan site occupancy was analyzed using IEF (Isoelectric focusing) analysis and Q-TOF Mass Spectrometry.

Specifically, the first column used in the purification process was TMAE which is an anion exchange resin, and IgD-hGH-His was partially isolated from a culture solution and eluted as a first eluate. Then, the first eluate was supplied to a HIS-Tag binding column, a metal affinity resin, which is a second column, and IgD-hGH-His was selectively eluted as a second eluate. Then, the second eluate was supplied to TMAE, an anion exchange resin, which is a third column, to remove a fraction with a low sialic acid content, and eluted as a third eluate. The third eluate was then supplied to a gel filtration column, which is a fourth column, to remove multimers and fragmented proteins, thereby obtaining a fourth eluate.

More specifically, it includes the following steps.

Step 1: equilibrating with a buffer containing TMAE, 0.5×25 cm (4 mL), v=150 cm/hr, 10 mM trolamine (pH 7.0). After loading the culture solution, the column was washed once with an equilibration buffer, and an elution buffer containing 10 mM trolamine and 250 mM sodium chloride (pH 7.0) was eluted in a linear gradient to obtain a first eluate.

Step 2: equilibrating with a buffer containing Ni-NTA His*Bind, 1.0×5 cm (4 mL), v=80 cm/hr, 10 mM sodium phosphate, 1 M sodium chloride, 10 mM imidazole (pH 7.0). After loading the first eluate, the column was washed once with an equilibrium buffer, and an elution buffer containing 10 mM sodium phosphate, 1 M sodium chloride, and 500 mM imidazole (pH 7.0) was eluted in a linear gradient to obtain a second eluate.

Step 3: Diafiltration

Step 4: Equilibrating with a buffer containing TMAE, 0.5×25 cm (4 mL), v=150 cm/hr, 10 mM trolamine (pH 7.0). After loading the second eluate, the column was washed once with an equilibrium buffer, and an elution buffer containing 10 mM trolamine and 100 mM sodium chloride (pH 7.0) was eluted in a linear gradient to obtain a third eluate.

Step 5: Ultrafiltration

Step 6: equilibrating with a buffer containing Sephacryl 5-100, 1.6×30 cm (60 mL), v=30 cm/hr, 20 mM sodium phosphate, 140 mM sodium chloride, pH 7.0. After loading the third eluate, the monomer fraction was eluted with an equilibration buffer to obtain a fourth eluate.

The isomer distribution of the obtained fourth eluate was shown in FIG. 3. In FIG. 3, the theoretical pI value of IgD-hGH-His is 6.65. The value lower than this means that IgD-hGH-His is O-Glycosylation and sialic acid is bound to this O-Glycan to becomes more acidic.

The results of analyzing IgD-hGH-His by Q-TOF Mass Spectrometry are shown in FIG. 4 (Y-axis: %; X-axis: mass; values of 7 to 21 shown above the peak are the numbers of O-Glycans). As shown in FIG. 4, in IgD-hGH-His, 0-Glycans were distributed from 8 to 21, and the average number of O-Glycans was 14.7.

1.1.3. IgA-hGH (AHAA)

In the recombinant vector pDHDD-D1G1 constructed in Example 1.1.1, a recombinant vector pAHAA-D1G1 was constructed to have the same configuration, except that the coding genes of three IgD hinges (one on the N-terminus side and two on the C-terminus side of hGH, three in total) were replaced with the coding genes of the IgA1 hinges, respectively., and then expressed in the same manner as in Example 1.1.1 to produce a fusion polypeptide having a configuration of IgA1 hinge (IgA; SEQ ID NO: 2)—human growth hormone (hGH; SEQ ID NO: 3)—IgA1 hinge (IgA; SEQ ID NO: 2)—IgA1 hinge (IgA; SEQ ID NO: 2) (see FIG. 1; hereinafter referred to as 'IgA-hGH'). The fusion polypeptide IgA-hGH theoretically has 24 O-Glycans. The fusion polypeptide IgA-hGH produced through expression of the recombinant vector was purified by referring to the method described in Example 1.1.1.

As a result of analyzing the purified IgA-hGH by Q-TOF Mass Spectrometry, the average number of O-Glycans in IgA-hGH was 12.8 in Fraction 3, 14.3 in Fraction 4, and 15.6 in Fraction 5.

1.1.4. IgD-hGH-IgA (DHAA)

7574 bp vector where the recombinant vector pDHDD-D1G1 produced in Example 1.1.1 was cut with BamHI and NotI was ligated with 489 bp of Insert I where pDHDD-DTG1 was cut with BamHI and KasI, and 383 bp of Insert II where the recombinant vector pAHAA-D1G1 used in Example 1.1.3 was cut with KasI and NotI, and thus the recombinant vector pDHAA-D1G1 was constructed so as to have the same configuration except that in the recombinant vector pDHDD-D1G1, 3 IgD hinges (1 on the N-terminus side and 2 on the C-terminus side of hGH, 3 in total), two on the 3' terminal side were replaced by the coding gene of the IgA1 hinge. The recombinant vector pDHAA-D1G1 was expressed in the same manner as in Example 1.1.1 to produce a fusion polypeptide having the configuration of IgD hinge (IgD; SEQ ID NO: 1)-human growth hormone (hGH; SEQ ID NO: 3)-IgA1 hinge (IgA; SEQ ID NO: 2)-IgA1 hinge (IgA; SEQ ID NO: 2). The fusion polypeptide IgD-hGH-IgA theoretically has 23 O-Glycans.

1.1.5. IgA-hGH-IgD (AHDD)

7574 bp vector where the recombinant vector pDHDD-D1G1 produced in Example 1.1.1 was cut with BamHI and NotI was ligated with 444 bp of Insert I where pAHAA-D1G1 used in Example 1.1.3 was cut with BamHI and KasI, and 473 bp of Insert II where pDHDD-D1G1 used in Example 1.1.1 was cut with KasI and NotI, and thus the recombinant vector pADD-D1G1 was constructed so as to have the same configuration except that one at the 5' terminal of the three IgD hinge coding genes was replaced by the coding gene for the IgA1 hinge, and then expressed in the same manner as in Example 1.1.1 to produce a fusion polypeptide having the configuration of IgA1 hinge (IgA; SEQ ID NO: 2)—human growth hormone (hGH; SEQ ID NO: 3)—IgD hinge (IgD; SEQ ID NO: 1)—IgD hinge (IgD; SEQ ID NO: 1) (see FIG. 1; hereinafter referred to as 'IgA-hGH-IgD'). The fusion polypeptide IgA-hGH-IgD theoretically has 22 O-Glycans.

1.2. Protein of Interest: GLP-1-Fc Fusion Protein

The fusion polypeptides Dulaglutide-ID (including one IgD hinge area) and Dulaglutide-ID2 (including two IgD hinge regions) (see FIG. 5) were prepared in which IgD hinge (ESPKAQASVPTAQPQAEGSLAKATTAPAT-TRNT; SEQ ID NO: 1) was fused with the target polypeptide (GLP-1 (Glucagon-like peptide-1)-Fc fusion protein: GLP-1-Fc). The GLP-1-Fc fusion protein exists as a dimer. The encoded amino acid sequence is summarized in Table 4 below.

TABLE 4

|  |  | Amino acid sequence (N-terminus→C-terminus) | SEQ ID NO |
|---|---|---|---|
| Signal Peptide (SP7.2) | | MHRPEAMLLL LTLALLGGPT WA | 4 |
| Target polypeptide (GLP-1-Fc) | Modified GLP-1 | HGEGTFTSDV SSYLEEQAAK EFIAWLVKGG G | 6 |
| | GS Linker | GGGGSGGGGS GGGGS | |
| | Modified IgG4 (IgG4 hinge-CH2-IgG4-CH3_modified) | AESKYGPPCP PCPAPEAAGG PSVFLFPPKP KDTLMISRTP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW | |

TABLE 4-continued

| | Amino acid sequence (N-terminus→C-terminus) | SEQ ID NO |
|---|---|---|
| | QEGNVFSCSV MHEALHNHYT QKSLSLSLG | |
| Hinge region of Immunoglobulin IgD (ID) | ESPKAQASSV PTAQPQAEGS LAKATTAPAT TRNT | 1 |

1.2.1. Dulaglutide-ID1

The expression vector pGJg4 (including the promoter of Korean Patent No. 10-1868139B1) expressing GLP-1-Fc, which is a variant of pcDNA3.1(+) (Invitrogen, Cat. No. V790-20), was used as a template, and PCR was performed using Primers JgG4mCH2_F and IgG4JD_R in Table 4 to obtain a PCR product (mIgG4) of 659 bp Modified IgG4. And, the pDHDD-D1G1 prepared in Example 1.1.1 was used as a template, and PCR was performed using Primers gG4D_F and ID_NotR in Table 4 to obtain PCR products of 129 bp (ID1) and 231 bp (ID2). The obtained 659 bp mIgG4 PCR Product and 129 bp ID PCR Product were purified, which was then used as a template. Overlapping PCR was performed using Primers JgG4mCH2_F and ID_NotR in Table 5 below to obtain a PCR product of 770 bp ('(N-terminus)-[lModified IgG4 Fc part (including BsrGI restriction site))-IgD hinge (IgDH1; SEQ ID NO: 1)-NotI restriction site]—gene encoding (C-terminus)').

TABLE 5

| Primer Name | DNA Sequence (5'→3') | SEQ ID NO |
|---|---|---|
| IgG4mCH2_F | CACCTGAGGCCGCCGGGGGACCG TCAGTCT | 19 |
| IgG4ID_R | CTTTGGAGACTCGCCCAGGGACA GGGACAG | 20 |
| IgG4ID_F | CTGGGCGAGTCTCCAAAGGCACA GGCCTCC | 21 |
| ID_NotR | TTCTTCTTC*GCGGCCGC*TTTATGT GTTACG | 22 |

A 7574 bp vector where pDHDD-D1G1 prepared in Example 1.1.1 was cut with BamHI and NotI was ligated with 607 bp of Insert I where pGIg4 was cut with BamHI and BsrGI and 403 bp of Insert II where the 770 bp PCR product obtained through the overlapping PCR was cut with BsrGI and NotI to prepare a recombinant vector pGIg4D-D1G1 for the production of a fusion polypeptide including the target polypeptide (GLP-1-Fc) and a hinge region of immunoglobulin (IgD) (total 309 aa (excluding signal peptide); O-Glycosylated sites—total 7, exists as dimers, so finally 14); hereinafter, referred to as 'Dulaglutide-ID1').

1.2.2. Dulaglutide-ID2

659 bp of mIgG4 PCR product and 231 bp of ID2 PCR product obtained in Example 1.2.1 were used as a template, and overlapping PCR was performed using Primers IgG4mCH2_F and ID_NotR in Table 4 to obtain a PCR product of 882 bp ('(N-terminus)-[Modified IgG4 Fc part (including BsrGI restriction site)-IgD hinge (IgDH1; SEQ ID NO: 1)-IgD hinge (IgDH1; SEQ ID NO: 1)-NotI restriction site)-gene encoding (C-terminus)').

A 7574 bp vector where pDHDD-D1G1 prepared in Example 1.1.1 was cut with BamHI and NotI was ligated with 607 bp of Insert I where pGIg4 was cut with BamHI and BsrGI and 505 bp of Insert II where the PCR product of 882 bp obtained through the overlapping PCR was cut with BsrGI and NotI to prepare a recombinant vector pGIg4DD-D1G1 for the production of a fusion polypeptide including the target polypeptide (GLP-1-Fc) and two hinge regions of immunoglobulin (IgD) (total 343 aa (excluding signal peptide); 0-Glycosylated sites-14 in total, 28 as it exists as dimer); hereinafter, referred to as 'Dulaglutide-ID2').

The fusion polypeptide Dulaglutide-ID2 produced through the expression of the recombinant vector was purified, and O-Glyan site occupancy was analyzed using isoelectric focusing (IEF) analysis and Q-TOF Mass Spectrometry.

Specifically, proteins were isolated and purified through Protein A affinity chromatography using the Fc region of substance, and then anion exchange chromatography and hydrophobic interaction chromatography were sequentially performed and purified.

The culture solution was filtered using a 0.22 um filtration membrane, injected into Protein A affinity resin equilibrated with an equilibration buffer (10 mM Sodium phosphate, 150 mM Sodium chloride, pH 7.4), and then washed with an equilibrium buffer. After washing, the protein was eluted with an elution buffer (100 mM Sodium citrate pH 3.5), and peaks were collected.

The collected eluate was subjected to a buffer exchange with 20 mM Tris pH 8.0.

The buffer exchanged sample was injected and purified into anion exchange chromatography (Source 15Q, GE Healthcare).

The equilibration buffer and elution buffer used were 20 mM Tris, pH 8.0, 20 mM Tris, 0.5 M NaCl, and pH 8.0, respectively. The equilibration buffer and the elution buffer were used as channels A and B, respectively, to elute the protein under concentration gradient conditions and collect peaks.

The collected protein solution was further purified using hydrophobic interaction chromatography (Butyl sepharose, GE Healthcare).

The equilibration buffer and elution buffer used were 0.1M sodium phosphate pH 6.0, 1.8 ammonium sulfate, pH 8.0, and 0.1M sodium phosphate pH 6.0, respectively. The equilibration buffer and the elution buffer were used as channels A and B, respectively, to elute the protein under concentration gradient conditions and collect peaks.

The isomer distribution of Dulaglutide-ID2 obtained by analyzing the collected peaks by isoelectric focusing (IEF) is shown in FIG. 6. In FIG. 6, the theoretical pI value of Dulaglutide-ID2 is 5.78, but in the case of Fraction #3, the value lower than this means that Dulaglutide-ID2 is O-Glycosylated, and this O-Glycan is attached to sialic acid and becomes more acidic.

As a result of analyzing Dulaglutide-ID2 Fraction #3 by Q-TOF Mass Spectrometry, ID could be performed up to 26, and the average number of O-Glycans was 17.5.

The finally purified protein solution was buffer-exchanged with the same excipients as Trulicity (Sodium citrate hydrate: 2.74 mg/mL, Anhydrous citric acid: 0.14 mg/mL, D-mannitol: 46.4 mg/mL, polysorbate 80: 0.20 mg/mL, pH 6.0-7.0), and concentrated and used as a test material for the animal PK test.

Example 2: Pharmacokinetic Properties (PK Profile) Test of Fusion Polypeptide (In Vivo)

2-1. Target Protein: Human Growth Hormone (hGH)

Fusion polypeptides IgD-hGH, IgD-hGH-His, IgA-hGH F3 (Fraction 3 of Example 1.1.3), IgA-hGH F4 (Fraction 4 of Example 1.1.3), and IgA-hGH F5 (Execution Fraction 5 of Example 1.1.3) prepared in Example 1.1 were subcutaneously administered to SD rats (Orientbio, 7 weeks old, about 300 g; n=3) at a dose of 2 mg/kg, and Pharmacokinetics were tested. Sampling was performed at 0, 0.5, 1, 2, 4, 6, 8, 24, 48 hours, and for comparison, hGH (Eutropin, LG Chem) was administered subcutaneously at a dose of 2 mg/kg in the same manner as above, and tested.

After administration to SD rat as described above, the blood collected by time-point was centrifuged to obtain a serum. ELISA was performed using Human Growth Hormone Quantikine ELISA Kit (R&D Systems), and the concentrations of hGH and fusion polypeptides (IgD-hGH, IgD-hGH-His, IgA-hGH FP3, IgA-hGH FP4 and IgA-hGH FP5) in the blood by time-point were confirmed. Using this data, parameters including AUC (area under the curve) were calculated using software for PK analysis (WinNonlin (Certara L. P.), etc.).

2-1-1. hGH vs. IgD-hGH

PK results of hGH and IgD-hGH are shown in Table 6 and FIG. 7.

TABLE 6

| Parameter | hGH Mean | hGH SD | IgD-hGH Mean | IgD-hGH SD |
|---|---|---|---|---|
| Cmax (ng/mL) | 1788 | 50.6 | 973 | 233 |
| Tmax (hr) | 1 | — | 4 | — |
| AUCinf (ng*hr/mL) | 4703 | 111 | 16027 | 2941 |
| AUClast (ng*hr/mL) | 4695 | 111 | 15845 | 2881 |
| $T_{1/2}$ (hr) | 2.17 | 1.79 | 7.11 | 0.327 |
| AUCextp (%) | 0.167 | 0.059 | 1.11 | 0.197 |

($C_{max}$: Maximum blood concentration, $T_{max}$: Time when peak blood concentration is reached, $AUC_{inf}$: Area under the blood concentration-time curve calculated by extrapolating from the last measurable blood collection time point to infinite time, $AUC_{last}$: Area under the blood concentration-time curve until the last measurable blood collection time point, $T_{1/2}$: elimination half-life, $AUC_{Extp}$(%): [($AUC_{inf}$-$AUC_{last}$)/$AUC_{inf}$]*100)

As can be seen in Table 6 and FIG. 7, it can be confirmed that the half-life of the hGH fused with the hinge region (IgD-hGH) increased by about 3.3 times compared to the hGH not fused with the hinge region.

2-1-2. hGH vs. IgD-hGH-His

PK results of hGH and IgD-hGH-His are shown in Table 7 and FIG. 8.

TABLE 7

| Parameter | hGH Mean | hGH SD | IgD-hGH-His Mean | IgD-hGH-His SD |
|---|---|---|---|---|
| Cmax (ng/mL) | 502.22 | 39.88 | 886.67 | 195.63 |
| Tmax (hr) | 1 | — | 4 | — |
| AUCinf (ng*hr/mL) | 1028.80 | 120.03 | 13436.05 | 2680.39 |
| AUClast (ng*hr/mL) | 1003.74 | 115.76 | 13332.39 | 2710.64 |
| $T_{1/2}$ (hr) | 2.55 | 0.20 | 6.61 | 0.71 |
| AUCextp (%) | 2.43 | 0.23 | 0.82 | 0.39 |

($C_{max}$: Maximum blood concentration, $T_{max}$: Time when peak blood concentration is reached, $AUC_{inf}$: Area under the blood concentration-time curve calculated by extrapolating from the last measurable blood collection time point to infinite time, $AUC_{last}$: Area under the blood concentration-time curve until the last measurable blood collection time point, $T_{1/2}$: elimination half-life, $AUC_{Extp}$(%): [($AUC_{inf}$-$AUC_{last}$)/$AUC_{inf}$]*100)

As can be seen in Table 7 and FIG. 8, it can be confirmed that the half-life of hGH (IgD-hGH-His) fused with the hinge region with His-Tag increased by about 2.6 times compared to the hGH not fused with the hinge region.

2-1-3. IgA-hGH (Effect on PK by O-Glycan Number)

In order to see the effect of the number of O-glycans on PK, PK results for each IgA-hGH fraction are shown in Table 8 and FIG. 9.

TABLE 8

| Parameter | IgA-hGH FP3 (Average number of O-glycan: 12.8) Mean | IgA-hGH FP3 SD | IgA-hGH FP4 (Average number of O-glycan: 14.3) Mean | IgA-hGH FP4 SD | IgA-hGH FP5 (Average number of O-glycan: 15.6) Mean | IgA-hGH FP5 SD |
|---|---|---|---|---|---|---|
| Cmax (ng/mL) | 290 | 80.5 | 305 | 102 | 195 | 32.8 |
| Tmax (hr) | 2 | — | 4 | — | 2 | — |
| AUCinf (ng*hr/mL) | 2510 | 474 | 2832 | 814 | 2186 | 89.2 |
| AUClast (ng*hr/mL) | 2509 | 475 | 2826 | 816 | 2160 | 96.8 |
| $T_{1/2}$ (hr) | 1.98 | 0.205 | 2.53 | 0.287 | 3.56 | 0.335 |
| AUCextp (%) | 0.050 | 0.035 | 0.240 | 0.182 | 1.21 | 0.573 |

($C_{max}$: Maximum blood concentration, $T_{max}$: Time when peak blood concentration is reached, $AUC_{inf}$: Area under the blood concentration-time curve calculated by extrapolating from the last measurable blood collection time point to infinite time, $AUC_{last}$: Area under the blood concentration-time curve until the last measurable blood collection time point, $T_{1/2}$: elimination half-life, $AUC_{Extp}$(%): [($AUC_{inf}$-$AUC_{last}$)/$AUC_{inf}$]*100) As can be seen in Table 8 and FIG. 9, it can be confirmed that the half-life increases as the number of O-glycan increases.

2-2. Target Protein: GLP-1-Fc Fusion Protein (GLP-1-Fc, Dulaglutide)

Fusion polypeptide Dulaglutide-ID2 prepared in Example 1.2 was subcutaneously administered to SD rats (Orientbio, 7 weeks old, about 300 g; n=3) at a dose of 0.1 mg/kg, and Pharmacokinetics were tested. Sampling was performed at 0, 0.5, 1, 2, 4, 6, 8, 24, 48, 96 and 144 hours, and for comparison, Dulaglutide (Trulicity, Lilly Korea) was administered subcutaneously at a dose of 0.1 mg/kg in the same manner as above, and tested.

After administration to the SD rat as above, the blood collected by time-point was centrifuged to obtain a serum. ELISA was performed using Anti-GLP-1 antibody (Novous-Bio) and Anti-Human IgG4 Fc Antibody (Sigma-Aldrich), and the concentrations of Dulaglutide and fusion polypeptide Dulaglutide-ID2 in the blood by time-point were confirmed. Using this data, parameters including AUC (area under the curve) were calculated using software for PK analysis (WinNonlin (Certara L. P.), etc.).

The obtained results are shown in Table 9 and FIG. 10.

TABLE 9

| Parameter | Dulaglutide | | Dulaglutide-ID2 | |
|---|---|---|---|---|
| | Mean | SD | Mean | SD |
| Cmax (ng/mL) | 268 | 24.2 | 46.8 | 2.43 |
| Tmax (hr) | 24 | — | 24 | — |
| AUCinf (ng*hr/mL) | 11500 | 1230 | 3430 | 535 |
| AUClast (ng*hr/mL) | 11700 | 1200 | 3870 | 786 |
| T½ (hr) | 26.9 | 3.06 | 40.9 | 7.04 |
| AUCextp (%) | 1.97 | 0.542 | 10.9 | 4.09 |

($C_{max}$: Maximum blood concentration, $T_{max}$: Time when peak blood concentration is reached, $AUC_{inf}$: Area under the blood concentration-time curve calculated by extrapolating from the last measurable blood collection time point to infinite time, $AUC_{last}$: Area under the blood concentration-time curve until the last measurable blood collection time point, $T_{1/2}$: elimination half-life, $AUC_{Extp}$(%): [($AUC_{inf}$–$AUC_{last}$)/$AUC_{inf}$]*100) As can be seen in Table 9 and FIG. 10, it can be confirmed that the half-life of GLP-1-Fc (Dulaglutide-ID2) fused with the hinge region increased by about 1.5 times as compared with Dulaglutide, which is not fused with the hinge area. Further, Cmax was about ⅕, and AUClast was about ⅓.

From the above description, those skilled in the art will understand that the present disclosure can be implemented in other specific forms without changing the technical idea or essential features thereof. In this regard, it should be understood that the embodiments described above are illustrative in all respects and non-limiting. The scope of the present disclosure should be construed that all changes or modifications derived from the meaning and scope of the claims to be described later rather than the above detailed description and the equivalent concepts thereof are included in the scope of the present disclosure.

The invention claimed is:

1. A fusion polypeptide comprising the structure of the following formula:

N'—(Z)n-Y—(Z)m-C' in the above formula,

N' is the N-terminus of the fusion polypeptide, C' is the C-terminus of the fusion polypeptide, Y is a target polypeptide, Z is an O-glycosylatable polypeptide region, n is the number of O-glycosylatable polypeptide regions bound to the N-terminus of the target polypeptide, and is an integer of 1, and m is the number of O-glycosylatable polypeptide regions bound to the C-terminus of the target polypeptide, and is an integer of 2 or 3, wherein each of the O-glycosylatable polypeptide regions is independently selected from the group consisting of:

(1) a hinge region of Immunoglobulin D (IgD), (2) a hinge region of Immunoglobulin A (IgA), (3) a polypeptide comprising the amino acid sequence of SEQ ID NO: 1, (4) a polypeptide comprising 5 or more consecutive amino acids of the amino acid sequence of SEQ ID NO: 1 and containing 3 to 7 O-glycosylated residues, (5) a polypeptide comprising 34 or more consecutive amino acids of Immunoglobulin D (IgD) and containing the polypeptide of (3) or (4), (6) a polypeptide comprising the amino acid sequence of SEQ ID NO: 2, (7) a polypeptide comprising 8 or more consecutive amino acids of the amino acid sequence of SEQ ID NO: 2 and containing 3 to 8 O-glycosylated residues, and (8) a polypeptide comprising 19 or more consecutive amino acids of Immunoglobulin A (IgA) and containing the polypeptide of (6) or (7), the fusion polypeptide is O-glycosylated, and the total number of O-glycans contained in the fusion polypeptide is 13 or more per the target polypeptide.

2. The fusion polypeptide according to claim 1, wherein each of the O-glycosylatable polypeptide regions is independently selected from the group consisting of:

(1) a polypeptide comprising the amino acid sequence of SEQ ID NO: 1, (2) a polypeptide comprising 5 or more consecutive amino acids of the amino acid sequence of SEQ ID NO: 1 and containing SEQ ID NO: 9, or 7 or more consecutive amino acids of the amino acid sequence of SEQ ID NO: 1 and containing SEQ ID NO: 10, (3) a polypeptide comprising 34 or more consecutive amino acids of Immunoglobulin D (IgD) and containing the polypeptide of (1) or (2), (4) a polypeptide comprising the amino acid sequence of SEQ ID NO: 2, (5) a polypeptide comprising 8 or more consecutive amino acids of the amino acid sequence of SEQ ID NO: 2 and containing SEQ ID NO: 12, and (6) a polypeptide comprising 19 or more consecutive amino acids of Immunoglobulin A (IgA) and containing the polypeptide of (4) or (5).

3. The fusion polypeptide according to claim 1, wherein an in vivo half-life of the target polypeptide bound to the O-glycosylatable polypeptide regions in the fusion polypeptide increases by 1.5 times as compared with the target polypeptide that is not bound to the O-glycosylated polypeptide regions.

4. A pharmaceutical composition for treatment of a disease associated with a deficiency or functional abnormality of a target polypeptide, comprising the fusion polypeptide of claim 1.

5. A nucleic acid molecule encoding the fusion polypeptide of claim 1.

6. A recombinant vector comprising the nucleic acid molecule of claim 5.

7. A recombinant cell comprising the recombinant vector of claim 6.

8. A method for producing the fusion polypeptide of claim 1, the method comprising the step of culturing a recombinant cell comprising a recombinant vector containing a nucleic acid molecule encoding the fusion polypeptide.

9. A method of enhancing an in-vivo stability of a target polypeptide comprising the step of linking O-glycosylatable polypeptide regions to both the N- and C-termini of the target polypeptide, to generate the fusion polypeptide of claim 1, wherein the fusion polypeptide comprises the structure of the following formula:

N'—(Z)n-Y—(Z)m-C' in the above formula,

N' is the N-terminus of the fusion polypeptide, C' is the C-terminus of the fusion polypeptide, Y is a target polypeptide, Z is an O-glycosylatable polypeptide region, n is the number of O-glycosylatable polypeptide regions bound to the N-terminus of the target polypeptide, and is an integer of 1, and m is the number of O-glycosylatable polypeptide regions bound to the C-terminus of the target polypeptide, and is an integer of 2 or 3, and wherein each of the O-glycosylatable polypeptide regions is independently selected from the group consisting of:

(1) a hinge region of Immunoglobulin D (IgD), (2) a hinge region of Immunoglobulin A (IgA), (3) a polypeptide comprising the amino acid sequence of SEQ ID NO: 1, (4) a polypeptide comprising 5 or more consecutive amino acids of the amino acid sequence of SEQ ID NO: 1 and containing 3 to 7 O-glycosylated residues, (5) a polypeptide comprising 34 or more consecutive amino acids of Immunoglobulin D (IgD) and containing the polypeptide of (3) or (4), (6) a polypeptide comprising the amino acid sequence of SEQ ID NO: 2, (7) a polypeptide comprising 8 or more consecutive amino acids of the amino acid sequence of SEQ ID NO: 2 and containing 3 to 8 O-glycosylated residues, and (8) a polypeptide comprising 19 or more consecutive amino acids of Immunoglobulin A (IgA) and containing the polypeptide of (6) or (7), the fusion polypeptide is O-glycosylated, and the total number of O-glycans contained in the fusion polypeptide is 13 or more per the target polypeptide.

10. The method of enhancing an in-vivo stability of a target polypeptide according to claim 9, wherein each of the O-glycosylatable polypeptide regions is independently selected from the group consisting of:

(1) a polypeptide comprising the amino acid sequence of SEQ ID NO: 1, (2) a polypeptide comprising 5 or more consecutive amino acids of the amino acid sequence of SEQ ID NO: 1 and containing SEQ ID NO: 9, or 7 or more consecutive amino acids of the amino acid sequence of SEQ ID NO: 1 and containing SEQ ID NO: 10, (3) a polypeptide comprising 34 or more consecutive amino acids of Immunoglobulin D (IgD) and containing the polypeptide of (1) or (2), (4) a polypeptide comprising the amino acid sequence of SEQ ID NO: 2, (5) a polypeptide comprising 8 or more consecutive amino acids of the amino acid sequence of SEQ ID NO: 2 and containing SEQ ID NO: 12, and (6) a polypeptide comprising 19 or more consecutive amino acids of Immunoglobulin A (IgA) and containing the polypeptide of (4) or (5).

* * * * *